United States Patent
Lin et al.

(10) Patent No.: US 10,689,430 B2
(45) Date of Patent: Jun. 23, 2020

(54) INSULIN RECEPTOR PARTIAL AGONISTS

(71) Applicant: Merck Sharp & Dohme Corp., Rahway, NJ (US)

(72) Inventors: Songnian Lin, Holmdel, NJ (US); Lin Yan, East Brunswick, NJ (US); Pei Huo, Milburn, NJ (US); Dmitri Pissarnitski, Scotch Plains, NJ (US); Danqing Feng, Green Brook, NJ (US); Ravi Nargund, East Brunswick, NJ (US); Christina Madsen-Duggan, Scotch Plains, NJ (US); Yuping Zhu, Basking Ridge, NJ (US); Ahmet Kekec, Hoboken, NJ (US); Zhicai Wu, Montvale, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 16/301,010

(22) PCT Filed: May 23, 2017

(86) PCT No.: PCT/US2017/033900
§ 371 (c)(1),
(2) Date: Nov. 13, 2018

(87) PCT Pub. No.: WO2017/205309
PCT Pub. Date: Nov. 30, 2017

(65) Prior Publication Data
US 2019/0177393 A1    Jun. 13, 2019

Related U.S. Application Data

(60) Provisional application No. 62/341,171, filed on May 25, 2016.

(51) Int. Cl.
| | |
|---|---|
| *C07K 14/62* | (2006.01) |
| *A61K 38/28* | (2006.01) |
| *A61P 3/10* | (2006.01) |
| *A61K 38/00* | (2006.01) |

(52) U.S. Cl.
CPC .............. *C07K 14/62* (2013.01); *A61K 38/28* (2013.01); *A61P 3/10* (2018.01); *A61K 38/00* (2013.01); *C07K 2319/00* (2013.01)

(58) Field of Classification Search
CPC ........... A61K 38/00; A61K 38/28; A61P 3/10; C07K 14/62; C07K 2319/00
See application file for complete search history.

(56) References Cited

U.S. PATENT DOCUMENTS

| | | | |
|---|---|---|---|
| 3,907,763 A | 9/1975 | Brandenburg et al. | |
| 4,608,364 A * | 8/1986 | Grau | C07K 14/62 514/6.9 |
| 5,304,473 A | 4/1994 | Belagaje et al. | |
| 5,514,646 A | 5/1996 | Chance et al. | |
| 6,630,348 B1 | 10/2003 | Lee et al. | |
| 6,852,694 B2 | 2/2005 | Van Antwerp et al. | |
| 6,908,897 B2 | 6/2005 | Brandenburg et al. | |
| 9,593,156 B2 * | 3/2017 | Dimarchi | A61K 47/55 |
| 10,017,556 B2 | 7/2018 | Lin et al. | |
| 10,183,981 B2 * | 1/2019 | Lin | A61K 38/28 |
| 2002/0013269 A1 | 1/2002 | Balschmidt et al. | |
| 2002/0156234 A1 | 10/2002 | Rubroder et al. | |
| 2003/0113305 A1 | 6/2003 | Osborne et al. | |
| 2004/0198654 A1 * | 10/2004 | Glaesner | C07K 14/605 514/4.8 |
| 2009/0197800 A1 | 8/2009 | Schaffer et al. | |
| 2011/0166043 A1 | 7/2011 | Nagy et al. | |
| 2014/0162906 A1 | 6/2014 | Nagy et al. | |
| 2015/0274802 A1 | 10/2015 | Dimarchi et al. | |

FOREIGN PATENT DOCUMENTS

| | | | |
|---|---|---|---|
| EP | 0214826 A3 | 6/1987 | |
| WO | 9516708 A1 | 6/1995 | |
| WO | 9634882 A1 | 11/1996 | |
| WO | 2005054291 A1 | 6/2005 | |
| WO | 2006097521 A1 | 9/2006 | |
| WO | 2007096332 A1 | 8/2007 | |
| WO | 2007/104737 A1 | 9/2007 | |
| WO | 2007/104738 A2 | 9/2007 | |
| WO | 2007104734 A1 | 9/2007 | |
| WO | 2007104736 A2 | 9/2007 | |
| WO | 2009099763 A1 | 8/2009 | |
| WO | 2009132129 A2 | 10/2009 | |
| WO | 2010080606 A1 | 7/2010 | |
| WO | 2010080609 A1 | 7/2010 | |
| WO | WO2011059895 A2 | 12/2011 | |
| WO | WO2014052451 A2 | 4/2014 | |
| WO | WO2014141165 A1 | 9/2014 | |
| WO | WO2016081670 A2 | 5/2016 | |

OTHER PUBLICATIONS

Thermo—Technical Information. N-terminal Acetylation and C-Terminal Amidation of Peptides. 2004, 2 pages. (Year: 2004).*
Brandt, Sara J., Synthesis and Characterization of Insulin Receptor Partial Agonists as a Route to improved Diabetes Therapy, PhD Dissertation, Indiana University, 2015, pp. 1-207.
Brange, Jens et al., Designing Insulin for Diabetes Therapy by Protein Engineering, Current Opinion in Structural Biology, 1991, 934-940, 1.
Breiner et al., Heterogeneity of Insulin Receptors in Rat Tissues as Detected with the Partial Agonist, Molecular Pharmacology, 1993, Issue 2, pp. 271-276, 344.

(Continued)

*Primary Examiner* — Marcela M Cordero Garcia

(74) *Attorney, Agent, or Firm* — Janet E. Fair; Catherine D. Fitch

(57) ABSTRACT

Insulin dimers and insulin analog dimers that act as partial agonists at the insulin receptor are disclosed.

6 Claims, 6 Drawing Sheets

Specification includes a Sequence Listing.

(56) References Cited

OTHER PUBLICATIONS

Brems, David et al., Altering the Association Properties of Insulin by Amino Acid Replacement, Protein Engineering, 1992, 527-533, 5.
Deppe et al., Structure activity relationship of covalently dimerized insulin derivatives: correlation of partial agonist efficacy with cross linkage at lysine B29, Archives of Pharmacology, Springer, DE, 1994, pp. 213-217, 350.
Hashimoto, Muneaki et al., Synthesis of Palmitoyl Derivatives of Insulin and Their Biological Activities, Pharmaceutical Research, 1989, 171-176, 6.
International Search Report of PCT/US2015/061445 dated Jun. 17, 2016.
Joost et al., Quantitative Dissociation of Glucose Transport Stimulation and Insulin Receptor Tyrosine Kinase Activation in Isolated Adipocytes with a Covalent Insulin Dimer, Biochemical Pharmacology, 1989, vol. 14, pp. 2269-2277, 2338.
Knudsen et al., Agonism and Antagonism at the Insulin Receptor, PLos ONE, 2012, pp. 1-10, 17.
Kristensen et al., A single-chain insulin-like growth factor I/insulin hybrid binds with high affinity to the insulin receptor, Biochem. J., 1995, pp. 981-986, 305.
Mayer et al., Insulin Structure and Function, Biopolymers, 2007, No. 5, pp. 687-713, 788.
Means, Gary et al., Chemical Modifications of Proteins: History and Applications, Bioconjugate Chem., 1990, 2-12, 1.
Miller, Brian T., Acylation of Peptide Hydroxyl Groups with the Bolton—Hunter Reagent, Biochemical and Biophysical Research Communications, 1996, 377-382, 218.
Dimomi et al., Carbamylation of Insulin and its Biological Activity, Nephron, 1987, pp. 63-66, 46.
Previero et al., Specific O-Acylation of Hydroxylamino Acids in Presence of Free Amino Groups, Biochimica Et Biophysica Acta, 1972, 7-13, 263.
Roth et al., Effects of Covalently Linked Insulin Dimers on Receptor Kinase Activity and Receptor down Regulation, Febs Letters, 1984, Issue 2, pp. 360-364, 170.
Sang et al., Novel thioester reagents afford efficient and specific S-acylation of unprotected peptides under mild conditions in aqueous solution, J. Peptide Res, 2005, 169-180, 66.
Schuettler et al., Preparation and Properties of Covalently Linked Insulin Dimers, Biopolymers, 1982, pp. 317-330, 363.
Shimohigashi, Yasuyuki et al., Dehydro-Enkephalins—Synthesis and Biological Activity of Enkephalin, Int'l Journ Pept. Pro Res, 1982, 54-62, 19.
Shojaee-Moradie et al., Demonstration of a relatively hepatoselective effect of covalent insulin dimers on glucose metabolism in dogs, Diabetologia, 1995, pp. 1007-1013, 1038.
Tatnell et al., Covalently Linked Insulin Dimers—Their Metabolism and Biological Effects Invivo as Partial Competitive Antagonists of Insulin Clearance, Diabetologia, 1984, Issue 1, pp. 27-31, 27.
Tatnell et al., Evidence concerning the mechanism of insulin receptor interaction and the structure of teh insulin receptor from biological properties of covalently linked insulin dimers, Biochem. J., 1983, pp. 687-694, 216.
Vinther et al., Novel Covalently Linked Insulin Dimer Engineered to Investigate teh Function of Insulin Dimerization, PLos ONE, 2012, pp. 1-9, 7.
Weiland et al., Antagonistic Effects of a Covalently Dimerized Insulin Derivative on Insulin Receptors in 3T3-L1 Adipocytes, Proc. Natl. Acad. Sci. USA, 1990, pp. 1154-1158, 1187.
Written Opinion of PCT/US2015/061445 dated Jun. 17, 2016.
Zaykov et al., Poster P212-Exploration of the Structural and Mechanistic Basis for Partial Agonism of Insulin Dimers, American Peptide Symposium—Poster, Orlando Florida, 2015, Poster.

* cited by examiner

INSULIN RECEPTOR PARTIAL AGONISTS

CROSS-REFERENCE TO RELATED APPLICATIONS

This application is a U.S. National Phase application under 35 U.S.C. § 371 of PCT Application No. PCT/US2017/033900, filed May 23, 2017, which published as WO2017/205309 A1 on Nov. 30, 2017, and claims priority under 35 U.S.C. § 365(b) from U.S. provisional patent application No. 62/341,171, filed May 25, 2016.

REFERENCE TO SEQUENCE LISTING SUBMITTED ELECTRONICALLY

The sequence listing of the present application is submitted electronically via 10 EFS-Web as an ASCII formatted sequence listing with a file name "24335USPCT-SEQLIST-07NOV2018.txt", creation date of Nov. 7, 2018, and a size of 6.54 Kb. This sequence listing submitted via EFS-Web is part of the specification and is herein incorporated by reference in its entirety.

BACKGROUND OF THE INVENTION

(1) Field of the Invention

The present invention relates to insulin dimers and insulin analog dimers that act as partial agonists at the insulin receptor.

(2) Description of Related Art

Insulin is an essential therapy for type 1 diabetes mellitus (T1DM) patients and many type 2 mellitus diabetics (T2DMs), prescribed to close to one third of U.S. patients among all anti-diabetic drug users in the past decade. The worldwide market for insulins was US$20.4 billion in 2013 and is growing at a faster rate than all other anti-diabetic agents combined. However, challenges of current insulin therapies, including narrow TI to hypoglycemia and body weight gain, limit their wider adoption and potential for patients to achieve ideal glycemic control.

In addition to prandial insulin secretion in response to meals, the pancreas releases insulin at a "basal" rate, governed largely by plasma glucose levels to maintain appropriate fasting glucose regulation. This is achieved mainly by controlling hepatic glucose release, through endogenous insulin's hepato-preferring action. Modern insulin analogs include rapid acting and basal insulins, as well as mixtures of these two. Rapid-acting insulin analogs (RAA) are developed to control post-prandial hyperglycemia while insulins with extended duration of action regulate basal glucose levels. Long-acting insulins are used by all T1DM (in combination with prandial injections) and the majority of T2DM patients start their insulin therapy from a basal product. Basal insulin consumption is growing rapidly as the worldwide diabetes population (particularly T2DM) soars.

Despite continuous development efforts over the past several decades, available long-acting insulins are still not optimized compared to physiological basal insulin. This is partially because major focus was on improving PK flatness of these analogs but not fixing the relative over-insulinization of peripheral tissues, which contributes to increased hypoglycemia risk. As a result, hypoglycemia remains a key medical risk with huge burden on patients and causes significant morbidity and mortality.

BRIEF SUMMARY OF THE INVENTION

The present invention provides compounds comprising two insulin molecules covalently linked to form an insulin molecule dimer that may activate the insulin receptor with regular insulin-like potency but with reduced maximum activity. These compounds are insulin receptor partial agonists (IPRAs): they behave like other insulin analogs to lower glucose effectively but with lower risk of hypoglycemia.

Provided are insulin receptor partial agonist covalent insulin dimers formulated as novel and transformative basal insulins (once daily administration) that manifest an improved therapeutic index (TI) over current standard of care (SOC) basal insulins. In one embodiment, the IPRAs of the present invention may lower glucose effectively with reduced risk of hypoglycemia in diabetic minipig and has the property of a once daily (QD) basal insulin. The improved TI may empower practitioners to more aggressively dose IRPAs of the present invention to achieve target goals for control of fasting glucose. Tight control of fasting glucose and HbA1c by an IRPA may allow it to serve as 1) a stand-alone long-acting insulin with an enhanced efficacy and safety profile in T2DM and 2) an improved foundational basal insulin in T1DM (and some T2DM) for use with additional prandial rapid-acting insulin analogs (RAA) doses. Thus, the present invention provides the following embodiments.

The present invention provides an insulin dimer comprising a first B29 or B28 Lys of a first insulin heterodimer molecule having a first A-chain polypeptide and first B-chain polypeptide and a second B29 or B28 Lys of a second insulin heterodimer having a second A-chain polypeptide and second B-chain polypeptide conjugated together by a bifunctional linker selected from the group consisting Linker 1, Linker 2, Linker 3, Linker 4, Linker 5, Linker 6, Linker 7, Linker 8, Linker 9, Linker 10, Linker 11, Liner 12, Linker 13, Linker 14, Linker 15, Linker 16, Linker 17, Linker 18, Linker 19, Linker 20, Linker 21, Linker 22, Linker 23, Linker 24, Linker 25, Linker 26, Linker 27, Linker 28, Linker 29, Linker 30, Linker 31, Linker 32, Linker 33, Linker 34, Linker 35, Linker 36, Linker 37, Linker 38, Linker 39, Linker 40, Linker 41, Linker 42, Linker 43, Linker 44, Linker 45, Linker 46, Linker 47, Linker 48, Linker 49, Linker 50, Linker 51, Linker 52, Linker 53, Linker 54, Linker 55, Linker 56, Linker 57, Linker 58, Linker 59, Linker 60, Linker 61, Linker 62, Linker 63, Linker 64, and Linker 65.

In particular aspects of the insulin dimer, at least one of the first or second A-chain or B-chain polypeptides is conjugated at its N-terminal amino acid to a substituent or at least the N-terminal amino acids of the first insulin heterodimer molecule are conjugated to a substituent or the N-terminal amino acids of both the first insulin heterodimer and second insulin heterodimer are conjugated to a substituent.

In particular aspects of the insulin dimer, the substituent comprises an N-hydroxysuccinimide ester linked to a group having the general formula RC(O)—, where R can be R'CH$_2$, R'NH, R'O, and R' can be H, linear alkyl chain, amino acid, peptide, polyethylene glycol (PEG), saccharides.

In particular aspects of the insulin dimer, the substituent is a carbamoyl group, acetyl group, glycine, methyl group, methoxy acetyl, group, dimethyl group, isobutyl group, PEG1 group, AEG group, AEG-C6 alkyl group, 3-morpholinopropionate, or PEG2 group.

In particular aspects, when the linker is Linker 49 (suberic) then insulin dimer comprises at least one substituent that is 3-morpholinopropionate or only one heterodimer comprising the insulin dimer has a carbamoyl substituent on the N-terminal amino groups.

In particular aspects of the insulin dimer, the first insulin and the second insulin heterodimers are independently native human insulin, insulin lispro, insulin aspart, desB30 insulin, or insulin glargine.

In particular aspects of the insulin dimer, each A-chain polypeptide independently comprises the amino acid sequence GX$_2$X$_3$EQCCX$_8$SICSLYQLX$_{17}$NX$_{19}$CX$_{23}$ (SEQ ID NO:3) and each B-chain polypeptide independently comprises the amino acid sequence X$_{25}$LCGX$_{29}$X$_{30}$LVEALYLVCGERGFX$_{27}$YTX$_{31}$X$_{32}$ (SEQ ID NO:4) or X$_{22}$VNQX$_{25}$X$_{26}$CGX$_{29}$X$_{30}$LVEALYLVCGERGFX$_{27}$YTX$_{31}$X$_{32}$X$_{33}$X$_{34}$X$_{35}$ (SEQ ID NO:5) wherein X$_2$ is isoleucine or threonine; X$_3$ is valine, glycine, or leucine; X$_8$ is threonine or histidine; X$_{17}$ is glutamic acid or glutamine; X$_{19}$ is tyrosine, 4-methoxy-phenylalanine, alanine, or 4-amino phenylalanine; X$_{23}$ is asparagine or glycine; X$_{22}$ is or phenylalanine and desamino-phenylalanine; X$_{25}$ is histidine or threonine; X$_{26}$ is leucine or glycine; X$_{27}$ is phenylalanine or aspartic acid; X$_{29}$ is alanine, glycine, or serine; X$_{30}$ is histidine, aspartic acid, glutamic acid, homocysteic acid, or cysteic acid; X$_{31}$ is aspartic acid, proline, or lysine; X$_{32}$ is lysine or proline; X$_{33}$ is threonine, alanine, or absent; X$_{34}$ is arginine or absent; and X$_{35}$ is arginine or absent; with the proviso at least one of X$_{31}$ or X$_{32}$ is lysine.

The present invention further provides a composition comprising a first insulin or insulin analog heterodimer and a second insulin or insulin analog heterodimer each heterodimer including an A-chain polypeptide and a B-chain polypeptide, wherein the A-chain polypeptide and the B-chain polypeptide are linked together through interchain disulfide bonds; wherein the first and second insulin or insulin analog heterodimers are covalently linked together through a linking moiety joining the side chain of an amino acid at or near the carboxy terminus of the two respective B-chain polypeptides; wherein the linking moiety is selected from the group consisting of Linking moiety 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 42, 44, 45, 45, 47, 48, 49, 50, 51, 52, 53, 54, 55, 56, 57, 58, 59, 60, 61, 62, 63, 64 and 65; wherein the insulin is recombinant human insulin and the insulin analog is selected from the group consisting of insulin lispro, insulin aspart, and insulin glargine; and wherein the amino terminus of at least one of the A-chain polypeptides and the B-chain polypeptides of the first insulin polypeptide or second insulin polypeptide is covalently linked to a substituent.

In particular aspects of the insulin dimer, the first and second insulin or insulin analog heterodimers are the same or wherein the first and second insulin or insulin analog heterodimers are different.

In particular aspects of the insulin dimer, the linking moiety covalently links the first insulin or insulin analog heterodimer and the second insulin or insulin analog heterodimer via the epsilon amino group of a lysine residue at or near the carboxy terminus of their respective B-chain polypeptides.

In particular aspects of the insulin dimer, wherein the substituent has a general formula RC(O)—, where R can be R'CH2, R'NH, R'O, and R' can be H, linear alkyl chain, amino acid, peptide, PEG, saccharides, which in particular aspects RC(O)— may be acetyl, phenylacetyl, carbamoyl, N-alkyl carbamoyl, or alkoxycarbonyl. In particular aspects, the substituent is selected from the group consisting of acetyl, phenylacetyl, carbamoyl, N-alkyl carbamoyl, isobutyl, methoxy acetyl, glycine, aminoethylglucose (AEG), AEG-C6, PEG1, PEG2, N-dimethyl, 3-morpholinopropionate, and alkoxycarbonyl.

The present invention further provides a composition comprising an insulin dimer selected from the group consisting of Dimers 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85 and 86.

The present invention further provides a method for treating diabetes comprising administering to an individual with diabetes a therapeutically effective amount of a composition comprising the insulin receptor partial agonist of any one of insulin dimers. In particular aspects the diabetes is Type 1 diabetes, Type 2 diabetes, or gestational diabetes.

The present invention further provides a composition for the treatment of diabetes comprising the any one of the above insulin dimers. In particular aspects the diabetes is Type 1 diabetes, Type 2 diabetes, or gestational diabetes.

The present invention further provides for the use of any one of the above the insulin dimers for the manufacture of a medicament for the treatment of diabetes. In particular aspects the diabetes is Type 1 diabetes, Type 2 diabetes, or gestational diabetes.

The present invention further provides a composition comprising any one of the aforementioned insulin dimers and a glucagon-like protein 1 (GLP-1) receptor agonist. In particular aspects, the GLP-1 agonist is liraglutide, dulaglutide, or albiglutide.

Definitions

Insulin—as used herein, the term means the active principle of the pancreas that affects the metabolism of carbohydrates in the animal body and which is of value in the treatment of diabetes mellitus. The term includes synthetic and biotechnologically derived products that are the same as, or similar to, naturally occurring insulins in structure, use, and intended effect and are of value in the treatment of diabetes mellitus. The term is a generic term that designates the 51 amino acid heterodimer comprising the A-chain peptide having the amino acid sequence shown in SEQ ID NO: 1 and the B-chain peptide having the amino acid sequence shown in SEQ ID NO: 2, wherein the cysteine residues a positions 6 and 11 of the A chain are linked in a disulfide bond, the cysteine residues at position 7 of the A chain and position 7 of the B chain are linked in a disulfide bond, and the cysteine residues at position 20 of the A chain and 19 of the B chain are linked in a disulfide bond.

Insulin analog or analogue—the term as used herein includes any heterodimer analogue or single-chain analogue that comprises one or more modification(s) of the native A-chain peptide and/or B-chain peptide. Modifications include but are not limited to substituting an amino acid for the native amino acid at a position selected from A4, A5, A8, A9, A10, A12, A13, A14, A15, A16, A17, A18, A19, A21, B1, B2, B3, B4, B5, B9, B10, B13, B14, B15, B16, B17, B18, B20, B21, B22, B23, B26, B27, B28, B29, and B30; deleting any or all of positions B1-4 and B26-30; or conjugating directly or by a polymeric or non-polymeric linker one or more acyl, polyethylglycine (PEG), or saccharide moiety (moieties); or any combination thereof. As exemplified by the N-linked glycosylated insulin analogues disclosed herein, the term further includes any insulin heterodimer and single-chain analogue that has been modified to have at least one N-linked glycosylation site and in particular, embodiments in which the N-linked glycosylation site is linked to or occupied by an N-glycan. Examples of insulin analogues include but are not limited to the heterodimer and single-chain analogues disclosed in published international application WO20100080606, WO2009/099763, and WO2010080609, the disclosures of which are incorporated herein by reference. Examples of single-chain insulin analogues also include but are not limited to those disclosed in published International Applications WO9634882, WO95516708, WO2005054291, WO2006097521, WO2007104734, WO2007104736, WO2007104737, WO2007104738, WO2007096332, WO2009132129; U.S. Pat. Nos. 5,304,473 and 6,630,348; and Kristensen et al., Biochem. J. 305: 981-986 (1995), the disclosures of which are each incorporated herein by reference.

The term further includes single-chain and heterodimer polypeptide molecules that have little or no detectable activity at the insulin receptor but which have been modified to include one or more amino acid modifications or substitutions to have an activity at the insulin receptor that has at least 1%, 10%, 50%, 75%, or 90% of the activity at the insulin receptor as compared to native insulin and which further includes at least one N-linked glycosylation site. In particular aspects, the insulin analogue is a partial agonist that has less than 80% (or 70%) activity at the insulin receptor as does native insulin. These insulin analogues, which have reduced activity at the insulin growth hormone receptor and enhanced activity at the insulin receptor, include both heterodimers and single-chain analogues.

Single-chain insulin or single-chain insulin analog—as used herein, the term encompasses a group of structurally-related proteins wherein the A-chain peptide or functional analogue and the B-chain peptide or functional analogue are covalently linked by a peptide or polypeptide of 2 to 35 amino acids or non-peptide polymeric or non-polymeric linker and which has at least 1%, 10%, 50%, 75%, or 90% of the activity of insulin at the insulin receptor as compared to native insulin. The single-chain insulin or insulin analogue further includes three disulfide bonds: the first disulfide bond is between the cysteine residues at positions 6 and 11 of the A-chain or functional analogue thereof, the second disulfide bond is between the cysteine residues at position 7 of the A-chain or functional analogue thereof and position 7 of the B-chain or functional analogue thereof, and the third disulfide bond is between the cysteine residues at position 20 of the A-chain or functional analogue thereof and position 19 of the B-chain or functional analogue thereof.

Insulin dimer—as used herein, the term refers to a dimer comprising two insulin heterodimers linked together via their respective lysine residues at or near the C-terminus of their respective B-chain polypeptides (e.g., the B28 or B29 Lysine) via a linking moiety as disclosed herein.

Amino acid modification—as used herein, the term refers to a substitution of an amino acid, or the derivation of an amino acid by the addition and/or removal of chemical groups to/from the amino acid, and includes substitution with any of the 20 amino acids commonly found in human proteins, as well as atypical or non-naturally occurring amino acids. Commercial sources of atypical amino acids include Sigma-Aldrich (Milwaukee, Wis.), ChemPep Inc. (Miami, Fla.), and Genzyme Pharmaceuticals (Cambridge, Mass.). Atypical amino acids may be purchased from commercial suppliers, synthesized de novo, or chemically modified or derivatized from naturally occurring amino acids.

Amino acid substitution—as used herein refers to the replacement of one amino acid residue by a different amino acid residue.

Conservative amino acid substitution—as used herein, the term is defined herein as exchanges within one of the following five groups:

I. Small aliphatic, nonpolar or slightly polar residues:
Ala, Ser, Thr, Pro, Gly;
II. Polar, negatively charged residues and their amides:
Asp, Asn, Glu, Gln, cysteic acid and homocysteic acid;
III. Polar, positively charged residues:
His, Arg, Lys; Ornithine (Orn)
IV. Large, aliphatic, nonpolar residues:
Met, Leu, Ile, Val, Cys, Norleucine (Nle), homocysteine
V. Large, aromatic residues:
Phe, Tyr, Trp, acetyl phenylalanine Treat—As used herein, the term "treat" (or "treating", "treated", "treatment", etc.) refers to the administration of an IRPA of the present disclosure to a subject in need thereof with the purpose to alleviate, relieve, alter, ameliorate, improve or affect a condition (e.g., diabetes), a symptom or symptoms of a condition (e.g., hyperglycemia), or the predisposition toward a condition. For example, as used herein the term "treating diabetes" will refer in general to maintaining glucose blood levels near normal levels and may include increasing or decreasing blood glucose levels depending on a given situation.

Pharmaceutically acceptable carrier—as used herein, the term includes any of the standard pharmaceutical carriers, such as a phosphate buffered saline solution, water, emulsions such as an oil/water or water/oil emulsion, and various types of wetting agents suitable for administration to or by an individual in need. The term also encompasses any of the agents approved by a regulatory agency of the US Federal government or listed in the US Pharmacopeia for use in animals, including humans.

Pharmaceutically acceptable salt—as used herein, the term refers to salts of compounds that retain the biological activity of the parent compound, and which are not biologically or otherwise undesirable. Many of the compounds disclosed herein are capable of forming acid and/or base salts by virtue of the presence of amino and/or carboxyl groups or groups similar thereto.

Pharmaceutically acceptable base addition salts can be prepared from inorganic and organic bases. Salts derived from inorganic bases, include by way of example only, sodium, potassium, lithium, ammonium, calcium, zinc, and magnesium salts. Salts derived from organic bases include, but are not limited to, salts of primary, secondary and tertiary amines.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

Effective or therapeutically effective amount—as used herein refers to a nontoxic but sufficient amount of an insulin analog to provide the desired effect. For example one desired effect would be the prevention or treatment of hyperglycemia. The amount that is "effective" will vary from subject to subject, depending on the age and general condition of the individual, mode of administration, and the like. Thus, it is not always possible to specify an exact "effective amount." It is not always possible to determine the optimal effective amount prior to administration to or by an individual in need thereof. However, an appropriate "effective" amount in any individual case may be determined by one of ordinary skill in the art using routine experimentation.

Parenteral—as used herein, the term means not through the alimentary canal but by some other route such as intranasal, inhalation, subcutaneous, intramuscular, intraspinal, or intravenous.

DETAILED DESCRIPTION OF THE INVENTION

Figure 1:
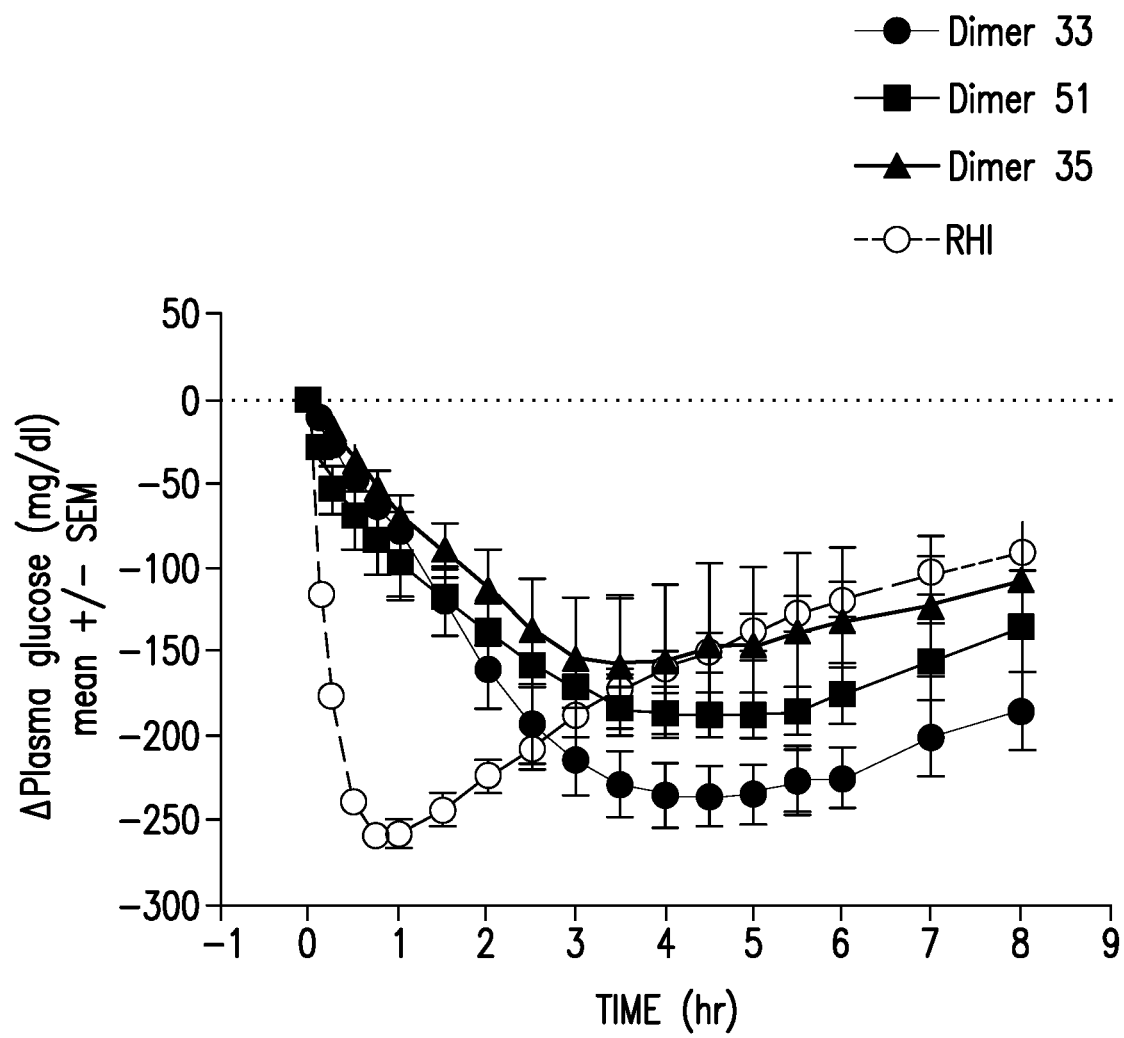
FIG. 1 shows the change in plasma glucose in diabetic minipigs over time for Dimers 33, 51, and 35 compared to recombinant human insulin (RHI). Dimers and RHI were administered at 0.69 nmol/kg.
Figure 2:
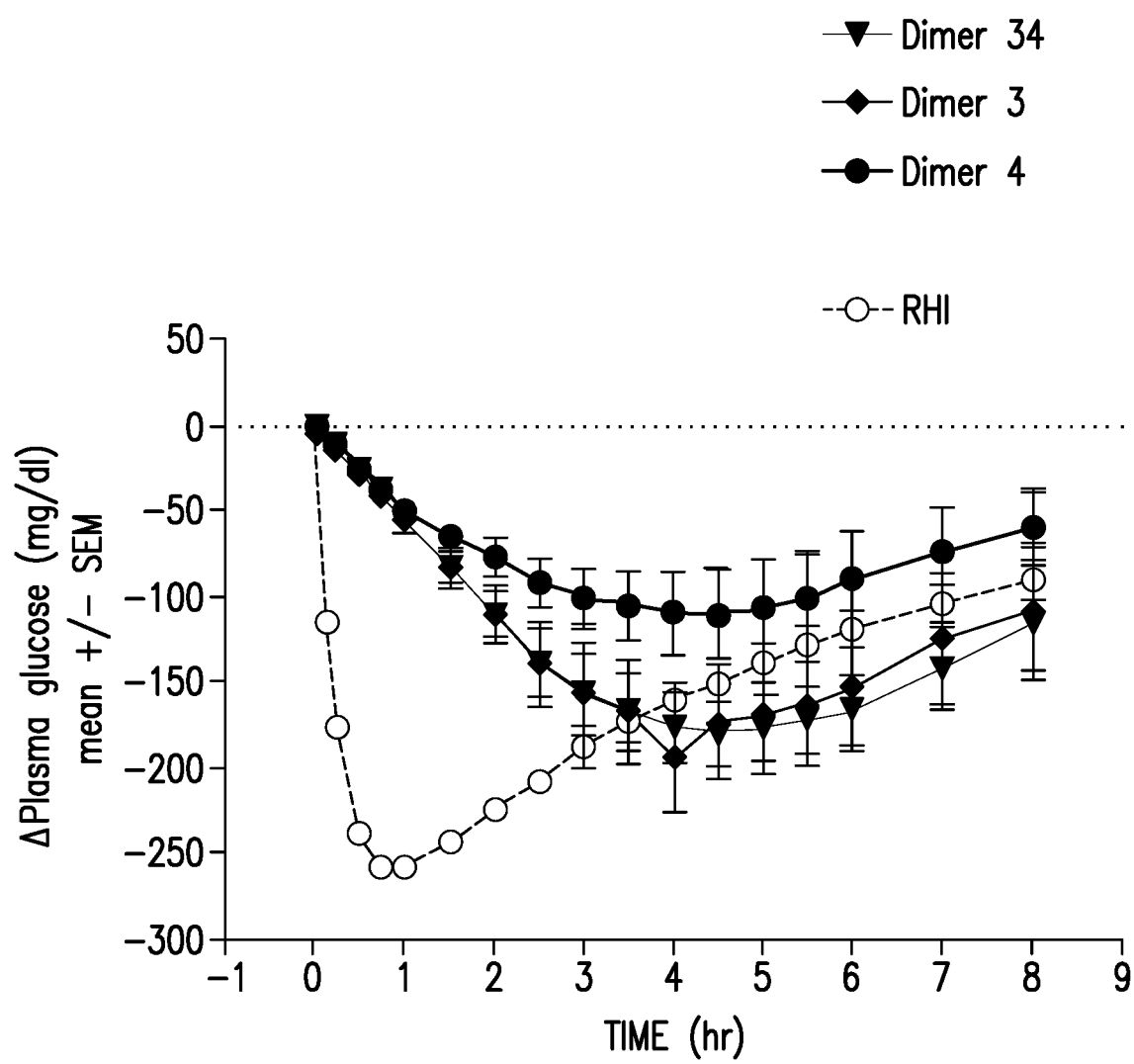
FIG. 2 shows the change in plasma glucose in diabetic minipigs over time for Dimers 34, 3, and 4 compared to recombinant human insulin (RHI). Dimers and RHI were administered at 0.69 nmol/kg.
Figure 3:
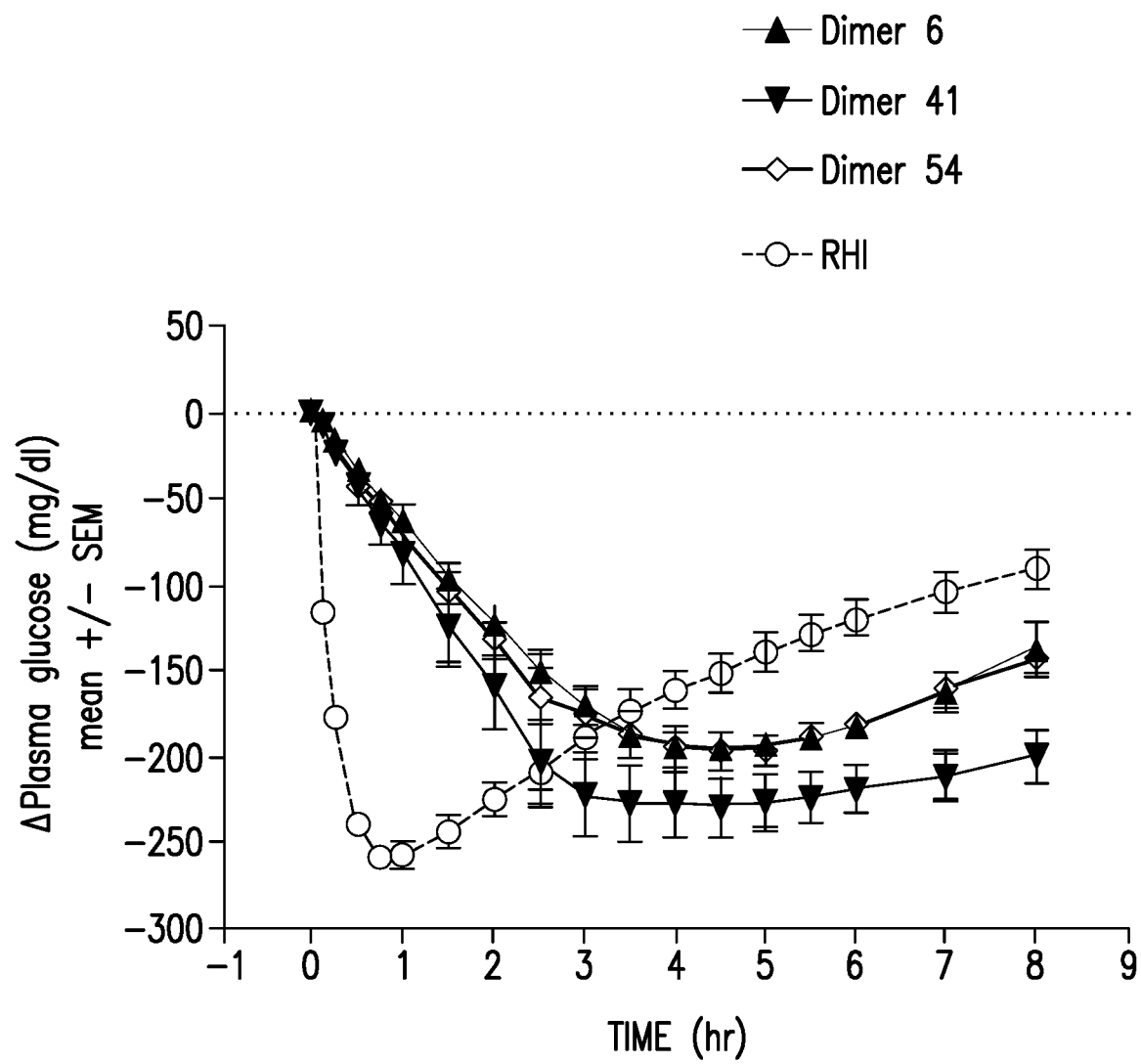
FIG. 3 shows the change in plasma glucose in diabetic minipigs over time for Dimers 6, 41, and 54 compared to recombinant human insulin (RHI). Dimers and RHI were administered at 0.69 nmol/kg.
Figure 4:
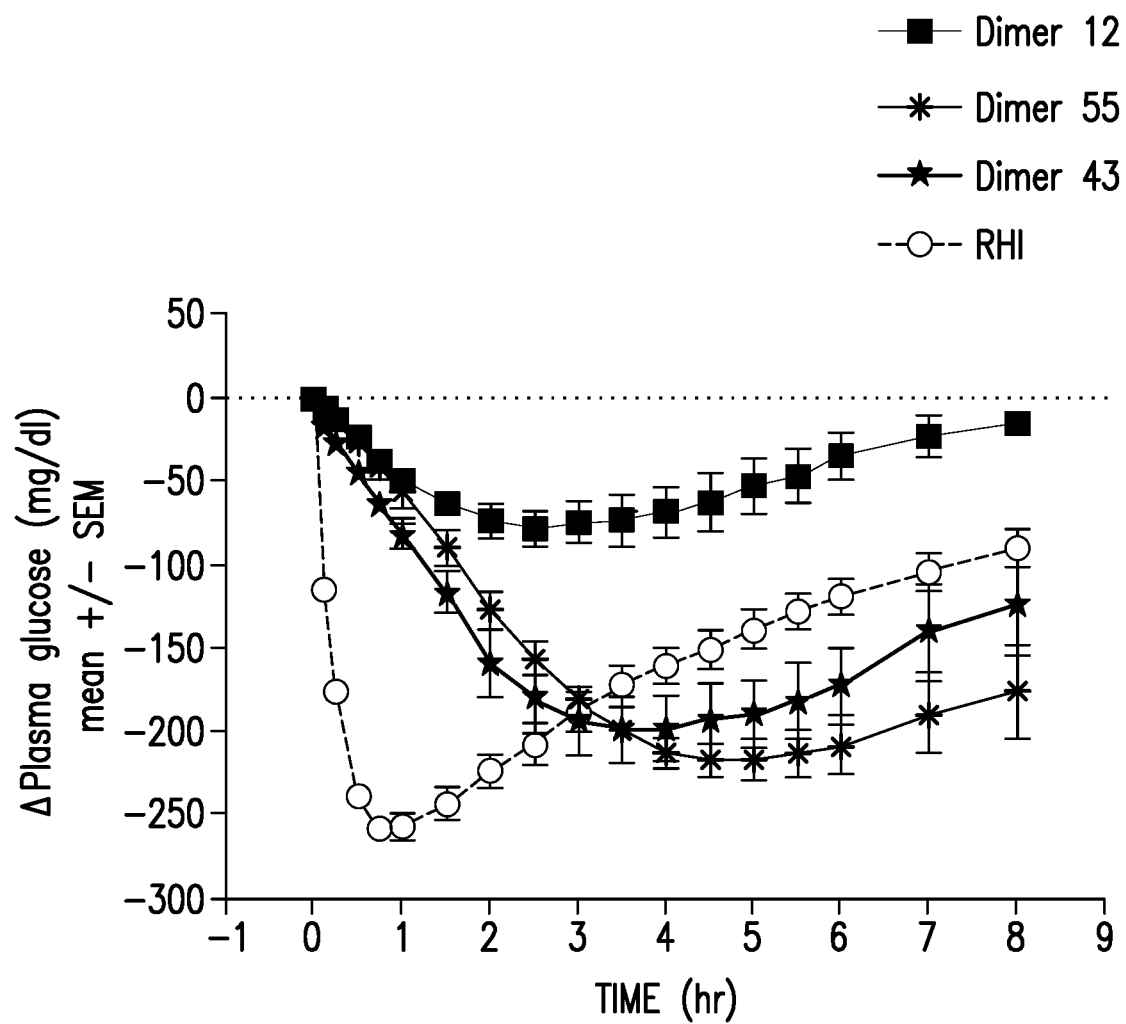
FIG. 4 shows the change in plasma glucose in diabetic minipigs over time for Dimers 12, 55, and 43 compared to recombinant human insulin (RHI). Dimers and RHI were administered at 0.69 nmol/kg.
Figure 5:
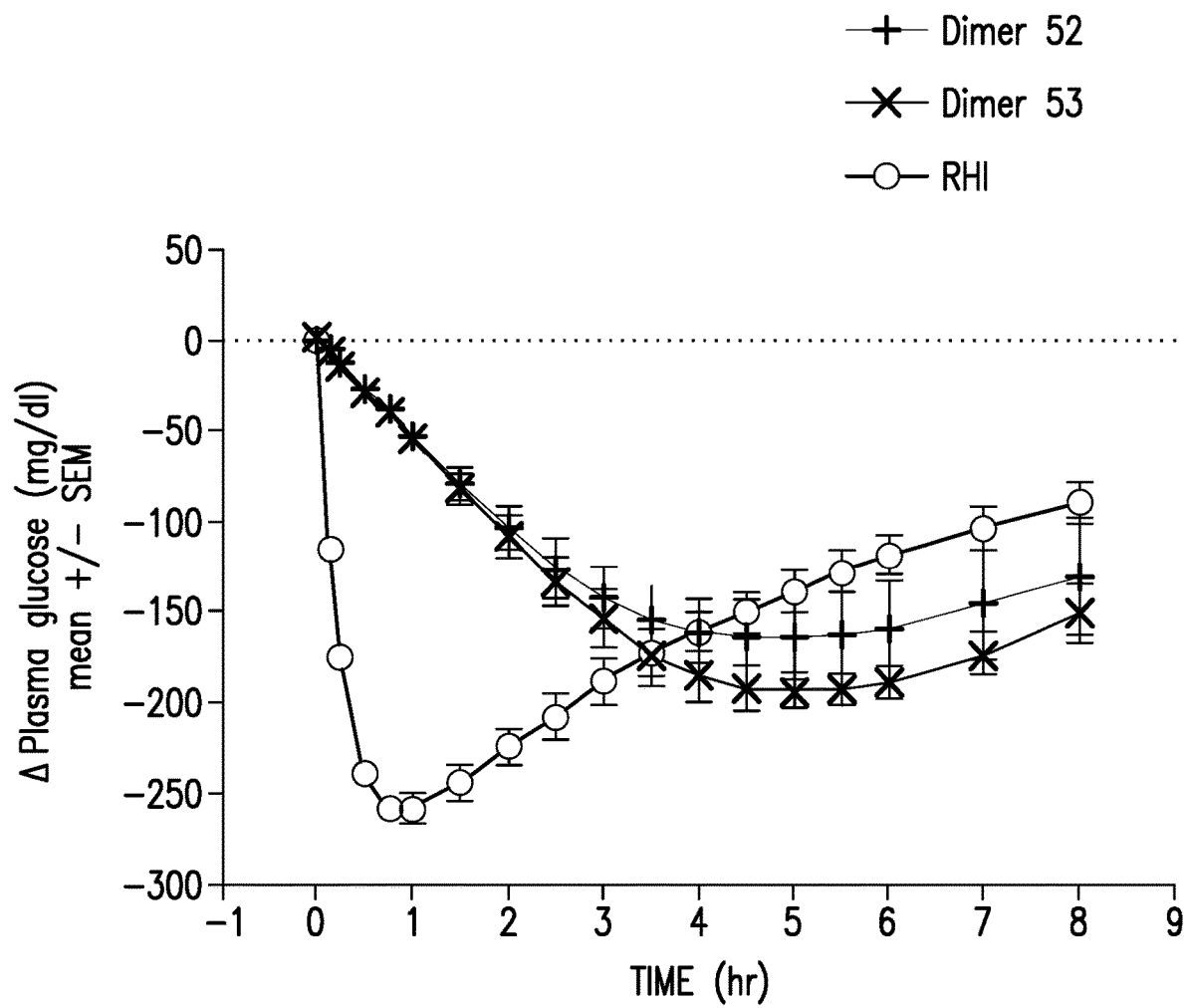
FIG. 5 shows the change in plasma glucose in diabetic minipigs over time for Dimers 52 and 53 compared to recombinant human insulin (RHI). Dimers and RHI were administered at 0.69 nmol/kg.
Figure 6:
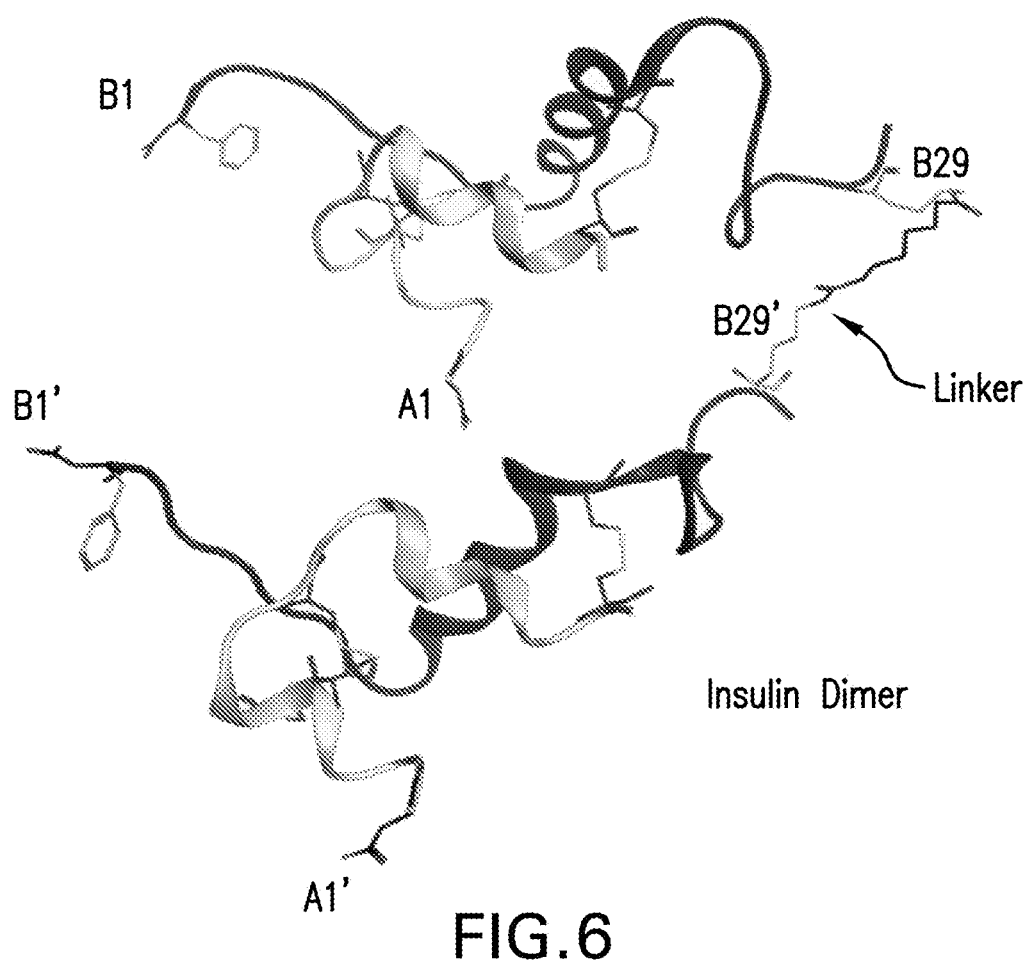
FIG. 6 shows a 3D schematic representation of an insulin dimer wherein the B29 Lysine of one insulin heterodimer to the B29' Lysine of the other insulin heterodimer.

The present invention provides compounds comprising two insulin molecules covalently linked to form a covalently-linked insulin dimer that may activate the insulin receptor with regular insulin-like potency and reduced maximum activity. These compounds are insulin receptor partial agonists (IRPA): they behave like other insulin analogs to lower glucose effectively but with lower risk of hypoglycemia. FIG. 6 shows a 3D representation of an insulin dimer.

Insulin dimers have been disclosed in Brandenburg et al. in U.S. Pat. No. 3,907,763 (1973); Tatnell et al., Biochem J. 216: 687-694 (1983); Shtittler and Brandenburg, Hoppe-Seyler's Z. Physiol. Chem, 363, 317-330, 1982; Weiland et al., Proc Natl. Acad. Sci. (USA) 87: 1154-1158 (1990); Deppe et al., Naunyn-Schmiedeberg's Arch Pharmacol (1994) 350:213-217; Brandenburg and Havenith in U.S. Pat. No. 6,908,897(B2) (2005); Knudsen et al., PLOS ONE 7: e51972 (2012); DiMarchi et al in WO2011/159895; DiMarchi et al. in WO 2014/052451; and Herrera et al., WO2014141165. More recently, insulin dimers have been described in Brant—*Synthesis and Characterization of Insulin Receptor Partial Agonists as a Route to Improved Diabetes Therapy*, Ph.D. Dissertation, Indiana University (April 2015) and Zaykov and DiMarchi, Poster P212-*Exploration of the structural and mechanistic basis for partial agonism of insulin dimers*, American Peptide Symposium, Orlando Fla. (Jun. 20-25 (2015). However, the inventors of the instant invention have discovered that the level of insulin activity and partial agonist activity of the dimers is a function of the dimeric structure, the sequence of the insulin analog, the length of the dimerization linker, and the site of dimerization that connects the two insulin polypeptides. The inventors have discovered that the insulin dimers of the present invention have reduced risk of promoting hypoglycemia when administered in high doses than native insulin or other insulin analogs when administered at high doses.

The present invention provides partial agonist covalently-linked insulin dimers formulated as a novel and transformative basal insulin (once daily administration) that manifests improved therapeutic index (TI) over current standard of care (SOC) basal insulins. These molecules may lower glucose effectively with reduced risk of hypoglycemia in diabetic minipig and have the property of a once daily (QD) basal insulin. The improved TI may enable practitioners to more aggressively dose IRPA insulin dimer to achieve target goals for control of fasting glucose. Tight control of fasting glucose and HbA1c may allow these molecules to serve as 1) a stand-alone long-acting insulin with an enhanced efficacy and safety profile in Type 2 diabetes mellitus (T2DM) and 2) an improved foundational basal insulin in Type 1 diabetes mellitus (T1DM) (and some T2DM) for use with additional prandial rapid-acting insulin analogs (RAA) doses.

An ideal long-acting insulin provides continuous control of fasting glucose in diabetics with highly stable and reproducible PK/PD. However, currently available basal insulins, even those with improved stability and reproducibility of PK/PD continue to have a narrow therapeutic index and hypoglycemia incidents increase as glucose levels approach euglycemia target. This can often lead to underdosing to avoid hypoglycemia. Treatment with an IRPA of the present invention is expected to alter this efficacy: hypoglycemia relationship by attenuating the rate of change in glucose lowering as dosing is increased.

Insulin A and B Chains

Disclosed herein are insulin or insulin analog dimers that have insulin receptor agonist activity. The level of insulin activity of the dimers is a function of the dimeric structure, the sequence of the insulin analog, the length of the dimerization linker, and the site of dimerization that connects the two insulin polypeptides. The insulin polypeptides of the present invention may comprise the native B and A chain sequences of human insulin (SEQ ID NOs: 1 and 2, respectively) or any of the known analogs or derivatives thereof that exhibit insulin agonist activity when linked to one another in a heteroduplex. Such analogs include, for example, proteins that having an A-chain and a B-chain that differ from the A-chain and B-chain of human insulin by having one or more amino acid deletions, one or more amino acid substitutions, and/or one or more amino acid insertions that do not destroy the insulin activity of the insulin analog.

One type of insulin analog, "monomeric insulin analog," is well known in the art. These are fast-acting analogs of human insulin, including, for example, insulin analogs wherein:

(a) the amino acyl residue at position B28 is substituted with Asp, Lys, Leu, Val, or Ala, and the amino acyl residue at position B29 is Lys or Pro;

(b) the amino acyl residues at any of positions B27 and B30 are deleted or substituted with a nonnative amino acid.

In one embodiment an insulin analog is provided comprising an Asp substituted at position B28 (e.g., insulin aspart (NOVOLOG); see SEQ ID NO:9) or a Lys substituted at position 28 and a proline substituted at position B29 (e.g., insulin lispro (HUMALOG); see SEQ ID NO:6). Additional monomeric insulin analogs are disclosed in Chance, et al., U.S. Pat. No. 5,514,646; Chance, et al., U.S. patent application Ser. No. 08/255,297; Brems, et al., Protein Engineering, 5:527-533 (1992); Brange, et al., EPO Publication No. 214,826 (published Mar. 18, 1987); and Brange, et al., Current Opinion in Structural Biology, 1:934-940 (1991). These disclosures are expressly incorporated herein by reference for describing monomeric insulin analogs.

Insulin analogs may also have replacements of the amidated amino acids with acidic forms. For example, Asn may be replaced with Asp or Glu. Likewise, Gln may be replaced with Asp or Glu. In particular, Asn(A18), Asn(A21), or Asp(B3), or any combination of those residues, may be replaced by Asp or Glu. Also, Gln(A15) or Gln(B4), or both, may be replaced by either Asp or Glu.

As disclosed herein insulin single chain analogs are provided comprising a B chain and A chain of human insulin, or analogs or derivative thereof, wherein the carboxy terminus of the B chain is linked to the amino terminus of the A chain via a linking moiety. In one embodiment the A chain is amino acid sequence GIVEQCCTSICSLY-QLENYCN (SEQ ID NO: land the B chain comprises amino acid sequence FVNQHLCGSH LVEALYLVCGERGFFYT-PKT (SEQ ID NO: 2) or a carboxy shortened sequence thereof having B30 deleted, and analogs of those sequences wherein each sequence is modified to comprise one to five amino acid substitutions at positions corresponding to native insulin positions selected from A5, A8, A9, A10, A14, A15, A17, A18, A21, B1, B2, B3, B4, B5, B9, B10, B13, B14, B20, B22, B23, B26, B27, B28, B29 and B30, with the proviso that at least one of B28 or B29 is lysine. In one embodiment the amino acid substitutions are conservative amino acid substitutions. Suitable amino acid substitutions at these positions that do not adversely impact insulin's desired activities are known to those skilled in the art, as demonstrated, for example, in Mayer, et al., Insulin Structure and Function, Biopolymers. 2007; 88(5):687-713, the disclosure of which is incorporated herein by reference.

In accordance with one embodiment the insulin analog peptides may comprise an insulin A chain and an insulin B chain or analogs thereof, wherein the A chain comprises an amino acid sequence that shares at least 70% sequence identity (e.g., 70%, 75%, 80%, 85%, 90%, 95%) over the length of the native peptide, with GIVEQCCTSICSLY-QLENYCN (SEQ ID NO: 1) and the B chain comprises an amino acid sequence that shares at least 60% sequence identity (e.g., 60%, 65%, 70%, 75%, 80%, 85%, 90%, 95%) over the length of the native peptide, with FVNQHLCG-SHLVEALYLVCGERGFFYTPKT (SEQ ID NO: 2) or a carboxy shortened sequence thereof having B30 deleted.

Additional amino acid sequences can be added to the amino terminus of the B chain or to the carboxy terminus of the A chain of the insulin polypeptides of the present invention. For example, a series of negatively charged amino acids can be added to the amino terminus of the B chain, including for example a peptide of 1 to 12, 1 to 10, 1 to 8 or 1 to 6 amino acids in length and comprising one or more negatively charged amino acids including for example glutamic acid and aspartic acid. In one embodiment the B chain amino terminal extension comprises 1 to 6 charged amino acids. In accordance with one embodiment the insulin polypeptides disclosed comprise a C-terminal amide or ester in place of a C-terminal carboxylate on the A chain.

In various embodiments, the insulin analog has an isoelectric point that has been shifted relative to human insulin. In some embodiments, the shift in isoelectric point is achieved by adding one or more arginine, lysine, or histidine residues to the N-terminus of the insulin A-chain peptide and/or the C-terminus of the insulin B-chain peptide. Examples of such insulin polypeptides include $Arg^{A0}$-human insulin, $Arg^{B31}Arg^{B32}$-human insulin, $Gly^{A21}Arg^{B31}Arg^{B32}$-human insulin, $Arg^{A0}Arg^{B31}Arg^{B32}$-human insulin, and $Arg^{A0}Gly^{A21}Arg^{B31}Arg^{B32}$-human insulin. By way of further example, insulin glargine (LANTUS; see SEQ ID NOs: 7 and 8) is an exemplary long-acting insulin analog in which $Asn^{A21}$ has been replaced by glycine, and two arginine residues have been covalently linked to the C-terminus of the B-peptide. The effect of these amino acid changes was to shift the isoelectric point of the molecule, thereby producing a molecule that is soluble at acidic pH (e.g., pH 4 to 6.5) but insoluble at physiological pH. When a solution of insulin glargine is injected into the muscle, the pH of the solution is neutralized and the insulin glargine forms microprecipitates that slowly release the insulin glargine over the 24 hour period following injection with no pronounced insulin peak and thus a reduced risk of inducing hypoglycemia. This profile allows a once-daily dosing to provide a patient's basal insulin. Thus, in some embodiments, the insulin analog comprises an A-chain peptide wherein the amino acid at position A21 is glycine and a B-chain peptide wherein the amino acids at position B31 and B32 are arginine. The present disclosure encompasses all single and multiple combinations of these mutations and any other mutations that are described herein (e.g., $Gly^{A21}$-human insulin, $Gly^{A21}Arg^{B31}$-human insulin, $Arg^{B31}Arg^{B32}$-human insulin, $Arg^{B31}$-human insulin).

In particular aspects of the insulin receptor partial agonists, one or more amidated amino acids of the insulin analog are replaced with an acidic amino acid, or another amino acid. For example, asparagine may be replaced with aspartic acid or glutamic acid, or another residue. Likewise, glutamine may be replaced with aspartic acid or glutamic acid, or another residue. In particular, $Asn^{A18}$, $Asn^{A21}$, or $Asn^{B3}$, or any combination of those residues, may be replaced by aspartic acid or glutamic acid, or another residue. $Gln^{A15}$ or $Gln^{B4}$, or both, may be replaced by aspartic acid or glutamic acid, or another residue. In particular aspects of the insulin receptor partial agonists, the insulin analogs have an aspartic acid, or another residue, at position A21 or aspartic acid, or another residue, at position B3, or both.

One skilled in the art will recognize that it is possible to replace yet other amino acids in the insulin analog with other amino acids while retaining biological activity of the molecule. For example, without limitation, the following modifications are also widely accepted in the art: replacement of the histidine residue of position B10 with aspartic acid ($His^{B10}$ to $Asp^{B10}$), replacement of the phenylalanine residue at position B1 with aspartic acid (PheB1 to AspB1); replacement of the threonine residue at position B30 with alanine (ThrB30 toAlaB30); replacement of the tyrosine residue at position B26 with alanine (TyrB26 to AlaB26); and replacement of the serine residue at position B9 with aspartic acid (SerB9 to AspB9).

In various embodiments, the insulin analog has a protracted profile of action. Thus, in certain embodiments, the insulin analog may be acylated with a fatty acid. That is, an amide bond is formed between an amino group on the insulin analog and the carboxylic acid group of the fatty acid. The amino group may be the alpha-amino group of an N-terminal amino acid of the insulin analog, or may be the epsilon-amino group of a lysine residue of the insulin analog. The insulin analog may be acylated at one or more of the three amino groups that are present in wild-type human insulin may be acylated on lysine residue that has been introduced into the wild-type human insulin sequence. In particular aspects of the insulin receptor partial agonists, the insulin analog may be acylated at position A1, B1, or both A1 and B1. In certain embodiments, the fatty acid is selected from myristic acid ($C_{14}$), pentadecylic acid ($C_{15}$), palmitic acid ($C_{16}$), heptadecylic acid ($C_{17}$) and stearic acid ($C_{18}$).

Examples of insulin analogs can be found for example in published International Application WO9634882, WO95516708; WO20100080606, WO2009/099763, and WO2010080609, U.S. Pat. No. 6,630,348, and Kristensen et al., Biochem. J. 305: 981-986 (1995), the disclosures of which are incorporated herein by reference). In further embodiments, the in vitro glycosylated or in vivo N-glycosylated insulin analogs may be acylated and/or pegylated.

In accordance with one embodiment, an insulin analog is provided wherein the A chain of the insulin peptide comprises the sequence GIVEQCCX$_8$SICSLYQLX$_{17}$NX$_{19}$CX$_{23}$ (SEQ ID NO: 3) and the B chain comprising the sequence X$_{25}$LCGX$_{29}$X$_{30}$LVEALYLVCGERGFFYTX$_{31}$X$_{32}$ (SEQ ID NO: 4) wherein $X_8$ is threonine or histidine;
$X_{17}$ is glutamic acid or glutamine;
$X_{19}$ is tyrosine, 4-methoxy-phenylalanine, or 4-amino phenylalanine;
$X_{23}$ is asparagine or glycine;
$X_{25}$ is histidine or threonine;
$X_{29}$ is alanine, glycine or serine;
$X_{30}$ is histidine, aspartic acid, glutamic acid, homocysteic acid, or cysteic acid;
$X_{31}$ is proline or lysine; and
$X_{32}$ is proline or lysine, with the proviso that at least one of $X_{31}$ or $X_{32}$ is lysine.

In a further embodiment, the B chain comprises the sequence X$_{22}$VNQX$_{25}$LCGX$_{29}$X$_{30}$LVEALYLVCGERGFFYTX$_{31}$X$_{32}$X$_{33}$X$_{34}$X$_{35}$ (SEQ ID NO: 5) wherein $X_{22}$ is or phenylalanine and desamino-phenylalanine;
$X_{25}$ is histidine or threonine;
$X_{29}$ is alanine, glycine, or serine;
$X_{30}$ is histidine, aspartic acid, glutamic acid, homocysteic acid, or cysteic acid;
$X_{31}$ is aspartic acid, proline, or lysine;
$X_{32}$ is lysine or proline;
$X_{33}$ is threonine, alanine, or absent;
$X_{34}$ is arginine or absent; and
$X_{35}$ is arginine or absent;
With the proviso at least one of $X_{31}$ or $X_{32}$ is lysine.

Linking Moiety

The insulin dimers disclosed herein are formed between a first and second insulin polypeptide wherein each insulin polypeptide comprises an A chain and a B chain. The first and second insulin polypeptides may be two chain insulin analogs (i.e., wherein the A and B chains are linked only via inter-chain disulfide bonds between internal cysteine residues) wherein the first and second insulin polypeptides are linked to one another to form the dimer by a covalent bond, bifunctional linker, or using copper(I) catalyzed alkyne-azide cycloaddition (CuAAC) click chemistry or copper-free click chemistry to link linking moieties on the respective B chains. In accordance with one embodiment the first and second insulin polypeptides are linked to one another by a bifunctional linker joining the side chain of the B28 or B29 lysine of the B chain of the first insulin polypeptide to the side chain of the B28 or B29 amino acid of the B chain of the second insulin polypeptide.

The following table shows exemplary linkers, which may be used to construct the dimers of the present invention. The linkers shown comprise 2,5-dioxopyrrolidin-1yl or isocyanate groups for conjugating to the epsilon amino group of the B29 or B28 lysine or aldehyde group for conjugation via reductive amination, or alkyne groups for conjugation to the epsilon amino group of the B29 or B28 lysine if azido groups are appended to B29 or B28 lysine residues prior to conjugation.

Table of Linkers

| Linker No. | Structure | Name |
|---|---|---|
| 1 | 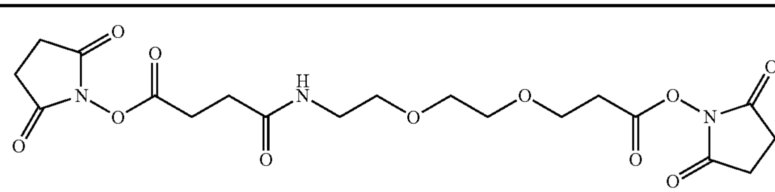 | C4-N-PEG2 |
| 2 | 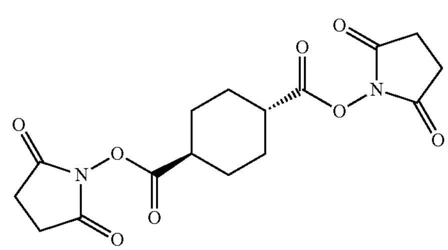 [SMILES: O=C1CCC(=O)N1OC(=O)[C@H]1CC[C@H](C(=O)ON2C(=O)CCC2=O)CC1] | transcyclohexane-1,4-diacid |

-continued

Table of Linkers

| Linker No. | Structure | Name |
|---|---|---|
| 3 | 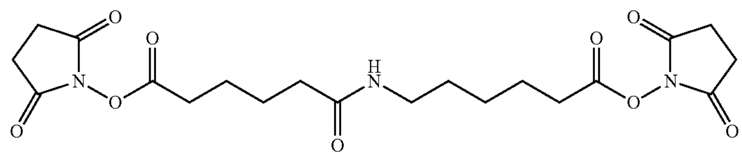 [SMILES: O=C(CCCCC(=O)ON1C(=O)CCC1=O)NCCCCCC(=O)ON1C(=O)CCC1=O] | C6 + NC6 |
| 4 | 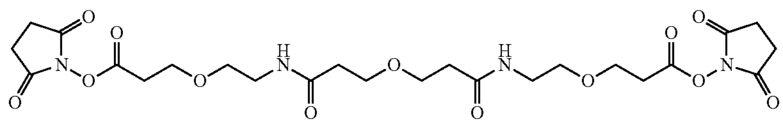 [SMILES: O=C(CCOCCC(=O)NCCOCCC(=O)ON1C(=O)CCC1=O)NCCOCCC(=O)ON1C(=O)CCC1=O] | PEG1-N-PEG1-N-PEG1 |
| 5 | 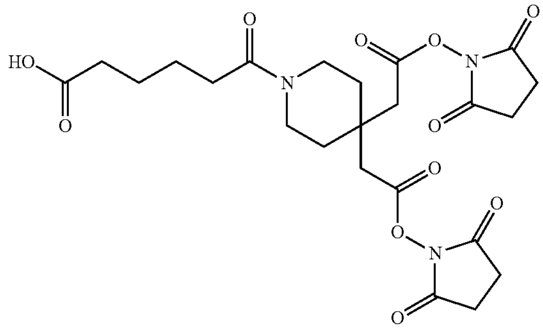 [SMILES: O=C(O)CCCCC(=O)N1CCC(CC(=O)ON2C(=O)CCC2=O)(CC(=O)ON2C(=O)CCC2=O)CC1] | 2,2'-(1-(5-carboxypentanoyl)piperidine-4,4-diyl)diacetic |
| 6 | 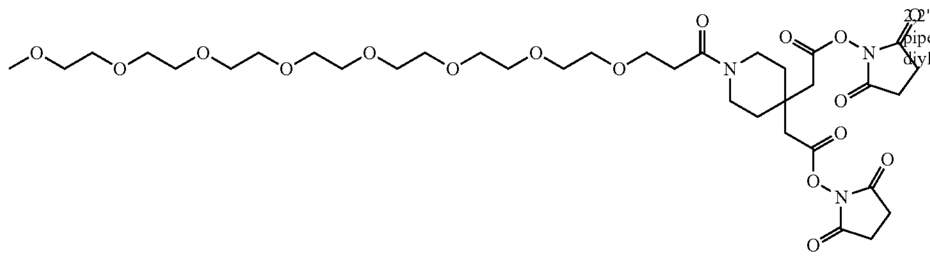 | 2,2'-((1-PEG8)-piperidine-4,4-diyl)diacetic |
| 7 | 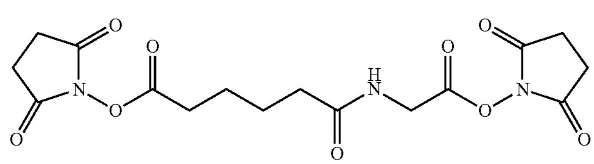 [SMILES: O=C(CCCCC(=O)ON1C(=O)CCC1=O)NCC(=O)ON1C(=O)CCC1=O] | C6-glycine |
| 8 | 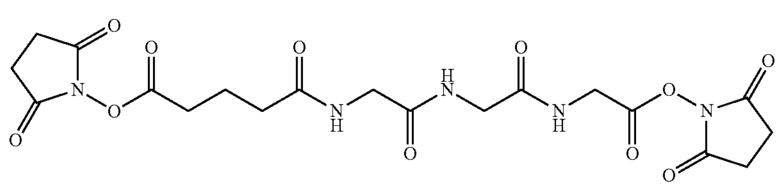 [SMILES: O=C(CCCC(=O)ON1C(=O)CCC1=O)NCC(=O)NCC(=O)NCC(=O)ON1C(=O)CCC1=O] | C5-Gly-Gly-Gly |
| 9 | 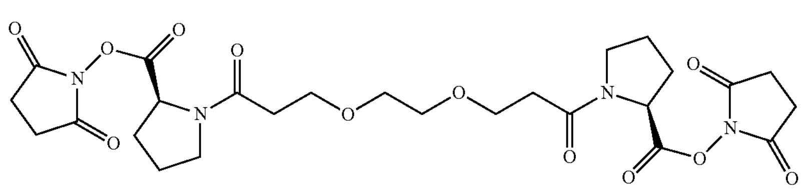 [SMILES: O=C(ON1C(=O)CCC1=O)[C@@H]1CCCN1C(=O)CCOCCOCCC(=O)N1CCC[C@H]1C(=O)ON1C(=O)CCC1=O] | D-PRO-PEG2-D-PRO |

-continued
Table of Linkers
| Linker No. | Structure | Name |
|---|---|---|
| 10 | 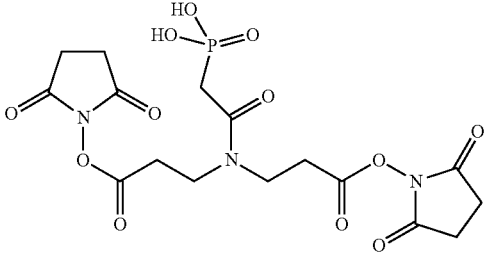 [SMILES: O=C(CCN(CCC(=O)ON1C(=O)CCC1=O)C(=O)CP(=O)(O)O)ON1C(=O)CCC1=O] | H2O3PCH2CO-imido-bis-acetic |
| 11 | 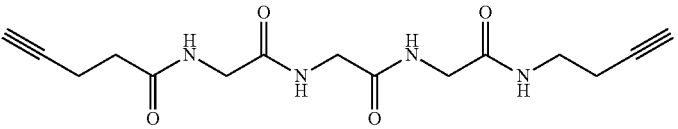 [SMILES: C#CCCNC(=O)CNC(=O)CNC(=O)CNC(=O)CCC#C] | NCO-NCO-NCO-dialkyne |
| 12 | 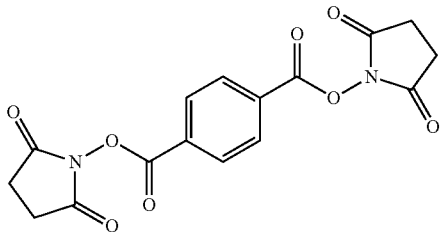 [SMILES: O=C(ON1C(=O)CCC1=O)c1ccc(C(=O)ON2C(=O)CCC2=O)cc1] | Terphthalic |
| 13 | 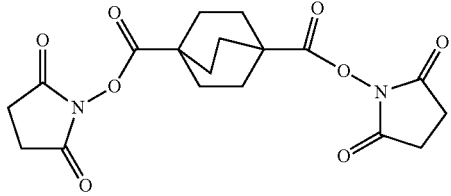 [SMILES: O=C1CCC(=O)N1OC(=O)C12CCC(C(=O)ON3C(=O)CCC3=O)(CC1)CC2] | Biocyclo[2.2.2]-octane-1,4-diacid |
| 14 | 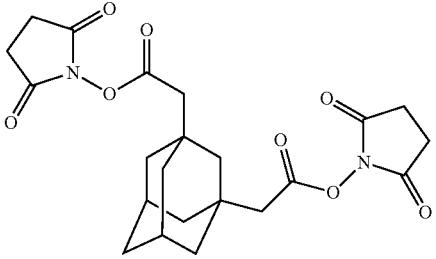 [SMILES: O=C(CC12CC3CC(C1)CC(CC(=O)ON1C(=O)CCC1=O)(C3)C2)ON1C(=O)CCC1=O] | Adamantane-1,3-diacetic |
| 15 | 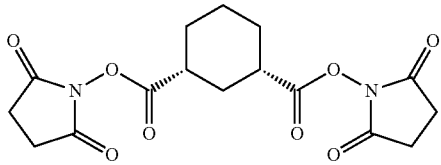 [SMILES: O=C(ON1C(=O)CCC1=O)[C@@H]1CCC[C@H](C(=O)ON2C(=O)CCC2=O)C1] | Ciscyclohexane-1,3-diacid |
| 16 | 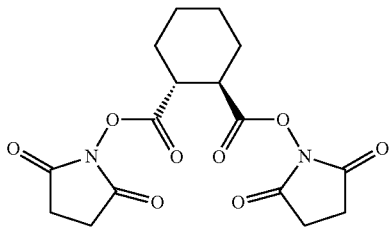 [SMILES: O=C(ON1C(=O)CCC1=O)[C@@H]1CCCC[C@H]1C(=O)ON1C(=O)CCC1=O] | Transcyclo-hexane-1,2-diacid |

-continued

Table of Linkers

| Linker No. | Structure | Name |
|---|---|---|
| 17 | 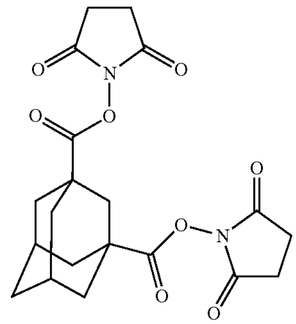 [SMILES: O=C1CCC(=O)N1OC(=O)C12CC3CC(C1)CC(C(=O)ON1C(=O)CCC1=O)(C3)C2] | Adamantane-1,3-diacid |
| 18 | 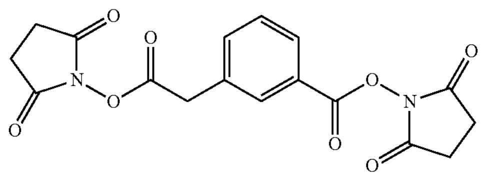 [SMILES: O=C(Cc1cccc(C(=O)ON2C(=O)CCC2=O)c1)ON1C(=O)CCC1=O] | 3-carboxyl-benzene-acetic acid |
| 19 | 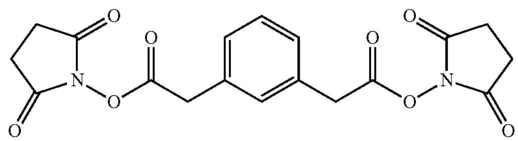 [SMILES: O=C(Cc1cccc(CC(=O)ON2C(=O)CCC2=O)c1)ON1C(=O)CCC1=O] | 1,3-benzene-diacetic |
| 20 | 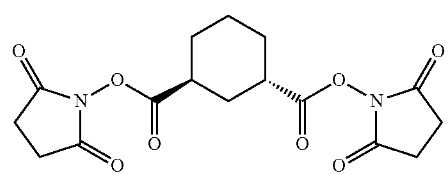 [SMILES: O=C(ON1C(=O)CCC1=O)[C@H]1CCC[C@H](C(=O)ON2C(=O)CCC2=O)C1] | transcyclohexane1,3-diacid |
| 21 | 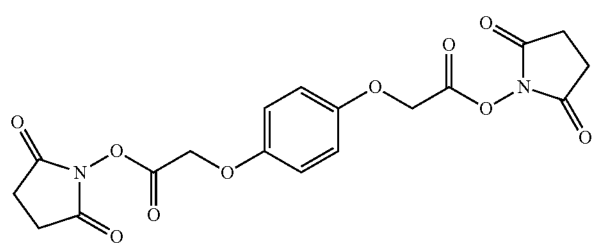 | 1,4-phenylene-bis(oxy)acetic |
| 22 | 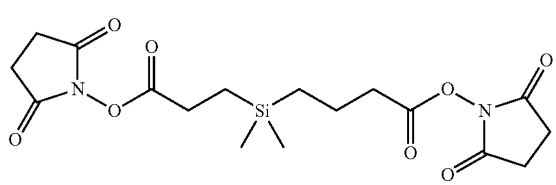 [SMILES: C[Si](C)(CCCC(=O)ON1C(=O)CCC1=O)CCC(=O)ON1C(=O)CCC1=O] | 4-((2-carboxy-ethyl)dimethyl-silyl)butanoic |
| 23 | 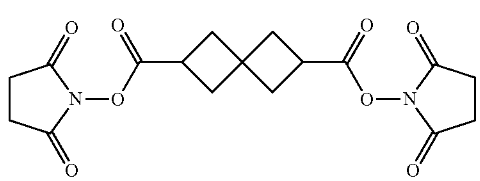 [SMILES: O=C(ON1C(=O)CCC1=O)C1CC2(C1)CC(C(=O)ON1C(=O)CCC1=O)C2] | Spiro[3.3]-heptane-2,6-diacidic |

-continued

Table of Linkers

| Linker No. | Structure | Name |
|---|---|---|
| 24 | 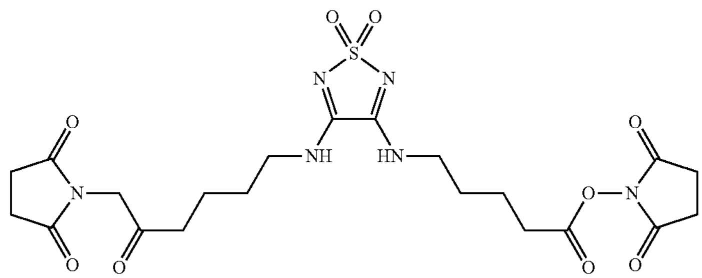 [SMILES: O=C(CCCCNC1=NS(=O)(=O)N=C1NCCCCC(=O)ON1C(=O)CCC1=O)CN1C(=O)CCC1=O] | 5,5'-((1,1-dioxido-1,2,5-thiadiazole-3,4-diyl)bis(azanediyl))-dipentanoic |
| 25 | 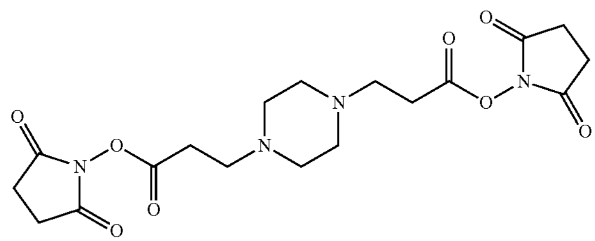 [SMILES: O=C(CCN1CCN(CCC(=O)ON2C(=O)CCC2=O)CC1)ON1C(=O)CCC1=O] | 3,3'-(piperazine-1,4-diyl)dipropionic |
| 26 | 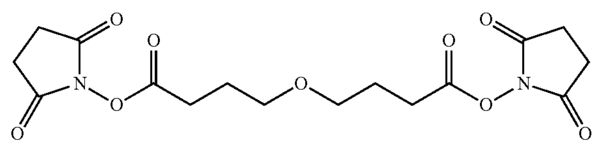 [SMILES: O=C(CCCOCCCC(=O)ON1C(=O)CCC1=O)ON1C(=O)CCC1=O] | 4,4'-oxydibutyric |
| 27 | 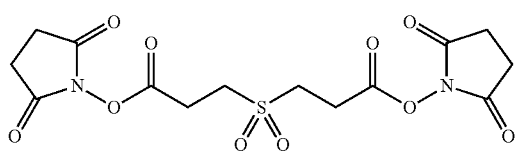 [SMILES: O=C(CCS(=O)(=O)CCC(=O)ON1C(=O)CCC1=O)ON1C(=O)CCC1=O] | 4,4'-3,3'-sulfonyl-dipropionic |
| 28 | 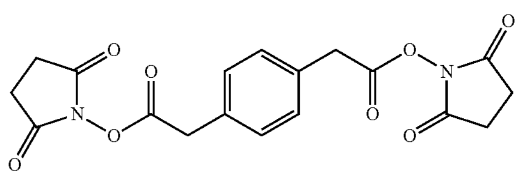 [SMILES: O=C(Cc1ccc(CC(=O)ON2C(=O)CCC2=O)cc1)ON1C(=O)CCC1=O] | 2,2'-(1,4-phenylene)-diacetic |
| 29 | 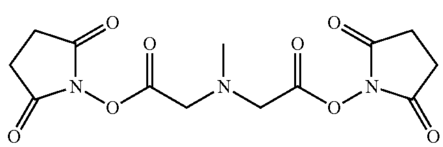 [SMILES: CN(CC(=O)ON1C(=O)CCC1=O)CC(=O)ON1C(=O)CCC1=O] | 2,2'-(methyl-azanediyl)diacetic |
| 30 | 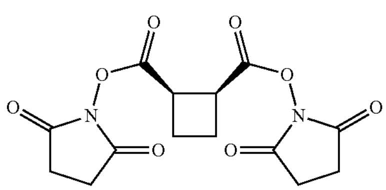 [SMILES: O=C(ON1C(=O)CCC1=O)[C@H]1CC[C@H]1C(=O)ON1C(=O)CCC1=O] | (1R,2S)-cyclobutane-1,2-dicarboxylic |
| 31 | 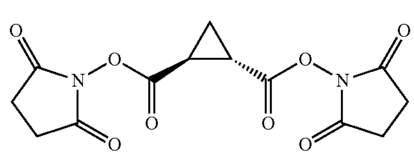 [SMILES: O=C(ON1C(=O)CCC1=O)[C@H]1C[C@@H]1C(=O)ON1C(=O)CCC1=O] | (1R,2R)-cyclopropane-1,2-dicarboxylic |

| Linker No. | Structure | Name |
|---|---|---|
| 32 | 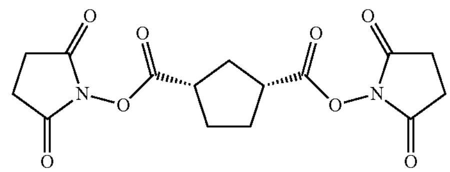 [SMILES: O=C(ON1C(=O)CCC1=O)[C@@H]1CC[C@H](C(=O)ON2C(=O)CCC2=O)C1] | (1R,3S)-cyclopentane-1,3-dicarboxylic |
| 33 | 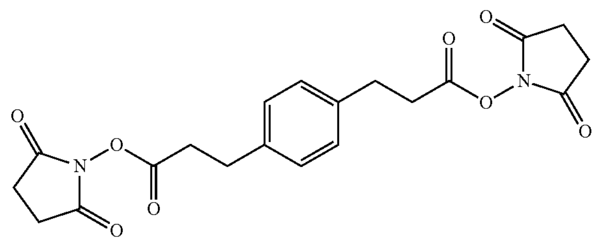 [SMILES: O=C(CCc1ccc(CCC(=O)ON2C(=O)CCC2=O)cc1)ON1C(=O)CCC1=O] | 3,3'-(1,4-phenylene)-dipropionic |
| 34 | 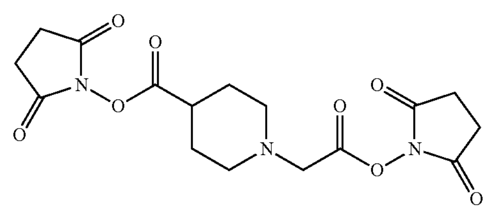 [SMILES: O=C(CN1CCC(C(=O)ON2C(=O)CCC2=O)CC1)ON1C(=O)CCC1=O] | 1-(carboxymethyl)-piperidine-4-carboxylic |
| 35 | 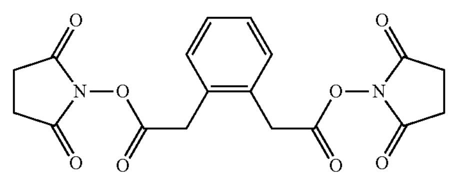 [SMILES: O=C(Cc1ccccc1CC(=O)ON1C(=O)CCC1=O)ON1C(=O)CCC1=O] | 2,2'-(1,2-phenylene)diacetic |
| 36 | 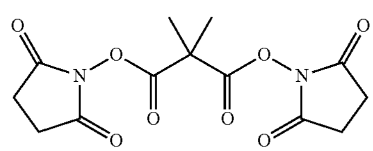 [SMILES: CC(C)(C(=O)ON1C(=O)CCC1=O)C(=O)ON1C(=O)CCC1=O] | dimethylmalonic |
| 37 | 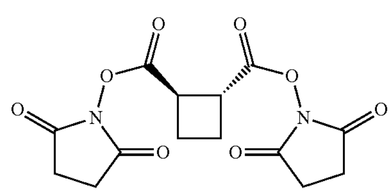 [SMILES: O=C(ON1C(=O)CCC1=O)[C@@H]1CC[C@H]1C(=O)ON1C(=O)CCC1=O] | (1R,2R)-cyclobutane-1,2-dicarboxylic |
| 38 | 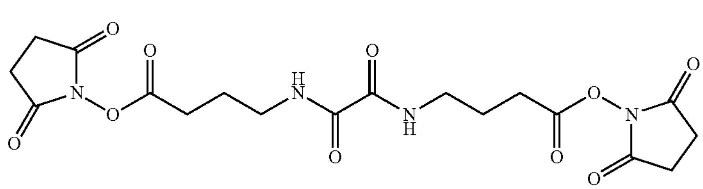 [SMILES: O=C(CCCNC(=O)C(=O)NCCCC(=O)ON1C(=O)CCC1=O)ON1C(=O)CCC1=O] | 4,4'-(oxalylbis-(azanediyl)dibutyric |

Table of Linkers

| Linker No. | Structure | Name |
|---|---|---|
| 39 | 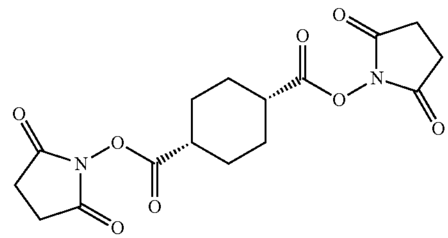 [SMILES: O=C1CCC(=O)N1OC(=O)[C@H]1CC[C@@H](C(=O)ON2C(=O)CCC2=O)CC1] | cis-cyclohexane-1,4-diacid |
| 40 | 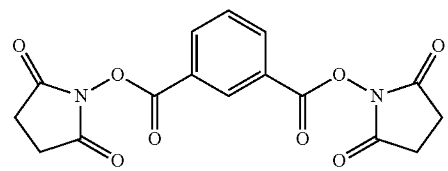 [SMILES: O=C(ON1C(=O)CCC1=O)c1cccc(C(=O)ON2C(=O)CCC2=O)c1] | 1,3-benzene-dicarboxylic |
| 41 | 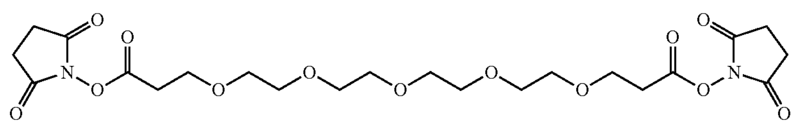 [SMILES: O=C(CCOCCOCCOCCOCCOCCC(=O)ON1C(=O)CCC1=O)ON1C(=O)CCC1=O] | PEG3 |
| 42 | 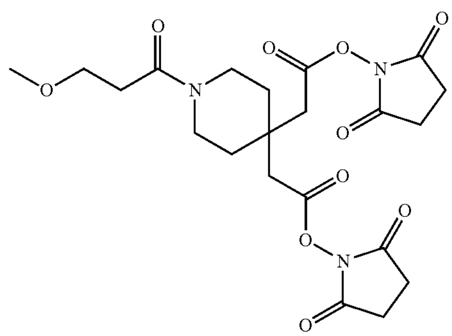 [SMILES: COCCC(=O)N1CCC(CC(=O)ON2C(=O)CCC2=O)(CC(=O)ON2C(=O)CCC2=O)CC1] | 2,2'-(1-(5-Carboxypenta-noyl)piperidine-4,4-diyl)diacetic |
| 43 | 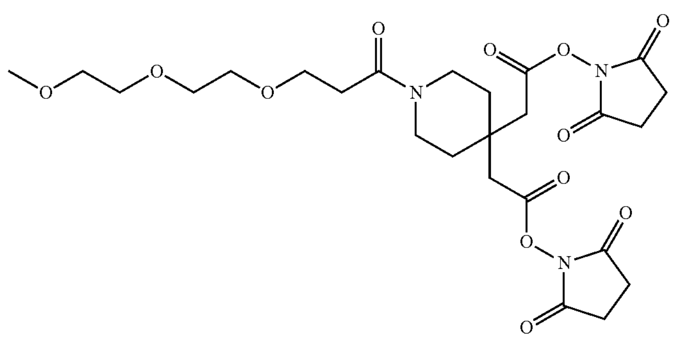 [SMILES: COCCOCCOCCC(=O)N1CCC(CC(=O)ON2C(=O)CCC2=O)(CC(=O)ON2C(=O)CCC2=O)CC1] | 2,2'-((1-PEG3)-piperidine-4,4-diyl)diacetic |
| 44 | 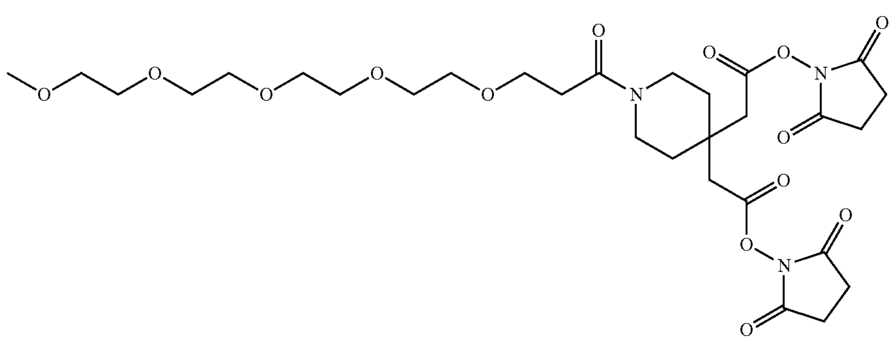 [SMILES: COCCOCCOCCOCCOCCC(=O)N1CCC(CC(=O)ON2C(=O)CCC2=O)(CC(=O)ON2C(=O)CCC2=O)CC1] | 2,2'-((1-PEG5)-piperidine-4,4-diyl)diacetic |

Table of Linkers

| Linker No. | Structure | Name |
|---|---|---|
| 45 | 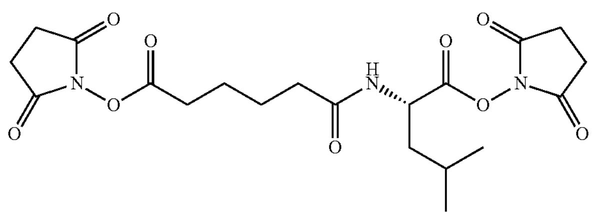 [SMILES: CC(C)C[C@H](NC(=O)CCCCC(=O)ON1C(=O)CCC1=O)C(=O)ON1C(=O)CCC1=O] | C6-leucine |
| 46 | 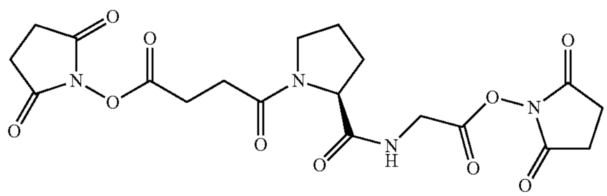 [SMILES: O=C(CCC(=O)N1CCC[C@H]1C(=O)NCC(=O)ON1C(=O)CCC1=O)ON1C(=O)CCC1=O] | C4-L-Pro-Gly |
| 47 | 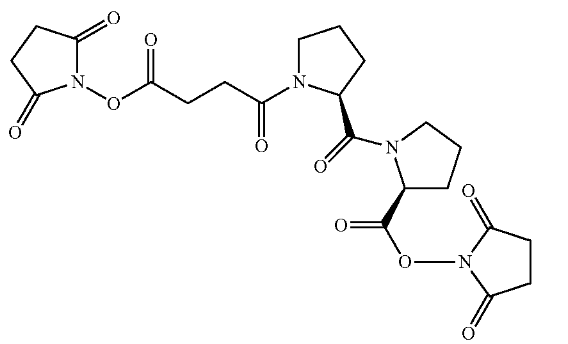 [SMILES: O=C(CCC(=O)N1CCC[C@H]1C(=O)N1CCC[C@H]1C(=O)ON1C(=O)CCC1=O)ON1C(=O)CCC1=O] | C4-L-Pro-L-Pro |
| 48 | 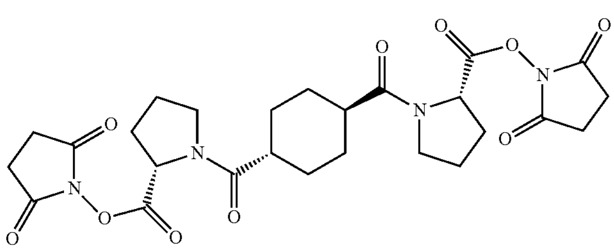 [SMILES: O=C(ON1C(=O)CCC1=O)[C@@H]1CCCN1C(=O)[C@H]1CC[C@H](C(=O)N2CCC[C@H]2C(=O)ON2C(=O)CCC2=O)CC1] | L-Pro-Cyclohexane-dicarbonyl-L-Pro |
| 49 | 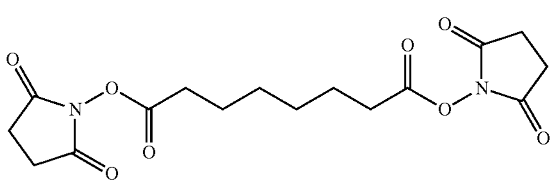 [SMILES: O=C(CCCCCCC(=O)ON1C(=O)CCC1=O)ON1C(=O)CCC1=O] | suberic |
| 50 | 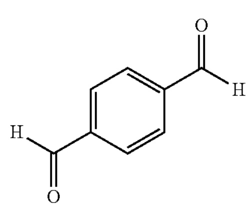 | 1,4-benzenedi-carboxaldehyde |

27
28
-continued
| Table of Linkers | | |
|---|---|---|
| Linker No. | Structure | Name |
| 51 | 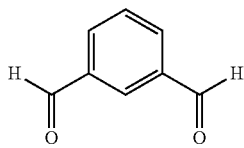 | 1,3-benzenedi-carboxaldehyde |
| 52 | 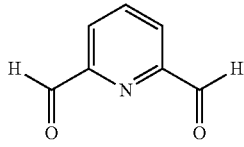 | 2,6-pyridinedi-carboxaldehyde |
| 53 | 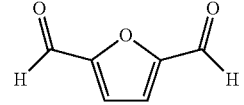 | 2,5-furandi-carboxaldehyde |
| 54 | 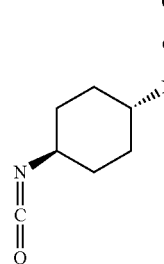 | N,N'-(transcyclo-hexane-1,4-diyl)-diformamide |
| 55 | 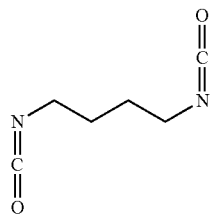 | 1,1'-(butane-1,4-diyl)diurea |
| 56 | 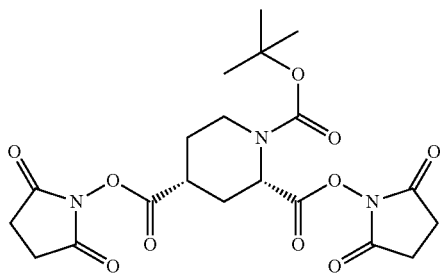 [SMILES: CC(C)(C)OC(=O)N1CC[C@@H](C(=O)ON2C(=O)CCC2=O)C[C@H]1C(=O)ON1C(=O)CCC1=O] | cis-rac-piperidine-2,4-diacid |

Table of Linkers (continued)

| Linker No. | Structure | Name |
|---|---|---|
| 57 | 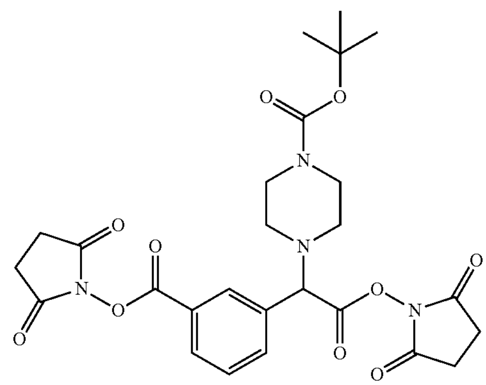 [SMILES: CC(C)(C)OC(=O)N1CCN(C(C(=O)ON2C(=O)CCC2=O)c2cccc(C(=O)ON3C(=O)CCC3=O)c2)CC1] | 3-(carboxy-(piperazin-2-yl)methyl)benzoic acid |
| 58 | 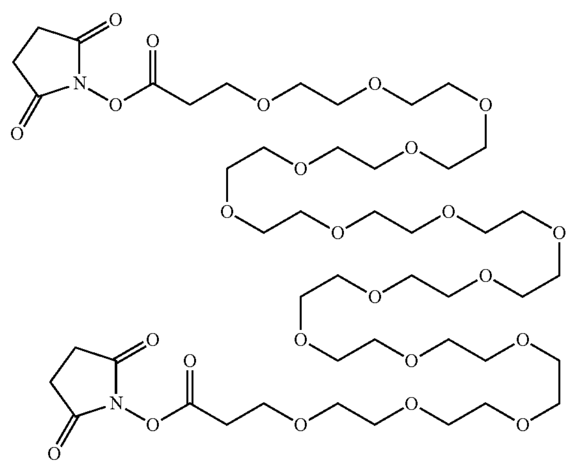 [SMILES: O=C(CCOCCOCCOCCOCCOCCOCCOCCOCCOCCOCCOCCOCCOCCOCCOCCOCCOCCC(=O)ON1C(=O)CCC1=O)ON1C(=O)CCC1=O] | PEG17 |
| 59 | 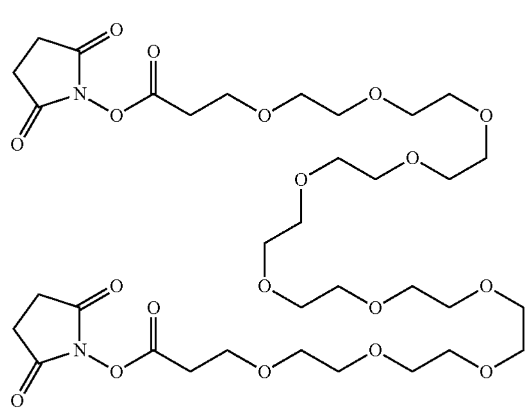 [SMILES: O=C(CCOCCOCCOCCOCCOCCOCCOCCOCCOCCOCCOCCC(=O)ON1C(=O)CCC1=O)ON1C(=O)CCC1=O] | PEG11 |

| Linker No. | Structure | Name |
|---|---|---|
| 60 | 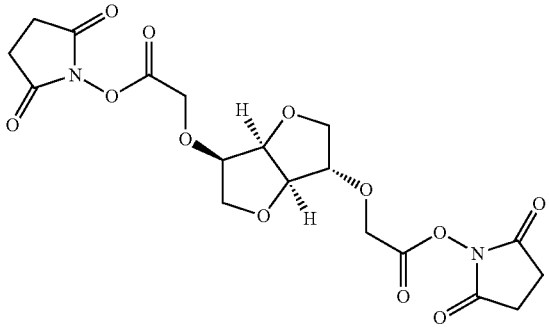 [SMILES: O=C(CO[C@H]1CO[C@H]2[C@@H]1OC[C@H]2OCC(=O)ON1C(=O)CCC1=O)ON1C(=O)CCC1=O] | Isosorbide |
| 61 | 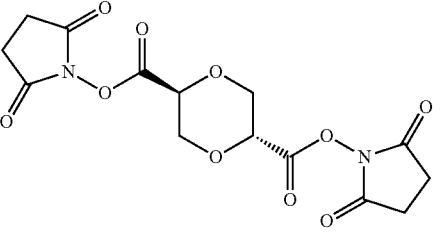 [SMILES: O=C(ON1C(=O)CCC1=O)[C@@H]1CO[C@@H](C(=O)ON2C(=O)CCC2=O)CO1] | 1,4-dioxane-2,5-dicarboxylate |
| 62 | 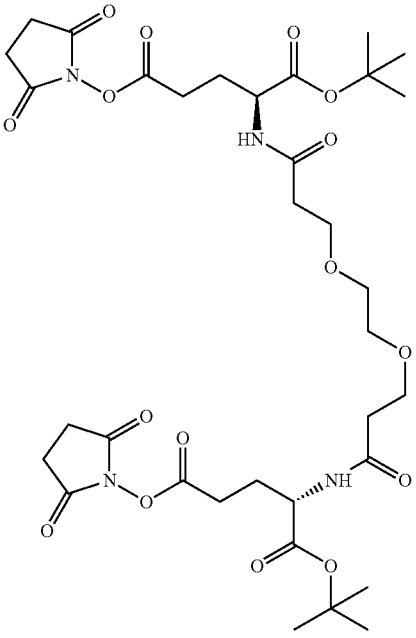 [SMILES: CC(C)(C)OC(=O)[C@H](CCC(=O)ON1C(=O)CCC1=O)NC(=O)CCOCCOCCC(=O)N[C@@H](CCC(=O)ON1C(=O)CCC1=O)C(=O)OC(C)(C)C] | Isoglu-PEG2-isoglu |

Table of Linkers

| Linker No. | Structure | Name |
|---|---|---|
| 63 | 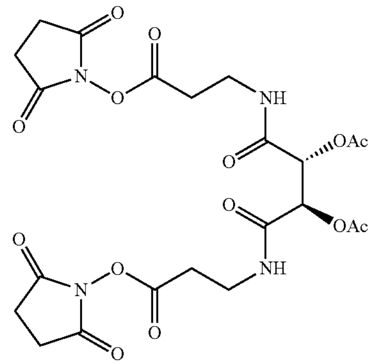 [SMILES: CC(=O)O[C@@H](C(=O)NCCC(=O)ON1C(=O)CCC1=O)[C@@H](OC(C)=O)C(=O)NCCC(=O)ON1C(=O)CCC1=O] | C3-tartaric-C3 |
| 64 | 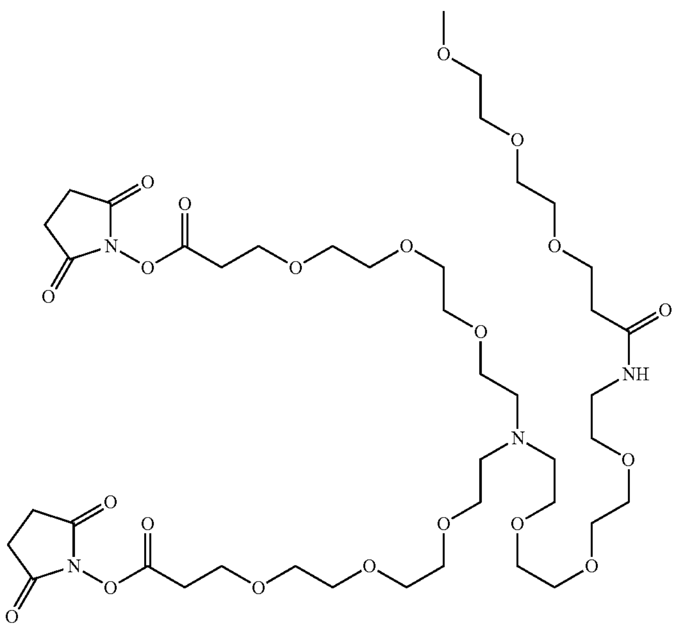 [SMILES: COCCOCCOCCC(=O)NCCOCCOCCOCCN(CCOCCOCCOCCC(=O)ON1C(=O)CCC1=O)CCOCCOCCOCCC(=O)ON1C(=O)CCC1=O] | Bis(PEG3)Amine-(MPEG3-PEG3) |

Conjugation of a bifunctional linker to the epsilon amino group of the lysine residue at position B29 or B28 of the B-chain polypeptide of two insulin or insulin analog molecules to form the insulin dimer linked by a linking moiety may be schematically shown as

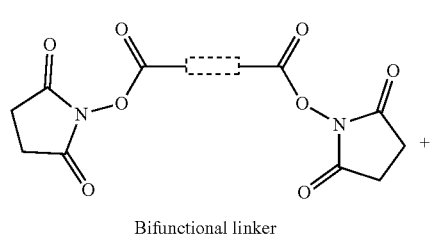

wherein the insulin 1 and insulin 2 molecules may be the same or different and the bifunctional linker and resulting and linking moiety following conjugation may have the structure of any linker and resulting linking moiety disclosed herein. Various linkers are shown with protecting groups attached thereto, e.g., Linker 56, Linker 57, and Linker 62. Following conjugation, the protecting group is removed from the linker to provide the corresponding linking moiety shown in the Table of Linking Moieties shown below.

When the bifunctional linker is Linker 11, then the insulin molecules comprise a linker comprising a terminal azide group capable of forming a 1,4 di-substituted triazole with the alkyne groups at the ends of Linker 11. For example, the linker comprising a terminal azide group may be

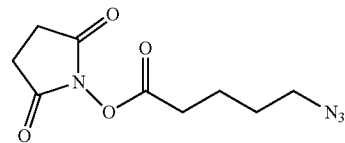 [SMILES: [N-]=[N+]=NCCCCC(=O)ON1C(=O)CCC1=O]

which is conjugated to the epsilon amino group of the B29 and B29' Lysine or the epsilon amino group of the B28 and B28' Lysine of the insulin heterodimers to form the structure

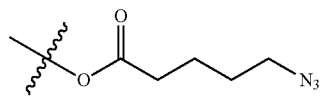 [SMILES: *OC(=O)CCCCN=[N+]=[N-]]

wherein the wavy line identifies the bond between the linker and the epsilon amino group.

The following table shows exemplary linking moieties.

| No. | Linking Moieties Structure |
|---|---|
| 1 | ![structure] |
| 2 | ![structure] |
| 3 | ![structure] |
| 4 | ![structure] |
| 5 | ![structure] |

-continued
| No. | Linking Moieties Structure |
|---|---|
| 6 | 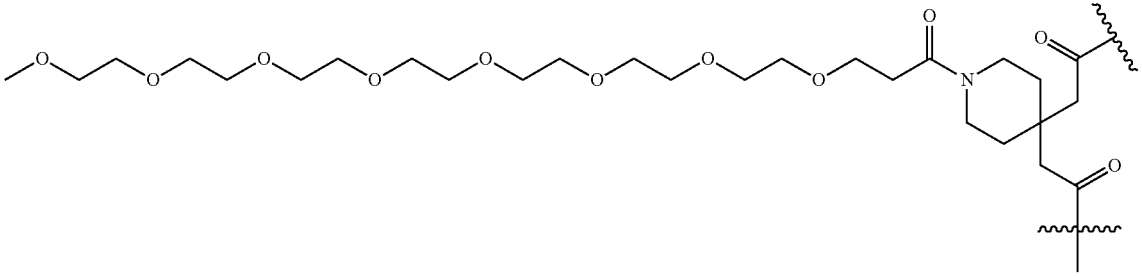 [SMILES: *C(=O)CC1(CC(*)=O)CCN(C(=O)CCOCCOCCOCCOCCOCCOCCOCCOC)CC1] |
| 7 | 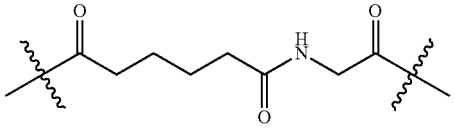 [SMILES: *C(=O)CCCCC(=O)NCC(*)=O] |
| 8 | 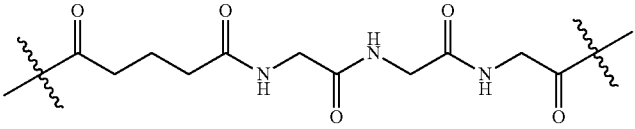 [SMILES: *C(=O)CCCC(=O)NCC(=O)NCC(=O)NCC(*)=O] |
| 9 | 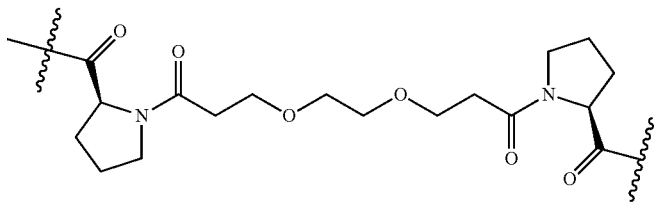 [SMILES: *C(=O)[C@@H]1CCCN1C(=O)CCOCCOCCC(=O)N1CCC[C@H]1C(*)=O] |
| 10 | 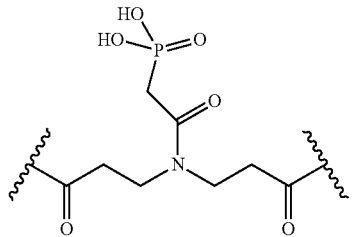 [SMILES: *C(=O)CCN(CCC(*)=O)C(=O)CP(=O)(O)O] |

-continued
| No. | Linking Moieties Structure |
|---|---|
| 11 | 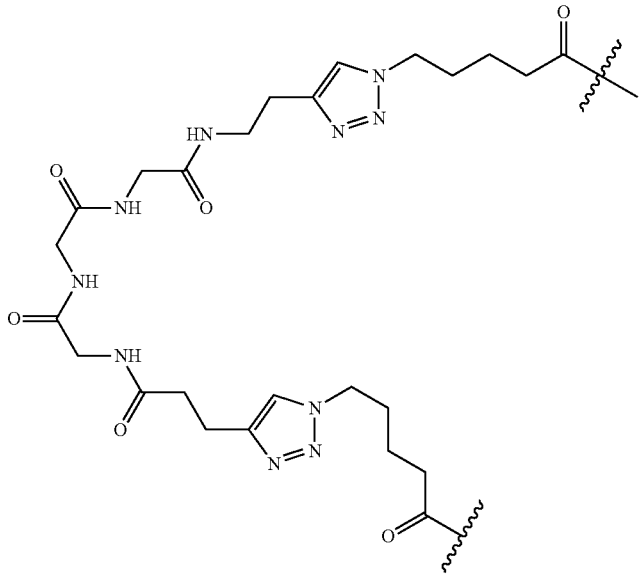 [SMILES: *C(=O)CCCCn1cc(CCNC(=O)CNC(=O)CNC(=O)CNC(=O)CCc2cn(CCCCC(*)=O)nn2)nn1] |
| 12 | 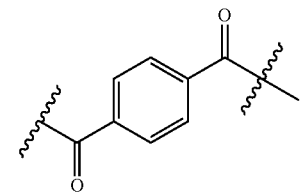 [SMILES: *C(=O)c1ccc(C(*)=O)cc1] |
| 13 | 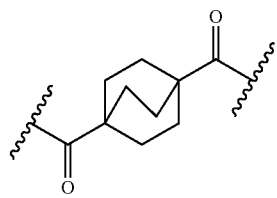 [SMILES: *C(=O)C12CCC(C(*)=O)(CC1)CC2] |
| 14 | 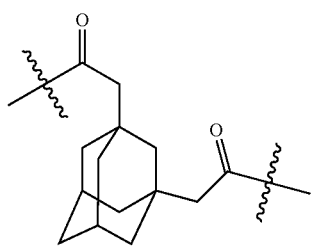 [SMILES: *C(=O)CC12CC3CC(C1)CC(CC(*)=O)(C3)C2] |
| 15 | 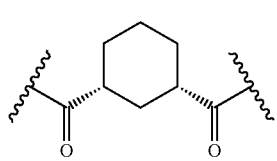 [SMILES: *C(=O)[C@@H]1CCC[C@H](C(*)=O)C1] |
| 16 | 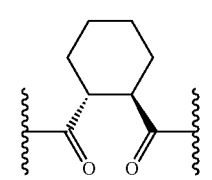 [SMILES: *C(=O)[C@@H]1CCCC[C@H]1C(*)=O] |

| | -continued |
|---|---|
| No. | Linking Moieties<br>Structure |
| 17 | 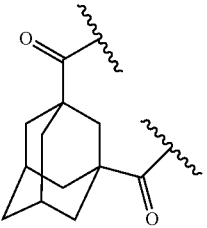 [SMILES: *C(=O)C12CC3CC(C1)CC(C(*)=O)(C3)C2] |
| 18 | 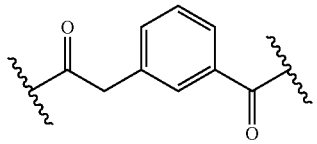 [SMILES: *C(=O)Cc1cccc(C(*)=O)c1] |
| 19 | 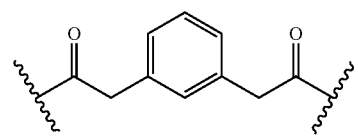 [SMILES: *C(=O)Cc1cccc(CC(*)=O)c1] |
| 20 | 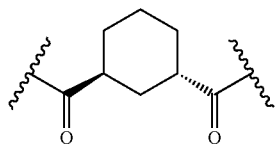 [SMILES: *C(=O)[C@H]1CCC[C@H](C(*)=O)C1] |
| 21 | 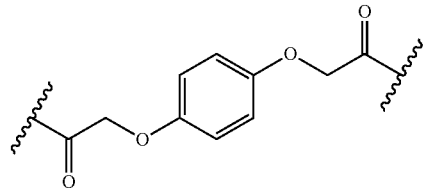 [SMILES: *C(=O)COc1ccc(OCC(*)=O)cc1] |
| 22 | 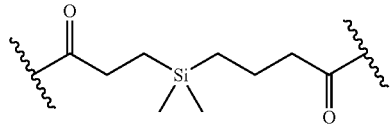 [SMILES: *C(=O)CCC[Si](C)(C)CCC(*)=O] |
| 23 | 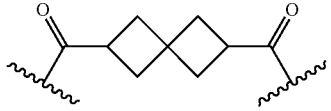 [SMILES: *C(=O)C1CC2(C1)CC(C(*)=O)C2] |
| 24 | 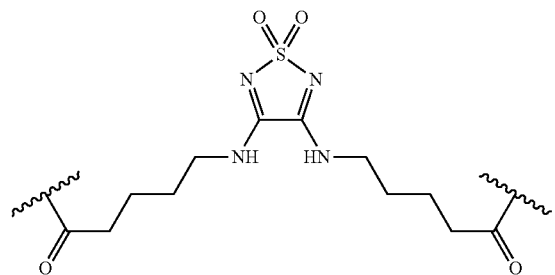 [SMILES: *C(=O)CCCCNC1=NS(=O)(=O)N=C1NCCCCC(*)=O] |

-continued

| No. | Linking Moieties Structure |
|---|---|
| 25 | |
| 26 | |
| 27 | |
| 28 | |
| 29 | |
| 30 | |
| 31 | |
| 32 | |
| 33 | |
| 34 | |

-continued

| | Linking Moieties |
|---|---|
| No. | Structure |

35

36

37

38

39

40

41

42

-continued

| No. | Linking Moieties Structure |
|---|---|
| 43 | |
| 44 | |
| 45 | |
| 46 | |
| 47 | |
| 48 | |

-continued

| No. | Linking Moieties Structure |
|---|---|
| 49 | ![structure 49] |
| 50 | ![structure 50] |
| 51 | ![structure 51] |
| 52 | ![structure 52] |
| 53 | ![structure 53] |
| 54 | ![structure 54] |
| 55 | ![structure 55] |
| 56 | ![structure 56] |

-continued

| No. | Linking Moieties Structure |
|---|---|
| 57 | |
| 58 | |
| 59 | |
| 60 | |
| 61 | |

| No. | Linking Moieties Structure |
|---|---|
| 62 | |
| 63 | |
| 64 | |

| No. | Linking Moieties Structure |
|-----|---------------------------|
| 65  | 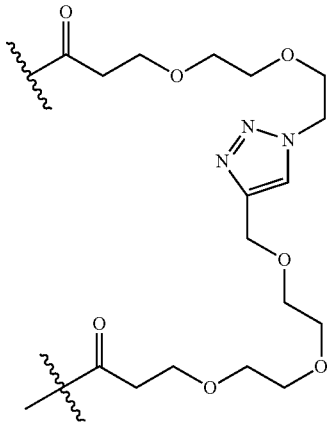 [SMILES: *C(=O)CCOCCOCCOCc1cn(CCOCCOCCC(*)=O)nn1]      |

The wavy line identifies the bond between the linker and the epsilon amino group Modification of Insulin Polypeptides In some embodiments, at least one of the A-chain polypeptides or B-chain polypeptides of the insulin receptor partial agonist is modified to comprise an acyl group. The acyl group can be covalently linked directly to an amino acid of the insulin polypeptide, or indirectly to an amino acid of the insulin polypeptide via a spacer, wherein the spacer is positioned between the amino acid of the insulin polypeptide and the acyl group. The insulin polypeptide may be acylated at the same amino acid position where a hydrophilic moiety is linked, or at a different amino acid position. For example, acylation may occur at any position including any amino acid of the A- or B-chain polypeptides as well as a position within the linking moiety, provided that the activity exhibited by the non-acylated insulin polypeptide is retained upon acylation. Non-limiting examples include acylation at positions A1 of the A chain and positions position B1 of the B chain.

In one specific aspect of the invention, the first and/or second insulin polypeptide (or derivative or conjugate thereof) is modified to comprise an acyl group by direct acylation of an amine, hydroxyl, or thiol of a side chain of an amino acid of the insulin polypeptide. In some embodiments, the first and/or second insulin polypeptide is directly acylated through the side chain amine, hydroxyl, or thiol of an amino acid. In this regard, an insulin polypeptide may be provided that has been modified by one or more amino acid substitutions in the A- or B-chain polypeptide sequence, including for example at positions A1, A14, A15, B1, B10, or B22 or at any position of the linking moiety with an amino acid comprising a side chain amine, hydroxyl, or thiol.

In some embodiments, the spacer between the first and/or second insulin polypeptide and the acyl group is an amino acid comprising a side chain amine, hydroxyl, or thiol (or a dipeptide or tripeptide comprising an amino acid comprising a side chain amine, hydroxyl, or thiol). In some embodiments, the spacer comprises a hydrophilic bifunctional spacer. In a specific embodiment, the spacer comprises an amino poly(alkyloxy)carboxylate. In this regard, the spacer can comprise, for example, $NH_2(CH_2CH_2O)_n(CH_2)_mCOOH$, wherein m is any integer from 1 to 6 and n is any integer from 2 to 12, such as, e.g., 8-amino-3,6-dioxaoctanoic acid, which is commercially available from Peptides International, Inc. (Louisville, Ky.). In one embodiment, the hydrophilic bifunctional spacer comprises two or more reactive groups, e.g., an amine, a hydroxyl, a thiol, and a carboxyl group or any combinations thereof. In certain embodiments, the hydrophilic bifunctional spacer comprises a hydroxyl group and a carboxylate. In other embodiments, the hydrophilic bifunctional spacer comprises an amine group and a carboxylate. In other embodiments, the hydrophilic bifunctional spacer comprises a thiol group and a carboxylate.

In some embodiments, the spacer between the first and/or second insulin polypeptide and the acyl group is a hydrophobic bifunctional spacer. Hydrophobic bifunctional spacers are known in the art. See, e.g., Bioconjugate Techniques, G. T. Hermanson (Academic Press, San Diego, Calif., 1996), which is incorporated by reference in its entirety. In certain embodiments, the hydrophobic bifunctional spacer comprises two or more reactive groups, e.g., an amine, a hydroxyl, a thiol, and a carboxyl group or any combinations thereof. In certain embodiments, the hydrophobic bifunctional spacer comprises a hydroxyl group and a carboxylate. In other embodiments, the hydrophobic bifunctional spacer comprises an amine group and a carboxylate. In other embodiments, the hydrophobic bifunctional spacer comprises a thiol group and a carboxylate. Suitable hydrophobic bifunctional spacers comprising a carboxylate and a hydroxyl group or a thiol group are known in the art and include, for example, 8-hydroxyoctanoic acid and 8-mercaptooctanoic acid.

In accordance with certain embodiments the bifunctional spacer can be a synthetic or naturally occurring amino acid comprising an amino acid backbone that is 3 to 10 atoms in length (e.g., 6-amino hexanoic acid, 5-aminovaleric acid, 7-aminoheptanoic acid, and 8-aminooctanoic acid). Alternatively, the spacer can be a dipeptide or tripeptide spacer having a peptide backbone that is 3 to 10 atoms (e.g., 6 to 10 atoms) in length. Each amino acid of the dipeptide or tripeptide spacer attached to the insulin polypeptide can be independently selected from the group consisting of: naturally-occurring and/or non-naturally occurring amino acids, including, for example, any of the D or L isomers of the naturally-occurring amino acids (Ala, Cys, Asp, Glu, Phe, Gly, His, Ile, Lys, Leu, Met, Asn, Pro, Arg, Ser, Thr, Val, Trp, Tyr), or any D or L isomers of the non-naturally occurring amino acids selected from the group consisting of: β-alanine (β-Ala), N-α-methyl-alanine (Me-Ala), aminobutyric acid (Abu), α-aminobutyric acid (γ-Abu), aminohexanoic acid (ε-Ahx), aminoisobutyric acid (Aib), aminomethylpyrrole carboxylic acid, aminopiperidinecarboxylic acid, aminoserine (Ams), aminotetrahydropyran-4-carboxylic acid, arginine N-methoxy-N-methyl amide, β-aspartic acid (β-Asp), azetidine carboxylic acid, 3-(2-benzothiazolyl)alanine, α-tert-butylglycine, 2-amino-5-ureido-n-valeric acid (citrulline, Cit), β-Cyclohexylalanine (Cha), acetamidomethylcysteine, diaminobutanoic acid (Dab), diaminopropionic acid (Dpr), dihydroxyphenylalanine (DOPA), dimethylthiazolidine (DMTA), γ-Glutamic acid (γ-Glu), homoserine (Hse), hydroxyproline (Hyp), isoleucine N-methoxy-N-methyl amide, methyl-isoleucine (MeIle), isonipecotic acid (Isn), methyl-leucine (MeLeu), methyl-lysine, dimethyl-lysine, trimethyl-lysine, methanoproline, methionine-sulfoxide (Met(O)), methionine-sulfone (Met(O2)), norleucine (Nle), methyl-norleucine (Me-Nle), norvaline (Nva), ornithine (Orn), para-aminobenzoic acid (PABA), penicillamine (Pen), methylphenylalanine (MePhe), 4-Chlorophenylalanine (Phe(4-Cl)), 4-fluorophenylalanine (Phe(4-F)), 4-nitrophenylalanine (Phe(4-NO2)), 4-cyanophenylalanine ((Phe (4-CN)), phenylglycine (Phg), piperidinylalanine, piperidinylglycine, 3,4-dehydroproline, pyrrolidinylalanine, sarcosine (Sar), selenocysteine (Sec), U-Benzyl-phosphoserine, 4-amino-3-hydroxy-6-methylheptanoic acid (Sta), 4-amino-5-cyclohexyl-3-hydroxypentanoic acid (ACHPA), 4-amino-3-hydroxy-5-phenylpentanoic acid (AHPPA), 1,2,3,4,-tetrahydro-isoquinoline-3-carboxylic acid (Tic), tetrahydropyranglycine, thienylalanine (Thi), U-Benzyl-phosphotyrosine, 0-Phosphotyrosine, methoxytyrosine, ethoxytyrosine, O-(bis-dimethylamino-phosphono)-tyrosine, tyrosine sulfate tetrabutylamine, methyl-valine (Me-Val), 1-amino-1-cyclohexane carboxylic acid (Acx), aminovaleric acid, beta-cyclopropyl-alanine (Cpa), propargylglycine (Prg), allylglycine (Alg), 2-amino-2-cyclohexyl-propanoic acid (2-Cha), tertbutylglycine (Tbg), vinylglycine (Vg), 1-amino-1-cyclopropane carboxylic acid (Acp), 1-amino-1-cyclopentane carboxylic acid (Acpe), alkylated 3-mercaptopropionic acid, 1-amino-1-cyclobutane carboxylic acid (Acb). In some embodiments the dipeptide spacer is selected from the group consisting of: Ala-Ala, β-Ala-β-Ala, Leu-Leu, Pro-Pro, γ-aminobutyric acid-γ-aminobutyric acid, and γ-Glu-γ-Glu.

The first and/or second insulin polypeptide may be modified to comprise an acyl group by acylation of a long chain alkane. In specific aspects, the long chain alkane comprises an amine, hydroxyl, or thiol group (e.g. octadecylamine, tetradecanol, and hexadecanethiol) which reacts with a carboxyl group, or activated form thereof, of the insulin polypeptide. The carboxyl group, or activated form thereof, of the insulin polypeptide can be part of a side chain of an amino acid (e.g., glutamic acid, aspartic acid) of the insulin polypeptide or can be part of the peptide backbone.

In certain embodiments, the first and/or second insulin polypeptide is modified to comprise an acyl group by acylation of the long chain alkane by a spacer which is attached to the insulin polypeptide. In specific aspects, the long chain alkane comprises an amine, hydroxyl, or thiol group which reacts with a carboxyl group, or activated form thereof, of the spacer. Suitable spacers comprising a carboxyl group, or activated form thereof, are described herein and include, for example, bifunctional spacers, e.g., amino acids, dipeptides, tripeptides, hydrophilic bifunctional spacers and hydrophobic bifunctional spacers. As used herein, the term "activated form of a carboxyl group" refers to a carboxyl group with the general formula R(C=O)X, wherein X is a leaving group and R is the insulin polypeptide or the spacer. For example, activated forms of a carboxyl groups may include, but are not limited to, acyl chlorides, anhydrides, and esters. In some embodiments, the activated carboxyl group is an ester with an N-hydroxysuccinimide (NHS) leaving group.

With regard to these aspects of the invention, in which a long chain alkane is acylated by the peptide, the insulin polypeptide or the spacer, the long chain alkane may be of any size and can comprise any length of carbon chain. The long chain alkane can be linear or branched. In certain aspects, the long chain alkane is a $C_4$ to $C_{30}$ alkane. For example, the long chain alkane can be any of a $C_4$ alkane, $C_6$ alkane, $C_8$ alkane, $C_{10}$ alkane, $C_{12}$ alkane, $C_{14}$ alkane, $C_{16}$ alkane, $C_{18}$ alkane, $C_{20}$ alkane, $C_{22}$ alkane, $C_{24}$ alkane, $C_{26}$ alkane, $C_{28}$ alkane, or a $C_{30}$ alkane. In some embodiments, the long chain alkane comprises a $C_8$ to $C_{20}$ alkane, e.g., a $C_{14}$ alkane, $C_{16}$ alkane, or a $C_{18}$ alkane.

In some embodiments, an amine, hydroxyl, or thiol group of the first and/or second insulin polypeptide is acylated with a cholesterol acid. In a specific embodiment, the peptide is linked to the cholesterol acid through an alkylated desamino Cys spacer, i.e., an alkylated 3-mercaptopropionic acid spacer. Suitable methods of peptide acylation via amines, hydroxyls, and thiols are known in the art. See, for example, Miller, Biochem Biophys Res Commun 218: 377-382 (1996); Shimohigashi and Stammer, Int J Pept Protein Res 19: 54-62 (1982); and Previero et al., Biochim Biophys Acta 263: 7-13 (1972) (for methods of acylating through a hydroxyl); and San and Silvius, J Pept Res 66: 169-180 (2005) (for methods of acylating through a thiol); Bioconjugate Chem. "Chemical Modifications of Proteins: History and Applications" pages 1, 2-12 (1990); Hashimoto et al., Pharmacuetical Res. "Synthesis of Palmitoyl Derivatives of Insulin and their Biological Activity" Vol. 6, No: 2 pp. 171-176 (1989).

The acyl group of the acylated peptide the first and/or second insulin polypeptide can be of any size, e.g., any length carbon chain, and can be linear or branched. In some specific embodiments of the invention, the acyl group is a $C_4$ to $C_{30}$ fatty acid. For example, the acyl group can be any of a $C_4$ fatty acid, $C_6$ fatty acid, $C_8$ fatty acid, $C_{10}$ fatty acid, $C_{12}$ fatty acid, $C_{14}$ fatty acid, $C_{16}$ fatty acid, $C_{18}$ fatty acid, $C_{20}$ fatty acid, $C_{22}$ fatty acid, $C_{24}$ fatty acid, $C_{26}$ fatty acid, $C_{28}$ fatty acid, or a $C_{30}$ fatty acid. In some embodiments, the acyl group is a $C_8$ to $C_{20}$ fatty acid, e.g., a $C_{14}$ fatty acid or a $C_{16}$ fatty acid. In some embodiments, the acyl group is urea.

In an alternative embodiment, the acyl group is a bile acid. The bile acid can be any suitable bile acid, including, but not limited to, cholic acid, chenodeoxycholic acid, deoxycholic acid, lithocholic acid, taurocholic acid, glycocholic acid, and cholesterol acid.

The acylated first and/or second insulin polypeptide described herein can be further modified to comprise a hydrophilic moiety. In some specific embodiments the hydrophilic moiety can comprise a polyethylene glycol (PEG) chain. The incorporation of a hydrophilic moiety can be accomplished through any suitable means, such as any of the methods described herein. In some embodiments the acylated single chain analog comprises an amino acid selected from the group consisting of a Cys, Lys, Orn, homo-Cys, or Ac-Phe, and the side chain of the amino acid is covalently bonded to a hydrophilic moiety (e.g., PEG). In one embodiment, the acyl group is attached to position A1, A14, A15, B1, B2, B10, or B22 (according to the amino acid numbering of the A and B chains of native insulin), optionally via a spacer comprising Cys, Lys, Orn, homo-Cys, or Ac-Phe.

Alternatively, the acylated first and/or second insulin polypeptide comprises a spacer, wherein the spacer is both acylated and modified to comprise the hydrophilic moiety. Non-limiting examples of suitable spacers include a spacer comprising one or more amino acids selected from the group consisting of Cys, Lys, Orn, homo-Cys, and Ac-Phe.

In some embodiments, the amino terminus of at least one N-terminal amino acid of at least one of the A-chain polypeptides and the B-chain polypeptides of the insulin receptor partial agonist is modified to comprise a substituent. The substituent may be covalently linked directly to the amino group of the N-terminal amino acid or indirectly to the amino group via a spacer, wherein the spacer is positioned between the amino group of the N-terminal amino acid of the insulin polypeptide and the substituent. The substituent may be an acyl moiety as discussed supra. The substituent may have the general formula RC(O)—, where R can be R'CH$_2$, R'NH, R'O, and R' can be H, linear alkyl chain, amino acid, peptide, polyethylene glycol (PEG), saccharides, which in particular aspects RC(O)— may be acetyl, phenylacetyl, carbamoyl, N-alkyl carbamoyl, or alkoxycarbonyl. In particular aspects, the substituent is a carbamoyl group, acetyl group, glycine, methyl group, methoxy group, dimethyl group, isobutyl group, PEG1 group, or PEG2 group (see Examples herein for structures of the substituents). Carbamolyation of insulin has been disclosed by Oimoni et al., Nephron 46: 63-66 (1987) and insulin dimers comprising a carbamoyl groups at the N-terminus has been disclosed in disclosed in published PCT Application No. WO2014052451 (E.g., MIU-90).

In particular embodiments, at least one N-terminal amino acid is conjugated via the N2 nitrogen to a substituent comprising an N-hydroxysuccinimide ester linked to a group having the general formula RC(O)—, where R can be R'CH$_2$, R'NH, R'O, and R' can be H, linear alkyl chain, amino acid, peptide, polyethylene glycol (PEG), saccharides, which in particular aspects RC(O)— may be acetyl, phenylacetyl, carbamoyl, N-alkyl carbamoyl, or alkoxycarbonyl. In particular aspects, the substituent is a carbamoyl group, acetyl group, glycine, methyl group, methoxy group, dimethyl group, isobutyl group, PEG1 group, or PEG2 group.

Exemplary substituents conjugated to the N-terminal amino group may be

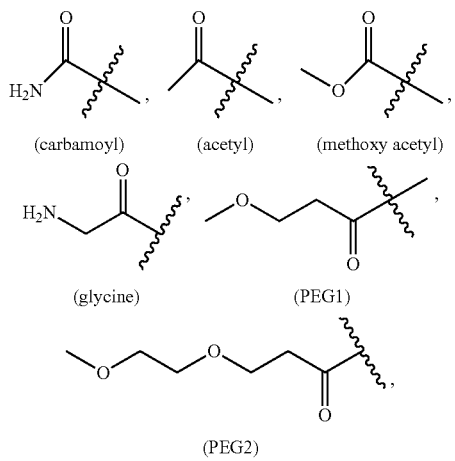

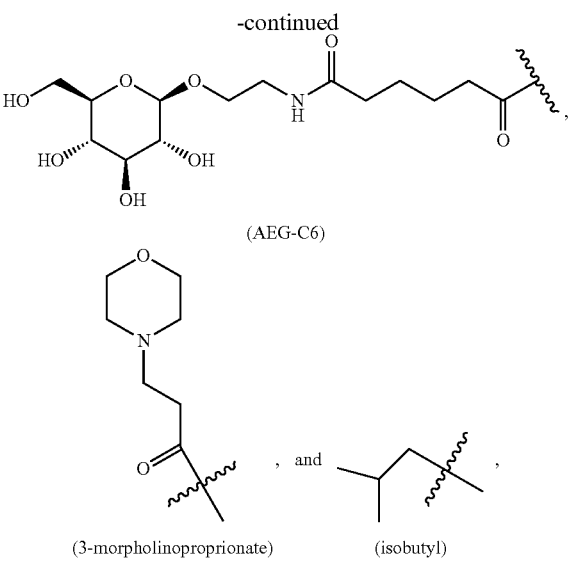

wherein the wavy line indicates the bond between the substituent and the N-terminal amino group. The substituent may also be

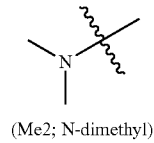

(Me2; N-dimethyl)

wherein the wavy line indicates the bond between Me2 and the alpha carbon of the N-terminal amino acid.

Exemplary Insulin Dimers

In particular embodiments, the present invention provides insulin dimers wherein a first B29 or B28 Lys of a first insulin heterodimer molecule having a first A-chain polypeptide and first B-chain polypeptide and a second B29 or B28 Lys of a second insulin heterodimer having a second A-chain polypeptide and second B-chain polypeptide are conjugated together by a bifunctional linker selected from the group consisting Linker 1, Linker 2, Linker 3, Linker 4, Linker 5, Linker 6, Linker 7, Linker 8, Linker 9, Linker 10, Linker 11, Liner 12, Linker 13, Linker 14, Linker 15, Linker 16, Linker 17, Linker 18, Linker 19, Linker 20, Linker 21, Linker 22, Linker 23, Linker 24, Linker 25, Linker 26, Linker 27, Linker 28, Linker 29, Linker 30, Linker 31, Linker 32, Linker 33, Linker 34, Linker 35, Linker 36, Linker 37, Linker 38, Linker 39, Linker 40, Linker 41, Linker 42, Linker 43, Linker 44, Linker 45, Linker 46, Linker 47, Linker 48, Linker 49, Linker 50, Linker 51, Linker 52, Linker 53, Linker 54, Linker 55, Linker 56, Linker 57, Linker 58, Linker 59, Linker 60, Linker 61, Linker 62, Linker 63, Linker 64, and Linker 65.

In particular embodiments, at least one of the first or second A-chain or B-chain polypeptides is conjugated at its N-terminal amino acid to a substituent as disclosed herein or at least the N-terminal amino acids of the first insulin heterodimer molecule are conjugated to a substituent as disclosed herein or the N-terminal amino acids of both the first insulin heterodimer and second insulin heterodimer are conjugated to a substituent. In particular embodiments, the substituent comprises an N-hydroxysuccinimide ester linked to a group having the general formula RC(O)—, where R can be R'CH$_2$, R'NH, R'O, and R' can be H, linear alkyl chain, amino acid, peptide, polyethylene glycol (PEG), saccharides, which in particular aspects RC(O)— may be acetyl, phenylacetyl, carbamoyl, N-alkyl carbamoyl, or alkoxycarbonyl. In particular aspects, the substituent is a carbamoyl group, acetyl group, glycine, methyl group, methoxy group, dimethyl group, isobutyl group, PEG1 group, AEG group, AEG-C6 alkyl group, or PEG2 group.

Exemplary insulin dimers include

Dimer 1

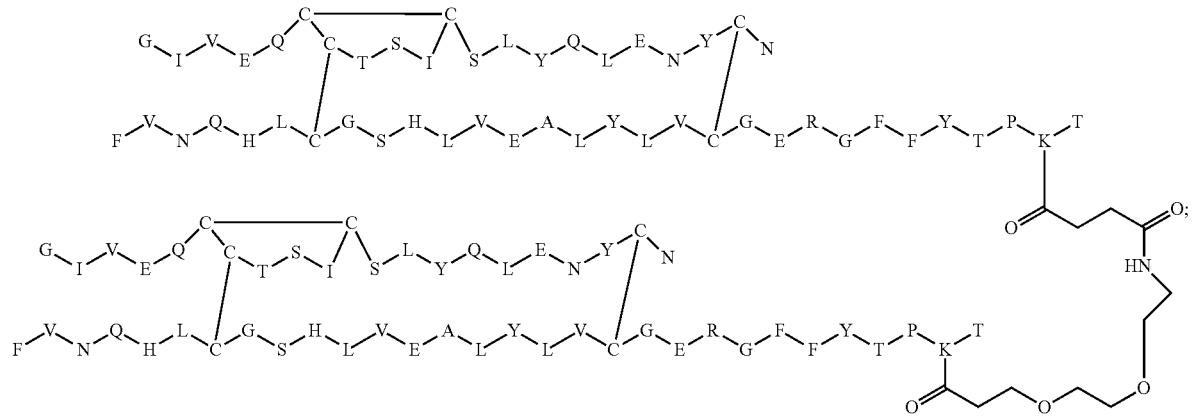

Dimer 2

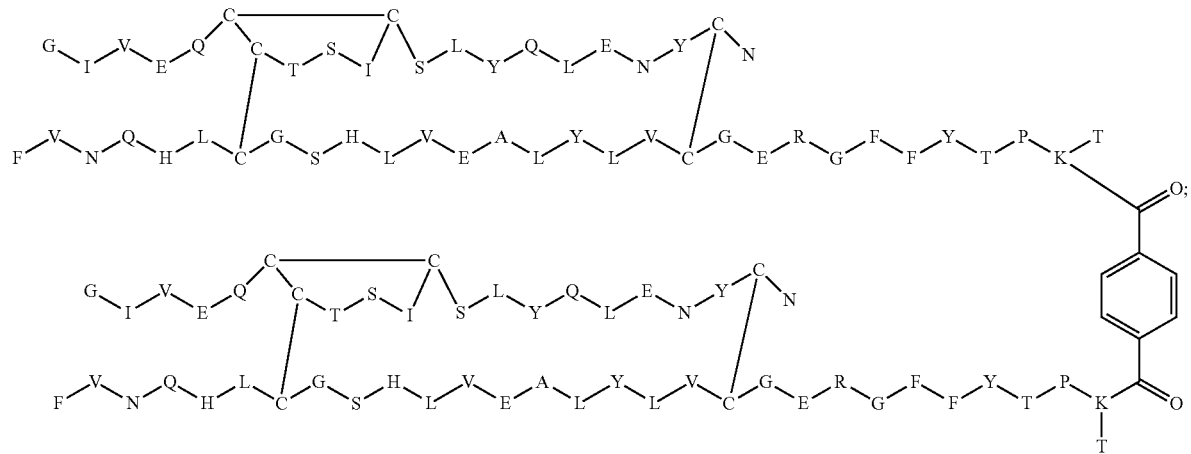

Dimer 3

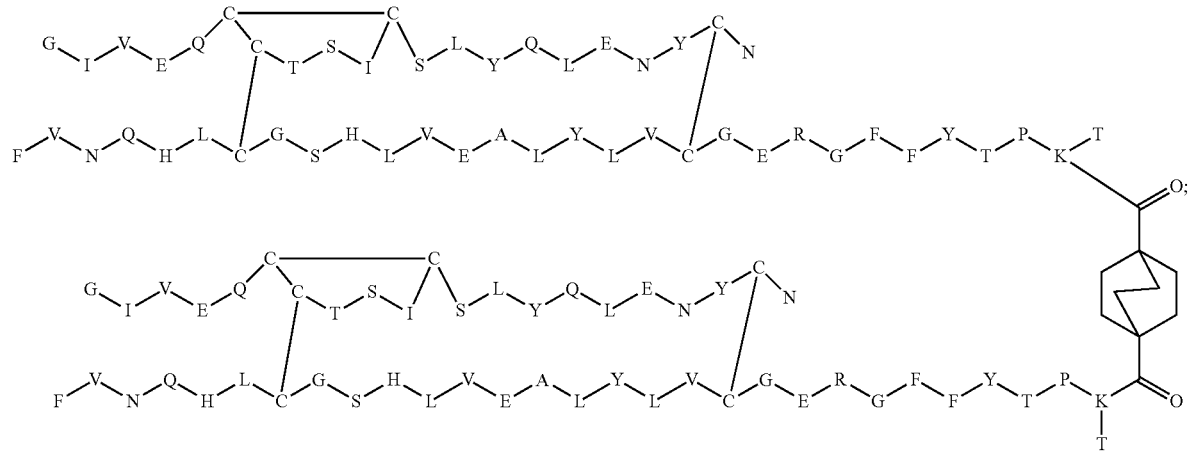

Dimer 4
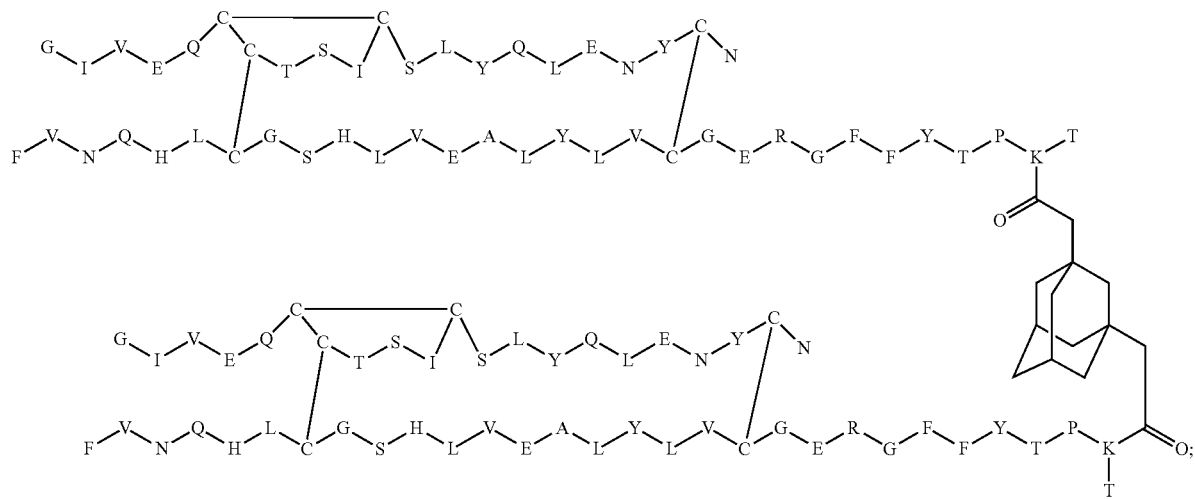
Dimer 5
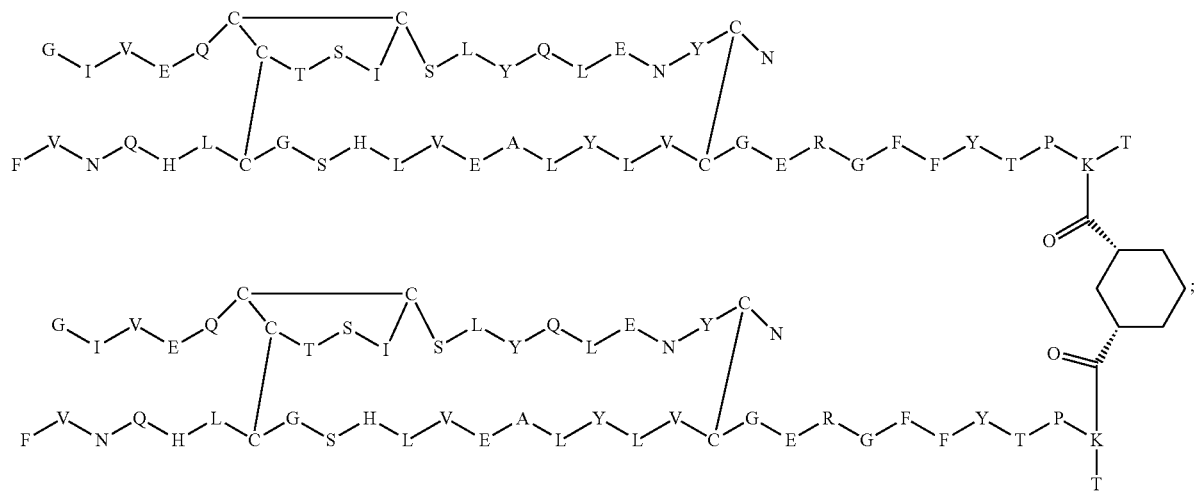
Dimer 6
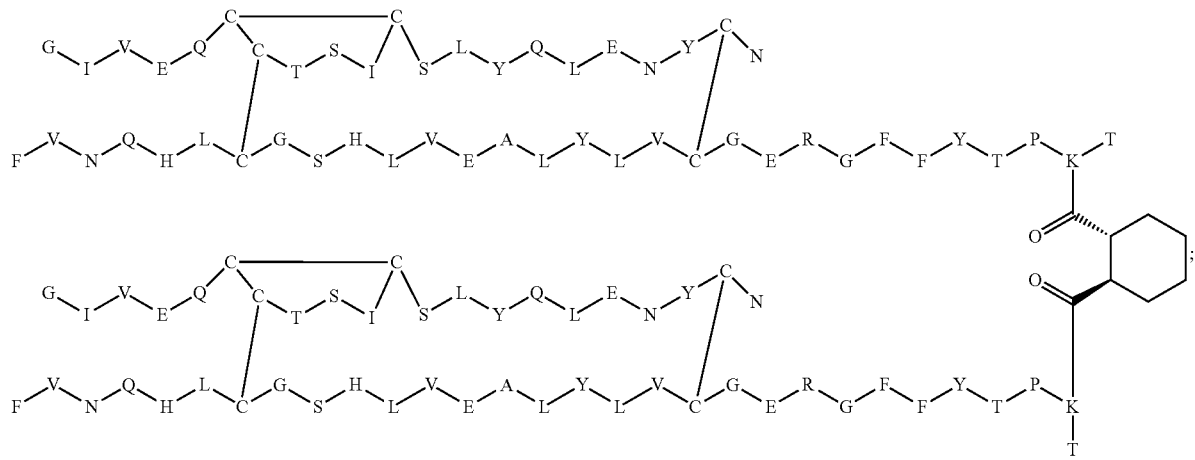

Dimer 7
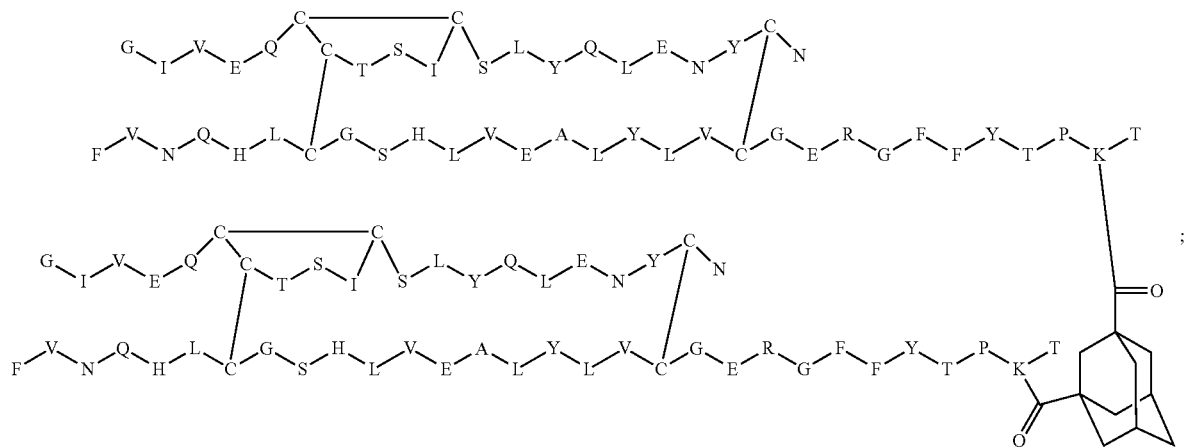
Dimer 8
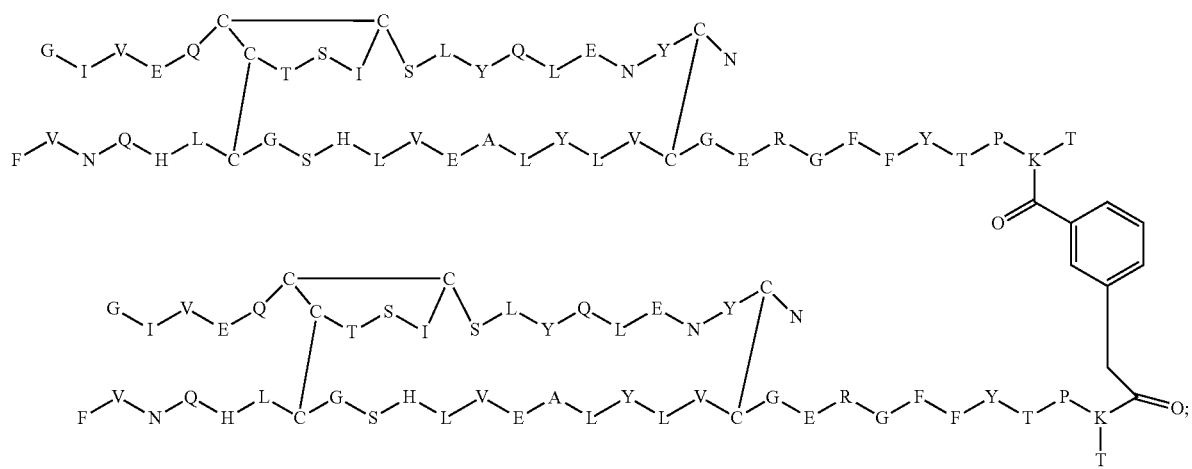
Dimer 9
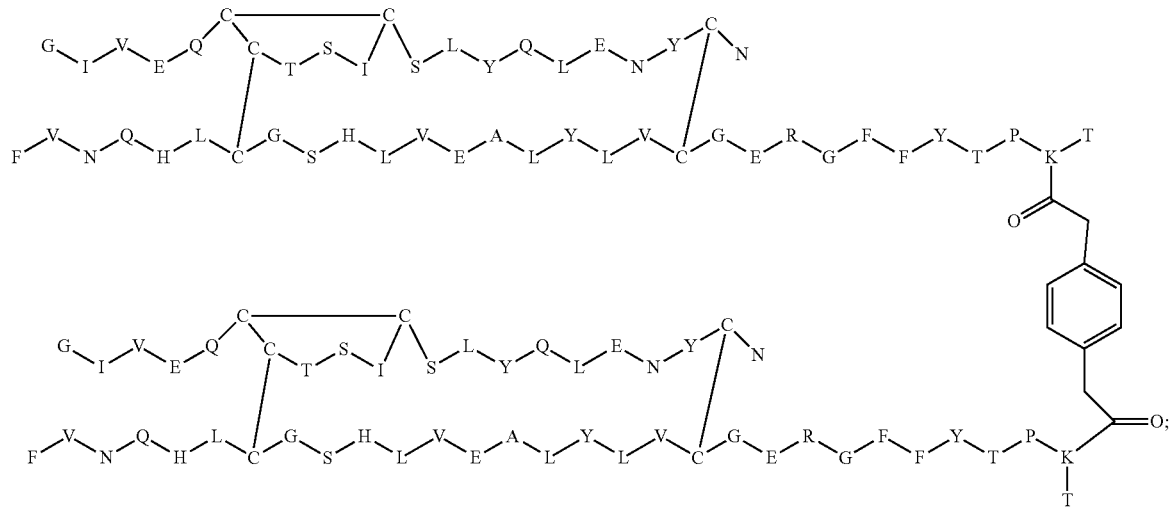

Dimer 10
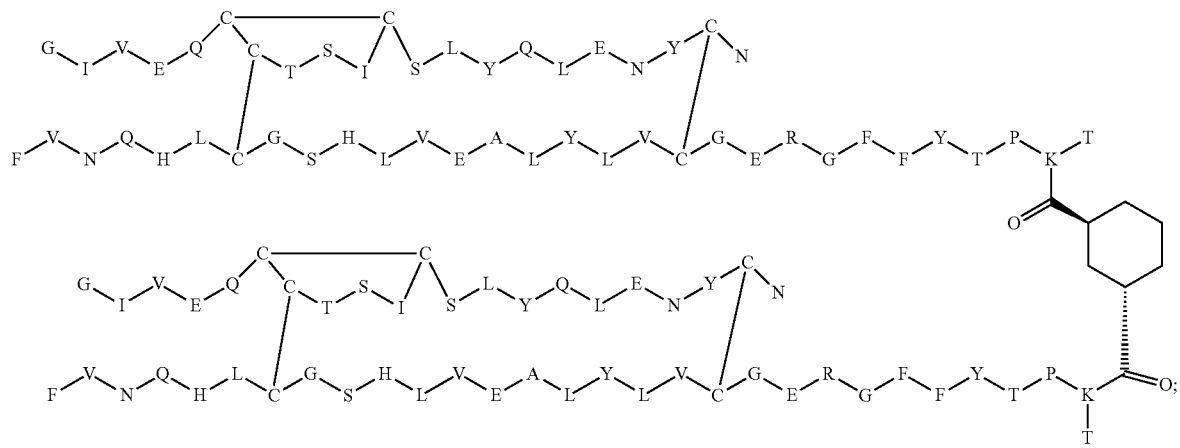
Dimer 11
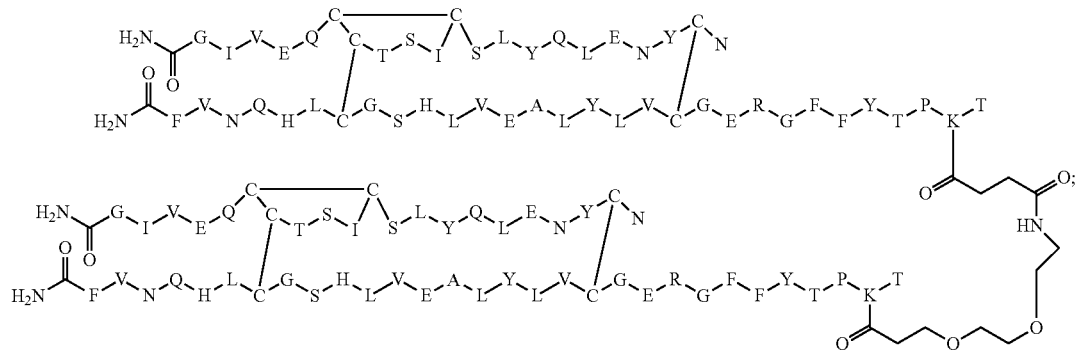
Dimer 12
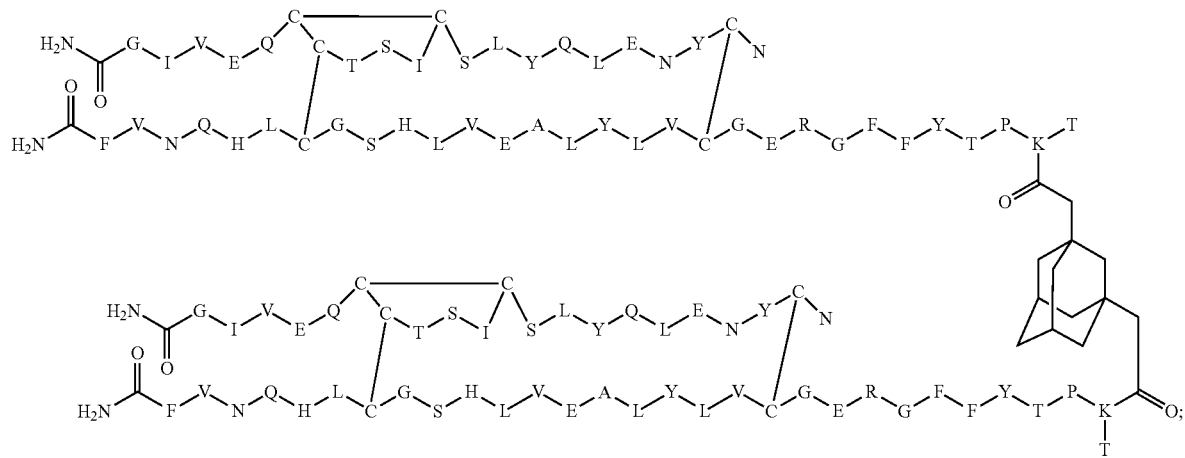

Dimer 13
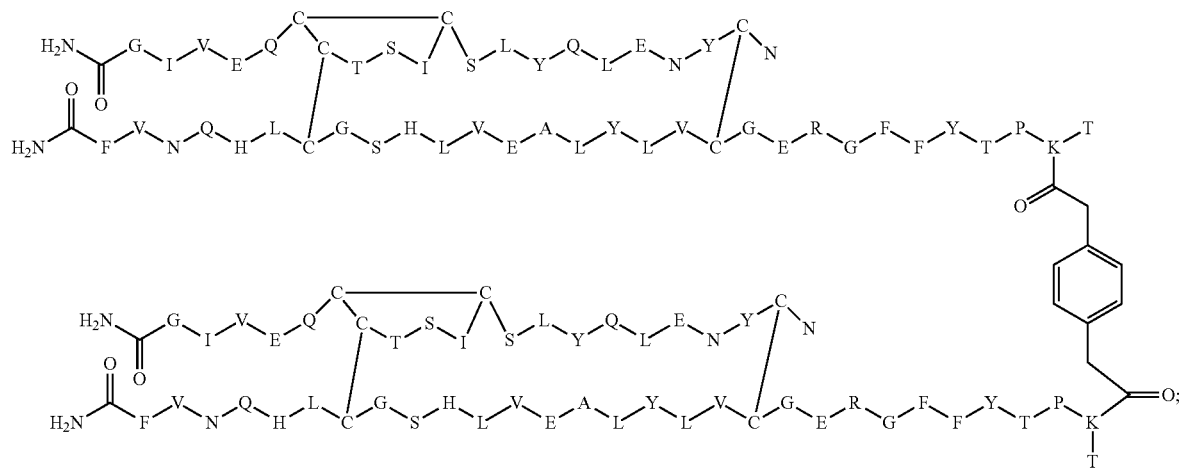
Dimer 14
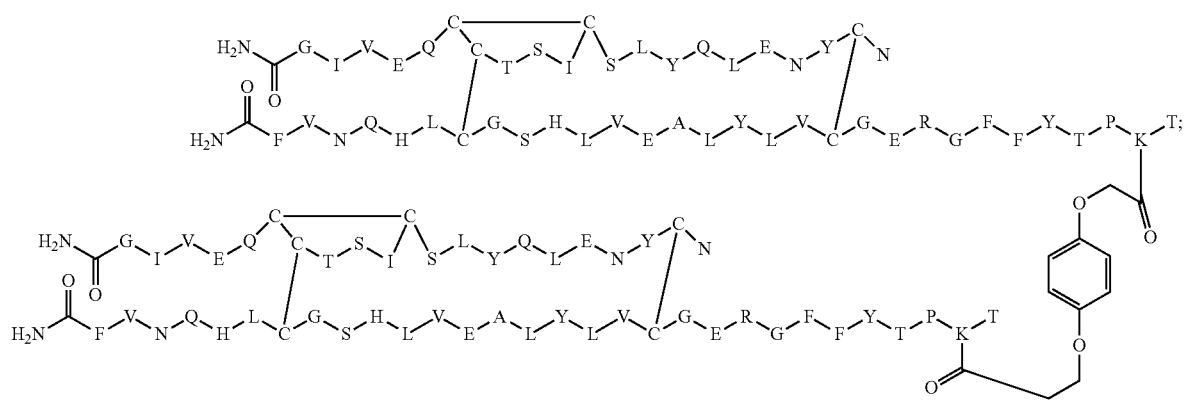
Dimer 15
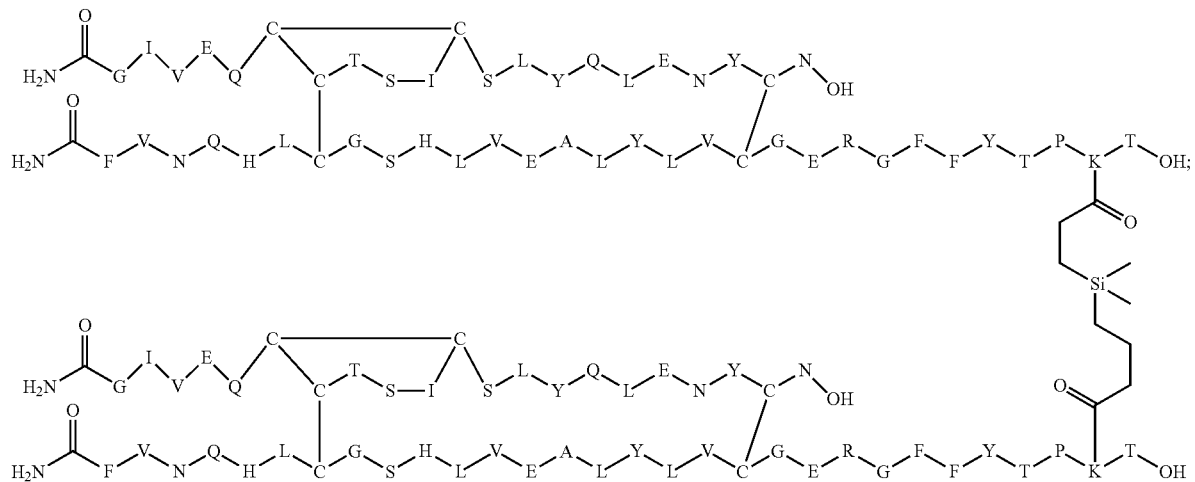

Dimer 16
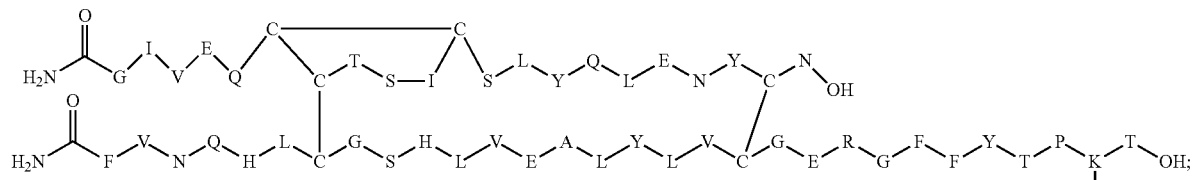
Dimer 17
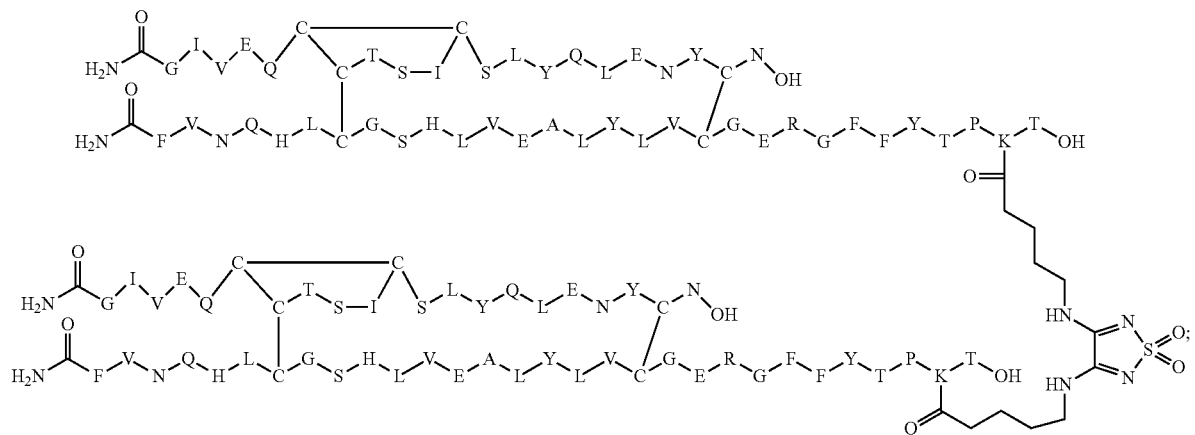
Dimer 18
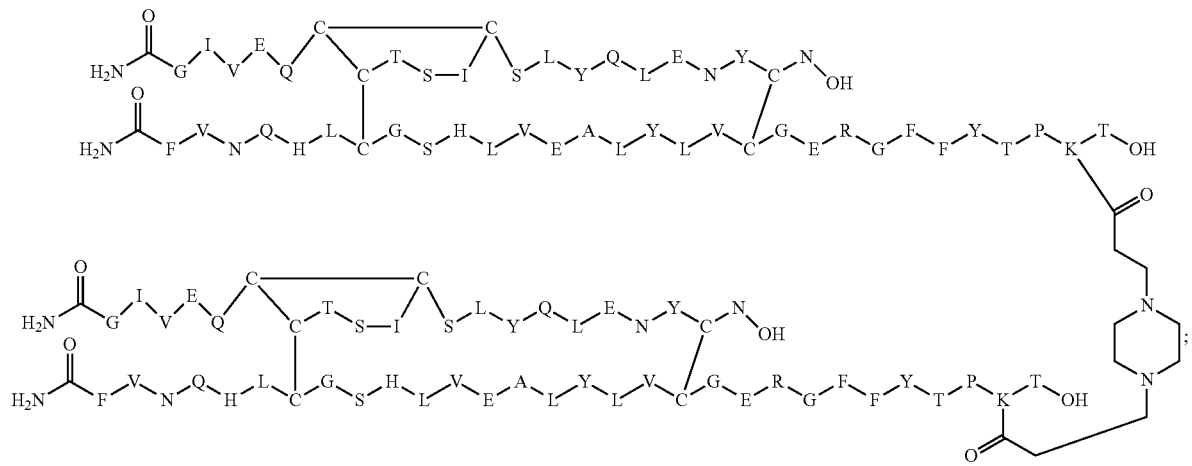

Dimer 19
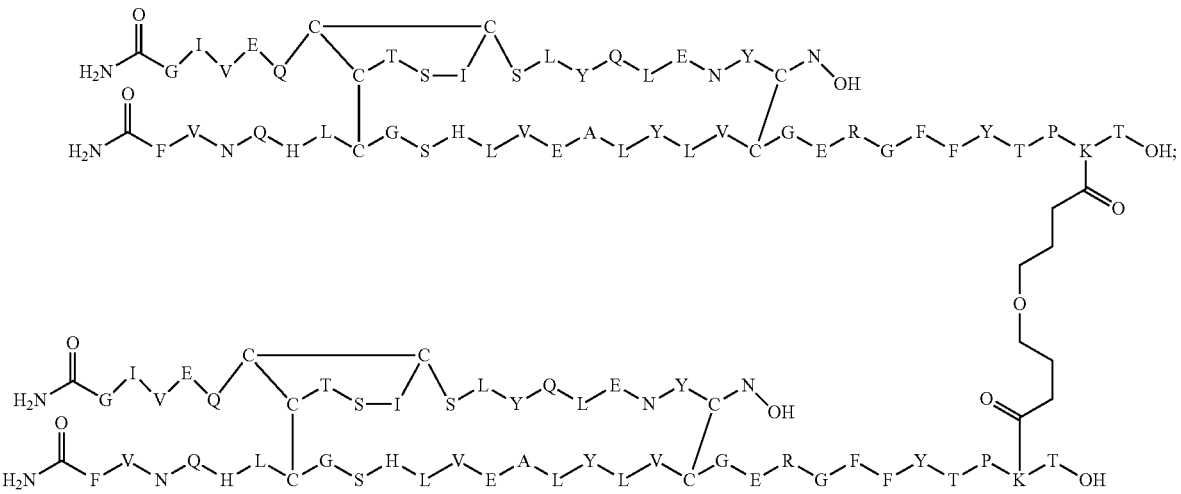
Dimer 20
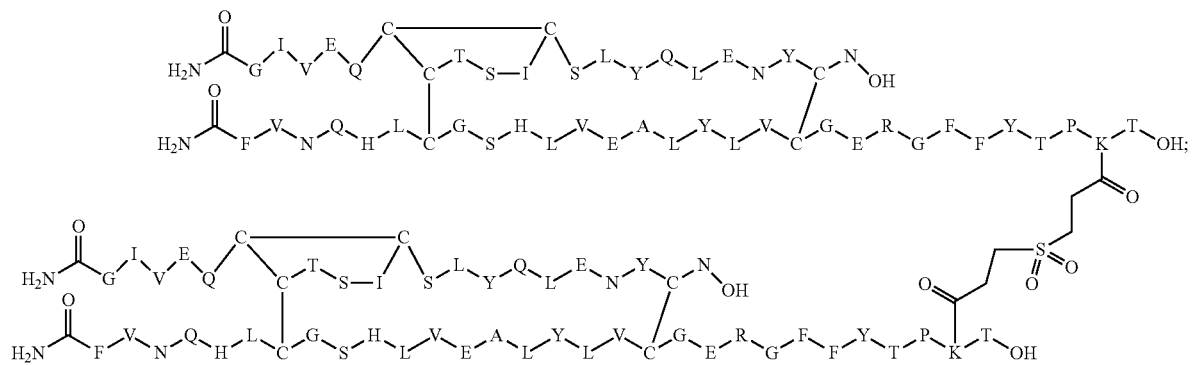
Dimer 21
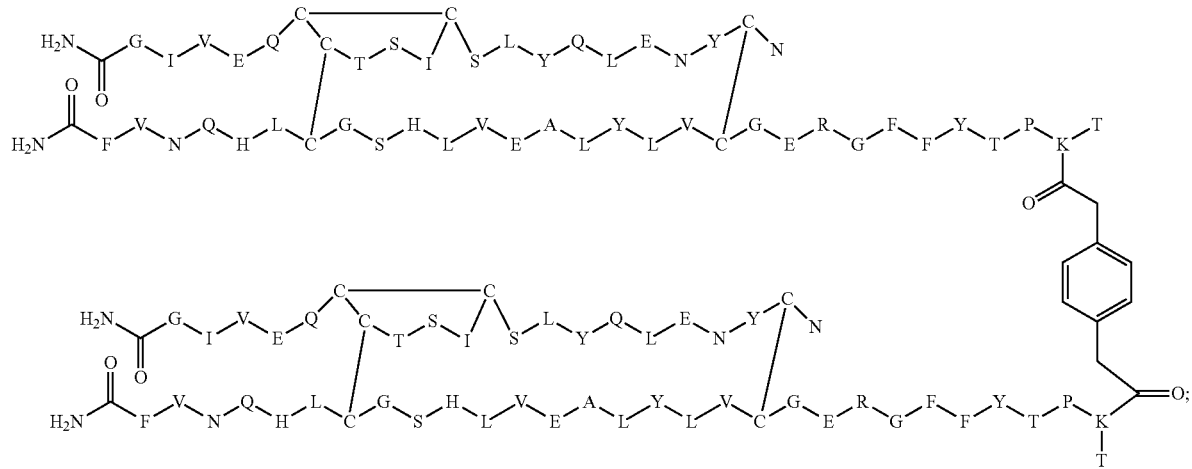

Dimer 22
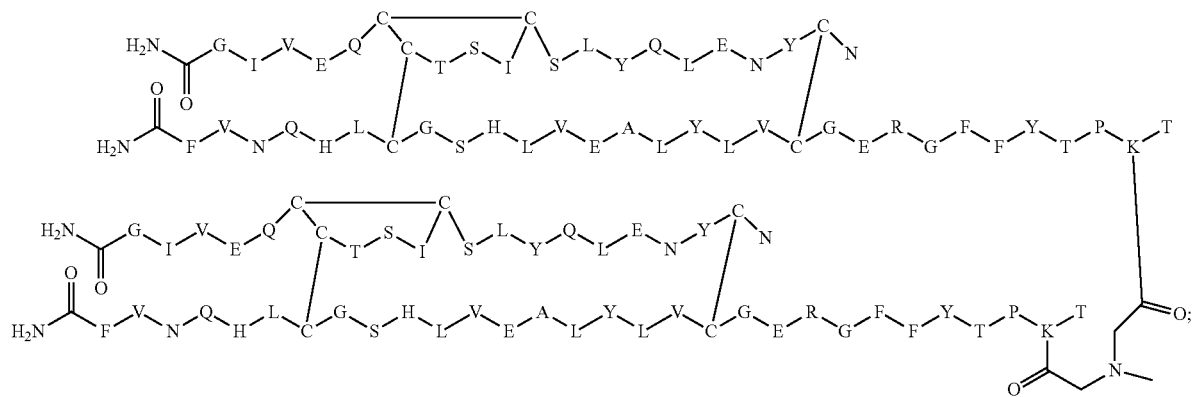
Dimer 23
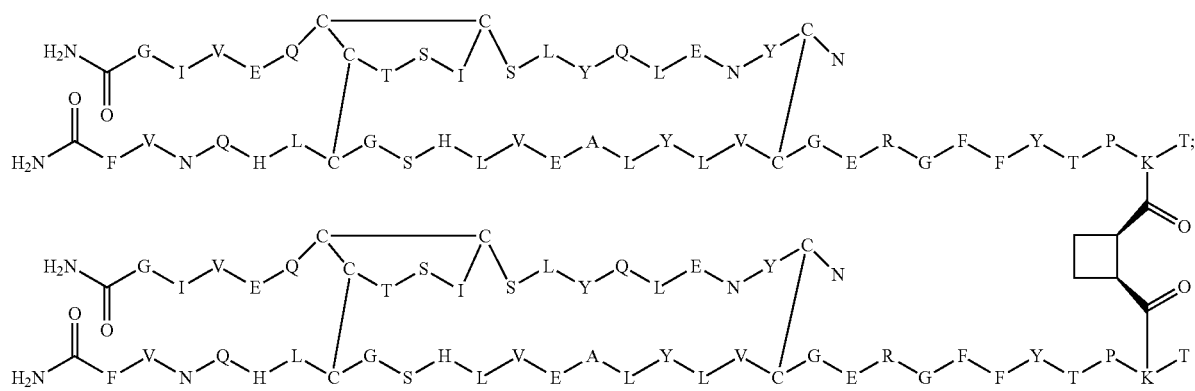
Dimer 24
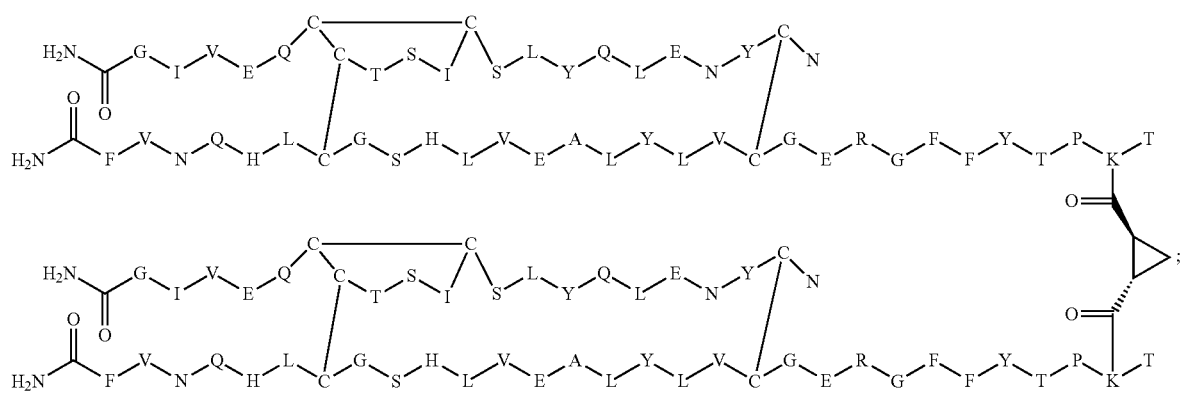

Dimer 25
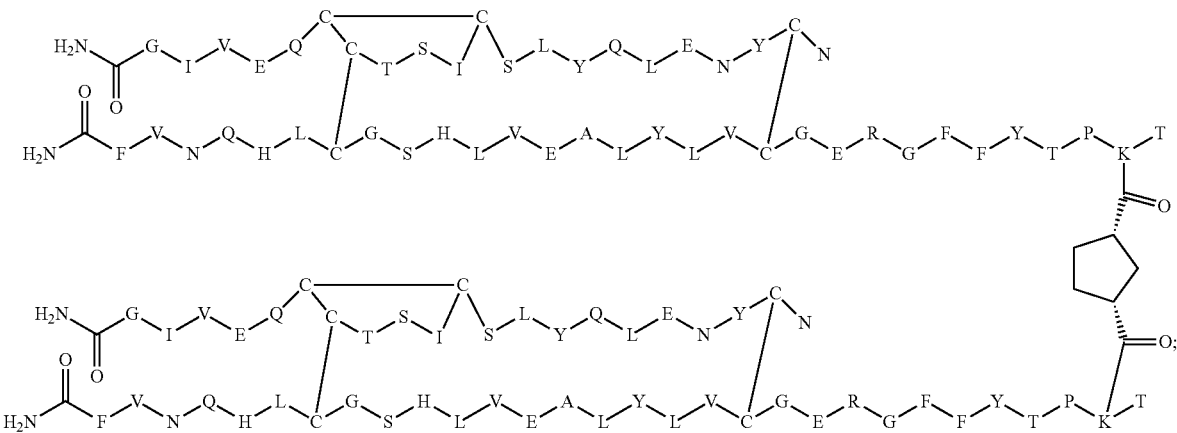
Dimer 26
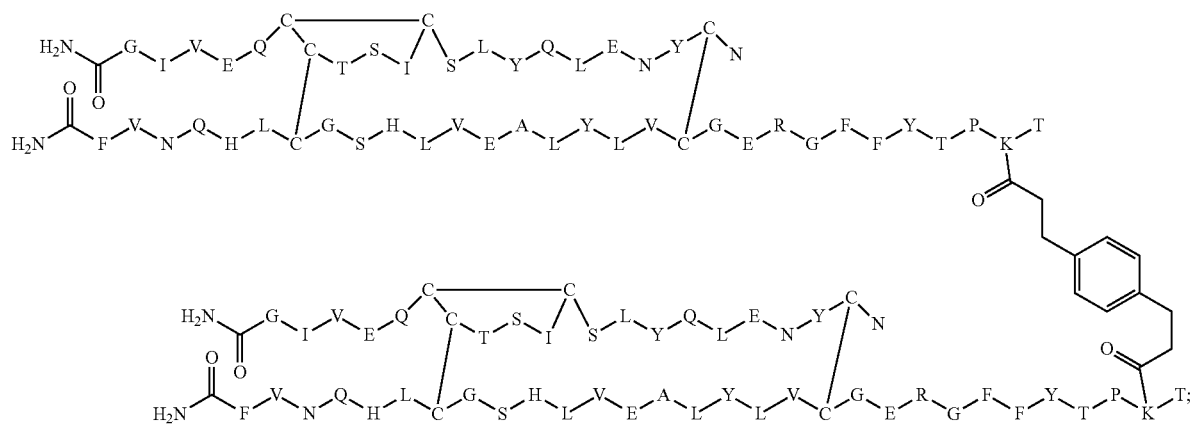
Dimer 27
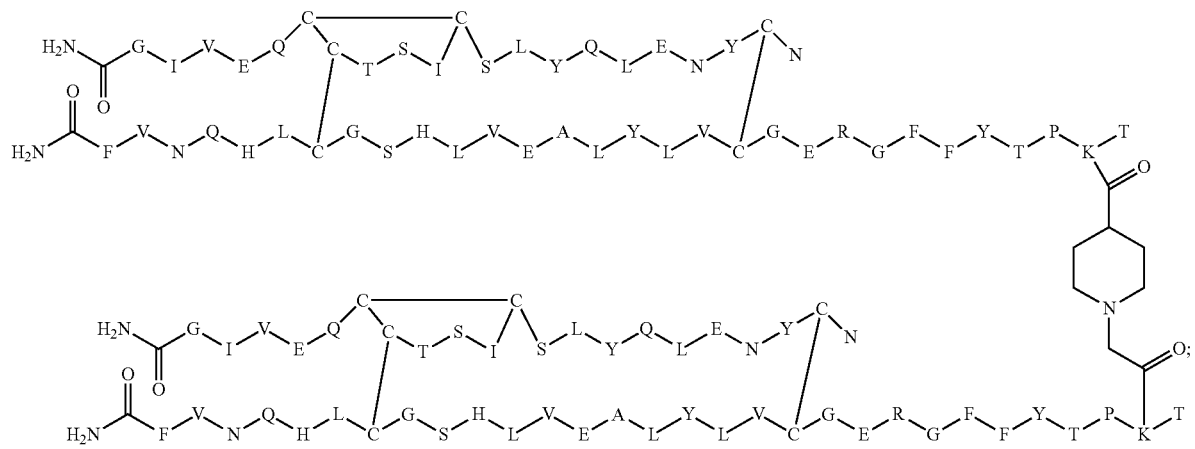

Dimer 28
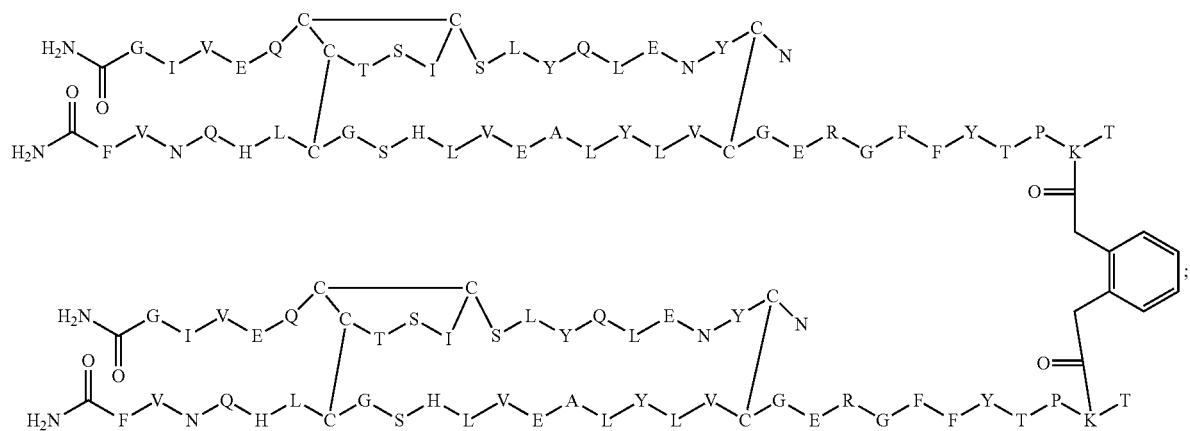
Dimer 29
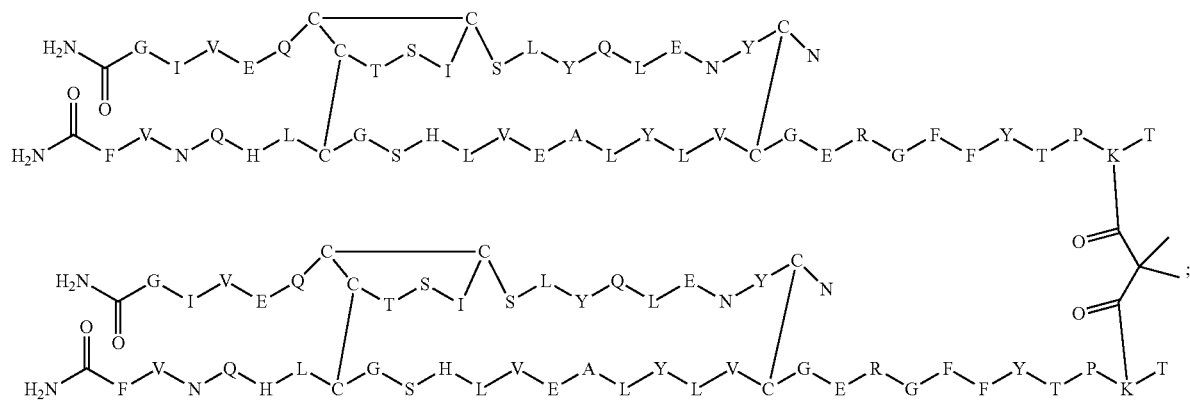
Dimer 30
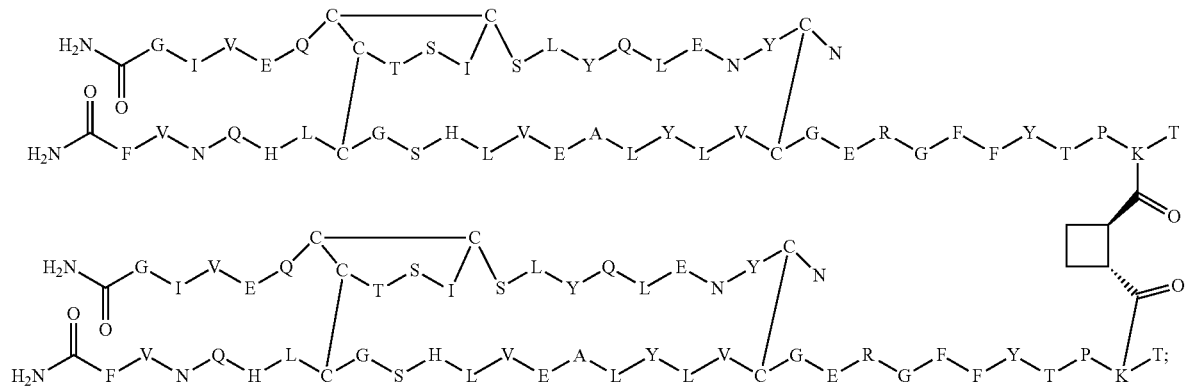

Dimer 31
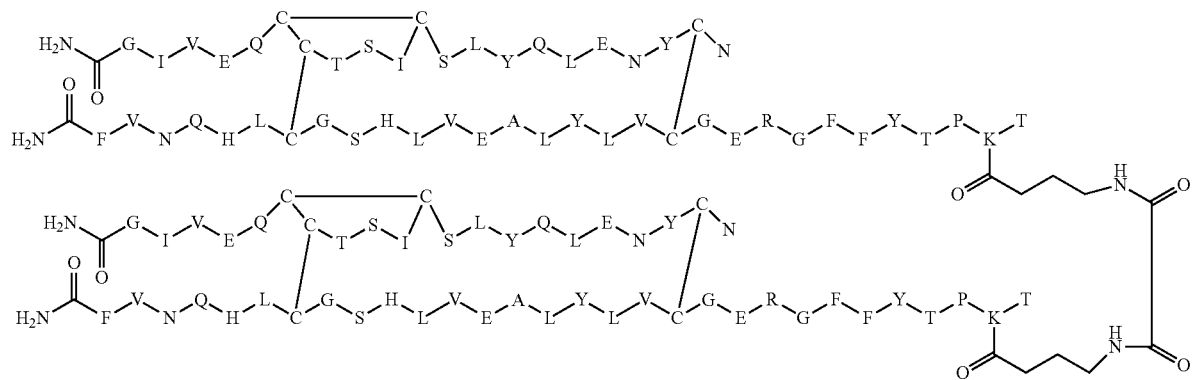
Dimer 32
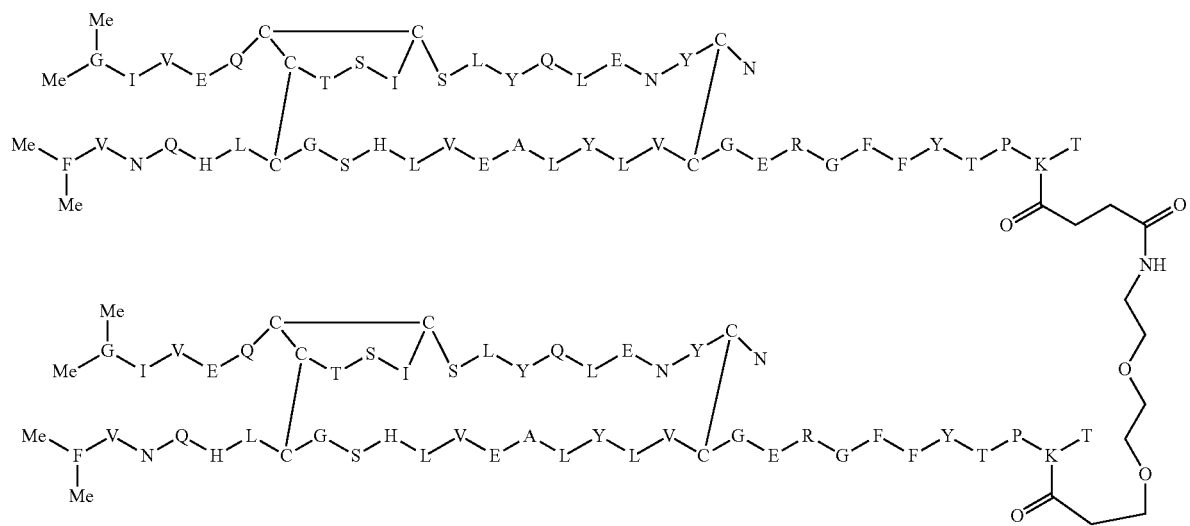
Dimer 33
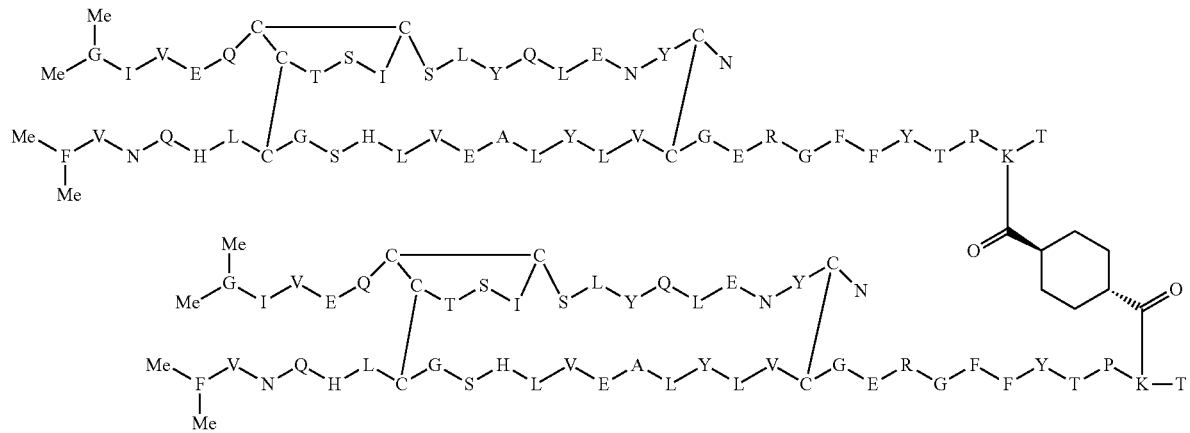

Dimer 34
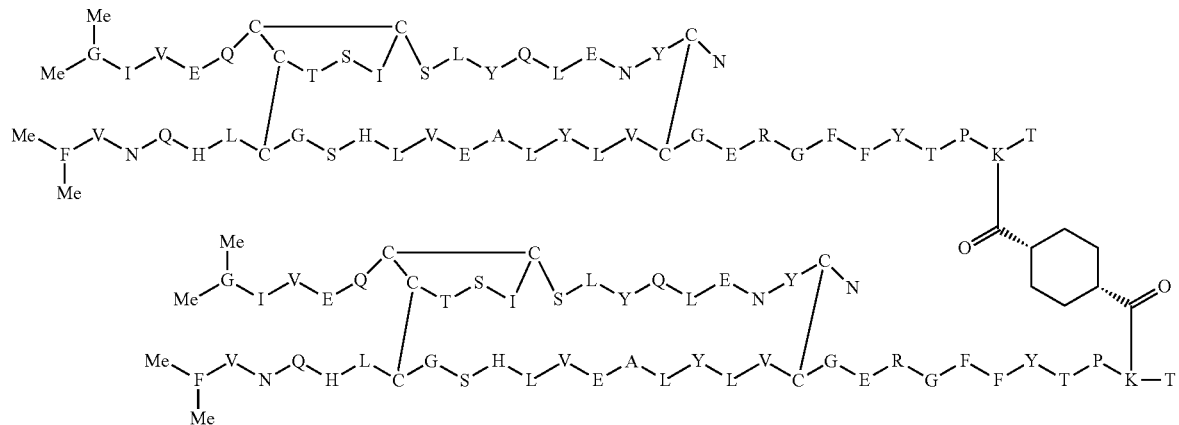
Dimer 35
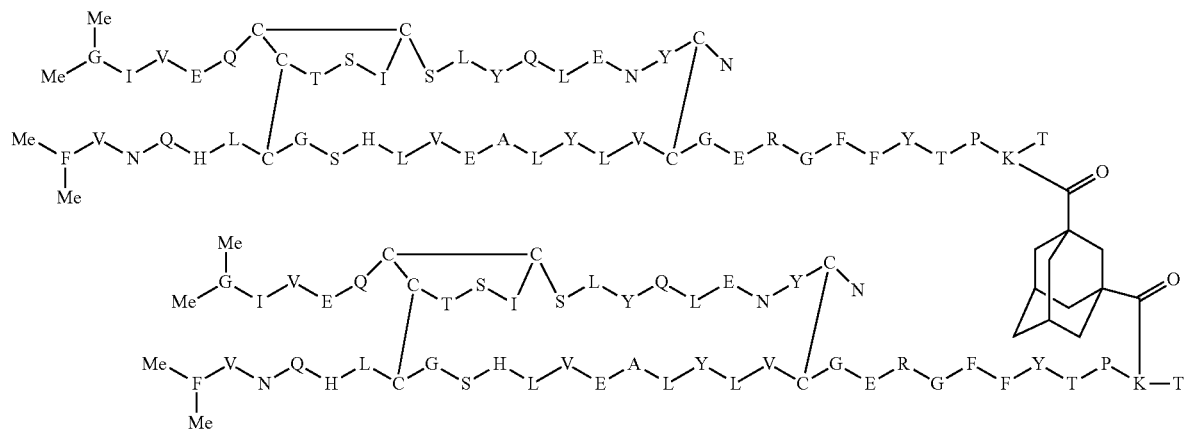
Dimer 36
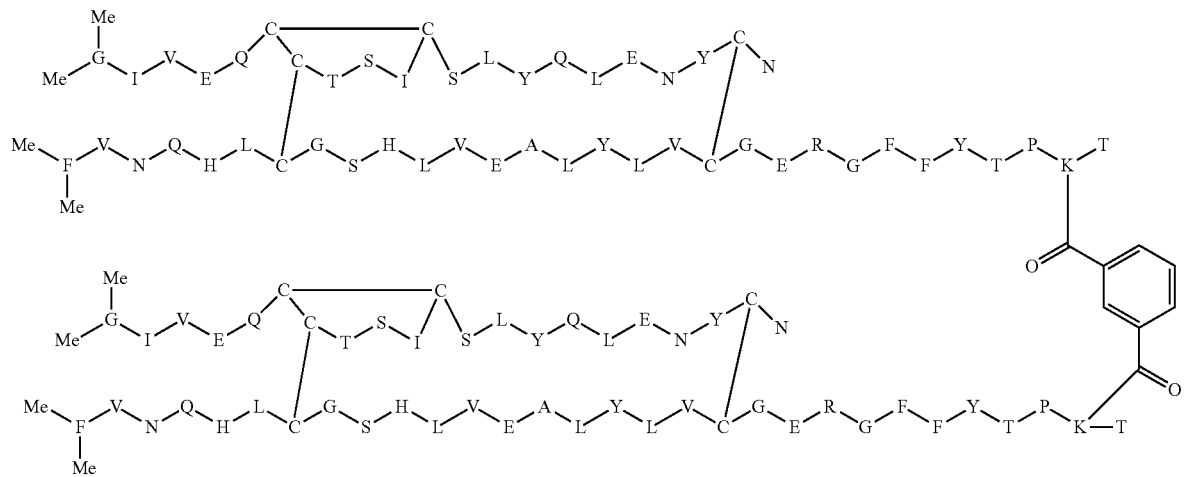

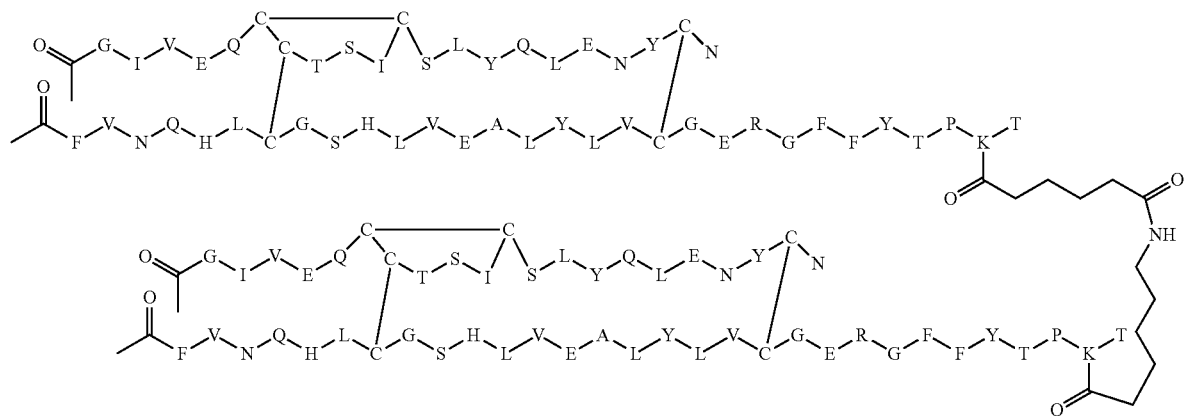
Dimer 37
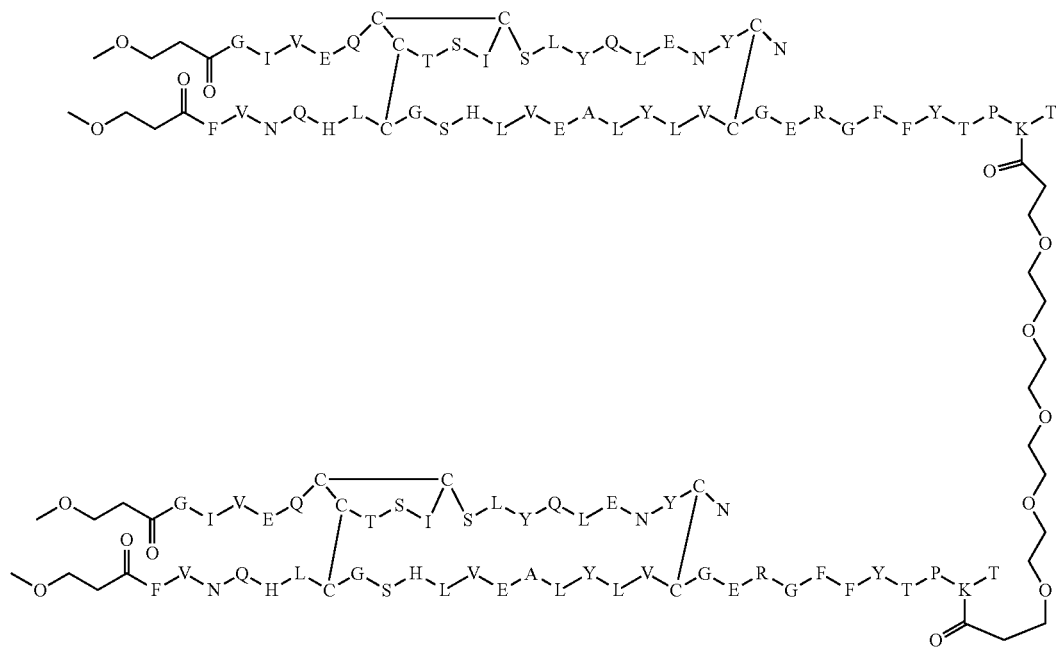
Dimer 38
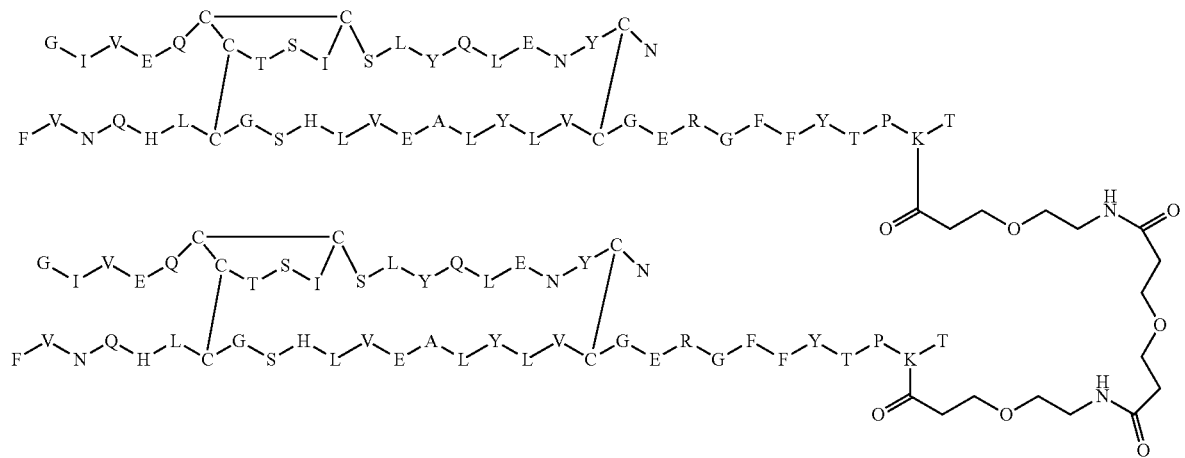
Dimer 39

Dimer 40
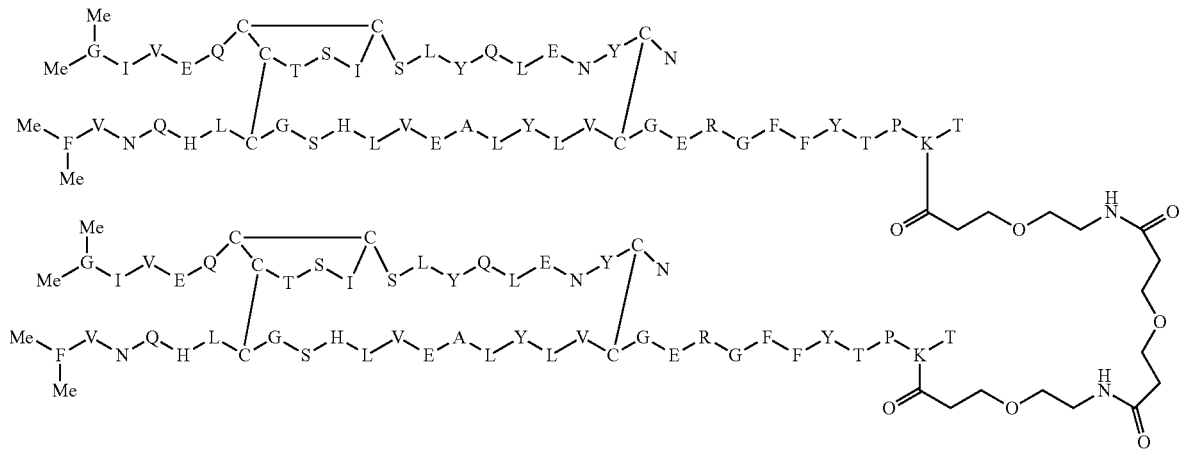
Dimer 41
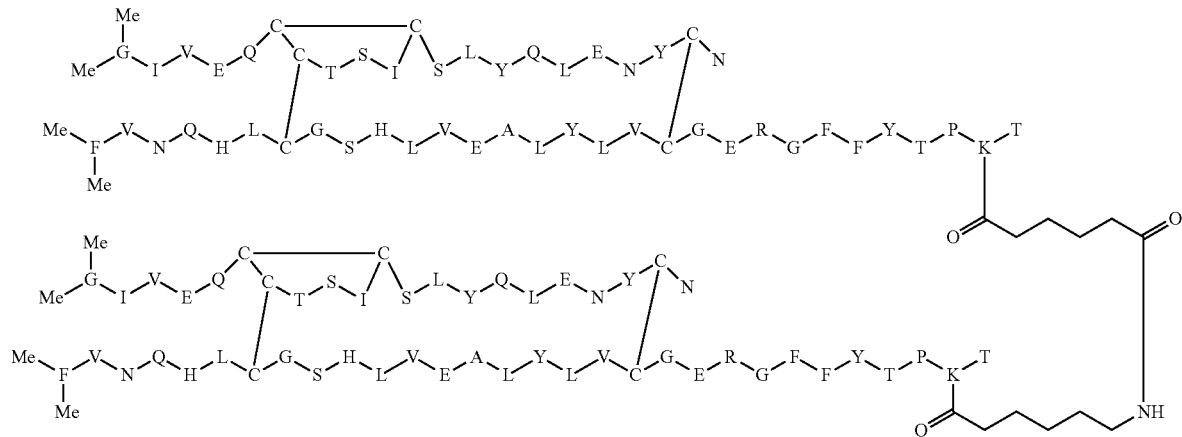
Dimer 42
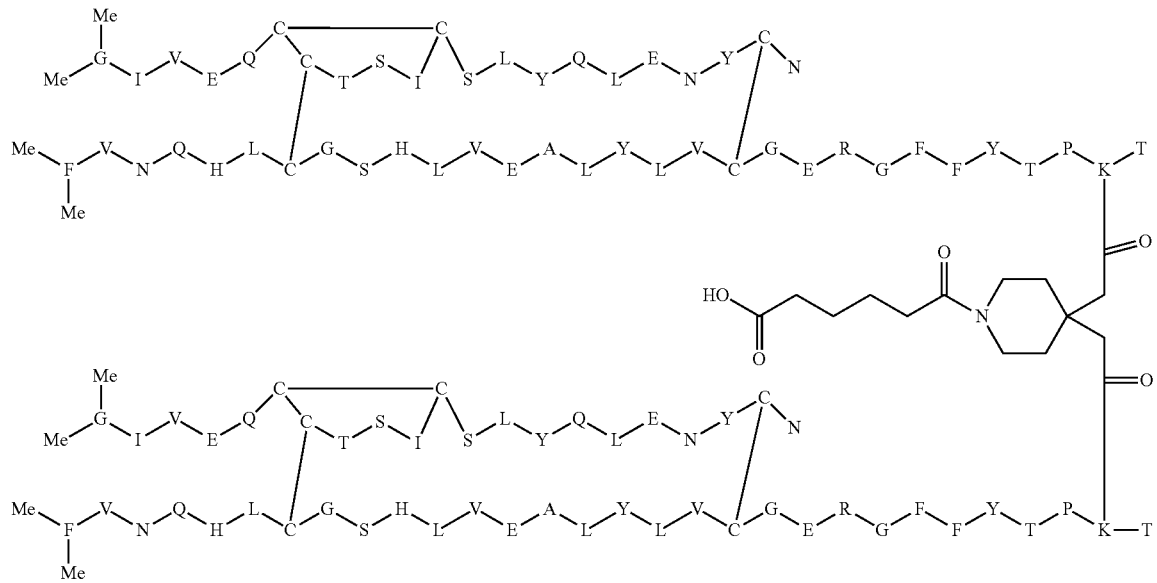

Dimer 43
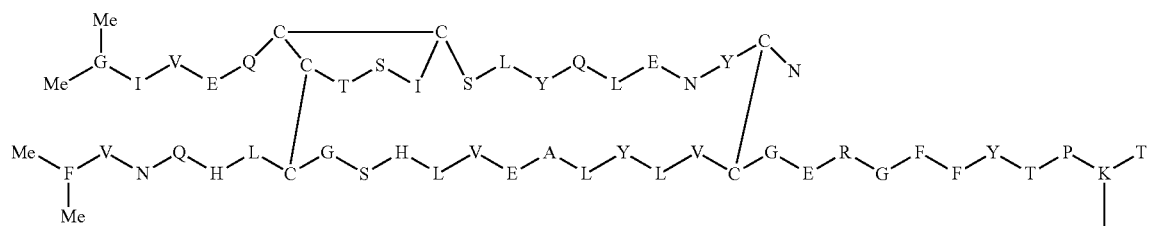
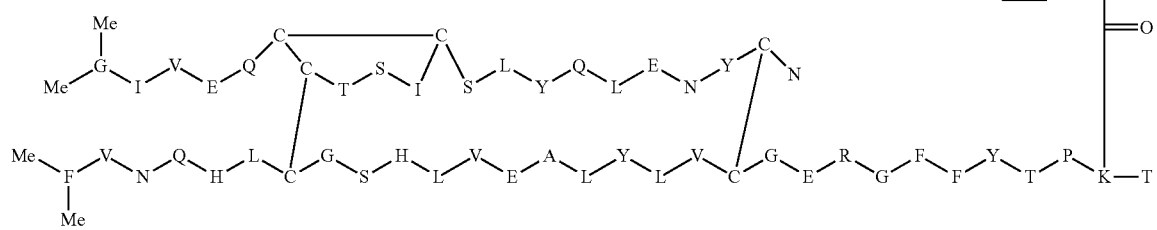
Dimer 44
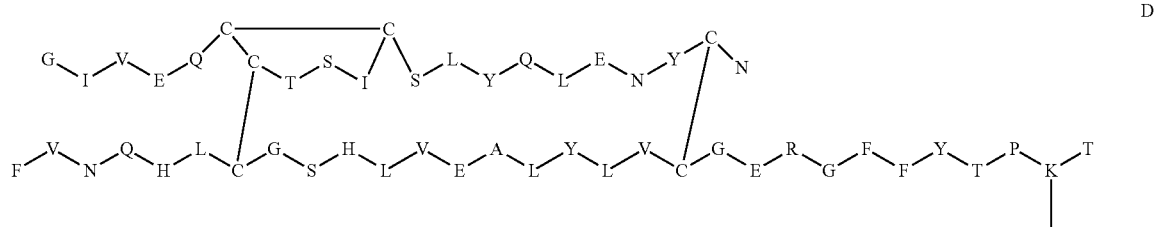
Dimer 45
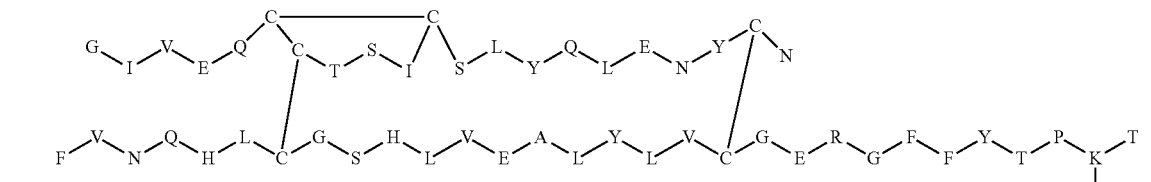
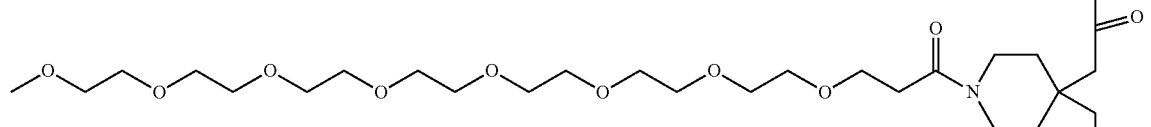
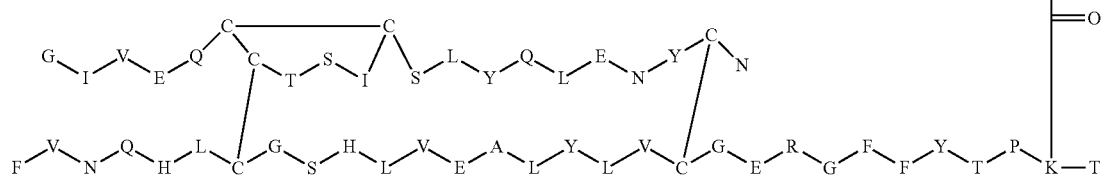

Dimer 46
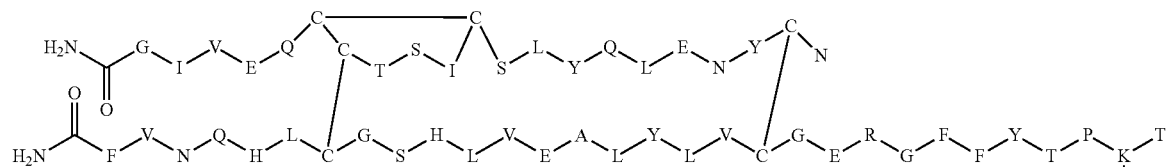
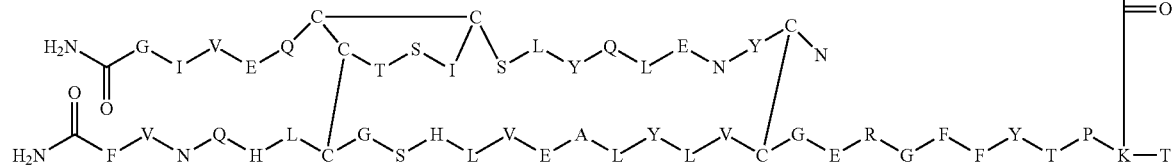
Dimer 47
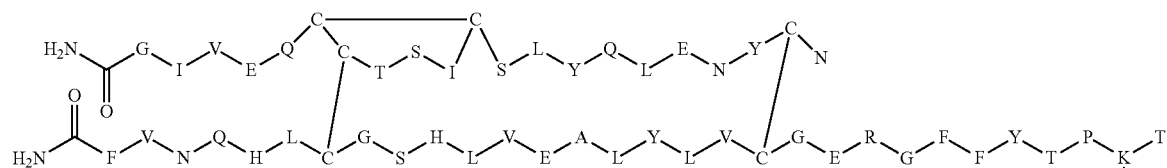
Dimer 48
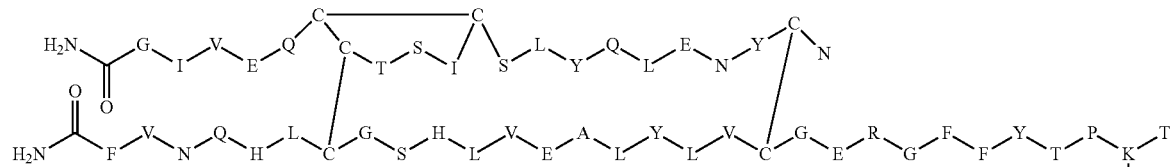
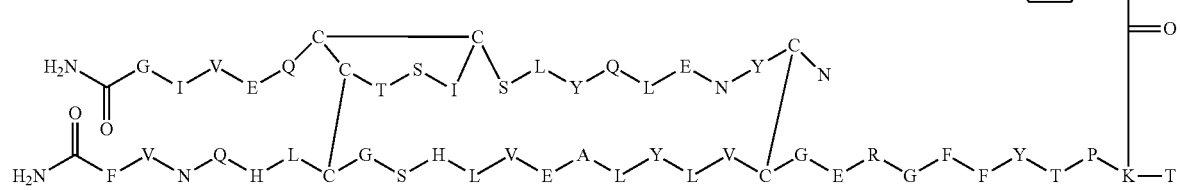

-continued
Dimer 49
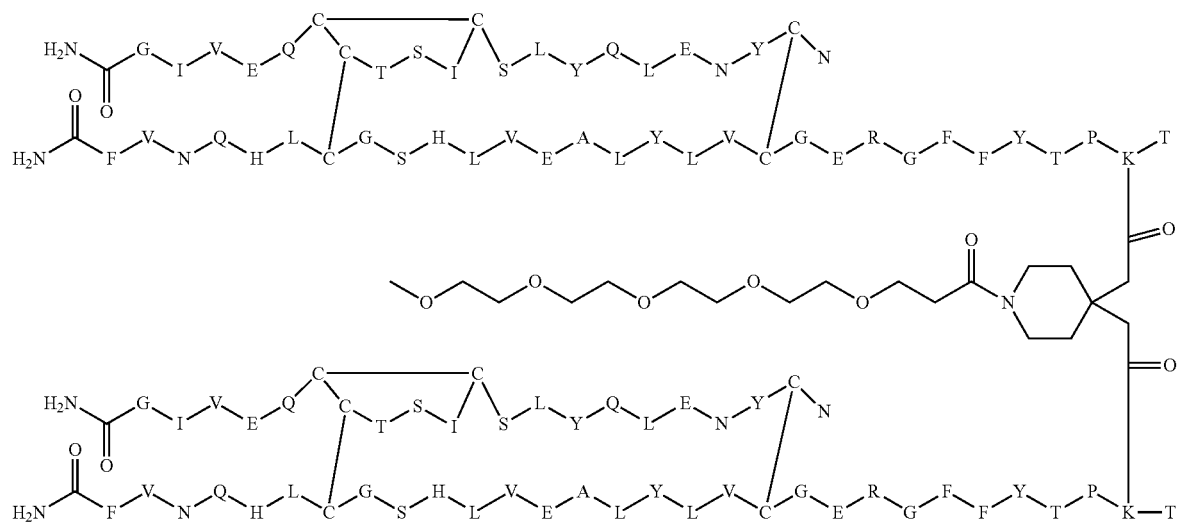
Dimer 50
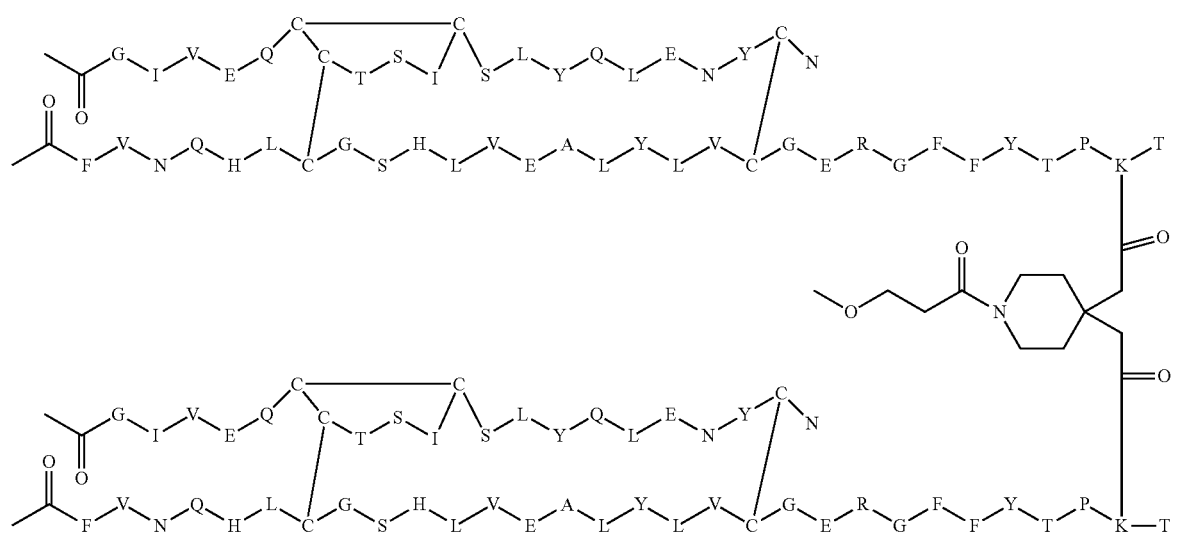
Dimer 51
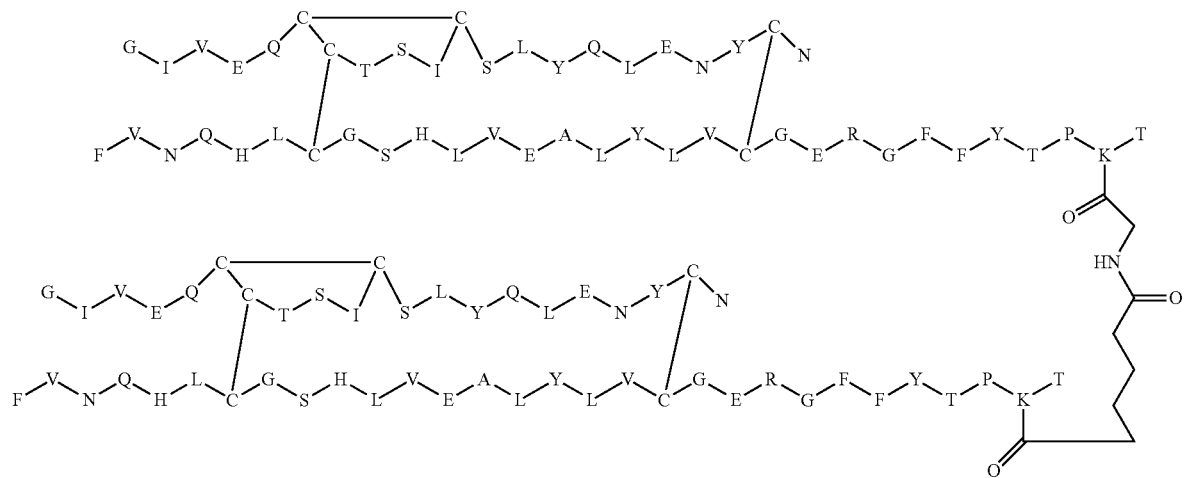

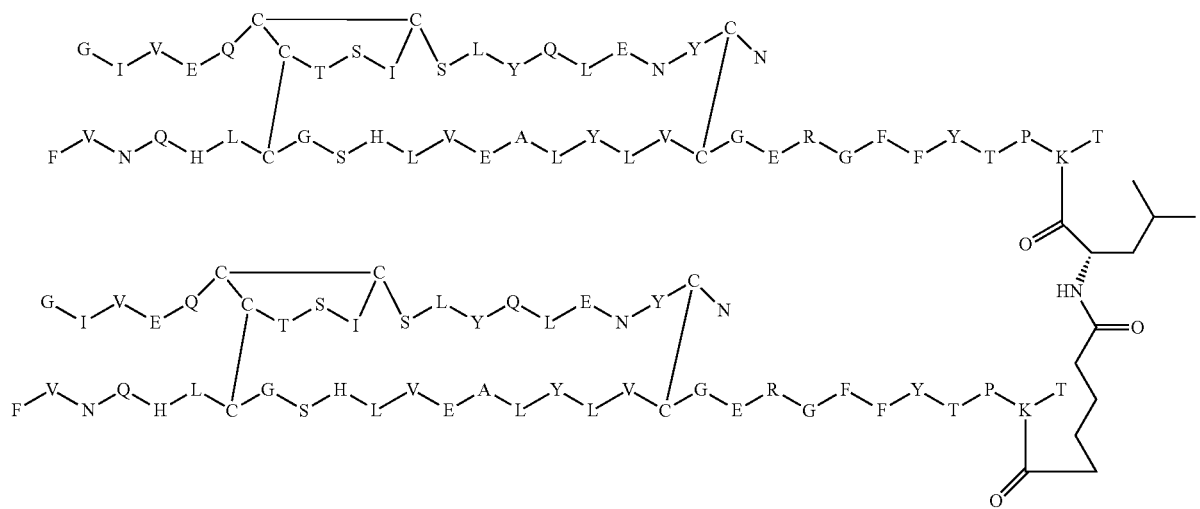
Dimer 52
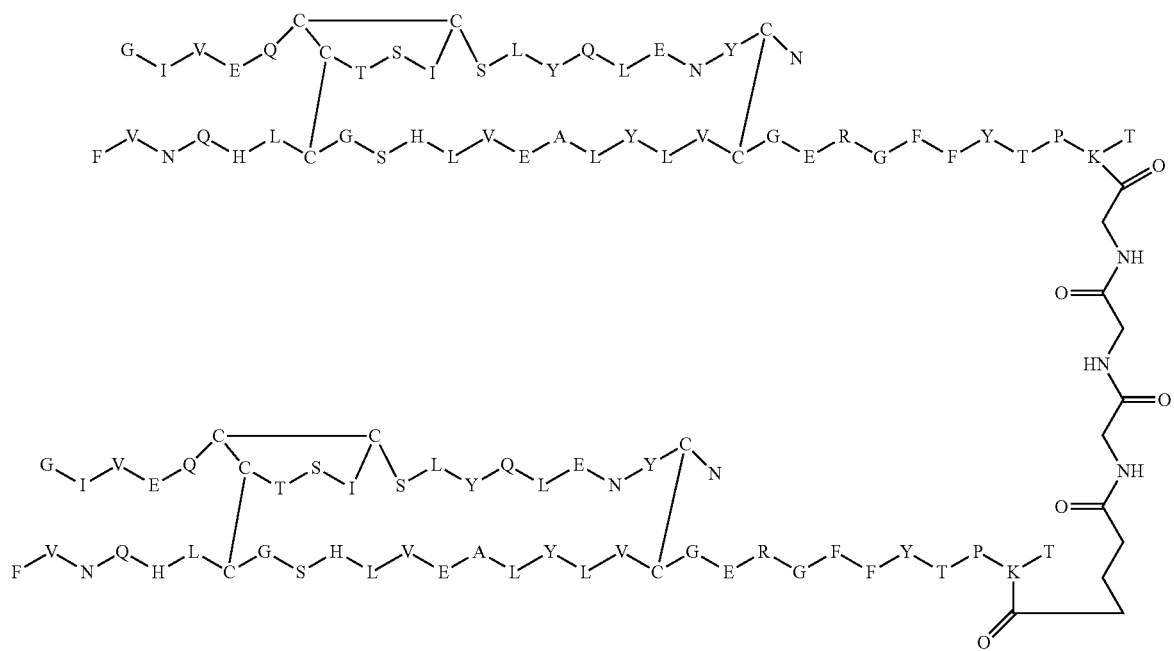
Dimer 53

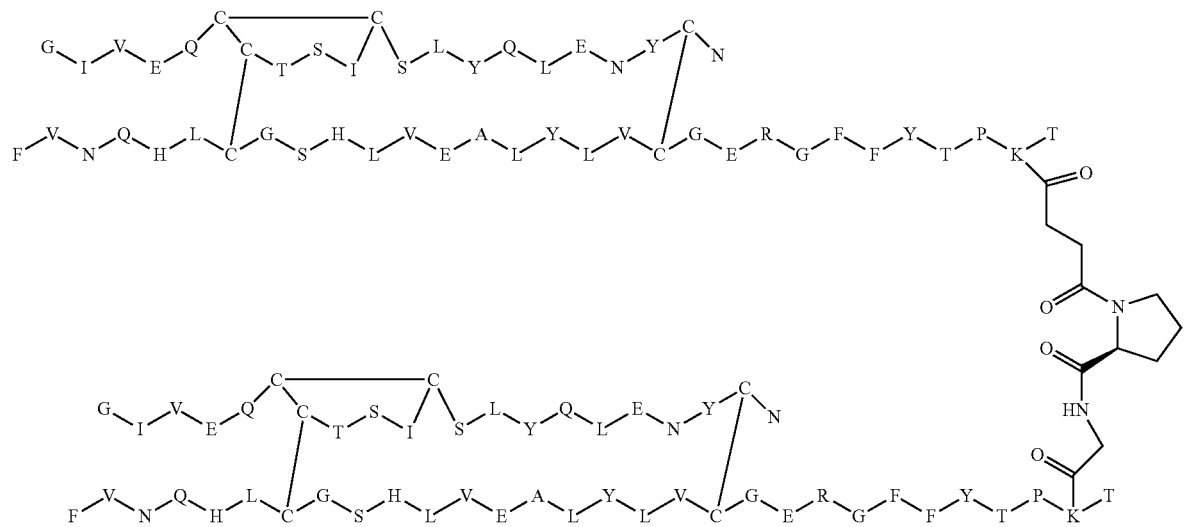
Dimer 54
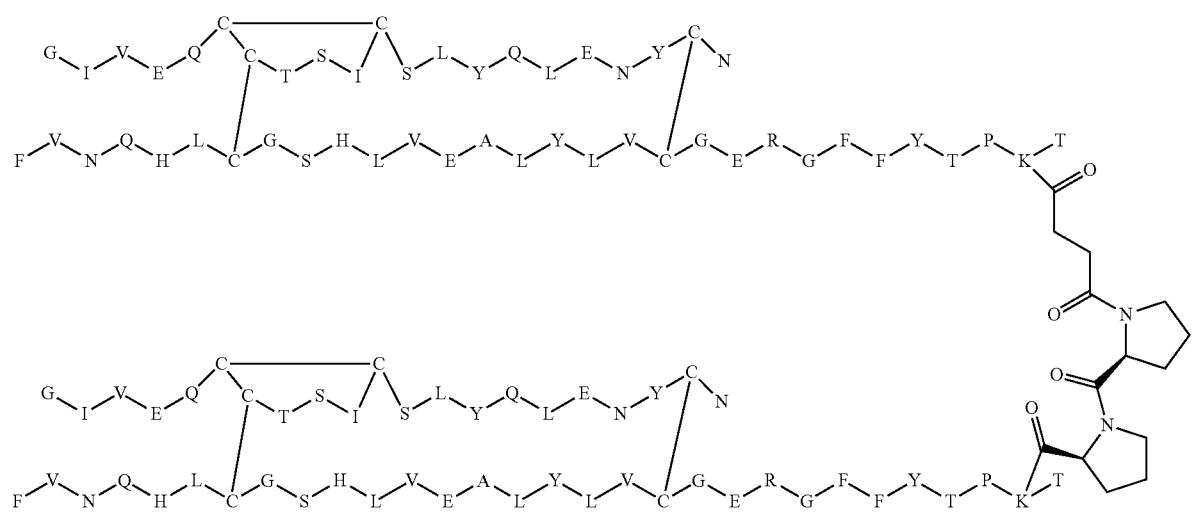
Dimer 55
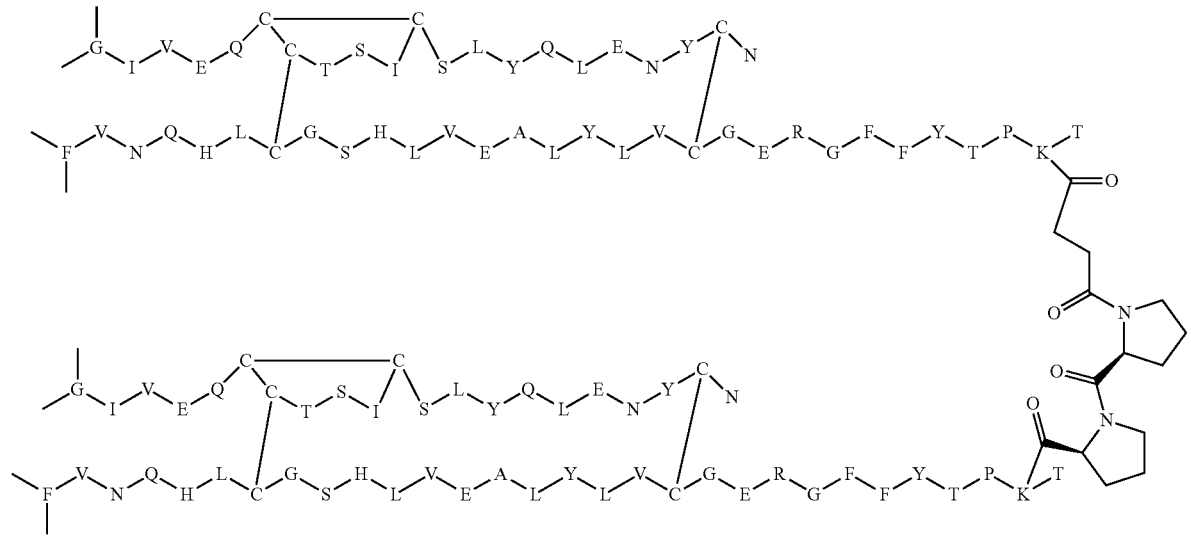
Dimer 56

Dimer 57
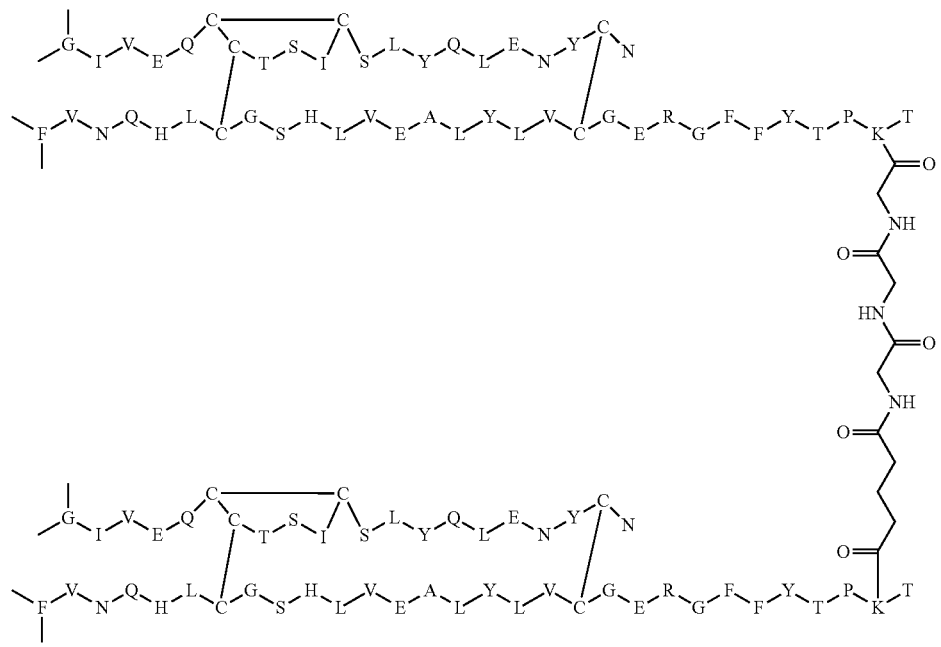
Dimer 58
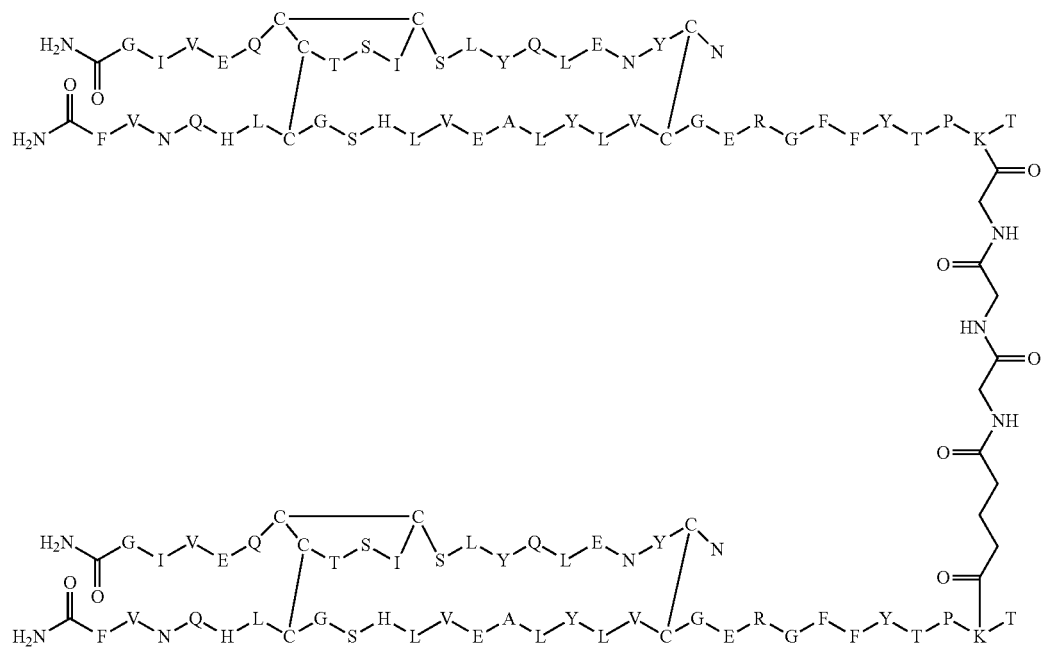

-continued
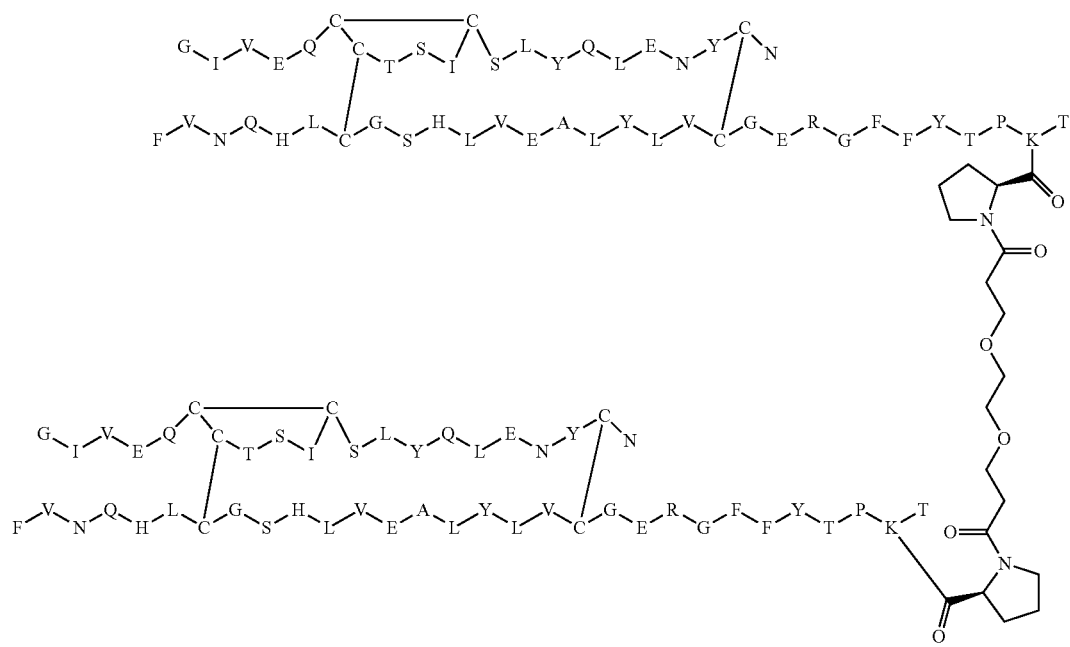
Dimer 59
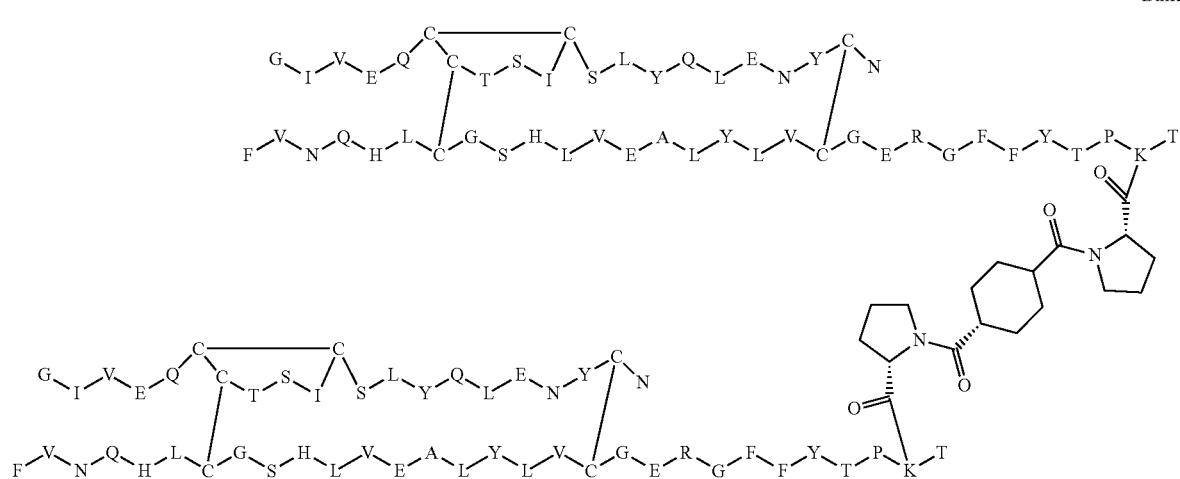
Dimer 60

Dimer 61
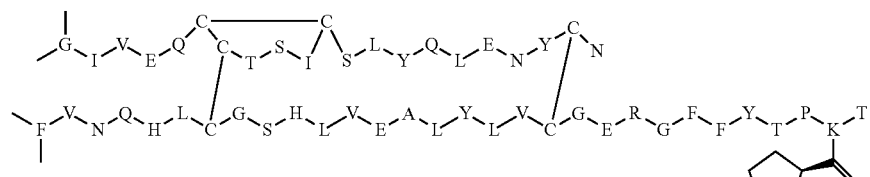
Dimer 62
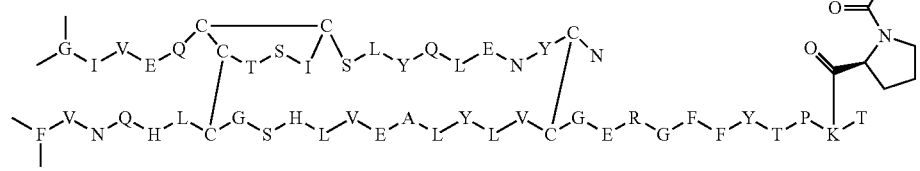
Dimer 63
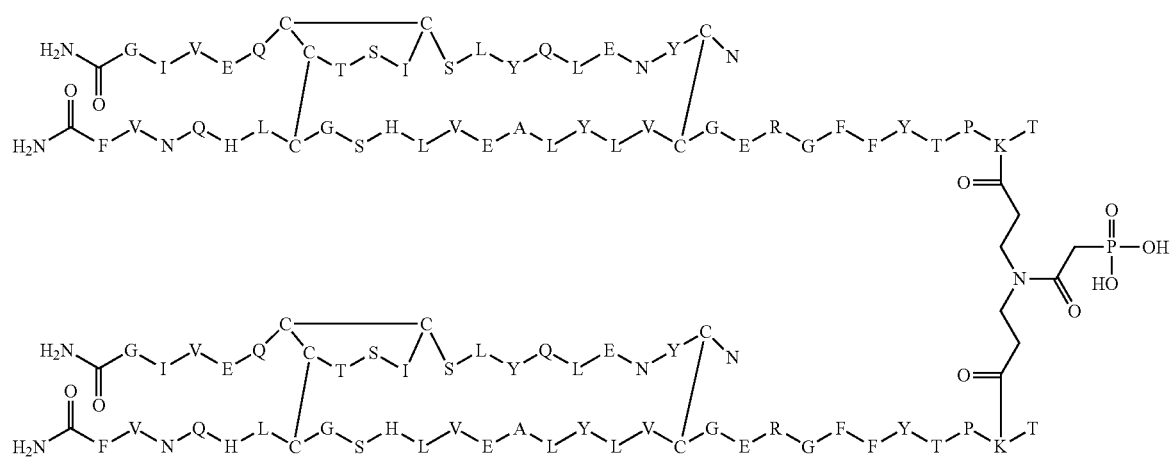
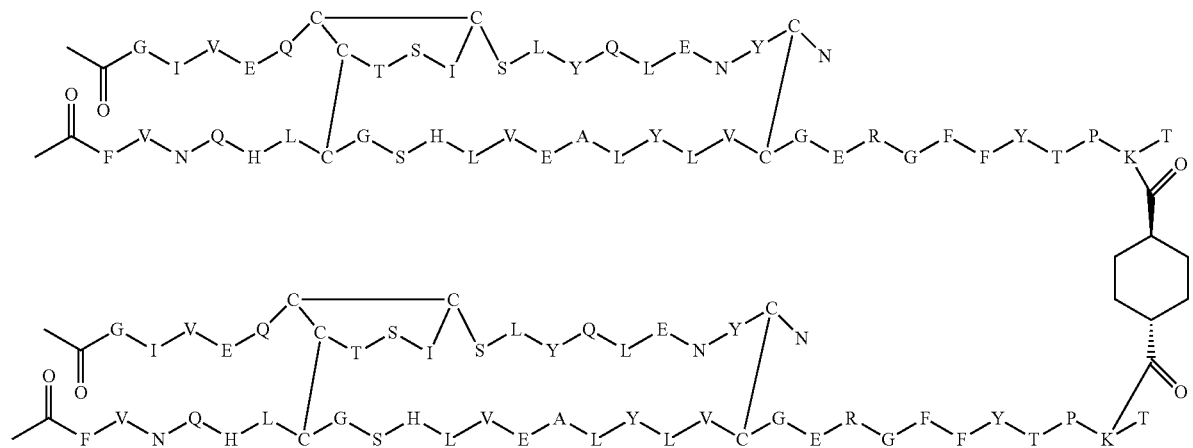

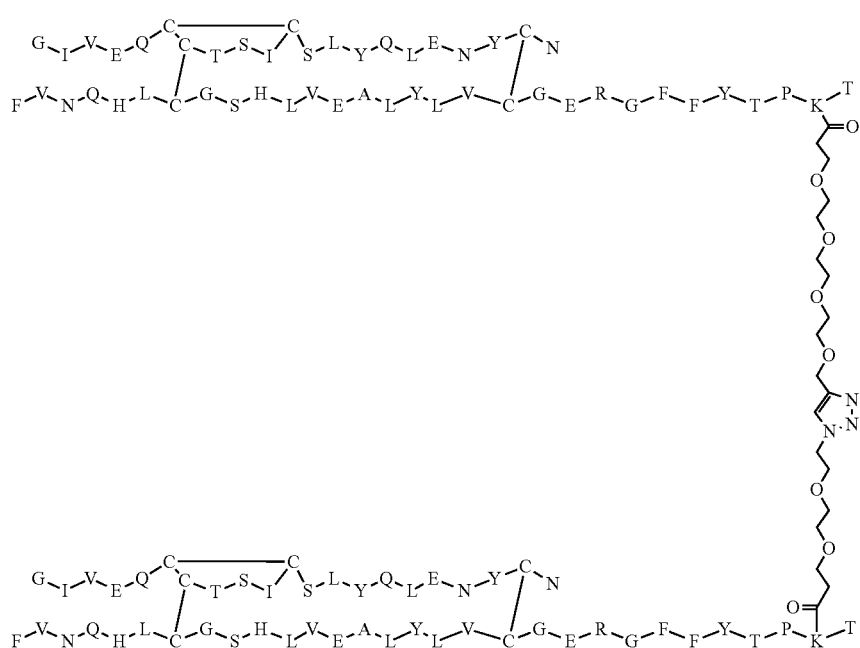
Dimer 64
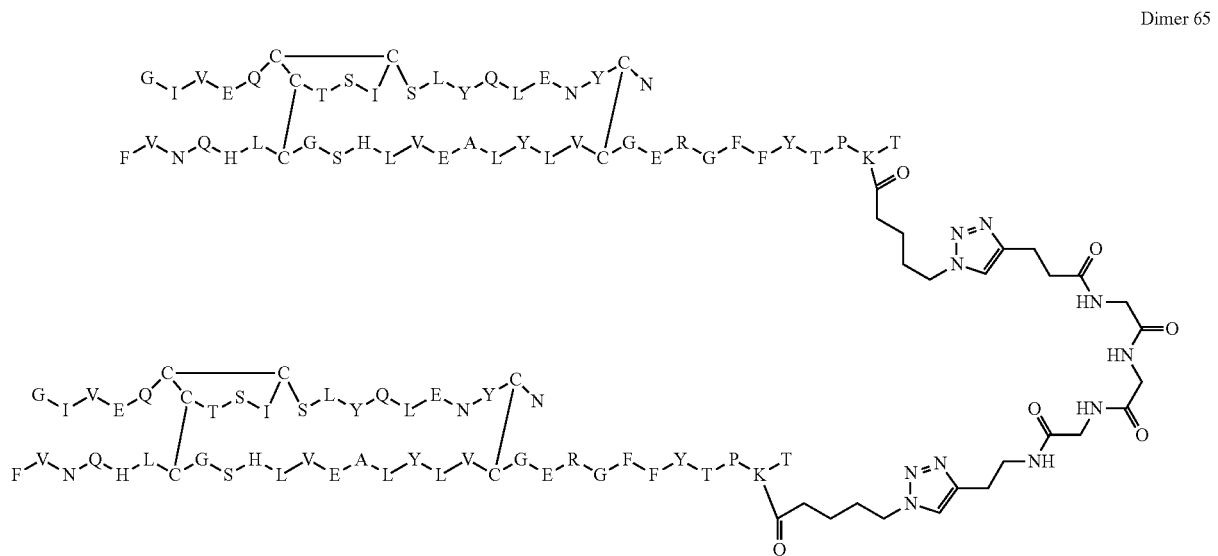
Dimer 65
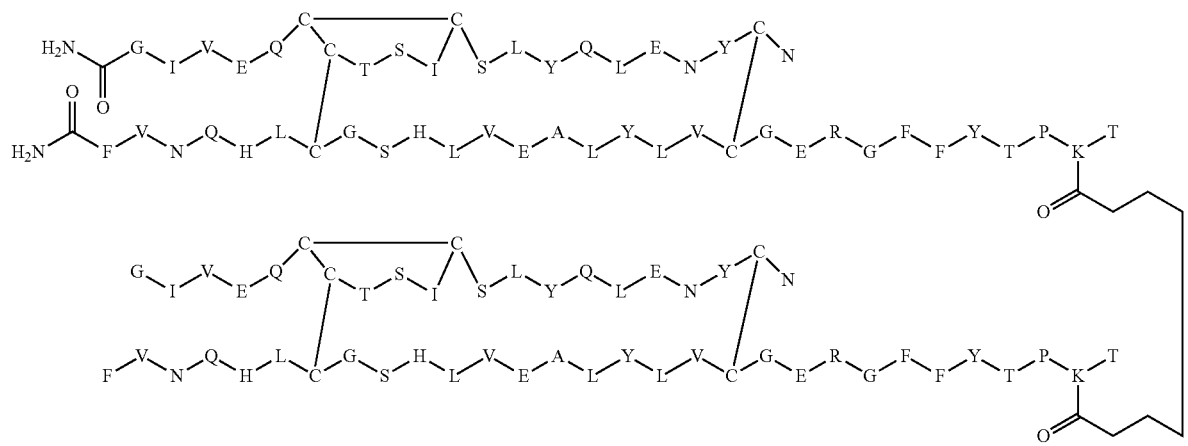
Dimer 66

-continued
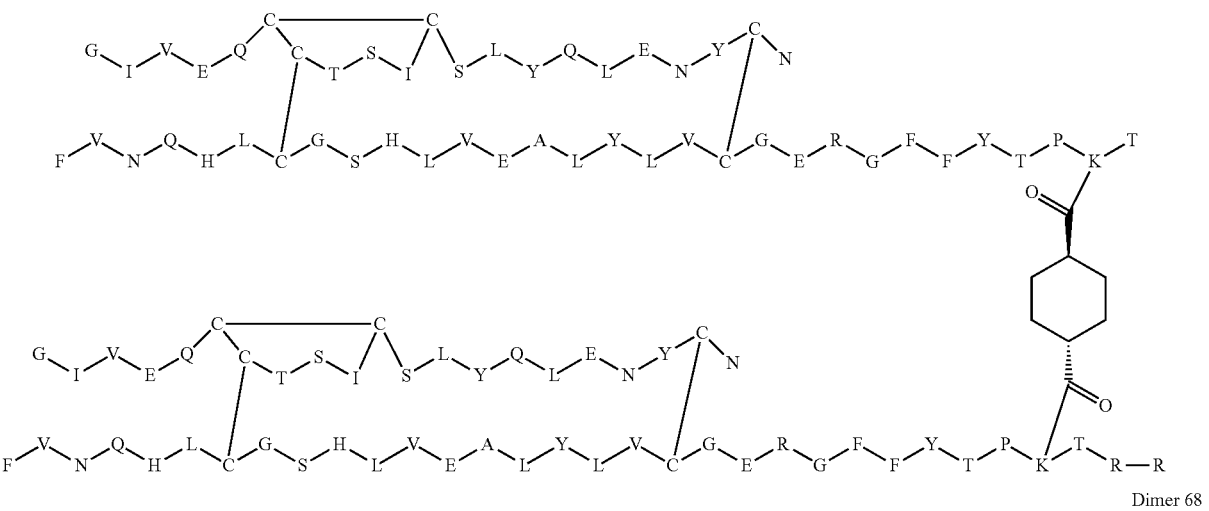
Dimer 67
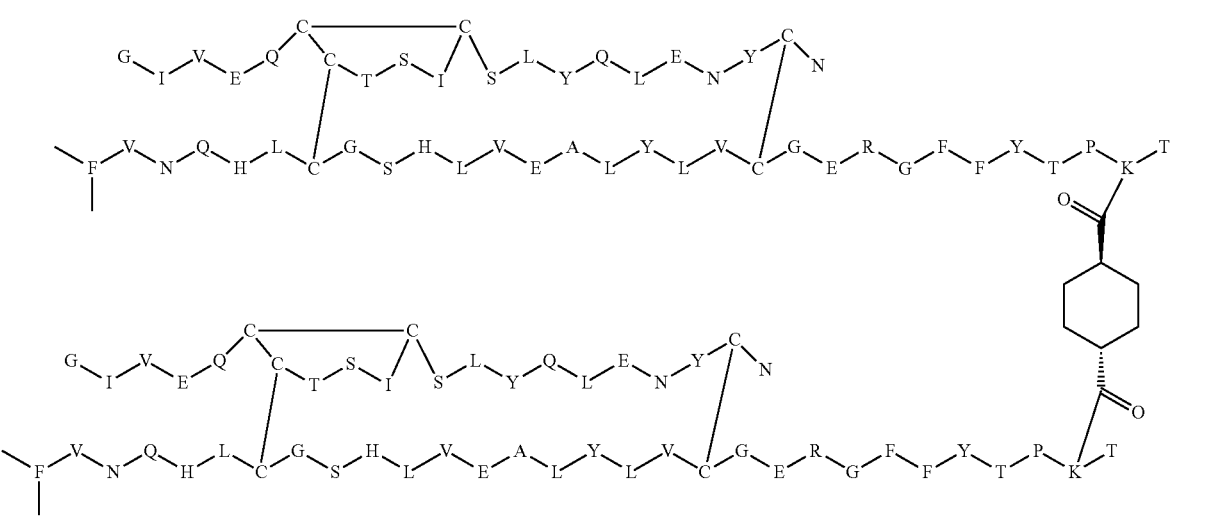
Dimer 68
Dimer 69
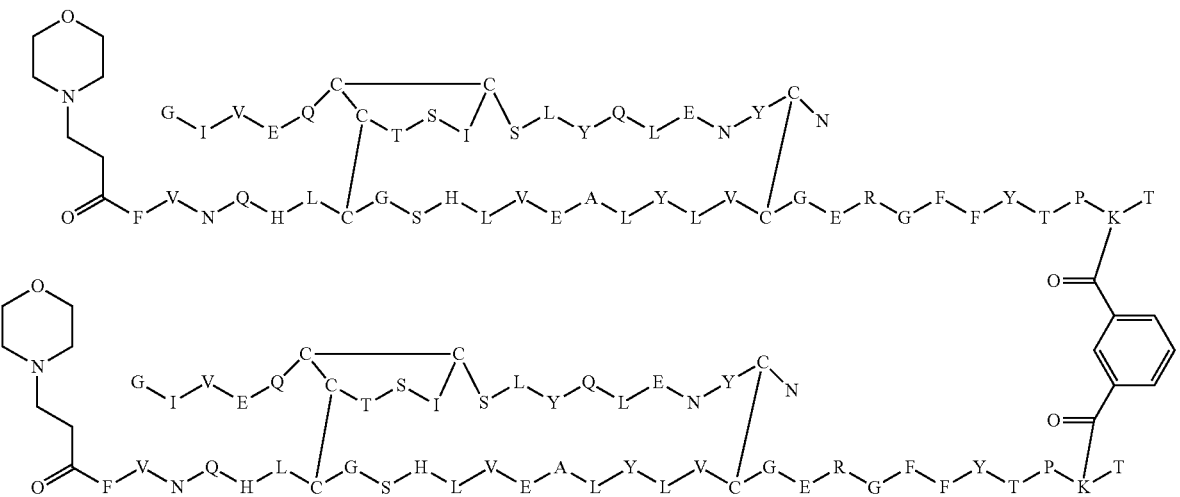

Dimer 70
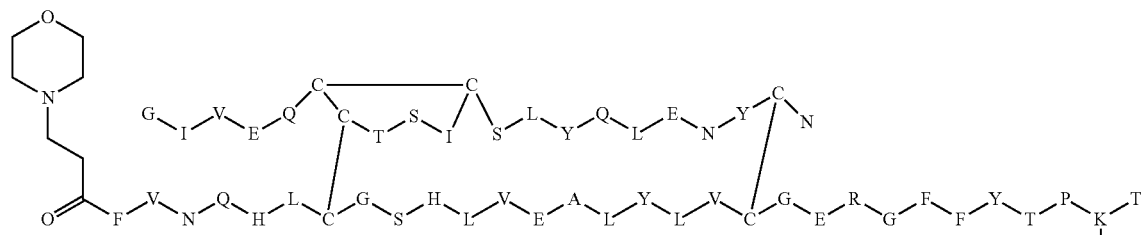
Dimer 71
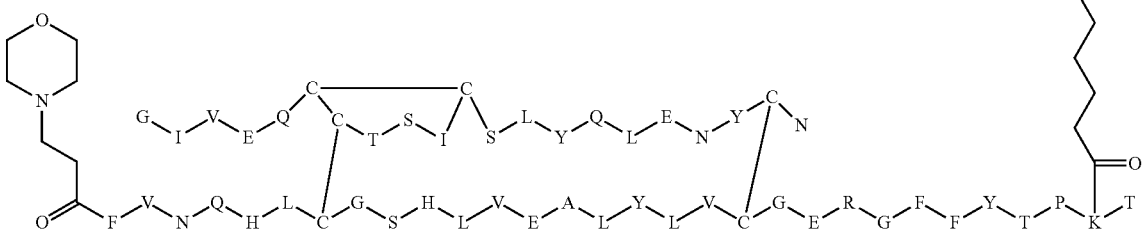
Dimer 72
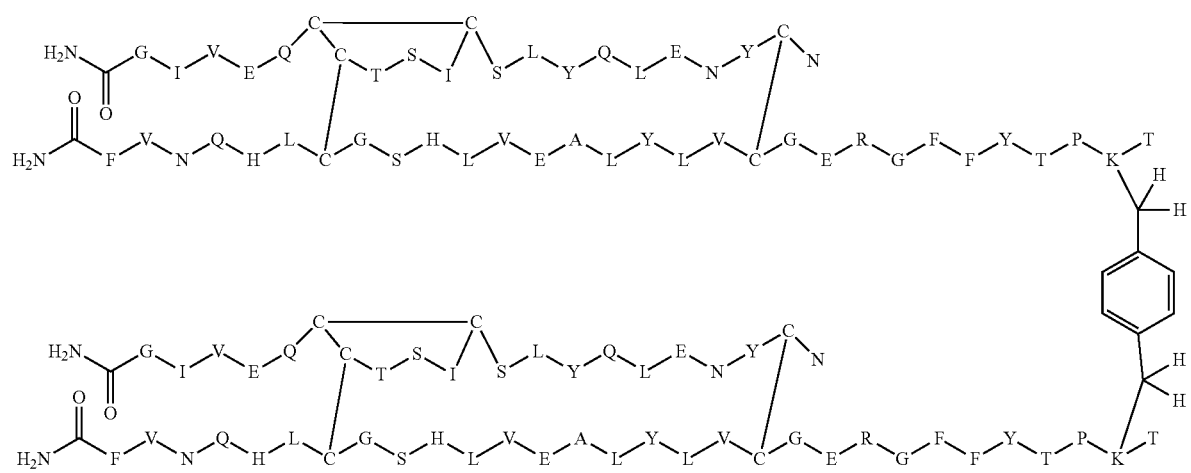
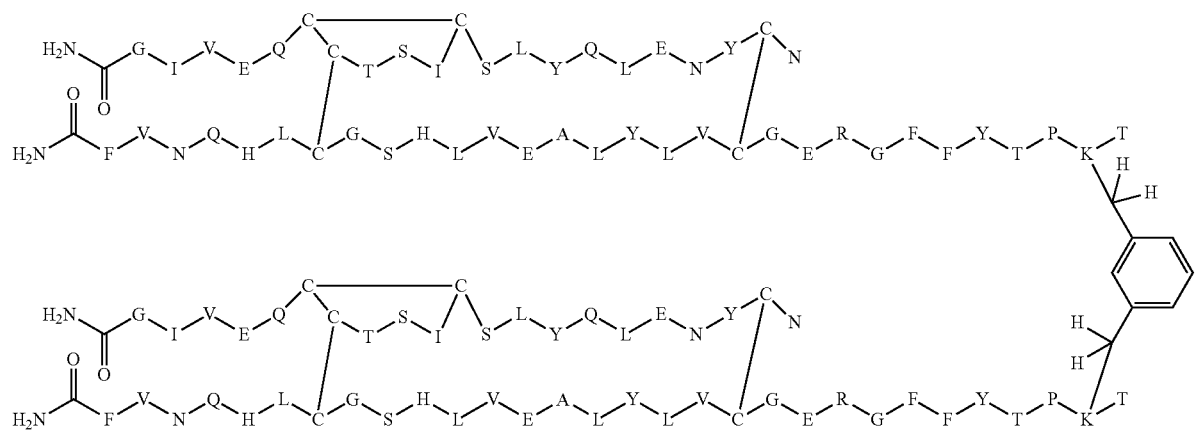

Dimer 73
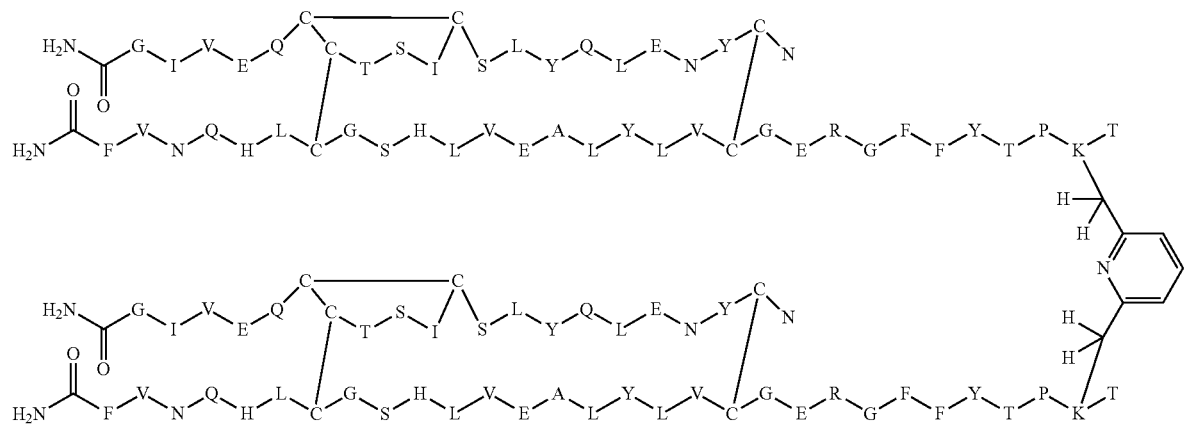
Dimer 74
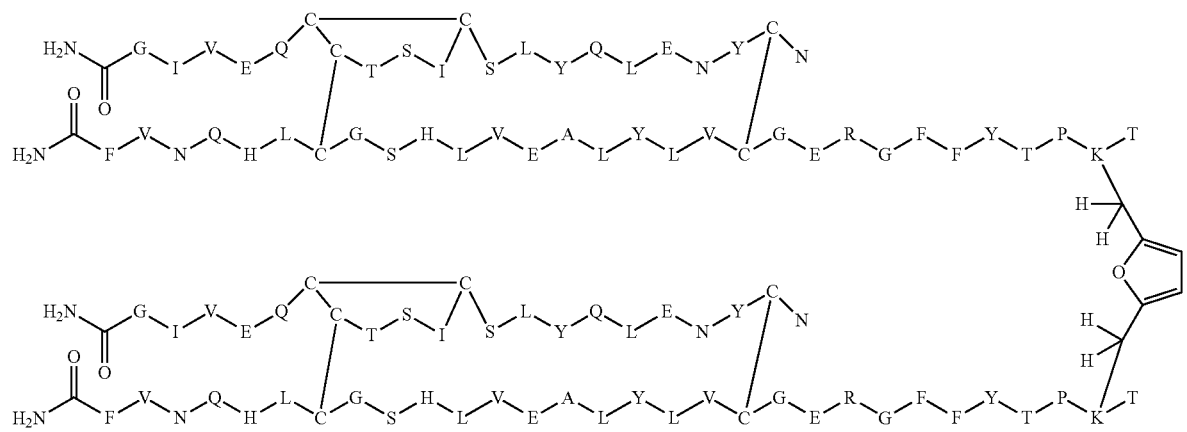
Dimer 75
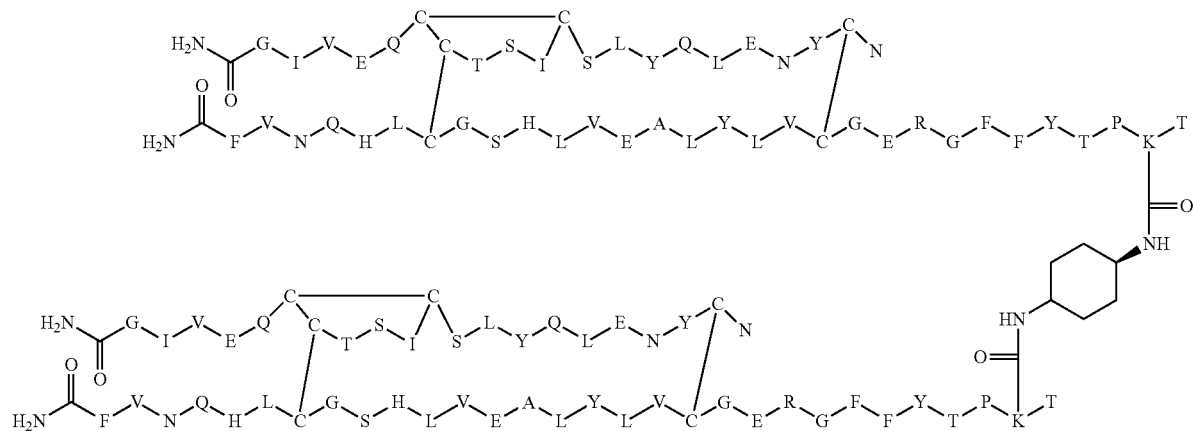

Dimer 76
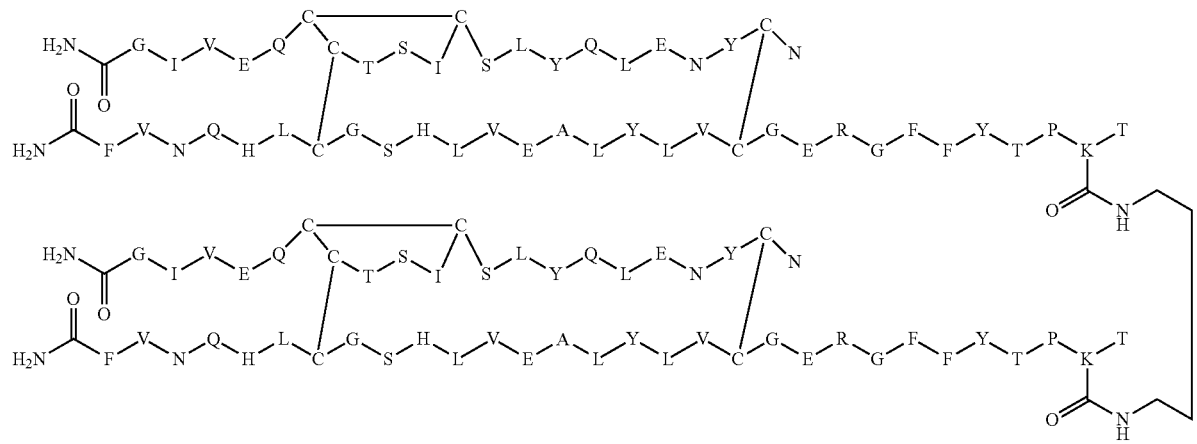
Dimer 77
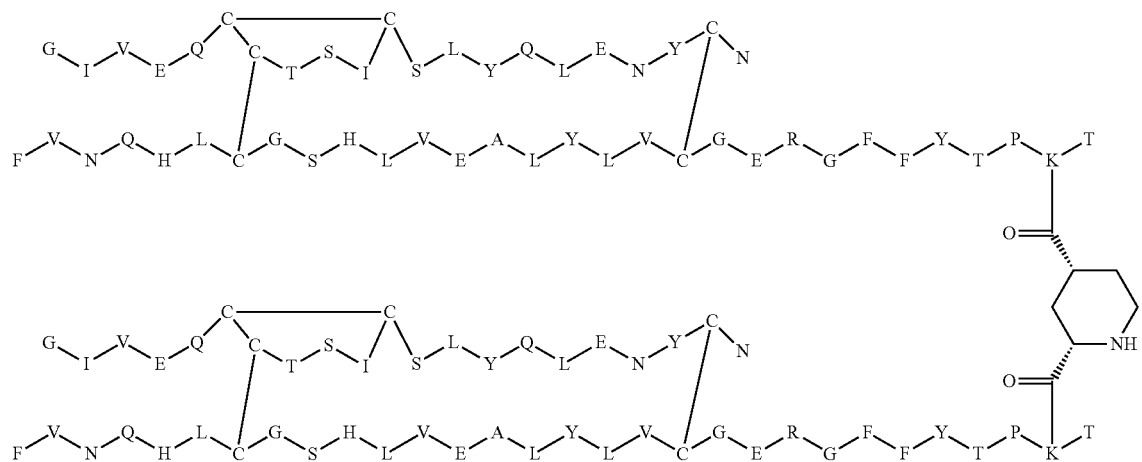
Dimer 78
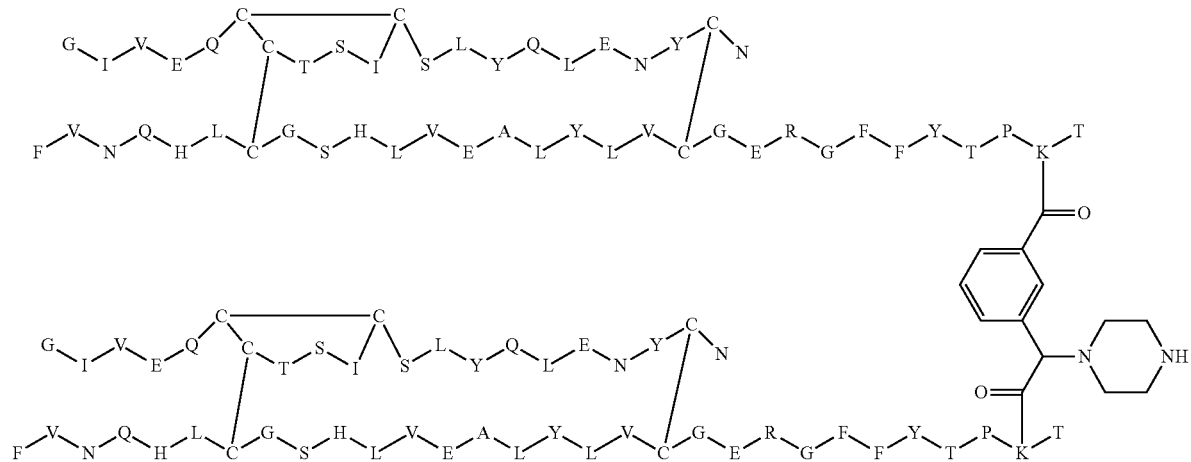

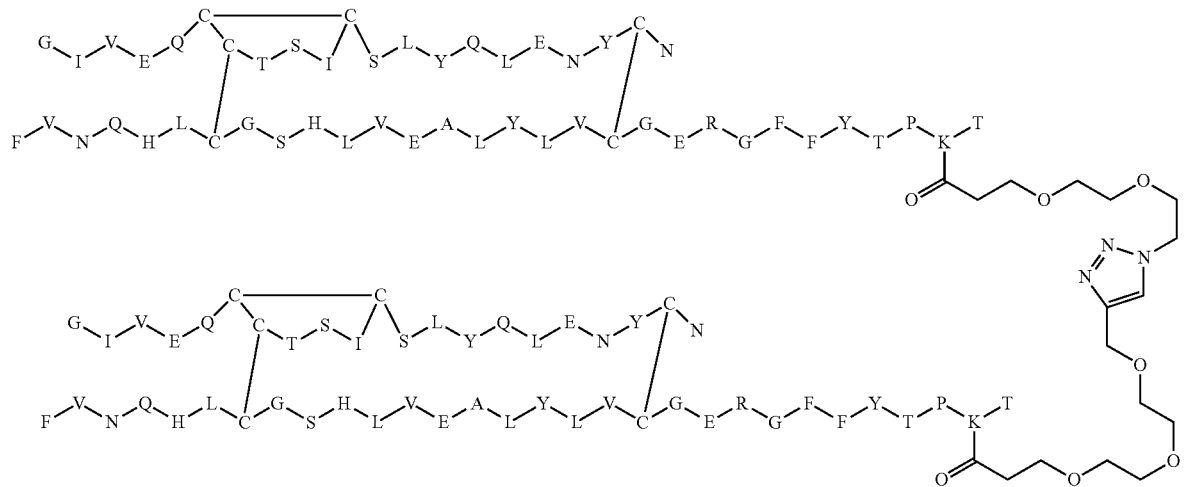
Dimer 79
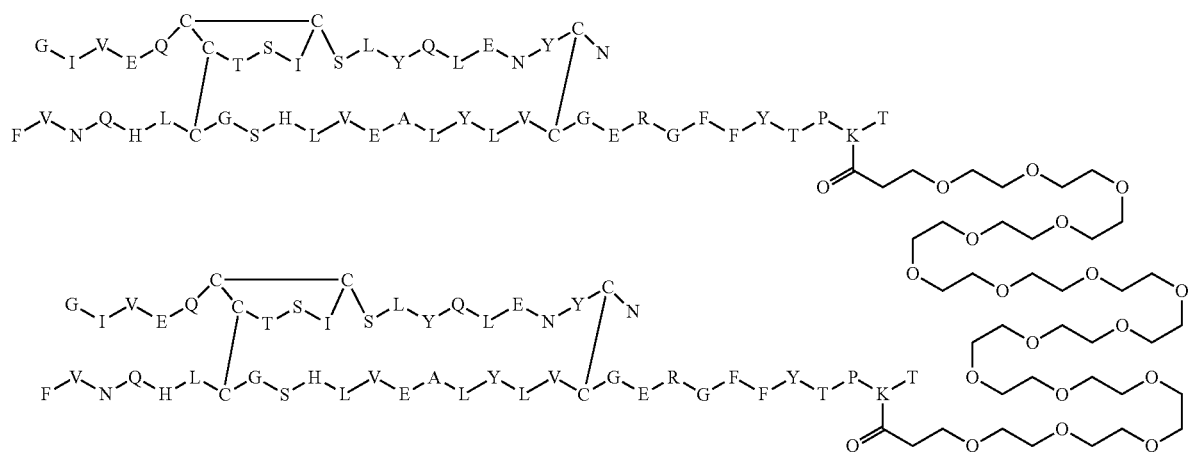
Dimer 80
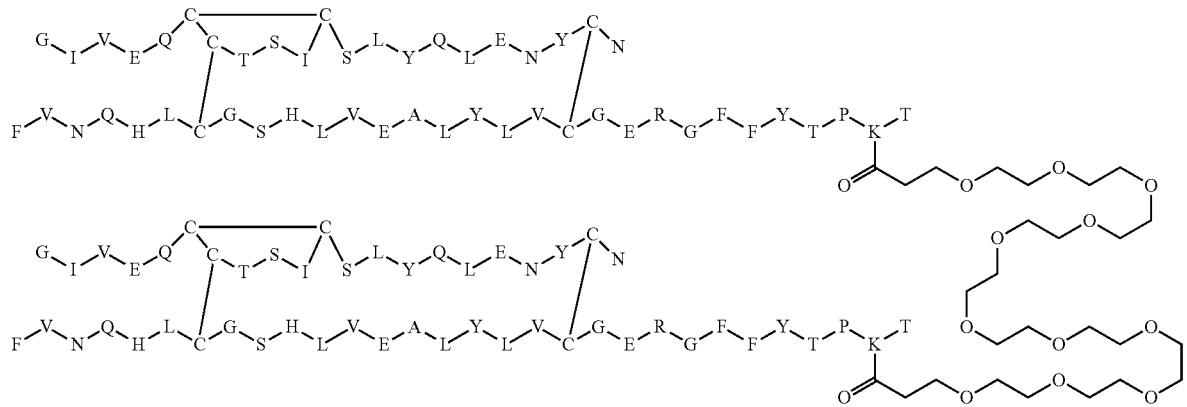
Dimer 81

-continued
Dimer 82
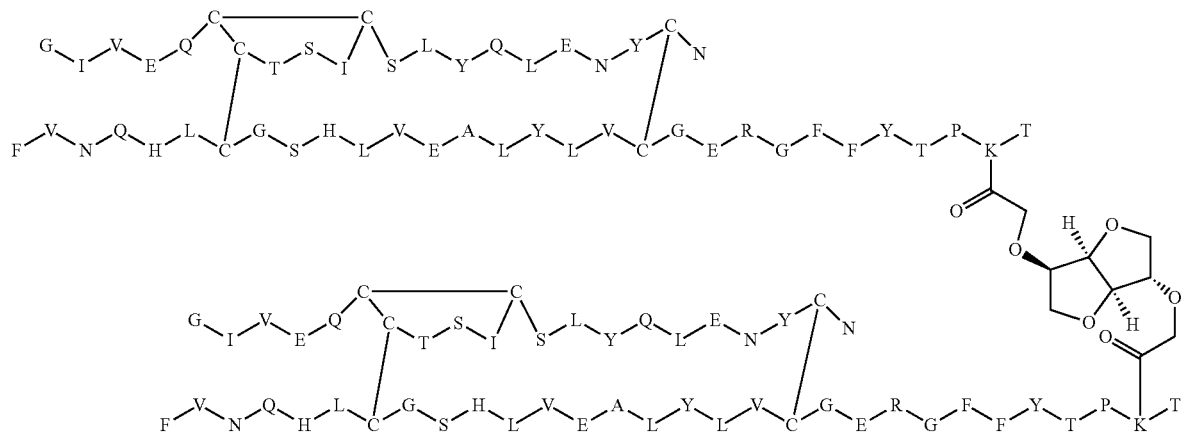
Dimer 83
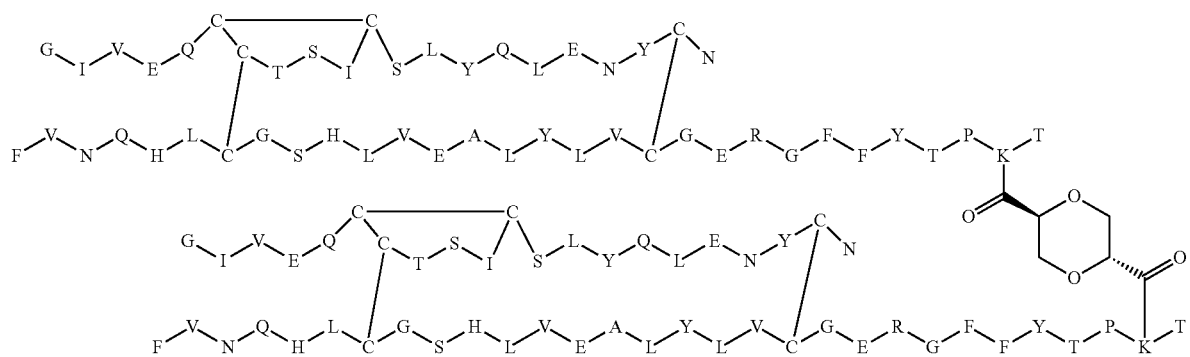
Dimer 84
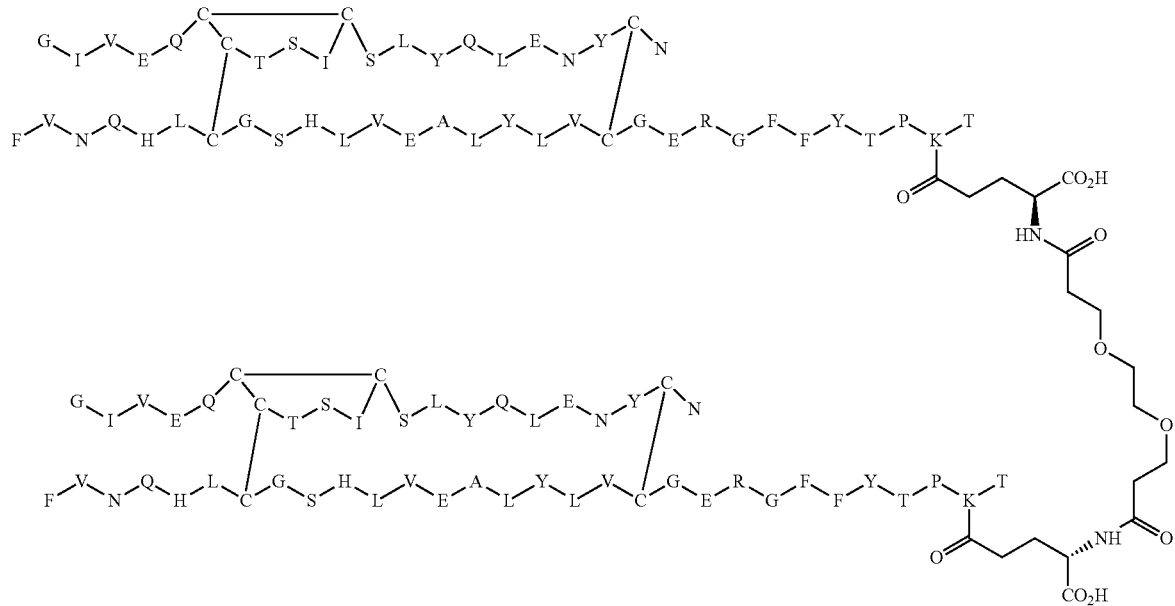

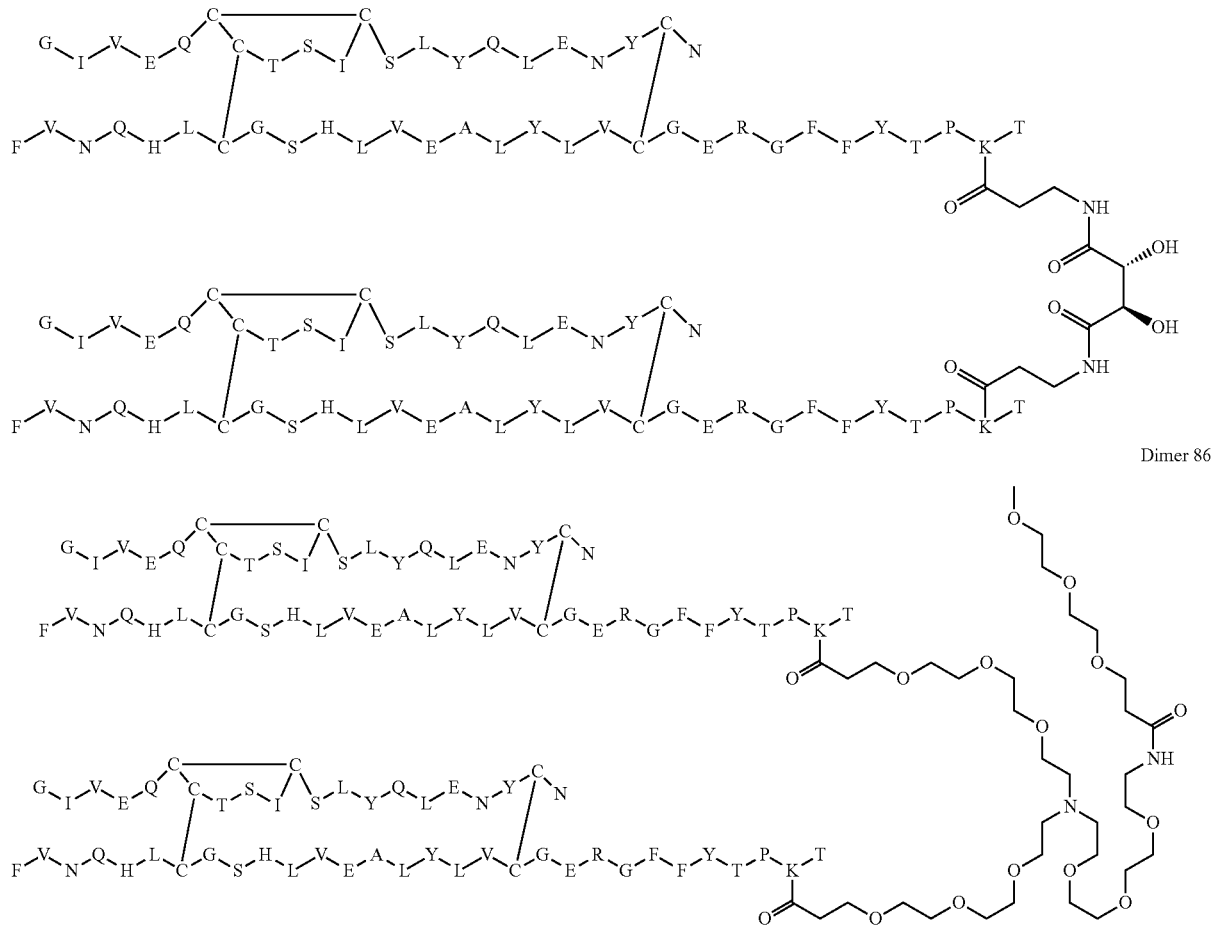

Dimer 85

Dimer 86 wherein the disulfide linkages between the $Cys_6$ and $Cys_{11}$ residues of the A-chain polypeptide and the disulfide linkages between the $Cys_7$ and $Cys_{20}$ of the A-chain to the $Cys_7$ and $Cys_{19}$ of the B-chain polypeptide, respectively, are represented by the solid line therebetween; wherein the linking moieties are covalently linked to the epsilon amino acid of the shown lysine residue wherein the A-chain polypeptide for Dimers 1-66 and 68-86 has the amino acid sequence shown in SEQ ID NO:1; the A-chain polypeptide for Dimer 67 has the amino acid sequence shown for SEQ ID NO:7; the B-chain polypeptide Dimers 1-66 and 68-86 has the amino acid sequence shown in SEQ ID NO:2 and the B-chain polypeptide for Dimer 67 has the amino acid sequence shown in SEQ ID NO:8.

Pharmaceutical Compositions

In accordance with one embodiment a pharmaceutical composition is provided comprising any of the novel insulin dimers disclosed herein, preferably at a purity level of at least 90%, 91%, 92%, 93%, 94%, 95%, 96%, 97%, 98% or 99%, and a pharmaceutically acceptable diluent, carrier or excipient. Such compositions may contain an insulin dimer as disclosed herein at a concentration of at least 0.5 mg/ml, 1 mg/ml, 2 mg/ml, 3 mg/ml, 4 mg/ml, 5 mg/ml, 6 mg/ml, 7 mg/ml, 8 mg/ml, 9 mg/ml, 10 mg/ml, 11 mg/ml, 12 mg/ml, 13 mg/ml, 14 mg/ml, 15 mg/ml, 16 mg/ml, 17 mg/ml, 18 mg/ml, 19 mg/ml, 20 mg/ml, 21 mg/ml, 22 mg/ml, 23 mg/ml, 24 mg/ml, 25 mg/ml or higher. In one embodiment the pharmaceutical compositions comprise aqueous solutions that are sterilized and optionally stored contained within various package containers. In other embodiments the pharmaceutical compositions comprise a lyophilized powder. The pharmaceutical compositions can be further packaged as part of a kit that includes a disposable device for administering the composition to a patient. The containers or kits may be labeled for storage at ambient room temperature or at refrigerated temperature.

The disclosed insulin dimers are believed to be suitable for any use that has previously been described for insulin peptides. Accordingly, the insulin dimers disclosed herein can be used to treat hyperglycemia, or treat other metabolic diseases that result from high blood glucose levels. Accordingly, the present invention encompasses pharmaceutical compositions comprising a insulin dimers as disclosed herein and a pharmaceutically acceptable carrier for use in treating a patient suffering from high blood glucose levels. In accordance with one embodiment the patient to be treated using a insulin dimer disclosed herein is a domesticated animal, and in another embodiment the patient to be treated is a human.

One method of treating hyperglycemia in accordance with the present disclosure comprises the steps of administering the presently disclosed insulin dimers to a patient using any standard route of administration, including parenterally, such as intravenously, intraperitoneally, subcutaneously or intramuscularly, intrathecally, transdermally, rectally, orally, nasally or by inhalation. In one embodiment the composition is administered subcutaneously or intramuscularly. In one embodiment, the composition is administered parenterally and the insulin polypeptide, or prodrug derivative thereof, is prepackaged in a syringe.

The insulin dimers disclosed herein may be administered alone or in combination with other anti-diabetic agents. Anti-diabetic agents known in the art or under investigation include native insulin, native glucagon and functional analogs thereof, sulfonylureas, such as tolbutamide (Orinase), acetohexamide (Dymelor), tolazamide (Tolinase), chlorpropamide (Diabinese), glipizide (Glucotrol), glyburide (Diabeta, Micronase, Glynase), glimepiride (Amaryl), or gliclazide (Diamicron); meglitinides, such as repaglinide (Prandin) or nateglinide (Starlix); biguanides such as metformin (Glucophage) or phenformin; thiazolidinediones such as rosiglitazone (Avandia), pioglitazone (Actos), or troglitazone (Rezulin), or other PPARy inhibitors; alpha glucosidase inhibitors that inhibit carbohydrate digestion, such as miglitol (Glyset), acarbose (Precose/Glucobay); exenatide (Byetta) or pramlintide; Dipeptidyl peptidase-4 (DPP-4) inhibitors such as vildagliptin or sitagliptin; SGLT (sodium-dependent glucose transporter 1) inhibitors; or FBPase (fructose 1,6-bisphosphatase) inhibitors.

Pharmaceutical compositions comprising the insulin dimers disclosed herein can be formulated and administered to patients using standard pharmaceutically acceptable carriers and routes of administration known to those skilled in the art. Accordingly, the present disclosure also encompasses pharmaceutical compositions comprising one or more of the insulin dimers disclosed herein, or a pharmaceutically acceptable salt thereof, in combination with a pharmaceutically acceptable carrier. For example, the pharmaceutical compositions comprising the insulin dimers disclosed herein may optionally contain zinc ions, preservatives (e.g., phenol, cresol, parabens), isotonicizing agents (e.g., mannitol, sorbitol, lactose, dextrose, trehalose, sodium chloride, glycerol), buffer substances, salts, acids and alkalis and also further excipients. These substances can in each case be present individually or alternatively as mixtures. Glycerol, dextrose, lactose, sorbitol and mannitol are customarily present in the pharmaceutical preparation in a concentration of 100-250 mM, NaCl in a concentration of up to 150 mM. Buffer substances, such as, for example, phosphate, acetate, citrate, arginine, glycylglycine or TRIS (i.e. 2-amino-2-hydroxymethyl-1,3-propanediol) buffer and corresponding salts, are present in a concentration of 5-250 mM, commonly from about 10-100 mM. Further excipients can be, inter alia, salts or arginine.

In one embodiment the pharmaceutical composition comprises a 1 mg/mL concentration of the insulin dimer at a pH of about 4.0 to about 7.0 in a phosphate buffer system. The pharmaceutical compositions may comprise the insulin dimer as the sole pharmaceutically active component, or the insulin dimer can be combined with one or more additional active agents.

All therapeutic methods, pharmaceutical compositions, kits and other similar embodiments described herein contemplate that insulin dimers include all pharmaceutically acceptable salts thereof.

In one embodiment the kit is provided with a device for administering the insulin dimers composition to a patient. The kit may further include a variety of containers, e.g., vials, tubes, bottles, and the like. Preferably, the kits will also include instructions for use. In accordance with one embodiment the device of the kit is an aerosol dispensing device, wherein the composition is prepackaged within the aerosol device. In another embodiment the kit comprises a syringe and a needle, and in one embodiment the insulin dimer composition is prepackaged within the syringe.

The compounds of this invention may be prepared by standard synthetic methods, recombinant DNA techniques, or any other methods of preparing peptides and fusion proteins. Although certain non-natural amino acids cannot be expressed by standard recombinant DNA techniques, techniques for their preparation are known in the art. Compounds of this invention that encompass non-peptide portions may be synthesized by standard organic chemistry reactions, in addition to standard peptide chemistry reactions when applicable.

The following examples are intended to promote a further understanding of the present invention.

EXAMPLES

General Procedures

All chemicals were purchased from commercial sources, unless otherwise noted. Reactions were usually carried out at ambient temperature or at room temperature unless otherwise noted. Reactions sensitive to moisture or air were performed under nitrogen or argon using anhydrous solvents and reagents. The progress of reactions was monitored by analytical thin layer chromatography (TLC), and ultra performance liquid chromatography-mass spectrometry (UPLC-MS). TLC was performed on E. Merck TLC plates precoated with silica gel 60E-254, layer thickness 0.25 mm. The plates were visualized using 254 nm UV and/or by exposure to cerium ammonium molybdate (CAM) orp-anisaldehyde staining solutions followed by charring. Ultra performance liquid chromatography (UPLC) was performed on a Waters Acquity™ UPLC® system.

UPLC-MS Method A: Waters Acquity™ UPLC® BEH C18 1.7 μm 1.0×50 mm column with gradient 10:90-95:5 v/v $CH_3CN/H_2O$+v 0.05% TFA over 2.0 min; flow rate 0.3 mL/min, UV wavelength 215 nm; UPLC-MS;

Method B: Waters Acquity™ UPLC BEH C18 1.7 μm 2.1×100 mm column with gradient 2:98-30:70 v/v $CH_3CN/H_2O$+v 0.05% TFA over 4.0 min and 30:70-95:5 v/v $CH_3CN/H_2O$+v 0.05% TFA over 40 sec; flow rate 0.3 mL/min, UV wavelength 200-300 nm; UPLC-MS;

Method C: Waters Acquity™ UPLC BEH C18 1.7 μm 2.1×100 mm column with gradient 20:80-90:10 v/v $CH_3CN/H_2O$+v 0.05% TFA over 4.0 min and 90:10-95:5 v/v $CH_3CN/H_2O$+v 0.05% TFA over 0.5 min; flow rate 0.3 mL/min, UV wavelength 200-300 nm; UPLC-MS;

Method D: Waters Acquity™ UPLC BEH C8 1.7 μm 2.1×100 mm column with gradient 10:90-55:45 v/v $CH_3CN/H_2O$+v 0.05% TFA over 4.0 min and 55:45-95:5 v/v $CH_3CN/H_2O$+v 0.05% TFA over 40 sec; flow rate 0.3 mL/min, UV wavelength 200-300 nm; UPLC-MS;

Method E: Waters Acquity™ UPLC BEH C8 1.7 μm 2.1×100 mm column with gradient 20:80-72.5:27.5 v/v $CH_3CN/H_2O$+v 0.05% TFA over 4.3 min and 72.5:27.5-95:5 v/v $CH_3CN/H_2O$+v 0.05% TFA over 0.5 min; flow rate 0.3 mL/min, UV wavelength 200-300 nm, and UPLC-MS;

Method F: Waters Acquity™ UPLC® BEH C8 1.7 μm 2.1×100 mm column with gradient 20:80-90:10 v/v $CH_3CN/H_2O$+v 0.1% TFA over 4.0 min and 90:10-95:5 v/v $CH_3CN/H_2O$+v 0.1% TFA over 0.4 min; flow rate 0.3 mL/min, UV wavelength 200-300 nm.

Method G: Waters Acquity™ UPLC BEH C18 1.7 μm 1×50 mm column with gradient 10:90-95:5 v/v CH$_3$CN/ H$_2$O+v 0.05% TFA over 2.0 min; flow rate 0.3 mL/min, UV wavelength 254 nm.

Mass analysis was performed on a Waters SQ Detector with electrospray ionization in positive ion detection mode and the scan range of the mass-to-charge ratio was 170-900 or a Waters Micromass® LCT Premier™ XE with electrospray ionization in positive ion detection mode and the scan range of the mass-to-charge ratio was 300-2000. The identification of the produced insulin conjugates or IRPA was confirmed by comparing the theoretical molecular weight to the experimental value that was measured using UPLC-MS. For the determination of the linkage positions, specifically, insulin dimers were subjected to DTT treatment (for a/b chain) or Glu-C digestion (with or without reduction and alkylation), and then the resulting peptides were analyzed by LC-MS. Based on the measured masses, the linkage positions were deduced.

Flash chromatography was performed using either a Biotage Flash Chromatography apparatus (Dyax Corp.) or a CombiFlash®Rf instrument (Teledyne Isco). Normal-phase chromatography was carried out on silica gel (20-70 μm, 60 Å pore size) in pre-packed cartridges of the size noted. Ion exchange chromatography was carried out on a silica-based material with a bonded coating of a hydrophilic, anionic poly(2-sulfoethyl aspartamide) (PolySULFOETHYL A column, PolyLC Inc., 250×21 mm, 5 μm, 1000 Å pore size). Reverse-phase chromatography was carried out on C18-bonded silica gel (20-60 μm, 60-100 Å pore size) in pre-packed cartridges of the size noted. Preparative scale HPLC was performed on Gilson 333-334 binary system using Waters DELTA PAK C4 15 μm, 300 Å, 50×250 mm column or KROMASIL® C8 10 μm, 100 Å, 50×250 mm column, flow rate 85 mL/min, with gradient noted. Concentration of solutions was carried out on a rotary evaporator under reduced pressure or freeze-dried on a VirTis Freezemobile Freeze Dryer (SP Scientific).

Abbreviations: acetonitrile (AcCN), aqueous (aq), 1-[bis (dimethylamino)methylene]-1H-1,2,3-triazolo[4,5-b]pyridinium 3-oxid hexafluorophosphate (HATU), dichloromethane (DCM), N,N-diisopropylethylamine or Hünig's base (DIPEA), N,N-dimethylacetamide (DMA), N,N-dimethylformamide (DMF), dimethyl sulfoxide (DMSO), ethyl acetate (EtOAc), N-(3-dimethylaminopropyl)-N'-ethylcarbodiimide hydrochloride (EDC), gram(s) (g), 1-hydroxybenzotriazole hydrate (HOBt), hour(s) (h or hr), isopropyl acetate (IPAc), mass spectrum (ms or MS), methyl tert-butyl ether (MTBE), microgram(s) (μg), microliter(s) (μL), micromole (μmol), milligram(s) (mg), milliliter(s) (mL), millimole (mmol), minute(s) (min), retention time (t$_R$), room temperature (rt), saturated (sat. or sat'd), saturated aq sodium chloride solution (brine), 1,1,3,3-tetramethylguanidine (TMG), 2,2,6,6-tetramethylpiperidine (TMP), triethylamine (TEA), trifluoroacetic acid (TFA), and N,N,N',N'-tetramethyl-O—(N-succinimidyl)uronium tetrafluoroborate (TSTU).

The term "RHI" refers to recombinant human insulin and is used to indicate that the insulin has the amino acid sequence characteristic of native, wild-type human insulin. As used herein in the tables, the term indicates that the amino acid sequence of the insulin comprising the dimer is that of native, wild-type human insulin.

Example 1

General Method A: Synthesis of $N^{6,29B},N^{6,29B'}$-Insulin Dimers Using Organic Base Condition In an appropriate sized container, insulin or insulin analog is suspended at room temperature in an organic solvent or mixed aqueous (aq)/organic solvents, e.g., DMSO, in the presence of a base, e.g., TMG. The mixture is allowed to stir gently until insulin is completely dissolved. To the resulting solution is added an activated ester intermediate (linker) in solution of organic solvents, such as DMSO or DMF. After UPLC chromatogram shows that a substantial portion of the reaction mixture has converted into $N^{6,29B},N^{6,29B'}$-insulin dimer (or $N^{6,29B},N^{6,29B'}$-insulin lispro dimer). The reaction mixture may be subjected directly to reverse phase HPLC purification (Waters C4 250×50 mm column, 10 μm, 1000 Å column or KROMASIL C8 250×50 mm, 10 μm, 100 Å column; Buffer A: 0.05-0.1% TFA in deionized water; Buffer B: 0.05-0.1% TFA in AcCN), or the reaction may be quenched by careful dilution with cold acidic H$_2$O (20×, pH about 3.0) at 0° C. and its pH is adjusted to a final pH of 2.5 using 1 N HCl (and 0.1 N NaOH if needed). The solution may first be concentrated by ultrafiltration, either through a tangential flow filtration (TFF) system or using Amicon Ultra-15 Centrifugal Units, with 1K, 3K or 10K MWCO membrane. The concentrated solution is usually first subjected to ion exchange chromatography (PolySULFOETHYL A column, PolyLC Inc., 250×21 mm, 5 μm, 1000 Å; Buffer A: 0.1% (v/v)H3PO4/25% AcCN; Buffer B: 0.1% (v/v)H3PO4/25% AcCN/0.5 M NaCl). Fractions containing B29-conjugate with desired purity are combined and concentrated using TFF system or Amicon Ultra-15. The concentrated solution is then subjected to reverse phase HPLC purification (Waters C4 250×50 mm column, 10 μm, 1000 Å column or KROMASIL C8 250×50 mm, 10 μm, 100 Å column; Buffer A: 0.05-0.1% TFA in deionized water; Buffer B: 0.05-0.1% TFA in AcCN). Fractions containing the desired insulin dimer are combined and freeze-dried or buffer exchanged using TFF system and/or Amicon Ultra-15 to give the $N^{6,29B},N^{6,29B'}$-Insulin dimers.

Example 2

General Method B: Synthesis of $N^{6,29B},N^{6,29B'}$-Insulin Dimers Using Aqueous Base Conditions.

In an appropriate sized container, insulin or insulin analog is dissolved, with gentle stirring, at room temperature in a mixed solvent: 2:3 v/v 0.1 M Na$_2$CO$_3$:AcCN. After the mixture cleared, the pH is adjusted to the value of 10.5-10.8 using alkaline solution, e.g., 0.1 N NaOH. In a separate vial, an activated ester intermediate (linker) is dissolved in an organic solvent, e.g., DMSO, at room temperature. Aliquots of the solution of the activated ester is added over a period of time to the solution containing insulin until UPLC chromatogram shows that most of the unmodified insulin has reacted and that a substantial portion of the reaction mixture has converted into $N^{6,29B},N^{6,29B'}$-insulin dimer (or $N^{6,29B},N^{6,29B'}$-insulin lispro dimer). The reaction is quenched by the addition of an amine nucleophile, e.g., 2-aminoethanol. The reaction solution is stirred at rt for 30 minutes. The resulting solution is carefully diluted with cold H$_2$O (20×) at 0° C. and its pH is adjusted to a final pH of 2.5 using 1 N HCl (and 0.1 N NaOH if needed). The solution is first concentrated by ultrafiltration, either through a tangential flow filtration (TFF) system or using Amicon Ultra-15 Centrifugal Units, with 1K, 3K or 10K MWCO membrane. The concentrated solution is usually first subjected to ion exchange chromatography (PolySULFOETHYL A column, PolyLC Inc., 250×21 mm, 5 μm, 1000 Å; Buffer A: 0.1% (v/v)H₃PO₄/25% AcCN; Buffer B: 0.1% (v/v)H₃PO₄/25% AcCN/0.5 M NaCl). Fractions containing B29-conjugate with desired purity are combined and concentrated using TFF system or Amicon Ultra-15. The resulting solution is then further purified by reverse phase HPLC (Waters C4 250×50 mm column, 10 μm, 1000 Å column or KROMASIL C8 250×50 mm, 10 μm, 100 Å column; Buffer A: 0.05-0.1% TFA in water; Buffer B: 0.05-0.1% TFA in AcCN). Fractions containing the title insulin dimer are combined and freeze-dried or buffer exchanged using TFF system and/or Amicon Ultra-15 to give the $N^{6,29B},N^{6,29B'}$-Insulin dimers.

Example 3

Synthesis of 2,5-dioxopyrrolidin-1-yl 4-((2-(2-(3-((2,5-dioxopyrrolidin-1-yl)oxy)-3-oxopropoxy)ethoxy)ethyl)amino)-4-oxobutanoate (C4+NH+PEG2, Linker 1) is described.

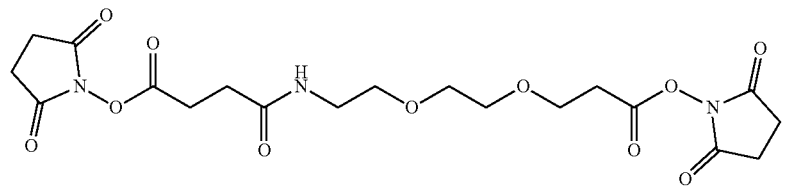 [SMILES: O=C(CCC(=O)ON1C(=O)CCC1=O)NCCOCCOCCC(=O)ON1C(=O)CCC1=O]

Step 1. 4-((2-(2-(2-carboxyethoxy)ethoxy)ethyl)amino)-4-oxobutanoic Acid

To a solution of tert-butyl 3-(2-(2-aminoethoxy)ethoxy) propanoate (250 mg, 1.072 mmol) in DMF (1.5 mL) at rt was added dihydrofuran-2,5-dione (107 mg, 1.072 mmol), and followed by Et₃N (0.149 ml, 1.072 mmol). The mixture was stirred at rt for 3 hr and then concentrated down to remove DMF. To the resulting residue at 0° C. was added 1 ml TFA and the mixture was allowed to stir at rt over night. After overnight, the solution was concentrated to give the diacid, which was used in the next step without further purification. UPLC-MS Method A: $t_R$=0.4 min, 278 (z=1).

Step 2. 2,5-dioxopyrrolidin-1-yl 4-((2-(2-(3-((2,5-dioxopyrrolidin-1-yl)oxy)-3-oxopropoxy)ethoxy)ethyl)amino)-4-oxobutanoate To a solution of the product of Step 1 (297 mg, 1.071 mmol) in DMF (1.5 ml) at rt was added TSTU (661 mg, 2.196 mmol), and followed by DIPEA (0.384 ml, 2.196 mmol). The mixture was stirred at rt for 3 hr and concentrated. The residue was purifiey by reverse phase chromatography using 120 g C18 column, elute with 0-40% AcCN in H₂O. Fractions containing the product were combined and freeze-dried to give title compound. UPLC-MS Method C: $t_R$=3.73 min, 472 (z=1).

Example 4

This example illustrates the synthesis of $N^{6,29B},N^{6,29B'}$-(Linker 1)bis[insulin human] (Dimer 1).

To a solution of RHI (500 mg, 0.085 mmol) and 1,1,3,3-tetramethylguanidine (0.216 mL, 1.722 mmol) in DMSO (5 mL) was added dropwise a solution of 2,5-dioxopyrrolidin-1-yl 4-((2-(2-(3-((2,5-dioxopyrrolidin-1-yl)oxy)-3-oxo- propoxy)ethoxy)ethyl)amino)-4-oxobutanoate (Linker 1) (20.29 mg, 0.043 mmol) in DMSO (500 μL) over 10 min in four portions. Upon completion, the reaction mixture was added dropwise to a mixture of IPAc/MTBE (v:v 4:1, 200 mL), and followed by addition of acetic acid (1.0 mL, 17.22 mmol). The resulting white precipitate was collected and rinsed with (IPAc, 100 mL) through filtration and then dried in vacuo. The white solid was re-dissolved in 25 mL of 20% AcCN/80% H₂O, the pH was adjusted to ~3 and then purified by reverse-phase chromatography on C8 phase gradient 28-36% of AcCN with 0.05% TFA in water with 0.05% TFA in 25 min. UPLC-MS Method D: $t_R$=2.62 min, m/z=1695 (z=7).

Example 5

The following dimers in Table 1 were prepared using either General Method A or General Method B or the procedure analogous to those described for EXAMPLE 4 but substituting appropriate N-hydroxysuccinimide esters—either commercially available or prepared using procedure analogous to those described for EXAMPLE 3 substituting appropriate carboxylic acids for 4-((2-(2-(2-carboxyethoxy)ethoxy)ethyl)amino)-4-oxobutanoic acid in Step 2—for Linker 1. The dimers were characterized using UPLC-MS Method D.

TABLE 1

| Dimer No. | Linking Moiety | $t_R$ (min) | [(M + 6)/6] or [(M + 7)/7] |
|---|---|---|---|
| 2 | ![structure] | 3.44 | 1679 |
| 3 | ![structure] | 3.46 | 1683 |

TABLE 1-continued

| Dimer No. | Linking Moiety | $t_R$ (min) | [(M + 6)/6] or [(M + 7)/7] |
|---|---|---|---|
| 4 | (adamantane diketone structure) | 3.77 | 1973 |
| 5 | (trans-cyclohexane diketone structure) | 3.54 | 1679 |
| 6 | (cis-cyclohexane diketone structure) | 3.88 | 1680 |
| 7 | (adamantane diketone structure) | 4.48 | 1687 |
| 8 | (1,3-phenylene diketone structure) | 3.62 | 1681 |
| 9 | (1,3-phenylene bis(acetyl) structure) | 3.61 | 1963 |
| 10 | (cyclohexane-1,3-diyl diketone structure) | 3.64 | 1680 |

The wavy line indicates the bond between the epsilon amino group of the B29 Lys of the insulin molecule.

Example 6

Synthesis of $N^{2,1A},N^{2,1B}$-bis(carbamoyl) Human Insulin (Analog 1) is described.

To a suspension of RHI (1 g, 0.172 mmol) in water (50 mL) was added a solution of potassium phosphate, dibasic (0.249 g, 1.429 mmol) in water (5.0 mL). After stirring at room temperature for 30 minutes, to the resulting mixture was added potassium cyanate (0.279 g, 3.44 mmol). The reaction mixture was allowed to stir for 16 hours. To stop the reaction, unreacted potassium cyanate was removed by TFF using MWCO 3K diafiltration device, and the product was isolated as a solid by lyophilization. The product contained about 10-35% of A1/B1/B29-tris-urea-RHI, which optionally could be removed by reverse-phase chromatography on C8 phase (Column KROMASIL, C8 10 μm 100 Å, 250×50 mm; solvent A=water/0.05% TFA, solvent B=AcCN/0.05% TFA), flow rate=85 mL/min, gradient B in A 26-34% over 30 min). UPLC-MS Method D: $t_R$=4.29 min, m/z=1475 (z=4). The N-terminal substituent has the structure

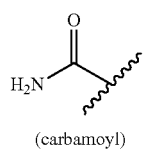

(carbamoyl)

wherein the wavy line indicates the bond between the substituent and the N nitrogen of the N-terminal amino acid residue.

Example 7

This example illustrates the synthesis of $N^{2,1A},N^{2,1A'}$, $N^{2,1B},N^{2,1B'}$-Tetrakis(carbamoyl)-$N^{6,B29}$, $N^{6,B29'}$-(Linker 1)bis[insulin human] (Dimer 11).

To a solution of $N^{2,1A},N^{2,1B}$-bis(carbamoyl) RHI (500 mg, 0.085 mmol, Analog 1) and TMP (0.430 mL, 2.55 mmol) in DMSO (5 mL) was added dropwise a solution of 2,5-dioxopyrrolidin-1-yl 4-((2-(2-(3-((2,5-dioxopyrrolidin-1-yl)oxy)-3-oxopropoxy)ethoxy)ethyl)amino)-4-oxobutanoate (Linker 1) (20.0 mg, 0.042 mmol) in 500 μL of DMSO. Upon completion, the reaction mixture was added dropwise to a mixture of IPAc/MTBE (v/v 4:1, 150 mL), and followed by addition of acetic acid (0.971 mL, 16.97 mmol). The resulting white precipitate was collected and rinsed with (3×50 mL of this IPAc/MTBE mixture) through filtration and then dried in vacuo. The white solid was re-dissolved in 22 mL of 15% AcCN/H₂O, pH was adjusted to—3 and then purified by reverse-phase chromatography on C8 phase gradient 28-36% $CH_3CN/H_2O$+0.05% TFA in 25 min. UPLC-MS Method D: $t_R$=3.83 min, m/z=1719 (z=7).

Example 8

The following dimers in Table 2 were prepared using either General Method A or General Method B or the procedure analogous to those described for EXAMPLE 7 but substituting appropriate N-hydroxysuccinimide esters—either commercially available or prepared using procedure analogous to those described for EXAMPLE 3 substituting appropriate carboxylic acids for 4-((2-(2-(2-carboxyethoxy)ethoxy)ethyl)amino)-4-oxobutanoic acid in Step 2—for Linker 1. The dimers were characterized using UPLC-MS Method G except for Dimer 12 and 29, which was characterized using UPLC-MS Method D.

TABLE 2

| Dimer No. | Linking Moiety | $t_R$ (min) | [(M + 7)/7] or [(M + 8)/8] |
|---|---|---|---|
| 12 | | 3.72 | 1716 |
| 13 | | 0.95 | 1708 |
| 14 | | 0.93 | 1712 |
| 15 | | 0.96 | 1711 |
| 16 | | 0.96 | 1707 |
| 17 | | 0.96 | 1730 |
| 18 | | 0.94 | 1499 |
| 19 | | 0.96 | 1707 |
| 20 | | 0.95 | 1710 |

TABLE 2-continued

| Dimer No. | Linking Moiety | $t_R$ (min) | [(M + 7)/7] or [(M + 8)/8] |
|---|---|---|---|
| 21 | | 0.89 | 1496 |
| 22 | | 0.88 | 1488 |
| 23 | | 0.89 | 1700 |
| 24 | | 0.88 | 1698 |
| 25 | | 0.88 | 1702 |
| 26 | | 0.88 | 1712 |
| 27 | | 0.88 | 1706 |
| 28 | | 0.89 | 1707 |
| 29* | | 3.64 | 1981 |
| 30 | | 0.88 | 1701 |

TABLE 2-continued

| Dimer No. | Linking Moiety | $t_R$ (min) | [(M + 7)/7] or [(M + 8)/8] |
|---|---|---|---|
| 31 | (structure: –C(O)–CH2CH2CH2–NH–C(O)–C(O)–NH–CH2CH2CH2–C(O)–) | 0.88 | 1717 |

The wavy line indicates the bond between the epsilon amino group of the B29 Lys of the insulin molecule.
*indicating z = 6

Example 9

This example illustrates the synthesis of $N^{2,1A},N^{2,1A'},N^{2,1B},N^{2,1B'}$-Octakis(methyl)-$N^{6,B29}$, $N^{6,B29'}$-(Linker 1)bis[insulin human] (Dimer 32).

Dissolved $N^{6,B29}$, $N^{6,B29'}$-(Linker 1)bis[insulin human] (Dimer 1) (90 mg, 7.59 µmol) in a mixture of AcCN/H2O (v/v 1:3, 8 mL, pH~3) and then adjusted pH value of the resulting solution to ~4 by dropwise addition of 0.1 N NaOH. To the resulting solution was added formaldehyde (20 µL, 0.269 mmol, 37 wt % in H2O stabilized with 10-15% CH3OH) and followed by dropwise addition of a freshly prepared solution of NaBH3CN (12.0 mg, 0.207 mmol) dissolved in 500 µL of H2O. After gentle stirring at rt for 1 hr, the pH of the reaction mixture was carefully acidified by dropwise addition of 1.0 N HCl to ~2.6. The resulting solution was subjected to reverse phase HPLC purification on C-8 phase gradient 27-36% of AcCN with 0.05% TFA in water with 0.05% TFA in 25 min. UPLC-MS Method D: $t_R$=2.23 min, m/z=1711 (z=7).

Example 10

Synthesis of bis(2,5-dioxopyrrolidin-1-yl) trans-cyclohexane-1,4-dicarboxylate (trans-cyclohexane 1,4-diacid, Linker 2) is described.

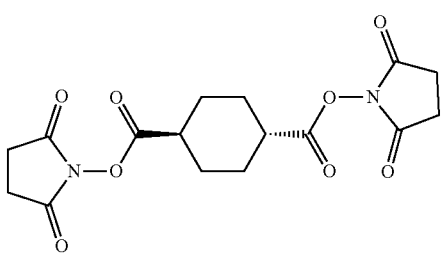 [SMILES: O=C1CCC(=O)N1OC(=O)[C@H]1CC[C@H](C(=O)ON2C(=O)CCC2=O)CC1]

To a solution of trans-cyclohexane-1,4-dicarboxylic acid (200 mg, 1.162 mmol) in DCM (11 mL) at 0° C. was added TSTU (734 mg, 2.439 mmol) and DIPEA (0.5 mL, 2.86 mmol). The resulting reaction mixture was stirred at rt for 1 hr. The product was crushed out in reaction solution as a white solid; filtered and washed with DCM (2×5 ml); and dried in vacuo to obtain the title compound. UPLC-MS calculated for C16H18N2O8, 366.11, observed m/z: 367.16 [M+1], $t_R$=3.20 min, using UPLC-MS Method A. $^1$H NMR (500 MHz, DMSO): δ 2.81-2.89 (m; 2H); 2.80 (s; 8H); 2.02-2.10 (m; 4H); 1.57-1.63 (m; 4H).

Example 11

The following octakis(methyl)-$N^{6,B29},N^{6,B29'}$ bis[insulin human] in Table 3 were prepared using the procedure analogous to those described for EXAMPLE 9 but substituting appropriate insulin dimers—prepared according to either General Method A or General Method B using N-hydroxysuccinimide esters that are either commercially available or prepared using procedure analogous to those described for EXAMPLE 3 substituting appropriate carboxylic acids for 4-((2-(2-(2-carboxyethoxy)ethoxy)ethyl)amino)-4-oxobutanoic acid in Step 2, for Linker 1—for $N^{6,B29}$, $N^{6,B29'}$-(Linker 1)bis[insulin human] (Dimer 1). These dimers were characterized using UPLC-MS Method D except for Dimer 36, which was characterized using UPLC-MS Method G.

TABLE 3

| Dimer No. | Linking Moiety | $t_R$ (min) | [M + 7]/7 |
|---|---|---|---|
| 33 | (trans-cyclohexane-1,4-dicarbonyl) | 3.61 | 1696 |
| 34 | (cis-cyclohexane-1,4-dicarbonyl) | 3.47 | 1696 |
| 35 | (adamantane-1,3-dicarbonyl) | 4.12 | 1704 |
| 36 | (benzene-1,3-dicarbonyl) | 0.86 | 1694 |

The wavy line indicates the bond between the epsilon amino group of the B29 Lys of the insulin molecule.

Example 12

Synthesis of 2,5-dioxopyrrolidin-1-yl 6-((6-((2,5-dioxopyrrolidin-1-yl)oxy)-6-oxohexyl)amino)-6-oxohexanoate (Linker 3; C6+NC6) is described.

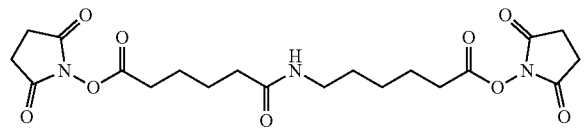 [SMILES: O=C(CCCCC(=O)ON1C(=O)CCC1=O)NCCCCCC(=O)ON1C(=O)CCC1=O]

Step 1 Benzyl 6-((6-(benzyloxy)-6-oxohexyl)amino)-6-oxohexanoate

To a mixture of adipic acid monobenzyl ester (600 mg, 2.54 mmol) and 6-(benzyloxy)-6-oxohexan-1-aminium 4-methylbenzenesulfonate (1.0 g, 2.54 mmol) in DMF (12.71 mL) was added HOBt (584 mg, 3.81 mmol), DIPEA (888 µL, 5.08 mmol), and EDC (731 mg, 3.81 mmol). After stirring overnight, the reaction mixture was partitioned between sat. NaHCO$_3$ and EtOAc. The organic phase was separated, washed with 1.0 M HCl and brine, dried over Na$_2$SO$_4$, and concentrated to give the title compound as a semi-solid and used in the next step without further purification. UPLC-MS Method A: $t_R$=1.26 min, m/z=440 (z=1).

Step 2 6-((5-Carboxypentyl)amino)-6-oxohexanoic Acid

A suspension of the product of Step 1 (1.08 g, 2.457 mmol) and Pearlman's catalyst (20% wt on carbon, 173 mg, 0.246 mmol) in MeOH (50 mL) was stirred under 50 psi H$_2$ overnight. The catalyst was filtered off and the filtrate was subjected to reverse-phase chromatography on C8 phase (Kromasil, C8 10 µm 100 Å, 250×50 mm; solvent A=water/0.05% TFA, solvent B=AcCN/0.05% TFA), flow rate=85 mL/min, gradient B in A 5-30% in 30 min. UPLC-MS Method A: $t_R$=0.40 min, m/z=260 (z=1).

Step 3 2,5-dioxopyrrolidin-1-yl 6-((6-((2,5-dioxopyrrolidin-1-yl)oxy)-6-oxohexyl)amino)-6-oxohexanoate To a solution of the product of Step 2 (50 mg, 0.193 mmol) in DMF (964 µL) was added TSTU (116 mg, 0.386 mmol). After cooled down to 0° C., to the mixture was added TEA (53.8 µL, 0.386 mmol). After stirring for 45 minutes, formation of the desired compound was observed: UPLC-MS Method A: $t_R$=0.71 min, m/z=453 [M+1]. The resulting 2,5-dioxopyrrolidin-1-yl 6-((6-((2,5-dioxopyrrolidin-1-yl)oxy)-6-oxohexyl)amino)-6-oxohexanoate was used as 0.2 M solution in DMF without purification.

Example 13

This example illustrates the synthesis of N$^{2,1A}$,N$^{2,1A'}$,N$^{2,1B}$,N$^{2,1B'}$-Tetrakis(acetyl or PEG1)-Dimers (Dimer 37 and 38).

To a solution of a dimer prepared using Linker 3 or commercial available Bis-PEG5-NHS ester (21 mg, 1.777 µmol, Broadpharm) in DMSO (2 mL) at rt was added TEA (3.96 µL, 0.028 mmol) and then a solution of 2,5-dioxopyrrolidin-1-yl acetate (2.23 mg, 0.014 mmol) in DMSO (100 µL) or other appropriate N-hydroxysuccinimide activated ester (i.e., 2,5-dioxopyrrolidin-1-yl PEG1 acetate) in DMSO (100 µL). After 3 hr, the reaction mixture was diluted with a mixture of water/AcCN (v/v 7:3+0.1% TFA, 12 mL), and pH was adjusted to 2.5. The resulting clear solution was concentrated by Amicon Ultra 15 Centrifuge Filters with 10K MWCO membrane. The resulting solution was first subjected to ion exchange chromatography (PolySULFOETHYL A, 250×21 mm, 5 µm, 1000 Å, 15 mL/min, gradient from 5% to 45% in 30 min; Buffer A: 0.1% (v/v) H$_3$PO$_4$/25% Acetonitrile in water; Buffer B: 0.1% (v/v) H$_3$PO$_4$/25% Acetonitrile/0.5 M NaCl in water). Fractions containing desired product with desired purity were combined and concentrated using Amicon Ultra-15 with 10K MWCO membrane. The resulting solution was then subjected to reverse phase HPLC (KROMASIL C8 250×50 mm, 10 µm, 100 Å column; Buffer A: 0.05% TFA in AcCN/H$_2$O; Buffer B: 0.05% AcCN; flow rate 85 mL/min). The desired fractions were combined and freeze-dried to give Dimer 36 and 37 as shown in Table 4. UPLC-MS Method D was used.

The N-terminal substituents have the structure

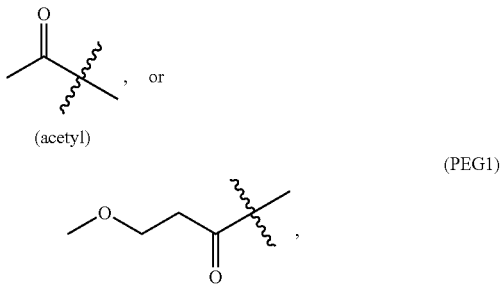

wherein the wavy line indicates the bond between the substituent and the N2 nitrogen of the N-terminal amino acid.

TABLE 4

| Dimer No. | Structure of Dimer showing the Linking moiety between the B29 and B29' Lysine residues | Insulin Type; Insulin N termini | $t_R$ (min) | [(M + 7)/7] |
|---|---|---|---|---|
| 37 | ![structure] | RHI; A1, B1, A1', B' = acetyl | 3.71 | 1716 |

TABLE 4-continued

| Dimer No. | Structure of Dimer showing the Linking moiety between the B29 and B29' Lysine residues | Insulin Type; Insulin N termini | $t_R$ (min) | $[(M + 7)/7]$ |
|---|---|---|---|---|
| 38 | ![structure] | RHI; A1, B1, A1', B' = PEG1 | 3.96 | 1753 |

The wavy line indicates the bond between the epsilon amino group of the B29 Lys of the insulin molecule.

Example 14

Synthesis of bis(2,5-dioxopyrrolidin-1-yl) 8,14-dioxo-4,11,18-trioxa-7,15-diazahenicosanedioate (Linker 4; PEG1+N-PEG1-N+PEG1) is described.

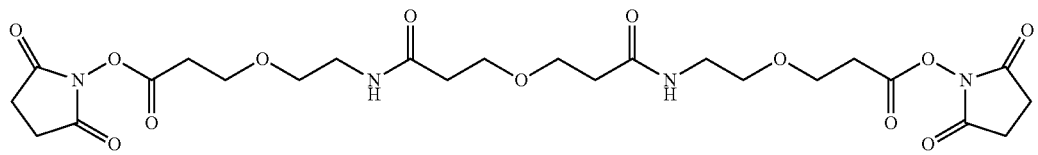 [SMILES: O=C(CCOCCC(=O)NCCOCCC(=O)ON1C(=O)CCC1=O)NCCOCCC(=O)ON1C(=O)CCC1=O]

Step 1 8,14-dioxo-4,11,18-trioxa-7,15-diazahenicosanedioic Acid

To a solution of tert-butyl 3-(2-aminoethoxy)propanoate (246 mg, 1.302 mmol) in DMF (1.5 ml) at rt was added bis(2,5-dioxopyrrolidin-1-yl) 3,3'-oxydipropanoate (232 mg, 0.651 mmol) and followed DIPEA (0.284 ml, 1.628 mmol). The mixture was allowed to stir at rt over night and concentrated to dryness. To the resulting residue at 0° C. was added 1.0 mL neat TFA, and the resulting mixture was allowed to stir at rt overnight. The mixture was concentrated to give the crude product, which was used without further purification. UPLC-MS Method A: $t_R$=0.7 min, m/z=393 (z=1).

Step 2 bis(2,5-dioxopyrrolidin-1-yl) 8,14-dioxo-4,11,18-trioxa-7,15-diazahenicosanedioate To a solution of the product of Step 1 (256 mg, 0.652 mmol) in DMF (1.5 ml) ar rt was added TSTU (403 mg, 1.337 mmol) and followed by DIPEA (0.234 ml, 1.337 mmol). The mixture was allowed to stir at rt overnight. The resulting mixture was concentrated and the residue was purified by on 120 g C18 column, elute with 0-30% AcCN in water. Fractions containing the desired product were combined and freeze-dried to give the title compound. UPLC-Method D: $t_R$=1.02 min, m/z=587 (z=1).

Example 15

The following dimers in Table 5 were prepared using Linker 3 and Linker 4 according to either General Method A or General Method B. Some resulting dimers were further chemically functionalized using procedures analogous to those described for EXAMPLES 9. The dimers were characterized using UPLC-MS Method D.

TABLE 5

| Dimer No. | Structure of Dimer showing the Linking moiety between the B29 and B29' Lysine residues | Insulin Type; Insulin N termini | $t_R$ (min) | [(M + 6)/ 6] or [(M + 7)/ 7] |
|---|---|---|---|---|
| 39 | | RHI; A1, B1, A1', B' = H | 2.62 | 1711 |
| 40 | | RHI; A1, B1, A1', B' = (CH$_3$)$_2$ | 3.62 | 1727 |
| 41 | | RHI; A1, B1, A1', B' = (CH$_3$)$_2$ | 4.06 | 1993 |

The wavy line indicates the bond between the epsilon amino group of the B29 Lys of the insulin molecule.

Example 16

Synthesis of 6-(4,4-bis(2-((2,5-dioxopyrrolidin-1-yl)oxy)-2-oxoethyl)piperidin-1-yl)-6-oxohexanoic acid (Linker 5) is described.

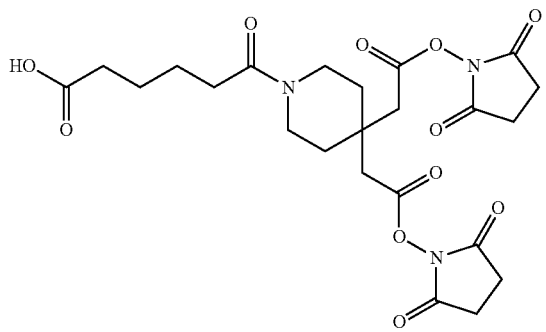 [SMILES: O=C(O)CCCCC(=O)N1CCC(CC(=O)ON2C(=O)CCC2=O)(CC(=O)ON2C(=O)CCC2=O)CC1]

Step 1 8,14-dioxo-4,11,18-trioxa-7,15-diazahenicosanedioic Acid

To a solution of 2,2'-(piperidine-4,4-diyl)diacetic acid (1019 mg, 5.06 mmol) in anhydrous DMF (25 mL) at 0° C. was added benzyl (2,5-dioxopyrrolidin-1-yl) adipate (1857 mg, 5.57 mmol) in DMF (3 ml) portionwise over a period of 15 min and followed by dropwise addition of TEA (1.694 ml, 12.15 mmol) over a period of 10 min. The reaction mixture was allowed to stir at rt under nitrogen overnight and then concentrated. The resulting residue was purified by reverse phase column chromatography on 120 g C18, eluting with AcCN/H$_2$O (gradient from 0% to 50%) to give the title compound after lyophilization. UPLC-Method C: $t_R$=3.66 min, m/z=420 (z=1).

Step 2 bis(2,5-dioxopyrrolidin-1-yl) 2,2'-(1-(6-(benzyloxy)-6-oxohexanoyl)piperidine-4,4-diyl)diacetate To a solution of the product of Step 1 (540 mg, 1.287 mmol) in DMF (15 ml) at 0° C. was added TSTU (969 mg, 3.22 mmol) and Hunig's base (0.675 ml, 3.86 mmol). The mixture was allowed to stir at 0° C. for 1 hr, and then at rt for 1 hr. The reaction mixture was concentrated and the residue was purified by reverse phase column chromatography on 100 g C18, eluting with AcCN/H$_2$O (gradient from 0% to 60% in 30 min). The desired fractions were combined and freeze-dried to give the title compound. UPLC-Method C: $t_R$=4.40 min, m/z=614 (z=1).

Step 3 6-(4,4-bis(2-((2,5-dioxopyrrolidin-1-yl)oxy)-2-oxoethyl)piperidin-1-yl)-6-oxohexanoic Acid A mixture of the product of Step 2 (500 mg, 0.815 mmol) and Pd/C (87 mg, 0.081 mmol) in acetone (20 mL) was degassed and then allowed to stir under a balloon of H$_2$ at rt for 2 hrs. The catalyst was filtered off through celite and washed with acetone, and filtrate was concentrated to give the crude title compound, which was used without further purification.

Example 17

Synthesis of bis(2,5-dioxopyrrolidin-1-yl) 2,2'-(1-(2,5,8,11,14,17,20,23-octaoxahexacosan-26-oyl)piperidine-4,4-diyl)diacetate (Linker 6) is described.

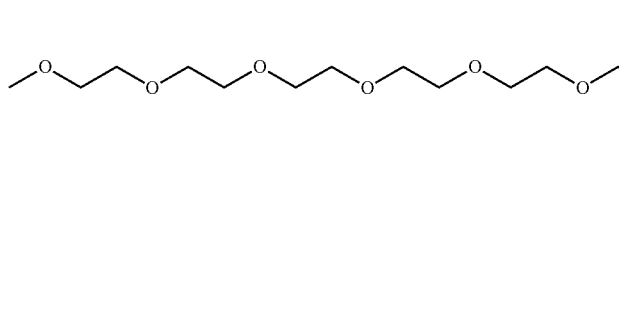

Example 18

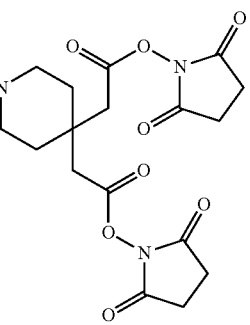

Step 1  2,2'-(1-(2,5,8,11,14,17,20,23-octaoxahexa-cosan-26-oyl)piperidine-4,4-diyl)diacetic Acid To a solution of 2,2'-(piperidine-4,4-diyl)diacetic acid (250 mg, 1.242 mmol) in anhydrous DMF (20 mL) at rt was added PEG-8 NHS Ester (992 mg, 1.947 mmol, Broadpharm) portionwise over a period of 15 min and then TEA (0.450 ml, 3.23 mmol). The resulting mixture was allowed to stir at rt overnight. The reaction mixture was then concentrated and the residue purified by reverse phase column chromatography on 100 g C18, eluting with AcCN/H$_2$O (gradient from 5% to 40%) to give the title compound after lyophilization. UPLC-Method C: $t_R$=2.43 min, m/z=596 (z=1).

Step 2  bis(2,5-dioxopyrrolidin-1-yl) 2,2'-(1-(2,5,8,11,14,17,20,23-octaoxahexacosan-26-oyl)piperidine-4,4-diyl)diacetate To a solution of the product of Step 1 (491 mg, 0.824 mmol) in DMF (24 mL) at 0° C. was added TSTU (620 mg, 2.061 mmol) and Hunig's base (0.396 ml, 2.267 mmol). The mixture was allowed to stir at 0° C. for 1 hr, and then at rt for 1 hr. The reaction mixture was concentrated and the residue was purified by reverse phase column chromatography on 100 g C18, eluting with AcCN/H$_2$O (gradient from 5% to 50%) to give the title compound lyophilization. UPLC-Method C: $t_R$=3.05 min, m/z=790 (z=1).

In Table 6, the following dimers, having generic linker structure as depicted on right (the wavy line indicates the bond between the epsilon amino group of the B29 Lys of the insulin molecule), were prepared using either General Method A or General Method B using Linker 5, Linker 6, or appropriate linkers, which were prepared using the procedure analogous to those described for EXAMPLE 17, substituting appropriate N-hydroxysuccinimide ester for PEG-8 NH Ester in Step 1. Some resulting dimers were further chemically functionalized using procedures analogous to those described for EXAMPLE 9 and EXAMPLE 13. These dimers were characterized using UPLC-MS Method D.

TABLE 6

| Dimer No. | R | Insulin Type; Insulin N termini | $t_R$ (min) | [(M + 6)/6] or [(M + 7)/7] |
|---|---|---|---|---|
| 42 | 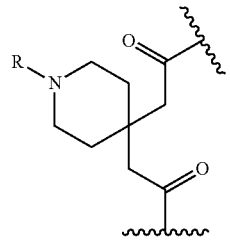 | RHI; A1, B1, A1', B' = (CH$_3$)$_2$ | 3.94 | 1986 |
| 43 | | RHI; A1, B1, A1', B' = (CH$_3$)$_2$ | 4.45 | 1997 |
| 44 | | RHI; A1, B1, A1', B' = H | 3.67 | 1979 |

TABLE 6-continued

| Dimer No. | R | Insulin Type; Insulin N termini | $t_R$ (min) | [(M + 6)/ 6] or [(M + 7)/ 7] |
|---|---|---|---|---|
| 45 | methoxy-(OCH₂CH₂)₇-C(O)- | RHI; A1, B1, A1', B' = H | 3.65 | 1740 |
| 46 | methoxy-CH₂CH₂-C(O)- | RHI; A1, B1, A1', B' = Urea | 3.84 | 1721 |
| 47 | methoxy-(OCH₂CH₂)₅-C(O)- | RHI; A1, B1, A1', B' = Urea | 3.87 | 1765 |
| 48 | methoxy-(OCH₂CH₂)₃-C(O)- | RHI; A1, B1, A1', B' = Urea | 3.84 | 1733 |
| 49 | methoxy-(OCH₂CH₂)₄-C(O)- | RHI; A1, B1, A1', B' = Urea | 3.81 | 1746 |
| 50 | methoxy-CH₂CH₂-C(O)- | RHI; A1, B1, A1', B' = acetyl | 3.82 | 1720 |

The wavy line indicates the bond connecting to the amino group of piperidine ring.

Example 19

Synthesis of 2,5-dioxopyrrolidin-1-yl 6-((2-((2,5-dioxopyrrolidin-1-yl)oxy)-2-oxoethyl)amino)-6-oxohexanoate (C6-Gly linker; Linker 7) is described.

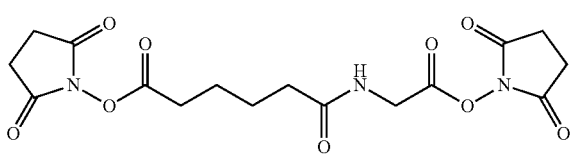 [SMILES: O=C(CCCCC(=O)ON1C(=O)CCC1=O)NCC(=O)ON1C(=O)CCC1=O]

Step 1 Benzyl(2,5-dioxopyrrolidin-1-yl) adipate

To a solution of 6-(benzyloxy)-6-oxohexanoic acid (5 g, 21.16 mmol) in DMF (10 mL) at 0° C. was added DIPEA (4.44 mL, 25.4 mmol) followed by TSTU (7.01 g, 23.28 mmol). The reaction was stirred at 0° C. for 1 hour and room temperature for 1 hour. The mixture was poured to ice-water/ethyl ether mixture (1/1, 100 mL). The mixture was extracted with ethyl ether (3×50 mL), washed with water (2×10 mL) and brine (10 mL). The organic layer was dried over MgSO₄, filtered through a pad of celite and concentrate to give the titled compound. UPLC-MS Method A: $t_R$=1.05 min, m/z=334 (z=1).

Step 2 2-((Carboxymethyl)amino)-6-oxohexanoic Acid

To a solution of glycine (225 mg, 3.0 mmol) in DMF (2.5 mL) was added the product of Step 1 (1.0 g, 3.0 mmol) in DMF (2.5 mL) drop wise followed by TEA (418 µL, 3.0 mmol). The reaction was stirred at room temperature for 18 hr. DMF was removed by under reduced pressure. The crude was purified by C18 reverse phase chromatography (eluted with 0-40% AcCN/water in 16 column volumes (CV)). Fractions containing desired product were combined, concentrated and lyophilized to give intermediate (6-(benzyloxy)-6-oxohexanoyl) glycine. To above intermediate in water (3 mL), was added Pd/C (10%, 160 mg, 0.15 mmol). The reaction was stirred at room temperature under hydrogen balloon for 18 hr. The mixture was filtered through a pad of celite, washed with MeOH/water (1/1, 10 mL). The filtrate was concentrated and lyophilized to give the titled compound. UPLC-MS Method A: $t_R$=0.28 min, m/z=204 [M+1].

Step 3. 2,5-dioxopyrrolidin-1-yl 6-((2-((2,5-dioxopyrrolidin-1-yl)oxy)-2-oxoethyl)amino)-6-oxohexanoate To a solution of the product of Step 2 (10 mg, 0.049 mmol) in DMF (0.5 mL) at 0° C. was added TEA (0.015 mL, 0.108 mmol) followed by TSTU (31.1 mg, 0.103 mmol). The reaction was warmed to rt and stirred at that temperature for 1 hr. TLC (EtOAc/MeOH/Water/AcCN: 2:1:1:1 (v/v/v/v)) showed formation of desired product (Rf: 0.25) and no starting material left. The crude material was used for constructing dimers without purification.

Example 20

Synthesis of 2,5-dioxopyrrolidin-1-yl 5-((2-((2-((2-((2,5-dioxopyrrolidin-1-yl)oxy)-2-oxoethyl)amino)-2-oxoethyl)amino)-2-oxoethyl)amino)-5-oxopentanoate (C5-GlyGlyGly linker; Linker 8) is described.

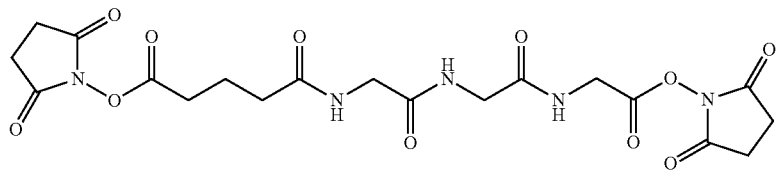 [SMILES: O=C(CCCC(=O)ON1C(=O)CCC1=O)NCC(=O)NCC(=O)NCC(=O)ON1C(=O)CCC1=O]

Step 1 (5-(tert-butoxy)-5-oxopentanoyl)glycylglycylglycine

To a solution of 5-tert-butoxy-5-oxypentanoic acid (600 mg, 3.19 mmol) in DMF (5 ml) at 0° C. was added quickly a solution of TSTU (960 mg, 3.19 mmol) in DMF (5 mL) and followed by dropwise addition of DIPEA (0.835 ml, 4.78 mmol). The mixture was allowed to stir at 0° C. for 1 hr, and then Glycyl-Glycyl-glycine (603 mg, 3.19 mmol) was added in one portion and followed by addition of DIPEA (0.835 ml, 4.78 mmol). After stirring at rt overnight, the reaction mixture was concentrated and the residue was purified on reverse phase chromatograph C18 column, eluting with MeCN/H$_2$O to obtain the title compound. UPLC-MS Method D: $t_R$=3.20 min, m/z=360 (z=1).

Step 2 5-((2-((2-(((carboxymethyl)amino)-2-oxoethyl)amino)-2-oxoethyl)amino)-5-oxopentanoic Acid A portion of the product of Step 1 (100 mg, 0.278 mmol) was dissolved in a premixed solution of 1:1 TFA:DCM (1 mL) and the reaction mixture was stirred for 2 hrs. The mixture was concentrated and solid obtained was redissolved in 30% MeCN/H$_2$O, 0.1% TFA (20 mL) and lyophilized overnight. The crude title compound was used without further purification. UPLC-MS Method D: $t_R$=1.04 min, m/z=304 (z=1).

Step 3 2,5-dioxopyrrolidin-1-yl 5-((2-((2-((2-((2,5-dioxopyrrolidin-1-yl)oxy)-2-oxoethyl)amino)-2-oxoethyl)amino)-2-oxoethyl)amino)-5-oxopentanoate Using the product of Step 2, the desired compound was prepared in similar fashion to Step 3, EXAMPLE 19. UPLC-MS Method A: $t_R$=0.79 min, m/z=498 (z=1).

Example 21

The following dimers in Table 7 were prepared using Linker 7, Linker 8, and linkers, prepared using procedures analogous to those described in EXAMPLE 19 and EXAMPLE 20, according to either General Method A or General Method B. Selected dimers were further chemically functionalized using procedures analogous to those described for EXAMPLES 9. The dimers were characterized using UPLC-MS Method D except for Dimer 53 and Dimer 55, which was characterized using UPLC-MS Method G.

TABLE 7

| Dimer No. | Structure of Dimer showing the Linking moiety between the B29 and B29' Lysine residues | Insulin Type; Insulin N termini | $t_R$ (min) | [(M + 6)/ 6] or [(M + 7)/ 7] |
|---|---|---|---|---|
| 51 | | RHI; A1, B1, A1', B' = H | 3.53 | 1964 |
| 52 | | RHI; A1, B1, A1', B' = H | 3.48 | 1974 |
| 53 | | RHI; A1, B1, A1', B' = H | 0.85 | 1698 |
| 54 | | RHI; A1, B1, A1', B' = H | 4.26 | 1694 |
| 55 | | RHI; A1, B1, A1', B' = H | 0.85 | 1700 |
| 56 | | RHI; A1, B1, A1', B' = $(CH_3)_2$ | 3.70 | 1716 |
| 57 | | RHI; A1, B1, A1', B' = $(CH_3)_2$ | 3.63 | 1715 |
| 58 | | RHI; A1, B1, A1', B' = Urea | 3.78 | 1723 |

The wavy line indicates the bond between the epsilon amino group of the B29 Lys of the insulin molecule.

Example 22

Synthesis of bis(2,5-dioxopyrrolidin-1-yl) (3,3'-(ethane-1,2-diylbis(oxy))bis(propanoyl))(S)-di-L-prolinate (Pro-PEG2-Pro linker; Linker 9) is described.

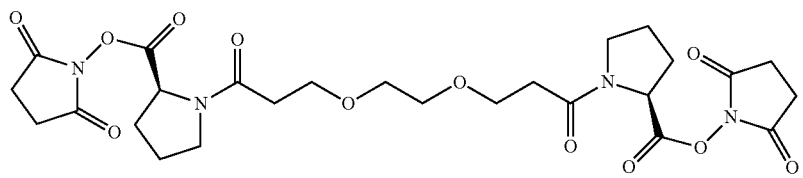 [SMILES: O=C(ON1C(=O)CCC1=O)[C@@H]1CCCN1C(=O)CCOCCOCCC(=O)N1CCC[C@H]1C(=O)ON1C(=O)CCC1=O]

Step 1 (2'S)-(3,3'-(ethane-1,2-diylbis(oxy))bis(propanoyl))di-L-proline

To a suspension of D-proline (144 mg, 1.249 mmol) in DMF (7 mL) at rt was added Bis-PEG$_2$-NHS ester (200 mg, 0.500 mmol, Broadpharm) and TMG (0.125 ml, 0.999 mmol). The reaction mixture was allowed to stir at rt overnight and purified using reverse phase C18, eluting with AcCN/H$_2$O to obtain the title compound. UPLC-MS Method A: $t_R$=0.59 min.

Step 2 bis(2,5-dioxopyrrolidin-1-yl) (3,3'-(ethane-1,2-diylbis(oxy))bis(propanoyl)) (S)-di-L-prolinate Using the product of Step 2, the desired compound was prepared in similar fashion to Step 3, EXAMPLE 19. UPLC-MS Method C: $t_R$=2.32 min, m/z=595 (z=1).

Example 23

The following dimers in Table 8 were prepared using Linker 9 or linkers, prepared using procedures analogous to those described in EXAMPLE 22 using appropriate bis-NHS esters, according to either General Method A or General Method B. Selected dimers were further chemically functionalized using procedures analogous to those described for EXAMPLES 9. These dimers were characterized using UPLC-MS Method D.

TABLE 8

| Dimer No. | Structure of Dimer showing the Linking moiety between the B29 and B29' Lysine residues | Insulin Type; Insulin N termini | $t_R$ (min) | [(M + 7)/7] |
|---|---|---|---|---|
| 59 | (structure) | RHI; A1, B1, A1', B' = H | 3.69 | 1713 |

TABLE 8-continued

| Dimer No. | Structure of Dimer showing the Linking moiety between the B29 and B29' Lysine residues | Insulin Type; Insulin N termini | $t_R$ (min) | [(M + 7)/ 7] |
|---|---|---|---|---|
| 60 | | RHI; A1, B1, A1', B' = H | 3.71 | 1708 |
| 61 | | RHI; A1, B1, A1', B' = (CH$_3$)$_2$ | 3.65 | 1729 |

The wavy line indicates the bond between the epsilon amino group of the B29 Lys of the insulin molecule.

Example 24

Synthesis of (2-(bis(3-((2,5-dioxopyrrolidin-1-yl)oxy)-3-oxopropyl)amino)-2-oxoethyl)phosphonic acid (Linker 10) described

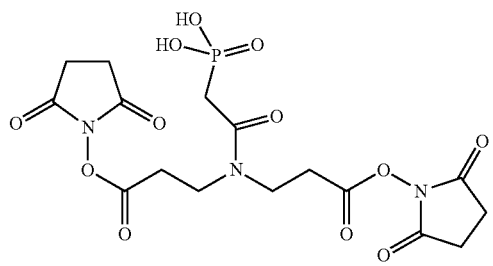 [SMILES: O=C(CCN(CCC(=O)ON1C(=O)CCC1=O)C(=O)CP(=O)(O)O)ON1C(=O)CCC1=O]

Step 1 2,5-dioxopyrrolidin-1-yl 2-(bis(benzyloxy)phosphoryl)acetate

To a solution of both dibenzylphosphonoacetic acid (500 mg, 1.561 mmol) and TSTU (517 mg, 1.717 mmol) in acetonitrile (7.8 mL) at 0° C. was added dropwise triethylamine (261 µl, 1.873 mmol). The reaction mixture was allowed to stir at 0° C. for 2 hrs, and concentrated. The residue was re-dissolved in 100 mL of EtOAc and washed with 50 mL of 1.0 M HCl, 50 mL of sat. sodium bicarbonate, and 50 mL of brine. The organic phase was ried over sodium sulfate, concentration and purified by chromatography on 40 g silica gel column, using gradient EtOAc/Hex of 0-80%, to give the title product. UPLC-MS Method C: $t_R$=3.50 min, m/z=418 (z=1).

Step 2 3,3'-((2-(bis(benzyloxy)phosphoryl)acetyl) azanediyl)dipropanoic Acid To a solution of 3,3'-azanediyldipropionic acid (102 mg, 0.630 mmol) in DMF (3.15 mL) was added 2,5-dioxopyrrolidin-1-yl 2-(bis(benzyloxy)phosphoryl)acetate from Step 1 (263 mg, 0.630 mmol) followed by triethylamine (351 µl, 2.52 mmol). The reaction mixture was allowed to stir for 1 hr and concentrated. The residue was purified by reverse phase C18 column (40 g, flow 40 mL/min, grad 0-60% in 30 min followed by hold) to give the title compound after lyophilization of desired fractions. UPLC-MS Method C: $t_R$=3.44 min, m/z=464 (z=1).

Step 3 bis(2,5-dioxopyrrolidin-1-yl) 3,3'-((2-(bis (benzyloxy)phosphoryl)acetyl)azanediyl)dipropionate To a solution of the product of Step 2 (187 mg, 0.404 mmol) in AcCN (3.8 mL) and DMF (1.0 mL) was added TSTU (255 mg, 0.847 mmol) followed by triethylamine (0.141 mL, 1.009 mmol). The reaction mixture was stirred for 1.5 hrs and more TSTU (24.30 mg, 0.081 mmol) was added. The reaction mixture was allowed to stir for 30 min, and diluted with 100 mL of EtOAc and washed with 100 mL of sat. sodium bicarbonate, 100 mL of 1M HCl, 100 mL of brine. Dried the organic phase over sodium sulfate, removed volatiles in vacuo, and used in the next step without further purification. UPLC-MS method C: Rt=4.04 min, m/z=658.205 (z=1).

Step 4 (2-(bis(3-((2,5-dioxopyrrolidin-1-yl)oxy)-3-oxopropyl)amino)-2-oxoethyl)phosphonic Acid To a solution of the product of Step 3 (285 mg, 0.433 mmol) in THF (4.33 mL) was added Pearlman's catalyst (60.9 mg, 0.087 mmol). The mixture was allowed to stir under a balloon of H$_2$ for 3 hrs. To the reaction mixture was added 1 mL of water to increase solubility of the forming product and continued to stir under H$_2$ for 3 more hrs. The catalyst was filtered off and the filtrate was concentrated to give the title product. UPLC-MS Method C: $t_R$=1.68 min, m/z=478 (z=1).

Example 25

The following dimers in Table 9 were prepared using Linker 2 and Linker 10 using either General Method A or General Method B. Selected dimers were further chemically functionalized using procedures analogous to those described for EXAMPLES 13. The dimers were characterized using UPLC-MS Method D.

TABLE 9

| Dimer No. | Structure of Dimer showing the Linking moiety between the B29 and B29' Lysine residues | Insulin Type; Insulin N termini | $t_R$ (min) | [(M + 7)/ 7] |
|---|---|---|---|---|
| 62 | ![structure] | RHI; A1, B1, A1', B' = Urea | 3.83 | 1720 |
| 63 | ![structure] | RHI; A1, B1, A1', B' = acetyl | 3.70 | 1704 |

The wavy line indicates the bond between the epsilon amino group of the B29 Lys of the insulin molecule.

The $N^{6,29B}$-acylated RHI Analog 2, Analog 3, and Analog 4 were prepared for use in constructing dimers using "click" chemistry and were prepared using General Method B or the procedure analogous to those described for EXAMPLE 4 but substituting recombinant human insulin and either (2,5-dioxopyrrolidin-1-yl pent-4-ynoate).

Example 26

General Method C: Synthesis of $N^{6,b29}$ Insulin Conjugates (Analogs)

In an appropriate sized container, insulin or insulin analog was dissolved, with gentle stirring, at room temperature in a mixed solvent: 2:3 v/v 0.1 M $Na_2CO_3$:AcCN. After the mixture cleared, the pH was adjusted to the value of 10.5-10.8 using alkaline solution, e.g., 0.1 N NaOH. In a separate vial, an activated ester intermediate (linking moiety) was dissolved in an organic solvent, e.g., DMSO, at room temperature. Aliquots of the solution of the activated ester (Linker) was added over a period of time to the solution containing insulin until UPLC chromatogram showed that most of the unmodified insulin had been reacted and that a substantial portion of the reaction mixture had been converted into B29-conjugated insulin. The reaction was quenched by the addition of an amine nucleophile, e.g., 2-aminoethanol. The reaction solution was stirred at room temperature for 30 minutes. The resulting solution was carefully diluted with cold $H_2O$ (20×) at 0° C. and its pH was adjusted to a final pH of 2.5 using 1 N HCl (and 0.1 N NaOH if needed). The solution was first concentrated by ultrafiltration, either through a tangential flow filtration (TFF) system or using Amicon Ultra-15 Centrifugal Units, with 1K, 3K or 10K MWCO membrane. The concentrated solution was usually first subjected to ion exchange chromatography (PolySULFOETHYL A column, PolyLC Inc., 250×21 mm, 5 µm, 1000 Å; Buffer A: 0.1% (v/v)$H_3PO_4$/25% AcCN; Buffer B: 0.1% (v/v)$H_3PO_4$/25% AcCN/0.5 M NaCl). Fractions containing B29-conjugate with desired purity were combined and concentrated using TFF system or Amicon Ultra-15. The resulting solution was then further purified by reverse phase HPLC (Waters C4 250×50 mm column, 10 µm, 1000 Å column or Kromasil C8 250×50 mm, 10 µm, 100 Å column; Buffer A: 0.05-0.1% TFA in water; Buffer B: 0.05-0.1% TFA in AcCN). Fractions containing the title conjugate were combined and freeze-dried or buffer exchanged using TFF system and/or Amicon Ultra-15 to give the title product.

Example 27

Synthesis of $N^{6,29B}$-5-azido-pentanoyl (Analog 2) is described.

In 20 mL scintillation vial, insulin (247.5 mg, 0.043 mmol) was dissolved, with gentle stirring, at room temperature in a mixed solvent (5 mL, 2:3 v/v 0.1 M $Na_2CO_3$: AcCN). After the mixture cleared, the pH was adjusted to the value of 10.5-10.8 using alkaline solution, e.g., 0.1 N NaOH. In a separate 8 mL scintillation vial, 2,5-dioxopyrrolidin-1-yl 5-azidopentanoate (10.24 mg, 0.043 mmol)

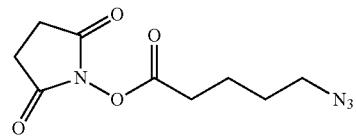 [SMILES: [N-]=[N+]=NCCCCC(=O)ON1C(=O)CCC1=O]

was dissolved in DMSO (500 µL) at rt. Aliquots of the solution of the activated ester was added over a period of time to the solution containing insulin until UPLC chromatogram showed that most of the unmodified insulin had been reacted and that a substantial portion of the reaction mixture had been converted into B29-conjugated insulin. The reaction was quenched by the addition of an amine nucleophile, e.g., 2-aminoethanol. The reaction solution was stirred at room temperature for 30 minutes. The resulting solution was carefully diluted with cold $H_2O$ (20×) at 0° C. and its pH was adjusted to a final pH of 2.5 using 1.0 N HCl (and 0.1 N NaOH if needed). The solution was first concentrated by ultrafiltration using Amicon Ultra-15 Centrifugal Units with 3K or 10K MWCO membrane. The concentrated solution was subjected to reverse phase HPLC (KROMASIL C8 250×50 mm, 10 µm, 100 Å column, 25-35% Buffer B in Buffer A over 20 min; Buffer A: 0.05%

TFA in water; Buffer B: 0.05% TFA in AcCN). Fractions containing Analog 2 were combined and then freeze-dried. UPLC-MS Method D: $t_R$=4.10 min, m/z=1484 (z=4).

Example 28

The following $N^{6,29B}$-acylated RHI analogs (Analog 3 and Analog 4) were prepared for use in constructing dimers using "click" chemistry. The analogs were prepared using General Method C or the procedure analogous to those described for EXAMPLE 30 but substituting the appropriate click linker selected from

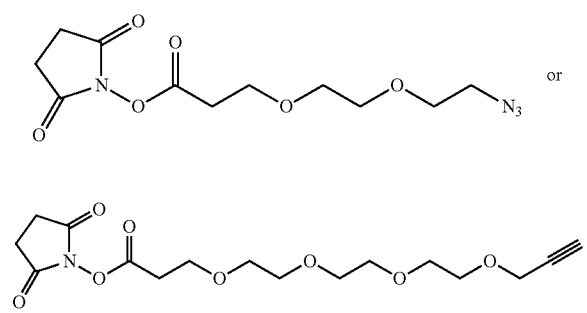

to make Analog 3 or Analog 4, respectively. The analogs were characterized using UPLC-MS Method D. Analogs 3 and 4 are shown in Table 10 below and used to make Dimer 64 shown in Example 29.

appropriate azido containing insulin intermediate (Analog) was dissolved, with gentle stirring, at rt in a mixed solvent of DMSO and water. Both solutions were combined, thoroughly mixed, degassed by gently bubbling $N_2$ through. To the resulting solution was added freshly prepared sodium ascorbate or ascorbic acid solution (final concentration is 0.5 mM) and, after thoroughly mixed, a solution of 10 mM $CuSO_4$ and tris[(1-benzyl-1H-1,2,3-triazol-4-yl)methyl] amine (i.e., TBTA ligand) in 55% DMSO. After degassed by gently bubbling $N_2$ through and mixed thoroughly, the mixture was stored at rt, with occasional mixing, overnight. The reaction mixture was carefully diluted with a mix solvent (v/v 7:3 AcCN/water with 0.05% TFA) at 0° C. and pH was adjusted to 2.50 using 0.1, 1.0 N HCl (and 0.1 N NaOH if needed). The solution was first concentrated by ultrafiltration, either through a tangential flow filtration (TFF) system or using Amicon Ultra-15 Centrifugal Units, with 1K, 3K, or 10K MWCO membrane. The concentrated solution was usually first subjected to ion exchange chromatography (PolySULFOETHYL A column, PolyLC Inc., 250×21 mm, 5 µm, 1000 Å; Buffer A: 0.1% (v/v)$H_3PO_4$/25% AcCN; Buffer B: 0.1% (v/v)$H_3PO_4$/25% AcCN/0.5 M NaCl). Fractions containing desired product with desired purity were combined and concentrated using TFF system or Amicon Ultra-15. The resulting solution was then further purified by reverse phase HPLC (Waters C4 250×50 mm column, 10 µm, 1000 Å column or KROMASIL C8 250×50 mm, 10 m, 100 Å column; Buffer A: 0.05-0.1% TFA in water; Buffer B: 0.05-0.1% TFA in AcCN). Fractions containing the desired product with desired purity were com-

TABLE 10

| Analog | Click Linker | $t_R$ (min) | [(M + 4)/4] |
|---|---|---|---|
| 3 | (structure) | 3.07 | 1499 |
| 4 | (structure) | 3.32 | 1514 |
| 6 | (structure) | 3.27 | 1502 |

The wavy line indicates the bond between the epsilon amino group of the B29 Lys of the insulin molecule.

Example 29

General Method D: Synthesis of $N^{6,29B},N^{6,29B'}$-Insulin Dimers Using $Cu^{2+}$-Catalyzed Click Chemistry.

In an appropriate sized container, appropriate acetylene containing insulin intermediate (Analog) was dissolved, with gentle stirring, at rt in a mixed solvent of DMSO and aq. triethylammonium acetate buffer (pH 7.0, final concentration 0.2 mM). In another appropriate sized container, bined and freeze-dried or buffer exchanged using TFF system and/or Amicon Ultra-15 to give the insulin dimers.

Table 11 lists Dimers 64, which was prepared using the appropriate intermediates following General Method D. The dime was characterized using UPLC-MS Method D, exhibiting either six charged, i.e. [(M+6)/6], (or seven charged, i.e. [(M+7)/7]) species of parent compound at certain retention time ($t_R$).

TABLE 11

| Dimer No. | First Insulin backbone | Second Insulin (') backbone | Structure of Dimer showing the Linking moiety between the B29 and B29' Lysine residues | $t_R$ (min) | [(M + 7)/ 7] |
|---|---|---|---|---|---|
| 64 | Analog 3 | Analog 4 | | 3.65 | 1721 |
| 79 | Analog 3 | Analog 6 | | 3.62 | 1715 |

The wavy line indicates the bond between the epsilon amino group of the B29 Lys and B29' Lys, respectively.

Example 30

Synthesis of N-(2-((2-((2-(but-3-yn-1-ylamino)-2-oxoethyl)amino)-2-oxoethyl)amino)-2-oxoethyl)pent-4-ynamide (Linker 11) is described.

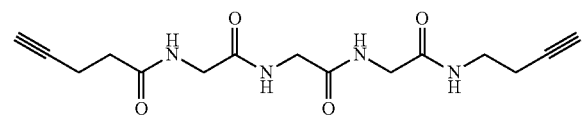 [SMILES: C#CCCNC(=O)CNC(=O)CNC(=O)CNC(=O)CCC#C]

Step 1 2-(2-(2-(pent-4-ynamido)acetamido)acetamido)acetic Acid

To a suspension of 2-(2-(2-aminoacetamido)acetamido) acetic acid (0.5 g, 2.64 mmol) in DMSO (6 ml) and DMF (24 mL) was added TEA (0.737 ml, 5.29 mmol) and followed by dropwise addition of a solution of 2,5-Dioxopyrrolidin-1-yl pent-4-ynoate (0.516 g, 2.64 mmol) in DMSO (6 mL). The reaction mixture was allowed to stir at rt overnight. Solid was filtered off and the filtrate was concentrated and ethyl ether was added. Precipitate was formed, collected via centrifuge, and purified on reverse phase C18 column, eluting with AcCN/H$_2$O to obtain the title compound. UPLC-MS Method B: $t_R$=2.15 min, m/z=539 [2m+e].

Step 2 N-(2-((2-((2-(but-3-yn-1-ylamino)-2-oxoethyl)amino)-2-oxoethyl)amino)-2-oxoethyl)pent-4-ynamide To a solution of the product from step 1 (45 mg, 0.167 mmol) in DMF (2 mL) was added HATU (63.5 mg, 0.167 mmol), but-3-yn-1-amine (46.2 mg, 0.669 mmol)) and DIPEA (0.088 mL, 0.501 mmol). The reaction mixture was allowed to stir at rt for 30 mins and directly purified on reverse phase C18 column, eluting with AcCN/H$_2$O to obtain the title compound. UPLC-MS Method B: $t_R$=3.57 min, m/z=321 (z=1).

Example 31

General Method E: Synthesis of $N^{6,29B},N^{6,29B'}$-Insulin Dimers Using Cu$^{2+}$-Catalyzed Double Click Chemistry.

In an appropriate sized container, appropriate azido containing insulin intermediate (Analog) was dissolved, with gentle stirring, at room temperature in a mixed solvent of DMSO and aq. triethylammonium acetate buffer (pH 7.0, final concentration 0.2 mM). In another appropriate sized container, appropriate bis-acetylene containing bridging or intermediate linker was dissolved, with gentle stirring, at room temperature in a mixed solvent of DMSO and water. Both solutions were combined, thoroughly mixed, degassed by gently bubbling N$_2$ through. To the resulting solution was added freshly prepared sodium ascorbate or ascorbic acid solution (final concentration is 0.5 mM) and, after thoroughly mixed, a solution of 10 mM CuSO$_4$ and tris[(1-benzyl-1H-1,2,3-triazol-4-yl)methyl]amine (i.e., TBTA ligand) in 55% DMSO. After degassed by gently bubbling N$_2$ through and mixed thoroughly, the mixture was stored at room temperature, with occasional mixing, overnight. The reaction mixture was carefully diluted with a mix solvent (v/v 7:3 AcCN/water with 0.05% TFA) at 0° C. and pH was adjusted to 2.50 using 0.1, 1.0 N HCl (and 0.1 N NaOH if needed). The solution was first concentrated by ultrafiltration, either through a tangential flow filtration (TFF) system or using Amicon Ultra-15 Centrifugal Units, with 1K, 3K, or 10K MWCO membrane. The concentrated solution was usually first subjected to ion exchange chromatography (PolySULFOETHYL A column, PolyLC Inc., 250×21 mm, 5 μm, 1000 Å; Buffer A: 0.1% (v/v)H$_3$PO$_4$/25% AcCN; Buffer B: 0.1% (v/v)H$_3$PO$_4$/25% AcCN/0.5 M NaCl). Fractions containing desired product with desired purity were combined and concentrated using TFF system or Amicon Ultra-15. The resulting solution was then further purified by reverse phase HPLC (Waters C4 250×50 mm column, 10 μm, 1000 Å column or KROMASIL C8 250×50 mm, 10 μm, 100 Å column; Buffer A: 0.05-0.1% TFA in water; Buffer B: 0.05-0.1% TFA in AcCN). Fractions containing the desired product with desired purity were combined and freeze-dried or buffer exchanged using TFF system and/or Amicon Ultra-15 to give the insulin dimers.

Table 12 lists Dimer 65 that was prepared using Analog 2 and the product of EXAMPLE 30 according to General Method E, which was characterized using UPLC-MS Method G, exhibiting seven charged, i.e. [(M+7)/7], species of parent compound at certain retention time ($t_R$).

Step 2: $N^{6,B29}$, $N^{6,B29'}$-(suberate)[$N^{2,1A}$,$N^{2,1B}$-bis (carbamoyl)] [Insulin Human]

To a solution of RHI (100 mg, 0.017 mmol) and TMG (64.8 μl, 0.517 mmol) in DMSO (1.01 mL) was added a solution of the product of Step 1 (106 mg, 0.017 mmol) in 2.0 mL of DMSO. The reaction mixture was stirred for 1 hr. The target m/z observed by UPLC. The mixture was diluted with 1:5 v/v CH$_3$CN/H$_2$O with 0.05% TFA and diafiltrated in Amicon 10K MWCO tubes to remove DMSO. The resulting solution was purified by ion-exchange (PolySUL-FOETHYL A column, PolyLC Inc., 250×21 mm, 5 μm, 1000 Å; Buffer A: 0.1% (v/v)H$_3$PO$_4$/25% AcCN; Buffer B: 0.1% (v/v)H$_3$PO$_4$/25% AcCN/0.5 M NaCl) and re-purified by reverse-phase chromatography chromatography (Kromasil, C8, 10 μM, 100 Å, 250×50 mm column; solvent A=water/ 0.05% TFA, solvent B=AcN/0.05% TFA, flow rate=85 mL/min, gradient B in A 26-35% in 30 min) to give the title compound after lyophilization. UPLC Method D: $t_R$=3.16 min, m/z=1974 (z=6).

Example 33

This example illustrates the synthesis of $N^{6,B29}$, $N^{6,B29'}$-(trans-cyclohexane-1,4-dicarboxylate)[insulin glargine] [insulin human] (Dimer 67).

TABLE 12

| Dimer No. | Structure of Dimer showing the Linking moiety between the B29 and B29' Lysine residues | $t_R$ (min) | [(M + 7)/ 7] |
|---|---|---|---|
| 65 | (structure image) | 0.83 | 1742 |

The wavy line indicates the bond between the epsilon amino group of the B29 Lys and B29' Lys, respectively.

Example 32

This example illustrates the synthesis of $N^{6,B29}$, $N^{6,B29'}$-(suberate)[$N^{2,1A}$,$N^{2,1B}$-bis(carbamoyl)insulin human] [insulin human] (Dimer 66).

Step 1: $N^{2,1A}$,$N^{2,1B}$-bis(carbamoyl)-$N^{6,29B}$-(8-((2,5-dioxopyrrolidin-1-yl)oxy)-8-oxooctanoyl) Human Insulin To a solution of bis(2,5-dioxopyrrolidin-1-yl) octanedioate (937 mg, 2.55 mmol) in DMSO (10.6 mL) was added TEA (236 μl, 1.697 mmol) and followed by dropwise addition with stirring of a solution of $N^{2,1A}$,$N^{2,1B}$-bis(carbamoyl) Human Insulin (1.0 g, 0.170 mmol) in DMSO (10.6 mL). After addition was complete (15 min), the reaction mixture was stirred for another 30 min. The reaction mixture was added into 50 mL of 1:5 v/v CH$_3$CN/H$_2$O with 0.05% TFA, dropwise with ice cooling (internal temperature not exceeded 20° C.), and pH maintained at 2.5-3 by addition of 1.0 M HCl. The product was purified by chromatography (Kromasil, C8, 10 μm, 100 Å, 250×50 mm column; solvent A=water/0.05% TFA, solvent B=CH$_3$CN/0.05% TFA, Flow=85 mL/min, gradient B in A 26-40% in 30 min). After lyophilization of fractions, the title compound was obtained. UPLC Method D, $t_R$=3.90 min, m/z=1538 (z=4).

Step 1: $N^{2,1A}$,$N^{2,1B}$-bis(trifluoroacetyl)-$N^{6,29B}$-(trans-4-(((2,5-dioxopyrrolidin-1-yl)oxy)carbonyl) cyclohexane-1-acyl) Human Insulin To a solution of bis(2,5-dioxopyrrolidin-1-yl) trans-cyclohexane-1,4-dicarboxylate (20 mg, 0.052 mmol) in anhydrous DMSO (1.0 mL) was added dropwise a solution of $N^{2,1A}$,$N^{2,1B}$-bis(trifluoroacetyl) RHI (110 mg, 0.018 mmol) and TMP (~20 eq, 80 μL) in 2 mL of anhydrous DMSO. The reaction mixture was stirred at rt for 5 min. Upon complition, the reaction mixture was added to a mixed solution of IPAc/MTBE (4:1 v/v, 50 mL). The resulting white suspension was collected through filtration and washed with (3×10 mL) of IPAc and dried in vacuo to give the titled compound, which was used in the following step without purification. UPLC-MS Method D: $t_R$=4.15 min, m/z=1564 (z=4).

Step 2: $N^{6,B29}$,$N^{6,B29'}$-(trans-cyclohexane-1,4-dicarboxylate)[insulin glargine] [$N^{2,1A}$,$N^{2,1B}$-bis(trifluoroacetyl)-Insulin Human]

To a solution of insulin glargine (110 mg, 0.018 mmol) and TMP (~40 eq; 150 μL) in 2 mL of DMA/H$_2$O (30% H$_2$O in DMA) was added dropwise a solution of the product from Step 1 in anhydrous DMSO (1.5 mL). The reaction mixture was stirred at rt for 2 hr. Upon completion, the reaction mixture was added to a solution of IPAc/t-amyl alcohol (2:1 v/v, ~50 mL). The resulting white precipitate was collected through filtration, washed with (3×10 mL) of IPAc and dried in vacuo, and purified on reverse phase HPLC (Kromasil C8 250×50 mm, 10 µm, 100 Å column; Buffer A: 0.05% TFA in water; Buffer B: 0.05% TFA in AcCN). Fractions containing the title conjugate were combined and freeze-dried to give the title product. UPLC-MS Method D: $t_R$=3.80 min, m/z=1744 (z=7).

Step 3: $N^{6,B29}$,$N^{6,B29'}$-(trans-cyclohexane-1,4-dicarboxylate)[insulin glargine][Insulin Human]

To a solution of the product of Step 2 (224 mg, 0.018 mmol) in 5 ml of 10% $CH_3CN$ in $H_2O$ at 0° C. was added dropwise $NH_4OH$ (28%, 5 mL). The mixture was stirred at the same temperature for 24 hrs. The crude reaction mixture was concentrated down to 5 mL with a 10K MWCO membrane Amicon centrifuge tube, and was further diafiltrated with 100 mL pH ~3.00 water to a final volume about 7.5 mL and purified by reverse phase HPLC (Kromasil C8 250×50 mm, 10 µm, 100 Å column; Buffer A: 0.05% TFA in water; Buffer B: 0.05% TFA in AcCN). Fractions containing the title conjugate were combined and freeze-dried to give the title product. UPLC-MS Method D: $t_R$=3.59 min, m/z=1716 (z=7).

Example 34

This example illustrates the synthesis of $N^{6,B29}$,$N^{6,B29'}$-(trans-cyclohexane-1,4-dicarboxylate)-bis[$N^{2,1B}$-bis(methyl)-insulin human] (Dimer 68).

Step 1: $N^{2,1B}$-bis(methyl) Human Insulin

Recombinant human insulin (1.02 g, 0.176 mmol) was suspended in $H_2O$ (50 mL) and the pH was adjusted to 2.5 with dropwise addition of acetic acid to fully dissolve the starting material. Then pH of the resulting mixture was adjusted to 4 with 1.0 N NaOH and the reaction mixture was clear. To the reaction mixture, formaldehyde (100 µL, 1.343 mmol) was added, after 10 min, was added 2-methylpyridine borane complex (42 mg, 0.393 mmol). The reaction mixture was stirred at rt for 1 hr. After completion, the reaction was quenched by adding ethanolamine (425 µl, 7.03 mmol). After stirring for 15 min, the pH of the reaction mixture was adjusted to ~3 with the addition of 1.0 N HCl and the resulting mixture was directly purified on HPLC (Kromasil C8 250×50 mm, 10 µm, 100 Å column; Buffer A: 0.05% TFA in water; Buffer B: 0.05% TFA in AcCN). Fractions containing the title conjugate were combined and freeze-dried to give the title product. UPLC-MS Method D: $t_R$=3.60 min, m/z=1460 (z=4).

Step 2: $N^{6,B29}$,$N^{6,B29'}$-(trans-cyclohexane-1,4-dicarboxylate)-bis[$N^{2,1B}$-bis(methyl)-insulin Human]

To a solution of the product of Step 1 (336 mg, 0.058 mmol) in a mixed solution of DMA (2.5 mL) and Water (718 µL) was added TMP (325 µl, 1.926 mmol). The mixture was stirred at rt until insulin analog was dissolved. Meanwhile, a solution of bis(2,5-dioxopyrrolidin-1-yl) trans-cyclohexane-1,4-dicarboxylate (10 mg, 0.027 mmol) in 200 µL of DMA was prepared. To the solution of insulin analog was added 50 µL of bis-NHS ester linker solution. The mixture was allowed to stir at rt for 15 min and the reaction progress was monitored by analyzing an aliquot of the reaction mixture using UPLC-MS Method D. This process was repeated until all activated ester solution was used up. Upon completion, the crude reaction mixture was added dropwise to a mixed solution of IPAc/t-amyl-OH (v/v 2:1, 100 mL). The resulting white precipitate was collected through filtration and rinsed with (3×50 ml of IPAc) and dried in vacuo for 1 hr. The crude product was then re-dissolved in 20 ml of 15% $CH_3CN$ in $H_2O$, the pH was adjusted to ~3 with the addition of 1.0 N HCl and directly purified on HPLC (Kromasil C8 250×50 mm, 10 µm, 100 Å column; Buffer A: 0.05% TFA in water; Buffer B: 0.05% TFA in AcCN). Fractions containing the title conjugate were combined and freeze-dried to give the title product. UPLC-MS Method D: $t_R$=3.63 min, m/z=1688 (z=7).

Example 35

Synthesis of $N^{2,1B}$-(3-morpholinopropionate) human insulin (Analog 5) is described.

Step 1.
2,5-dioxopyrrolidin-1-yl-3-morpholinopropanoate

To a solution of 3-morpholinopropanoic acid HCl salt (50 mg, 0.256 mmol) in DMF (0.4 mL) at 0° C. was added TEA (0.089 mL, 0.639 mmol) followed by addition of TSTU (85 mg, 0.281 mmol). The reaction was stirred at 0° C. for 1 hr and room temperature for 1 hr. The reaction mixture was used in next step without purification.

Step 2. $N^{2,1B}$-(3-morpholinopropionate) Human Insulin

To a solution of $N^{2,1A}$,$N^{6,29B}$-bis(Boc) human insulin (600 mg, 0.1 mmol) in DMSO (6 mL) was added TEA (0.278 mL, 1.997 mmol). The solution was stirred at 25° C. for 40 min. To above solution was added 2,5-dioxopyrrolidin-1-yl-3-morpholinopropanoate (51.2 mg, 0.2 mmol in 0.31 ml DMF/0.5 mL DMSO) via syringe pump over 30 min. The reaction mixture was stirred at 25° C. for 18 hr. The above reaction mixture was added to isopropyl acetate (35 ml) dropwise. The precipitated was collected by centrifugation, dried in vacuo overnight, and dissolved at 0° C. in neat TFA (2 ml). The resulting mixture was stirred at 0° C. for 1 hr. To the above solution was added ethyl ether (35 mL). The mixture was centrifuged. The supernatant was decanted. The white solid was dried in vacuo for 2 hr. The solid was then dissolved in AcCN/$H_2O$ with 0.05% TFA (2/8, 10 ml), purified by reverse phase HPLC to give the title product. UPLC-MS Method D: $t_R$=3.45 min, m/z=1488 (z=4).

Example 36

In Table 13 lists $N^{2,1B}$-acylated insulin dimers that were prepared using either General Method A or General Method B, substituting $N^{2,1B}$-(3-morpholinopropionate) human insulin for recombinant human insulin. These dimers were characterized using UPLC-MS Method D.

TABLE 13

| Dimer | Linking moiety | $t_R$ (min) | [(M + 7)/7] |
|---|---|---|---|
| 69 | 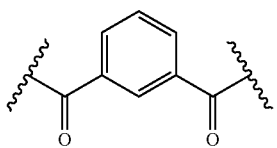 [SMILES: *C(=O)c1cccc(C(*)=O)c1] | 3.67 | 1719 |

TABLE 13-continued

| Dimer | Linking moiety | $t_R$ (min) | [(M + 7)/7] |
|---|---|---|---|
| 70 | (structure: O=C-(CH2)6-C=O with wavy lines) | 3.53 | 1720 |

The wavy line indicates the bond between the epsilon amino group of the B29 Lys of the insulin molecule.

Example 37

General Method F: Synthesis of $N^{6,29B},N^{6,29B'}$-Insulin Dimers Using Reductive Amination.

To a solution of $N^{2,1A},N^{2,1B}$-bis(carbamoyl)-Insulin (Analog 1) (30 mg, 5.09 μmol) in DMF with 5% HOAc (1.0 mL) was added terephthalaldehyde (0.1 mL, 3.4 mg/mL solution in DMF, 2.55 μmol) and followed by MP-CNBH$_3$ (0.020 mmol, Biotage). The mixture was allowed to stir at rt overnight and the filtered. The resulting solution was purified by reverse phase HPLC (Kromasil C8, 250×50 mm, 10 μm, 100 Å column; Buffer A: 0.05% TFA in AcCN/H$_2$O; Buffer B: 0.05% AcCN; flow rate 85 mL/min) to give the title compound after lyophilization. These dimers were characterized using UPLC-MS Method G.

TABLE 14

| Dimer | Linking aldehyde | $t_R$ (min) | [(M + 7)/7] |
|---|---|---|---|
| 71 | OHC-C6H4-CHO (para) | 0.87 | 1700 |
| 72 | OHC-C6H4-CHO (meta) | 0.87 | 1700 |
| 73 | OHC-pyridine-CHO | 0.87 | 1700 |
| 74 | OHC-furan-CHO | 0.91 | 1484 |

Example 38

General Method G: Synthesis of $N^{6,29B},N^{6,29B'}$-Insulin Dimers Using Bis-Isocyanate.

To a solution of $N^{2,1A},N^{2,1B}$-bis(carbamoyl)-Insulin (Analog 1) (30 mg, 5.09 mol) in DMSO (1.0 mL) was added TEA (0.028 mL, 0.204 mmol) and followed by (1R,4R)-1,4-diisocyanatocyclohexane (0.423 mg, 2.55 μmol). The mixture was allowed to stir at rt overnight and the filtered. The resulting solution was purified by reverse phase HPLC (Kromasil C8, 250×50 mm, 10 μm, 100 Å column; Buffer A: 0.05% TFA in AcCN/H$_2$O; Buffer B: 0.05% AcCN; flow rate 85 mL/min) to give the title compound after lyophilization. These dimers were characterized using UPLC-MS Method G.

TABLE 15

| Dimer | Linking isocyanate | $t_R$ (min) | [(M + 7)/7] |
|---|---|---|---|
| 75 | OCN-cyclohexyl-NCO | 0.88 | 1709 |
| 76 | OCN-(CH2)4-NCO | 0.88 | 1705 |

Example 39

Synthesis of 1-(tert-butyl) 2,4-bis(2,5-dioxopyrrolidin-1-yl) cis-piperidine-1,2,4-tricarboxylate (Linker 56) is described.

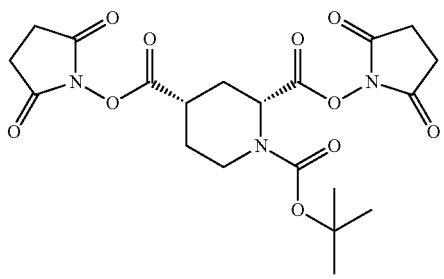 [SMILES: CC(C)(C)OC(=O)N1CC[C@H](C(=O)ON2C(=O)CCC2=O)C[C@@H]1C(=O)ON1C(=O)CCC1=O]

Step 1: cis-1-(tert-butoxycarbonyl)piperidine-2,4-dicarboxylic Acid

To a solution of 1-(tert-butoxycarbonyl)-2-(methoxycarbonyl)piperidine-4-carboxylic acid (215 mg, 0.748 mmol) in acetone (2 ml) was added 1.0 N NaOH (8 mL, 8.00 mmol). The resulting mixture was stirred at rt for 2 hr. Upon completion, the pH of the reaction mixture was adjusted to 3 with 1.0 N HCl and was extracted with ether (3×25 mL). The organic phases were combined, washed with water and brine, dried over Na$_2$SO$_4$ and concentrated to obtain the titled compound. UPLC-MS calculated for $C_{12}H_{19}NO_6$, 273.12, observed m/z: 547.30 [2M+H], $t_R$=3.12 min (UPLC-MS Method A).

Step 2: 1-(tert-butyl) 2,4-bis(2,5-dioxopyrrolidin-1-yl) cis-piperidine-1,2,4-tricarboxylate To a solution of the product of Step 1 (125 mg, 0.457 mmol) in DCM (5 mL) at 0° C. was added TSTU (300 mg, 0.997 mmol) and DIPEA (176 μL, 1.008 mmol). The resulting reaction mixture was stirred at rt for 2 hr and concentrated. The residue was purified by silica chromatography (0-100% EtOAc/hexanes) to provide the title compound. UPLC-MS calculated for $C_{20}H_{25}N_3O_{10}$, 467.15, observed m/z: 468 (z=1), $t_R$=4.74 min (UPLC-MS Method A).

General Method H: Synthesis of $N^{6,29B},N^{6,29B'}$-Insulin Dimers Using Organic Base Condition and Followed by TFA Treatment to Remove Boc Protecting Group In an appropriate sized container, insulin or insulin analog is suspended at room temperature in an organic solvent or mixed aq/organic solvents, e.g., DMSO, in the presence of a base, e.g., TEA, or 1,1,3,3-tetramethylguanidine (TMG). The mixture is allowed to stir gently until insulin is completely dissolved. To the resulting solution is added an activated ester intermediate in solution of organic solvents, such as DMSO or DMF. After UPLC, chromatogram shows that a substantial portion of the reaction mixture has converted into $N^{6,29B},N^{6,29B'}$-insulin dimer (or $N^{6,28B},N^{6,28B'}$-insulin lispro dimer), the reaction solution was transferred, via autopipette, to a 50 mL centrifuge tube containing IPAc/MTBE (v/v 4:1) (45 mL). The addition was made dropwise. The resulting white suspension was centrifuged (3000 rpm, 15 minutes, at 4° C.) to generate a clear supernatant and a white pellet. The supernatant was drawn off and white pellet was dried in vacuo. The white pellet containing crude intermediate was then dissolved in 2 mL of TFA at 0° C. and stirred for 10 minutes at same temperature. Upon completion of the de-boc reaction, the reaction solution was transferred, via autopipette, to a 50 mL centrifuge tube containing MTBE (45 mL). The addition was made dropwise. The resulting white suspension was centrifuged (3000 rpm, 15 minutes, at 4° C.) to generate a clear supernatant and a white pellet. The supernatant was drawn off and white pellet was dried in vacuo and re-dissolved in $CH_3CN/H_2O$ (v/v 1:4) solution. Reaction mixture may be subjected directly to reverse phase HPLC purification (Waters C4 250×50 mm column, 10 μm, 1000 Å column or Kromail C8 250×50 mm, 10 μm, 100 Å column; Buffer A: 0.05-0.1% TFA in deionized water; Buffer B: 0.05-0.1% TFA in AcCN), or the reaction may be quenched by careful dilution with cold acidic $H_2O$ (20×, pH ~3.0) at 0° C. and its pH is adjusted to a final pH of 2.5 using 1 N HCl (and 0.1 N NaOH if needed). The solution may first be concentrated by ultrafiltration, either through a tangential flow filtration (TFF) system or using Amicon Ultra-15 Centrifugal Units, with 1K, 3K or 10K MWCO membrane. The concentrated solution is usually first subjected to ion exchange chromatography (PolySULFOETHYL A column, PolyLC Inc., 250×21 mm, 5 μm, 1000 Å; Buffer A: 0.1% (v/v)$H_3PO_4$/25% AcCN; Buffer B: 0.1% (v/v)$H_3PO_4$/25% AcCN/0.5 M NaCl). Fractions containing B29-conjugate with desired purity are combined and concentrated using TFF system or Amicon Ultra-15. The concentrated solution is then subjected to reverse phase HPLC purification (Waters C4 250×50 mm column, 10 μm, 1000 Å column or Kromasil C8 250×50 mm, 10 m, 100 Å column; Buffer A: 0.05-0.1% TFA in deionized water; Buffer B: 0.05-0.1% TFA in AcCN). Fractions containing the desired insulin dimer are combined and freeze-dried or buffer exchanged using TFF system and/or Amicon Ultra-15 to give the $N^{6,29B},N^{6,29B'}$-Insulin dimers.

Table 16 lists Dimers 77 and 78, which were prepared using the appropriate linker following General Method H. These dimers were characterized using UPLC-MS Method D, exhibiting seven charged, i.e. [(M+7)/7,] species of parent compound at certain retention time ($t_R$).

TABLE 16

| Dimer No. | Structure of Dimer showing the Linking moiety between the B29 and B29' Lysine residues | Insulin Type; Insulin N termini | $t_R$ (min) | [(M + 7)/ 7] |
|---|---|---|---|---|
| 77 | (piperidine dicarboxamide linker) | RHI; A1, B1, A1', B1' = H | 3.61 | 1680 |
| 78 | (phenyl-piperazine linker) | RHI; A1, B1, A1', B1' = H | 3.16 | 1693 |

The wavy line indicates the bond between the epsilon amino group of the B29 Lys and B29' Lys, respectively.

Example 40

The following dimers in Table 17 were prepared using either General Method A or General Method B or the procedure analogous to those described for EXAMPLE 4 but substituting appropriate N-hydroxysuccinimide esters—either commercially available or prepared using procedure analogous to those described for EXAMPLE 3 substituting appropriate carboxylic acids for 4-((2-(2-(2-carboxyethoxy)ethoxy)ethyl)amino)-4-oxobutanoic acid in Step 2—for Linker 1. The dimers were characterized using UPLC-MS Method D.

TABLE 17

| Dimer No. | Linking Moiety | $t_R$ (min) | [(M + 6)/6] or [(M + 7)/7] |
|---|---|---|---|
| 80 | | 3.47 | 1779 |
| 81 | | 3.52 | 1741 |
| 82 | | 3.58 | 1692 |
| 83 | | 3.56 | 1680 |

TABLE 17-continued

| Dimer No. | Linking Moiety | $t_R$ (min) | [(M + 6)/6] or [(M + 7)/7] |
|---|---|---|---|
| 86 | | 3.47 | 1766 |

The wavy line indicates the bond between the epsilon amino group of the B29 Lys of the insulin molecule.

Example 41

Synthesis of 16,3-di-tert-butyl 1,18-bis(2,5-dioxopyrrolidin-1-yl) (3S,16S)-5,14-dioxo-8,11-dioxa-4,15-diazaoctadecane-1,3,16,18-tetracarboxylate (Linker 62) is described.

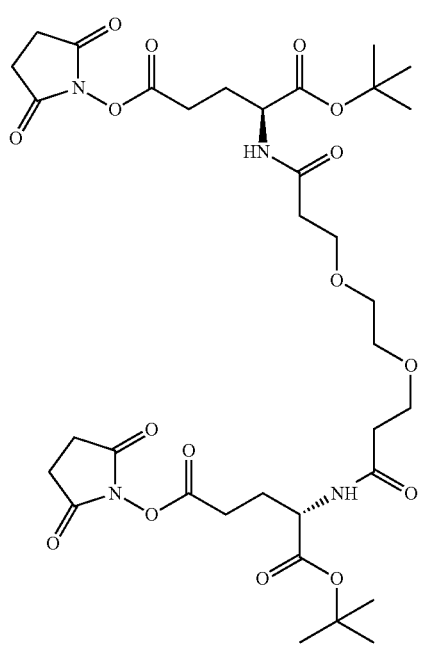 [SMILES: CC(C)(C)OC(=O)[C@H](CCC(=O)ON1C(=O)CCC1=O)NC(=O)CCOCCOCCC(=O)N[C@@H](CCC(=O)ON1C(=O)CCC1=O)C(=O)OC(C)(C)C]

Step 1: (4S,17S)-4,17-bis(tert-butoxycarbonyl)-6,15-dioxo-9,12-dioxa-5,16-diazaicosanedioic Acid To a solution of L-Glu-OtBu (406 mg, 1.998 mmol) and NaHCO₃ (369 mg, 4.40 mmol) in THF (6 mL) and H₂O (4 mL) at 0° C. was added bis(2,5-dioxopyrrolidin-1-yl) 3,3'-(ethane-1,2-diylbis(oxy))dipropionate (400 mg, 0.999 mmol) in THF (6 mL) slowly and the mixture was allowed to warm to rt and stirred overnight. The mixture was concentrated, diluted at rt with EtOAc, adjusted to pH ~2-3 with 0.3N HCl, extracted with EtOAc, washed with brine, dried over Na₂SO₄, filtered and concentrated in vacuo. The residue was purified by column chromatography over C18 (Isco 100 g, eluting with H₂O/AcCN 85:15 to 60:40; fractions analysed by LCMS and lyophilized, only the expected product was collected) to give the title compound. UPLC-MS Method A: $t_R$=3.94 min, m/z=577.28 (z=1).

Step 2: 16,3-di-tert-butyl 1,18-bis(2,5-dioxopyrrolidin-1-yl) (3S,16S)-5,14-dioxo-8,11-dioxa-4,15-diazaoctadecane-1,3,16,18-tetracarboxylate To a solution of (4S,17S)-4,17-bis(tert-butoxycarbonyl)-6,15-dioxo-9,12-dioxa-5,16-diazaicosane-1,20-dioic acid (300 mg, 0.520 mmol) in DMF (2 mL) at cooled 0° C. was added DIPEA (232 µL, 1.301 mmol) and TSTU (449 mg, 1.093 mmol). The reaction mixture was stirred at 0° C. for 30 mins and then TFA (120 µL, 1.561 mmol) was added. The mixture was purified on 150 g Biotage reverse phase, eluting with 0-100% AcCN/H₂O over 20 CV followed by 2 CV AcCN to give the title compound. UPLC-MS Method A: $t_R$=3.16 min, m/z=771.27 (z=1).

Example 42

Dimer 84 in Table 18 was prepared using Linker 62 following General Method H. The dimers were characterized using UPLC-MS Method D.

TABLE 18

| Dimer No. | Linking Moiety | $t_R$ (min) | [(M + 6)/6] or [(M + 7)/7] |
|---|---|---|---|
| 84 | ![structure] | 3.63 | 1721 |

The wavy line indicates the bond between the epsilon amino group of the B29 Lys of the insulin molecule.

Example 43

Synthesis of bis(2,5-dioxopyrrolidin-1-yl) 3,3'-(((2R,3R)-2,3-diacetoxysuccinyl)bis(azanediyl))dipropionate (Linker 63) is described.

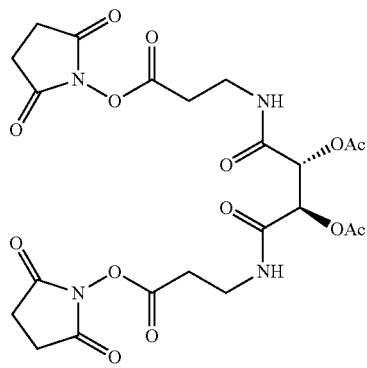 [SMILES: CC(=O)O[C@@H](C(=O)NCCC(=O)ON1C(=O)CCC1=O)[C@@H](OC(C)=O)C(=O)NCCC(=O)ON1C(=O)CCC1=O]

Step 1: dibenzyl 3,3'-(((2R,3R)-2,3-diacetoxysuccinyl)bis(azanediyl))dipropionate To a solution of (−)diacetyl-L-tartaric acid (1.0 g, 4.27 mmol) in DMF (21 mL) at rt was added β-alanine benzyl ester p-toluenesulfonate (3.0 g, 8.54 mmol), EDC (2.46 g, 12.81 mmol), HOBt (1.96 g, 12.81 mmol) and DIPEA (2.98 mL, 17.08 mmol). After stirring at rt overnight, the mixture was diluted with EtOAc (5×) and washed with equal volume of 1M HCl followed by sat'd NaHCO$_3$ and brine. The organic phase was separated and dried over MgSO$_4$, and concentrated. The residue was purified on 80 g SiO$_2$, grad 0-80% EtOAc/Hex over 30 min followed by hold (flow 80 mL/min) to give the title compound. UPLC-MS Method A: $t_R$=3.02 min, m/z=557.15 (z=1).

Step 2: 3,3'-(((2R,3R)-2,3-diacetoxysuccinyl)bis(azanediyl))dipropionic Acid A mixture of dibenzyl 3,3'-(((2R,3R)-2,3-diacetoxysuccinyl)bis(azanediyl))dipropionate (250 mg, 0.449 mmol) and Pearlman's Catalyst (31.5 mg, 0.045 mmol) in a mixed solvent of THF (5 mL) and acetic acid (1 mL) was shaken under 50 psi of H$_2$ over a period of 4 hr on a Parr shaker. The catalyst was removed by filtration and the filtrate was concentrated to give the title compound. UPLC-MS Method B: $t_R$=2.36 min, m/z=377.06 (z=1).

Step 3: bis(2,5-dioxopyrrolidin-1-yl) 3,3'-(((2R,3R)-2,3-diacetoxysuccinyl)bis(azanediyl))dipropionate To a solution of 3,3'-(((2R,3R)-2,3-diacetoxysuccinyl)bis(azanediyl))dipropionic acid (29 mg, 0.077 mmol) in DMF (771 μL) at rt was added TSTU (51.0 mg, 0.170 mmol). After all reagents dissolved, the mixture was cooled down to 0° C. and to which was added TMP (23.95 mg, 0.170 mmol). After stirring at 0° C. 30 min, the reaction was completed by UPLC-MS analysis and the crude product in solution was used as it was. UPLC-MS Method A: $t_R$=2.39 min, m/z=571.44 (z=1).

Example 44

This example illustrates the synthesis of $N^{6,B29}$, $N^{6,B29'}$-(C3-tartaric acid-C3)insulin human (Dimer 85).

Step 1: $N^{6,B29}$,$N^{6,B29'}$-(3,3'-(((2R,3R)-2,3-diacetoxysuccinyl)bis(azanediyl))dipropionate)insulin Human To a solution of insulin human (200 mg, 0.034 mmol) in DMSO (2 mL) was added TMP (195 mg, 1.378 mmol) followed by dropwise a solution of bis(2,5-dioxopyrrolidin-1-yl) 3,3'-(((2R,3R)-2,3-diacetoxysuccinyl)bis(azanediyl)) dipropionate (prepared as in EXAMPLE 43) in DMSO (1.5 mL). After stirring for 30 min, the reaction mixture was purified by reverse phase chromatography (Kromasil C8, 10 μm, 100 Å, 250×50 mm, solvent=0.05% TFA in H$_2$O, solvent B=0.05% TFA in AcCN, flow rate=85 min/mL, gradient 26-32% B in A over 30 min) to give the title compound. UPLC-MS Method D: $t_R$=3.62 min, m/z=1709.57 (z=7).

Step 23: $N^{6,B29}$,$N^{6,B29'}$-(C3-tartaric acid-C3)insulin Human

A solution of $N^{6,B29}$,$N^{6,B29'}$-(3,3'-(((2R,3R)-2,3-diacetoxysuccinyl)bis(azanediyl))dipropionate)insulin human (25 mg, 2.091 μmol) in NH$_4$OH (29%) (1.0 mL, 7.19 mmol) was stirred for 1 hr and then diluted with H$_2$O (15 mL). The resulting solution was concentrated using Amicon tubes to ~1 mL volume, and then adjusted the volume with 20% AcCN in H$_2$O with 0.05% TFA and pH to 2.5 mL with 1M HCl. The resulting mixture was purified by reverse phase chromatography on (Kromasil C8, 10 μm, 100 Å, size 250×50 mm; solvent A=H$_2$O with 0.05% TFA, solvent B=AcCN with 0.05% TFA, flow rate=85 mL/min, gradient B in A 26-34% in 30 min) to give the title compound. UPLC-MS Method D: $t_R$=3.61 min, m/z=1697.43 (z=7).

Example 45

Insulin Receptor Binding Assays were performed as follows.

IR binding assay was run in a scintillation proximity assay (SPA) in 384-well format using cell membranes prepared from CHO cells overexpressing human IR(B) grown in F12 media containing 10% FBS and antibiotics (G418, Penicillin/Strepavidin). Cell membranes were prepared in 50 mM Tris buffer, pH 7.8 containing 5 mM MgCl$_2$. The assay buffer contained 50 mM Tris buffer, pH 7.5, 150 mM NaCl, 1 mM CaCl$_2$, 5 mM MgCl$_2$, 0.1% BSA and protease inhibitors (Complete-Mini-Roche). Cell membranes were added to WGA PVT PEI SPA beads (5 mg/mL final concentration) followed by addition of insulin dimer molecules at appropriate concentrations. After 5-15 min incubation at room temperature, $^{125}$[I]-insulin was added at 0.015 nM final concentration for a final total volume of 50 µL. The mixture was incubated with shaking at room temperature for 1 to 12 hours followed by scintillation counting to determine $^{125}$[I]-insulin binding to IR and the titration effects of insulin dimer molecules on this interaction.

Example 46

Insulin Receptor (IR) AKT-Phosphorylation Assays were performed as follows.

IR AKT-Phosphorylation Assay: Insulin receptor activation can be assessed by measuring phosphorylation of the Akt protein, a key step in the insulin receptor signaling cascade. CHO cell lines overexpressing human IR were utilized in an HTRF sandwich ELISA assay kit (Cisbio "Phospho-AKT(Ser473) and Phospho-AKT(Thr308) Cellular Assay Kits"). Cells were grown in F12 media supplemented with 10% FBS, 400 µg/mL G418 and 10 mM HEPES. Prior to assay, the cells were incubated in serum free media for 2 to 4 hr. Alternatively, the cells could be frozen and aliquoted ahead of time in media containing 20% DMSO and used in the assay upon thawing, spin down and re-suspension. Cells were plated at 10,000 cells per well in 20 µL of the serum free F12 media in 384-well plates. Humulin and insulin glargine controls were run on each plate of test compounds. The titrated compounds were added to the cells (2 µL per well, final concentrations=1000 nM titrated down to 0.512 pM in 1:5 fold dilutions) and incubated at 37° C. for 30 min. The cells were lysed with 8 µL of the prepared lysis buffer provided in the CisBio kit and incubated at 25° C. for 1 hr. The diluted antibody reagents (anti-AKT-d2 and anti-pAKT-Eu3/cryptate) were prepared according to the kit instructions and then 10 µL was added to each well of cell lysate followed by incubation at 25° C. for 3.5 to 5 hr. The plate was read by in an Envision plate reader (Excitation=320 nm; Emission=665 nm) to determine the IR pAkt agonist activity with regard to both potency and maximum response for each compound. Alternatively, the compounds were tested in the same manner in the presence of 1.6 nM of Humulin to determine how each compound was able to compete against the full agonist activity of insulin.

Example 47

Table 19 shows the in vitro biological activity of the insulin dimers towards the insulin receptor (IR). The activities were measured by either ligand competition assays as described in EXAMPLE 45 or functional Akt-phosphorylation assays as described in EXAMPLE 46.

TABLE 19

| Dimer No. | IR Binding IC$_{50}$ (nM) | IR pAkt EC$_{50}$ (nM) | IR pAkt % Max |
|---|---|---|---|
| 1 | 2.31 | 0.15 | 56 |
| 2 | 4.19 | 0.26 | 70 |
| 3 | 2.57 | 0.99 | 81 |
| 4 | 1.76 | 0.46 | 87 |
| 5 | 0.28 | 1.21 | 83 |
| 6 | 1.91 | 0.18 | 45 |
| 7 | 1.43 | 0.22 | 49 |
| 8 | 0.77 | 0.08 | 45.5 |
| 9 | 3.65 | 0.08 | 31.5 |
| 10 | 2.44 | 0.11 | 50 |
| 11 | NA | 0.09 | 32 |
| 12 | 133 | 0.34 | 48 |
| 13 | 68.5 | 0.03 | 40 |
| 14 | 9.37 | 0.10 | 50 |
| 15 | 329 | 1.36 | 52 |
| 16 | 55 | 1.46 | 41 |
| 17 | 60 | 3.06 | 64 |
| 18 | 13.2 | 0.20 | 43 |
| 19 | 318 | 0.12 | 38 |
| 20 | 445 | 0.27 | 47 |
| 21 | 32.4 | 0.59 | 53 |
| 22 | >2511 | 0.39 | 56 |
| 23 | 9.77 | 0.98 | 47 |
| 24 | >2511 | 0.89 | 41 |
| 25 | 598 | 0.52 | 42 |
| 26 | 125 | 0.39 | 40 |
| 27 | 10.4 | 0.52 | 40 |
| 28 | 62 | 0.88 | 49 |
| 29 | 628 | 0.51 | 34.5 |
| 30 | 83.9 | 0.31 | 45 |
| 31 | 13.1 | 0.31 | 33 |
| 32 | 1.68 | 0.03 | 37 |
| 33 | 0.55 | 0.04 | 32 |
| 34 | 3.31 | 0.11 | 54 |
| 35 | 1.68 | 0.08 | 53 |
| 36 | 0.49 | 0.01 | 20 |
| 37 | 14.1 | 0.20 | 33.5 |
| 38 | 6.77 | 0.35 | 22 |
| 39 | 3.44 | 0.08 | 46 |
| 40 | 0.97 | 0.08 | 43 |
| 40 | 0.97 | 0.08 | 43 |
| 41 | 1.69 | 0.03 | 33 |
| 42 | 2.12 | 0.82 | 83 |
| 43 | 0.80 | 0.07 | 23 |
| 44 | 1.95 | 0.09 | 59 |
| 45 | 1.93 | 0.02 | 47 |
| 46 | 158 | 0.22 | 31 |
| 47 | 16.1 | 0.41 | 28 |
| 48 | 139 | 0.67 | 34 |
| 49 | 28.5 | 0.35 | 28 |
| 50 | 224 | 0.16 | 20 |
| 51 | 0.92 | 0.28 | 86 |
| 52 | 1.91 | 0.14 | 40 |
| 53 | 1.25 | 0.02 | 40 |
| 54 | 1.05 | 0.02 | 38 |
| 55 | 0.63 | 0.07 | 30 |
| 56 | 1.24 | 0.07 | 47 |
| 57 | 1.08 | 0.10 | 20 |
| 58 | 25.4 | 0.12 | 32 |
| 59 | 1.01 | 0.14 | 67 |
| 60 | 0.92 | 0.13 | 87 |
| 61 | 1.92 | 0.02 | 30 |
| 62 | 134 | 0.19 | 23 |
| 63 | 44.8 | 0.09 | 19 |
| 64 | 3.10 | 0.04 | 46 |
| 65 | 1.74 | 0.12 | 70 |
| 66 | 6.60 | 0.08 | 29.5 |
| 67 | 23.7 | 18.5 | 60.5 |
| 68 | 0.86 | 0.07 | 28 |
| 69 | 1.42 | 0.05 | 44 |
| 70 | 0.77 | 0.33 | 28.5 |
| 71 | 6.58 | 5.32 | 91 |
| 72 | 3.17 | 8.36 | 87 |
| 73 | 20.5 | 14.6 | 85 |
| 74 | 1.31 | 0.21 | 102 |
| 75 | 18.3 | 1.34 | 75 |
| 76 | 9.61 | 2.46 | 83 |

TABLE 19-continued

| Dimer No. | IR Binding $IC_{50}$ (nM) | IR pAkt $EC_{50}$ (nM) | IR pAkt % Max |
|---|---|---|---|
| 77 | 0.87 | 0.09 | 44.5 |
| 78 | 0.89 | 0.29 | 55 |
| 79 | 2.55 | 0.03 | 56 |
| 80 | 3.35 | 0.23 | 79 |
| 81 | 3.29 | 0.45 | 39 |
| 82 | 0.30 | 0.40 | 50 |
| 83 | 2.95 | 0.38 | 40 |
| 84 | 1.78 | 0.03 | 34 |
| 85 | 1.80 | 0.14 | 38 |
| 86 | 12.2 | 2.53 | 70 |

Example 48

The glucose lowering effect of Dimer 3, 4, 6, 12, 33, 34, 35, 41, 43, 51, 52, 53, 54, and 55 were compared to RHI in Diabetic Yucatan miniature pigs (D minipigs) as follows.

Yucatan minipigs were rendered Type 1 diabetic by Alloxan injections following a proprietary protocol developed by Sinclair Research Center (Auxvasse, Mo.). Induction is considered successful if basal glucose levels exceed 150 mg/dL. D minipigs with plasma glucose levels of approximately 300 mg/dl were utilized in these experiments.

Male Yucatan minipigs, instrumented with two Jugular vein vascular access ports (VAP), were used in these studies.

On the day of the study after an overnight fast, minipigs were placed in slings, and VAPs were accessed for infusion and sampling. At t=0 min, and after collecting two baseline blood samples for plasma glucose measurement (t=−30 minutes and t=0 minutes), minipigs were administered Humulin (recombinant human insulin, RHI) or insulin dimer as a single bolus IV, at 0.69 nmol/kg. Humulin and IRPA were formulated at 69 nmol/ml in a buffer containing Glycerin, 16 mg/mL; Metacresol, 1.6 mg/mL; Phenol, 0.65 mg/mL; Anhydrous Sodium Phosphate, Dibasic, 3.8 mg/mL; pH adjusted to 7.4 with HCl. After dosing, sampling continued for 480 minutes; time points for sample collection were −30 min, 0 min, 8 min, 15 min, 30 min, 45 min, 60 min, 90 min, 120 min, 150 min, 180 min, 210 min, 240 min, 270 min, 300 min, 330 min, 360 min, 420 min, 480 min. Blood was collected in K3-EDTA tubes, supplemented with 10 g/mL aprotinin, and kept on ice until processing, which occurred within 30 minutes of collection. After centrifugation at 3000 rpm, 4° C., for 8 min, plasma was collected and aliquoted for glucose measurement using a Beckman Coulter AU480 Chemistry analyzer and for compound levels measurement.

The results are shown in FIGS. 1-5. The results are presented as the change of glucose at any given time point to time 0 and show that the insulin dimers present less risk of promoting hypoglycemia than RHI.

Table of Sequences

| SEQ ID NO: | Description | Sequence |
|---|---|---|
| 1 | Homo sapiens insulin A chain | GIVEQCCTSICSLYQLENYCN |
| 2 | Homo sapiens insulin B chain | FVNQHLCGSHLVEALYLVCGERGFFYTPKT |
| 3 | Artificial sequence insulin A chain<br>$X_2$ is isoleucine or threonine;<br>$X_3$ is valine, glycine, or leucine;<br>$X_8$ is threonine or histidine;<br>$X_{17}$ is glutamic acid or glutamine;<br>$X_{19}$ is tyrosine, 4-methoxy-phenylalanine, alanine, or 4-amino phenylalanine;<br>$X_{23}$ is asparagine or glycine; | $GX_2X_3EQCCX_8SICSLYQLX_{17}NX_{19}CX_{23}$ |
| 4 | Artificial sequence insulin B chain<br>$X_{25}$ is histidine or threonine;<br>$X_{29}$ is alanine, glycine or serine;<br>$X_{30}$ is histidine, aspartic acid, glutamic acid, honnocysteic acid, or cysteic acid;<br>$X_{31}$ is proline or lysine; and<br>$X_{32}$ is proline or lysine, with the proviso that at least one of $X_{31}$ or $X_{32}$ is lysine | $X_{25}LCGX_{29}X_{30}LVEALYLVCGERGFX_{27}YTX_{31}X_{32}$ |
| 5 | $X_{22}$ is phenylalanine or desamino-phenylalanine;<br>$X_{25}$ is histidine or threonine;<br>$X_{26}$ is glycine or leucine;<br>$X_{27}$ is phenylalanine or aspartic acid;<br>$X_{29}$ is alanine, glycine, or serine;<br>$X_{30}$ is histidine, aspartic acid, glutamic acid, honnocysteic acid, or cysteic acid;<br>$X_{31}$ is aspartic acid, proline, or lysine;<br>$X_{32}$ is lysine or proline;<br>$X_{33}$ is threonine, alanine, or absent; | $X_{22}VNQX_{25}X_{26}CGX_{29}X_{30}LVEALYLVCGERGFX_{27}Y$<br>$TX_{31}X_{32}X_{33}X_{34}X_{35}$ |

Table of Sequences

| SEQ ID NO: | Description | Sequence |
|---|---|---|
| | $X_{34}$ is arginine or absent; and $X_{35}$ is arginine or absent; With the proviso at least one of $X_{31}$ or $X_{32}$ is lysine | |
| 6 | Artificial sequence insulin lispro B chain | FVNQHLCGSHLVEALYLVCGERGFFYTKPT |
| 7 | Artificial sequence insulin glargine A chain | GIVEQCCTSICSLYQLENYCG |
| 8 | Artificial sequence Insulin glargine B chain | FVNQHLCGSHLVEALYLVCGERGFFYTPKTRR |
| 9 | Artificial sequence Insulin aspart B chain | FVNQHLCGSHLVEALYLVCGERGFFYTDKT |
| 10 | Artificial sequence B: des30 | FVNQHLCGSHLVEALYLVCGERGFFYTPK |
| 11 | Artificial sequence A: Y19A | GIVEQCCTSICSLYQLENACN |

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

What is claimed:
1. An insulin dimer selected from the group consisting of:
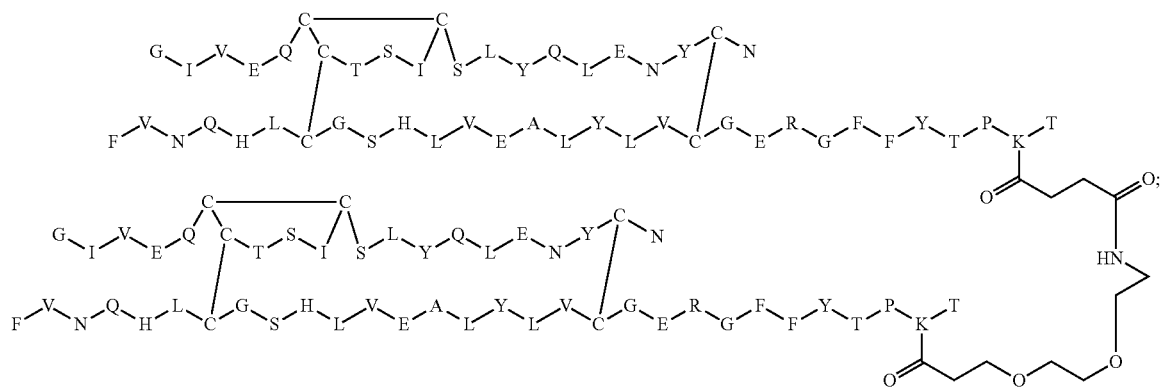
Dimer 1
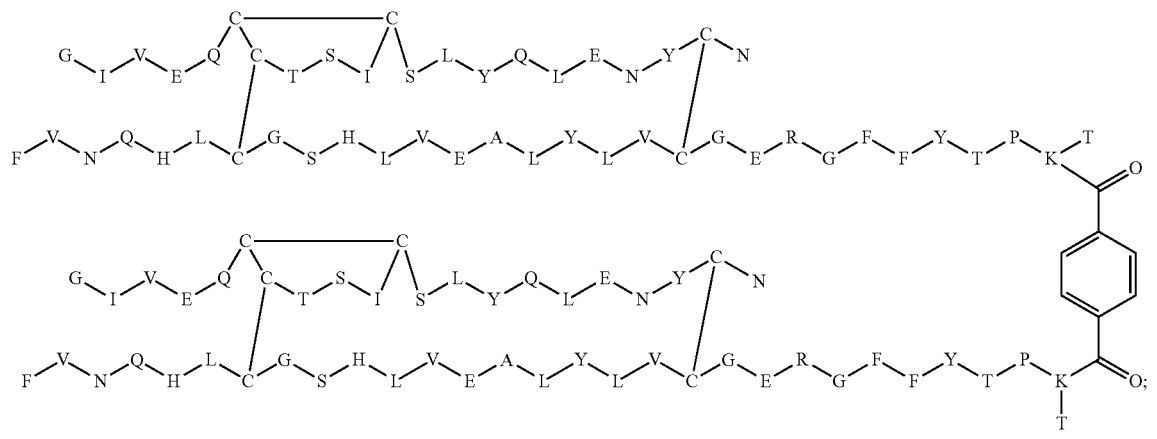
Dimer 2
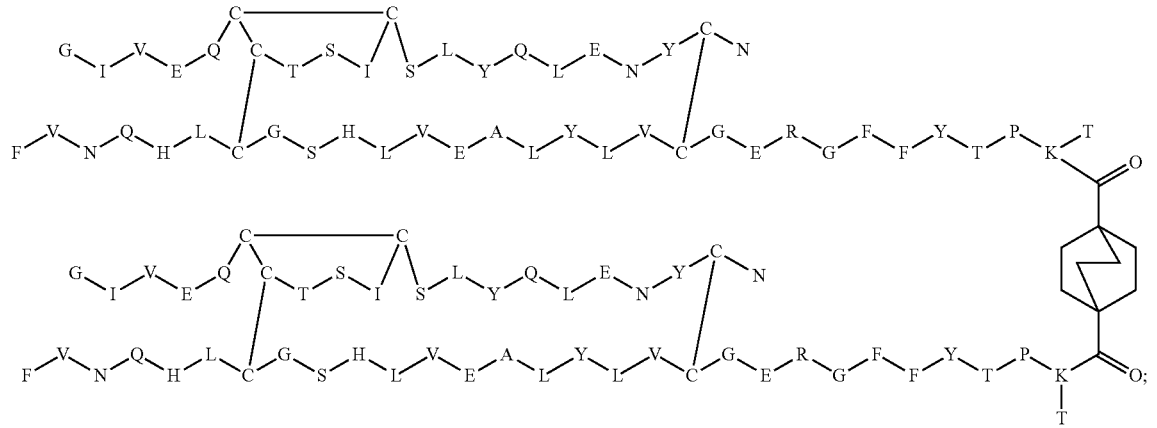
Dimer 3

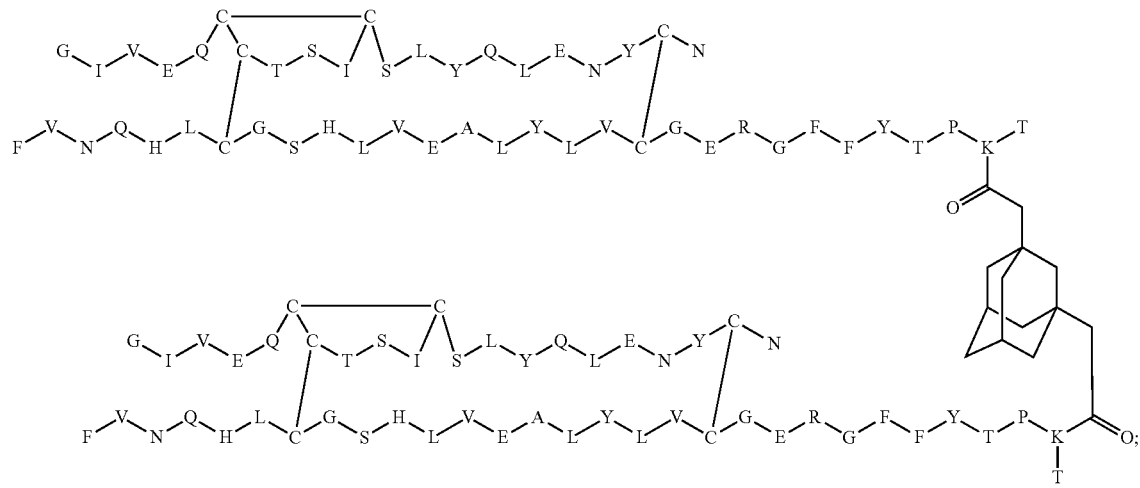
Dimer 4
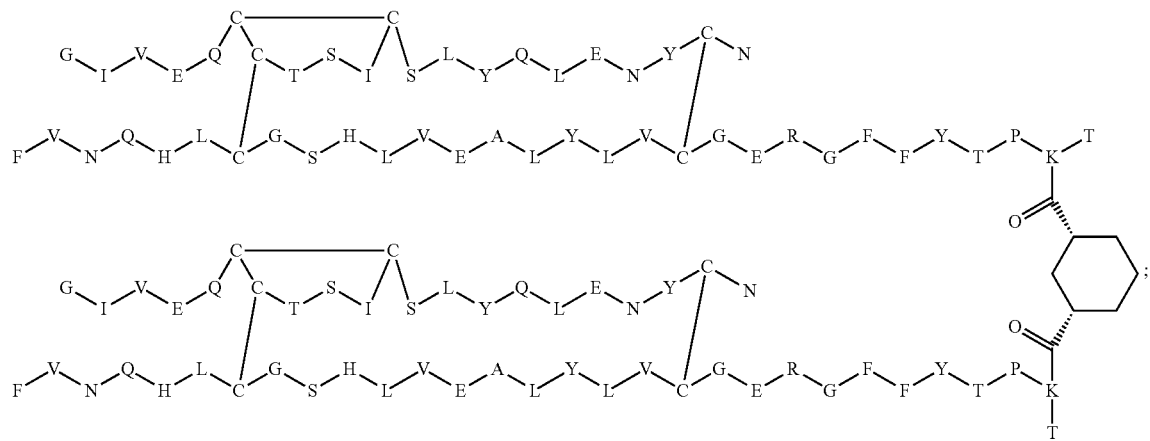
Dimer 5
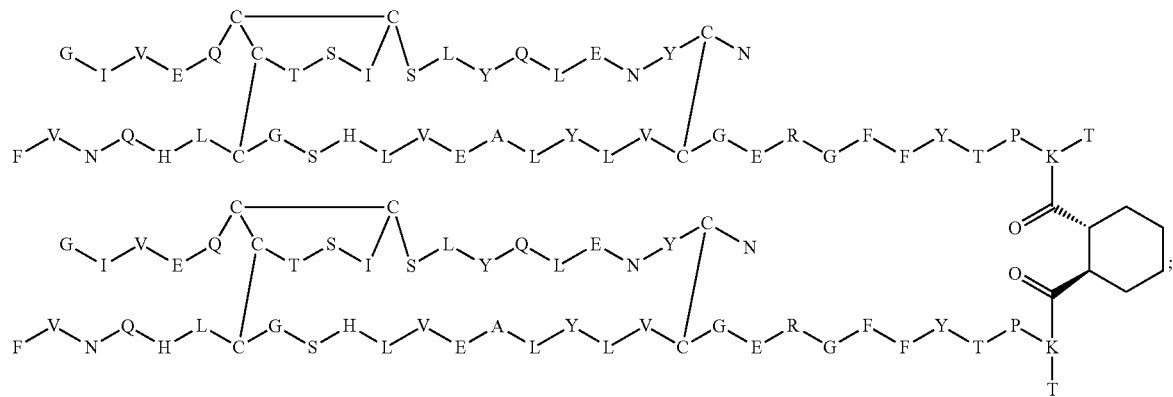
Dimer 6

Dimer 7
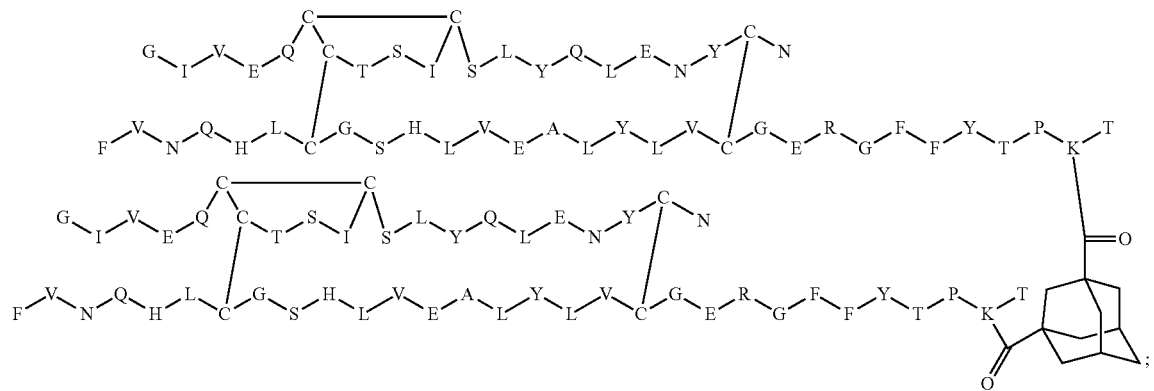
Dimer 8
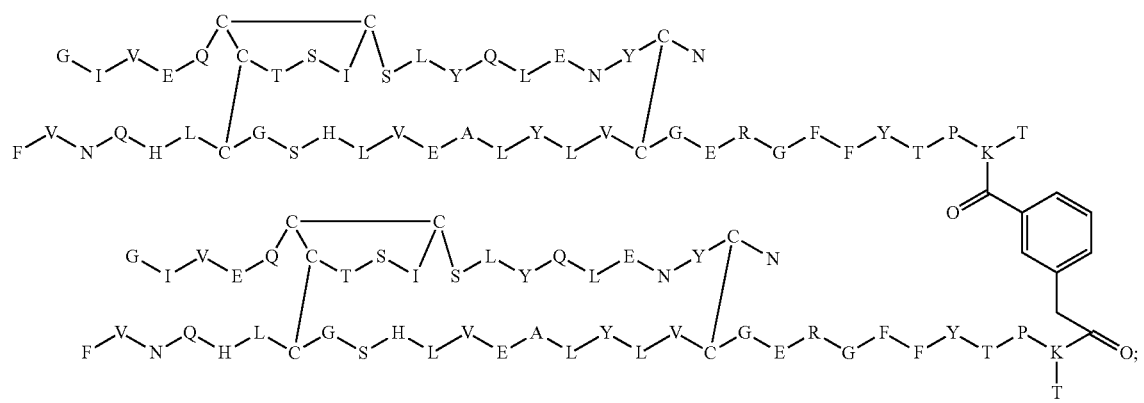
Dimer 9
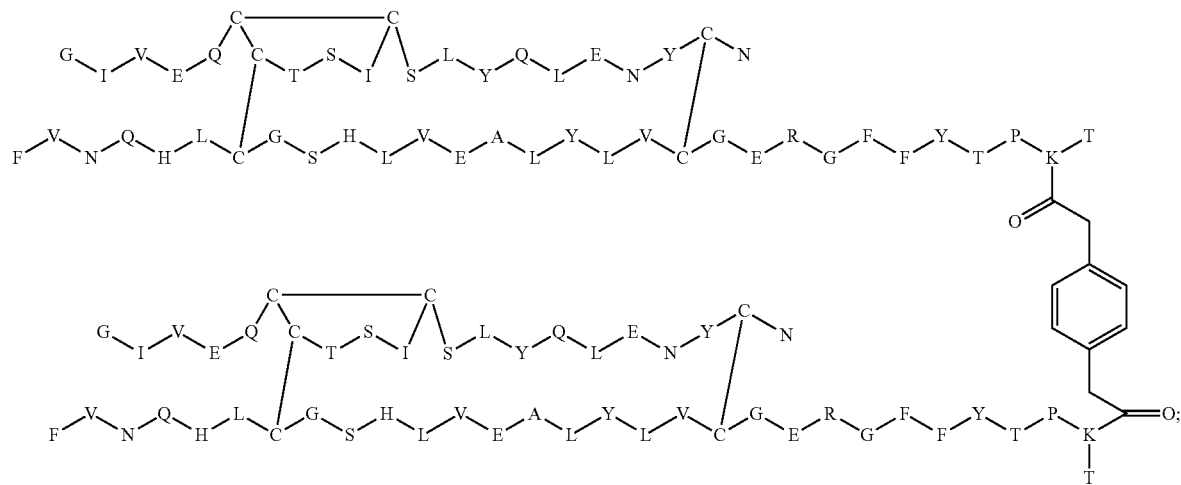

Dimer 10
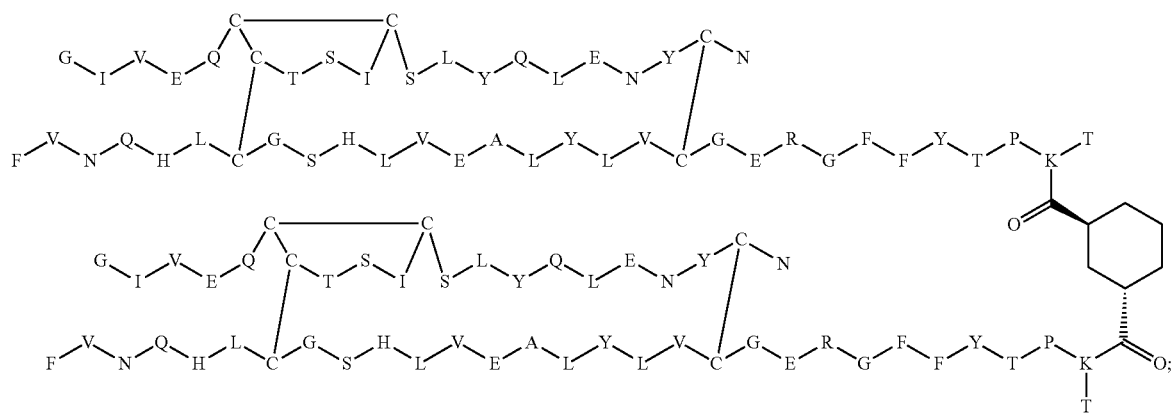
Dimer 11
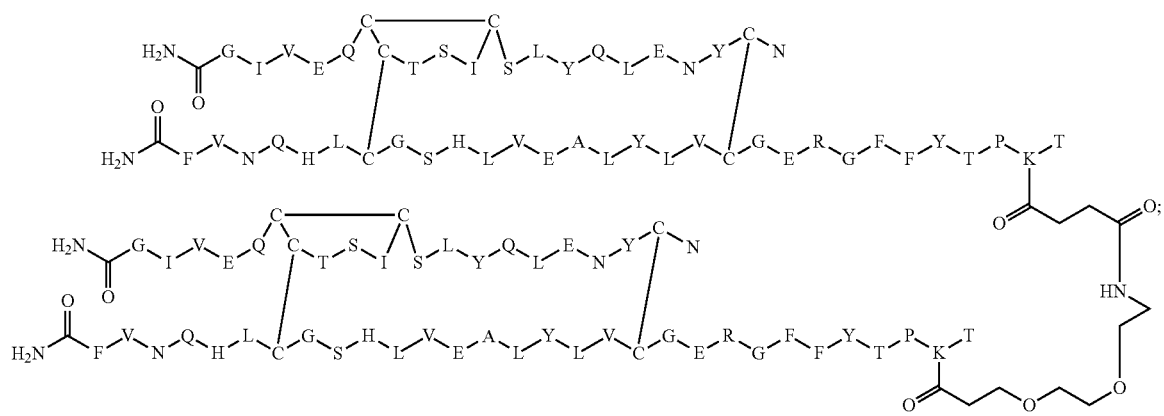
Dimer 12
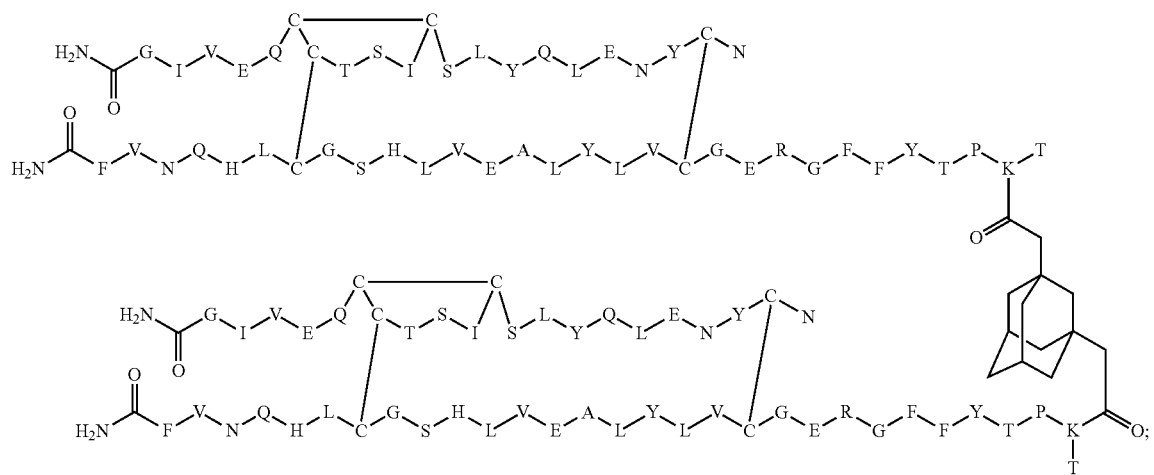

Dimer 13
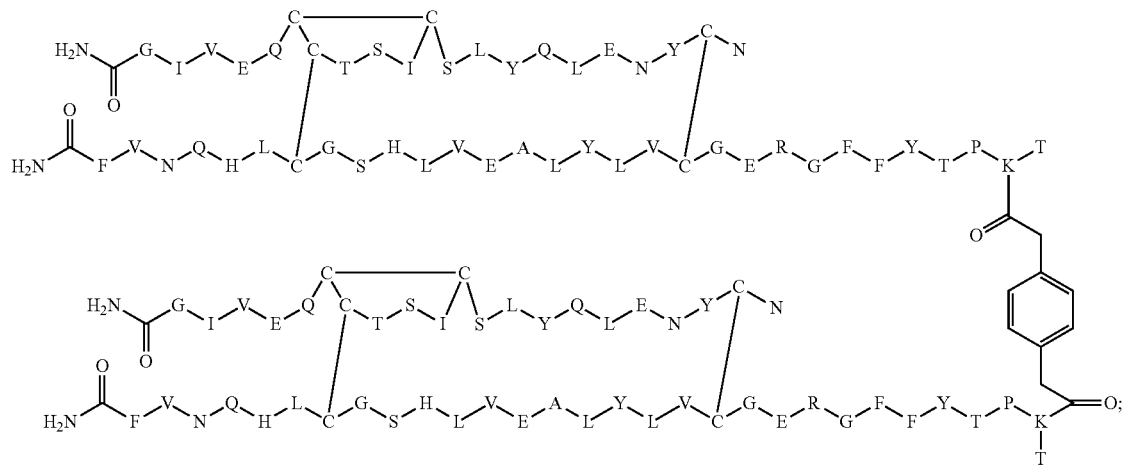
Dimer 14
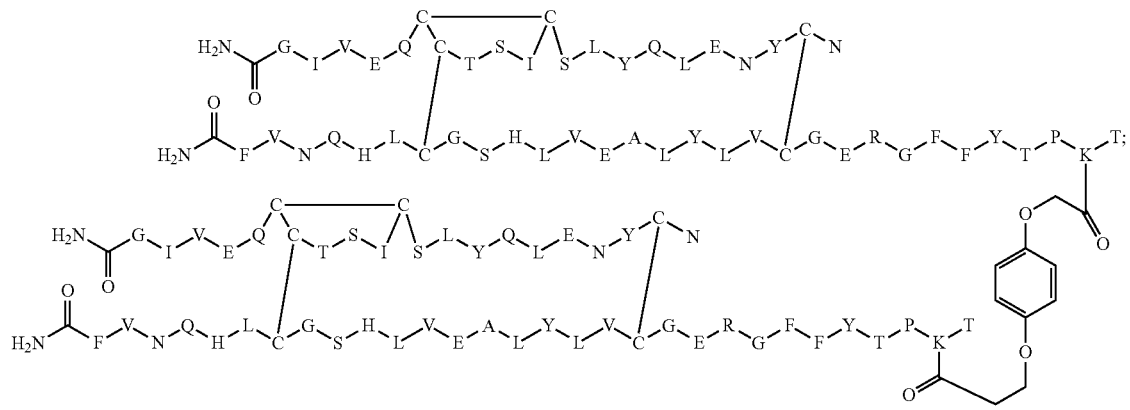
Dimer 15
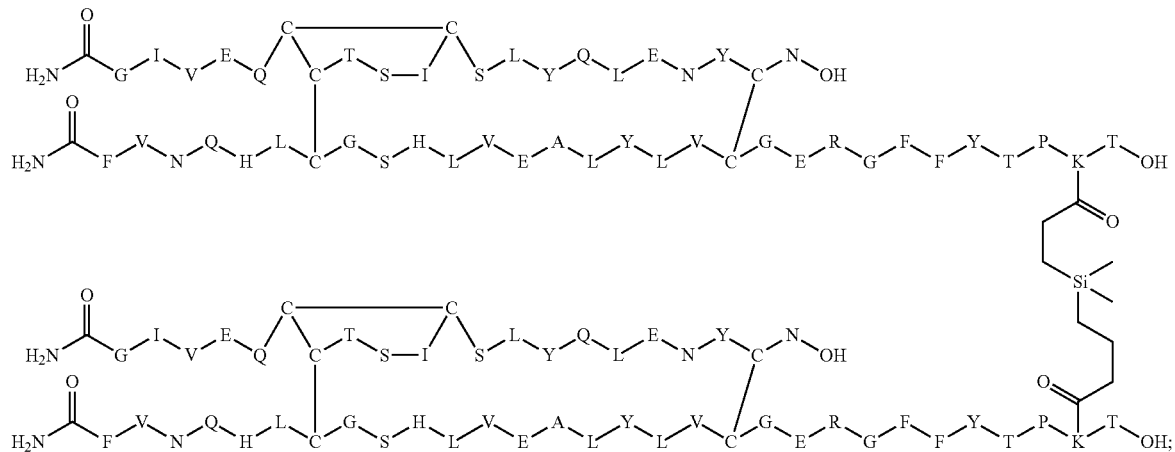

Dimer 16
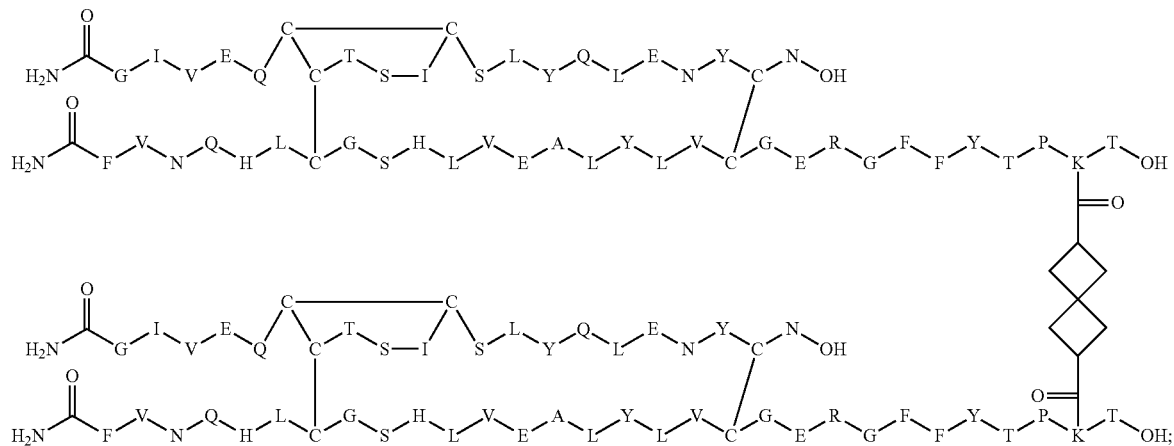
Dimer 17
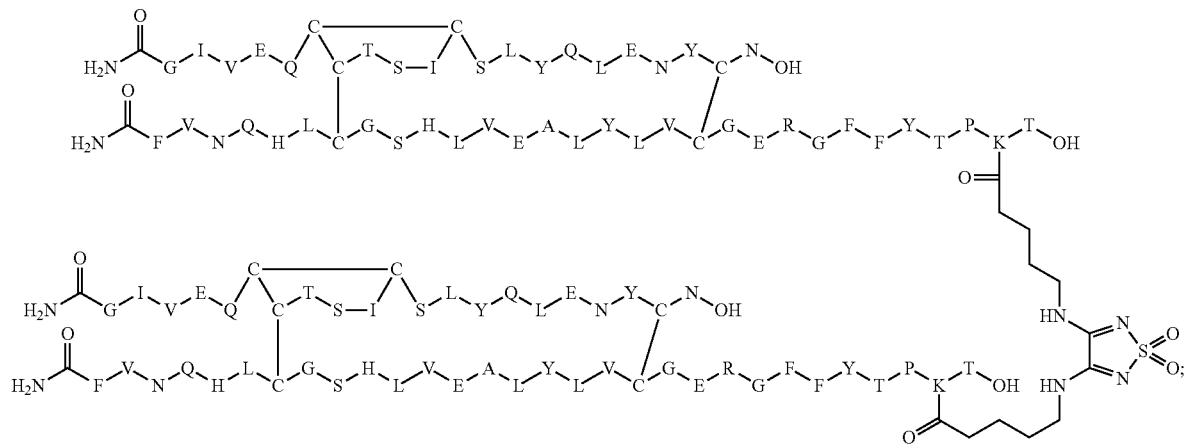
Dimer 18
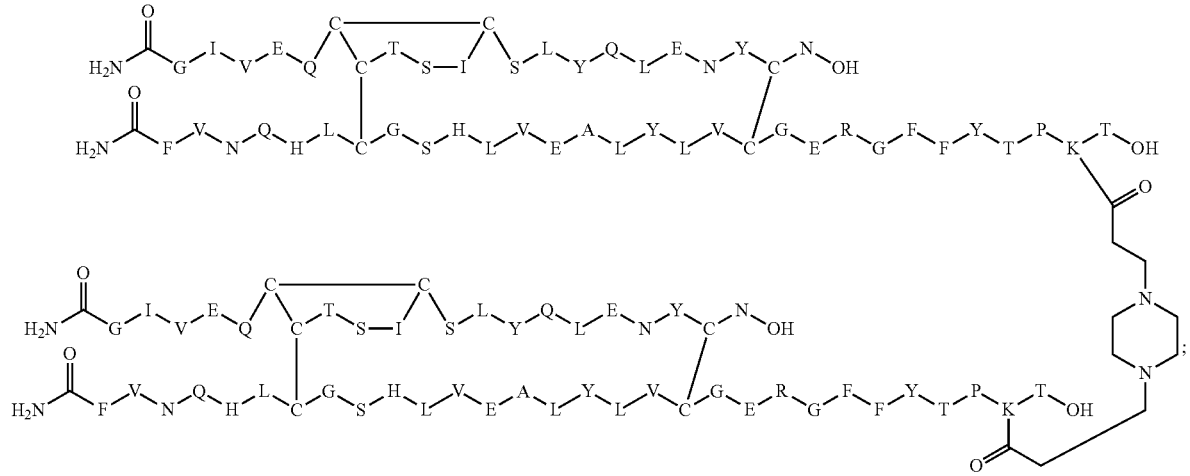

Dimer 19
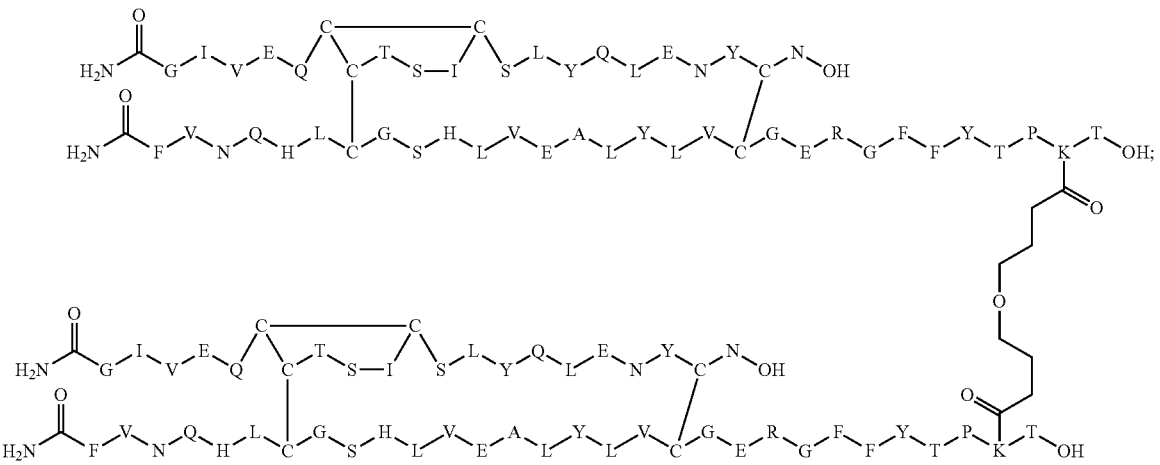
Dimer 20
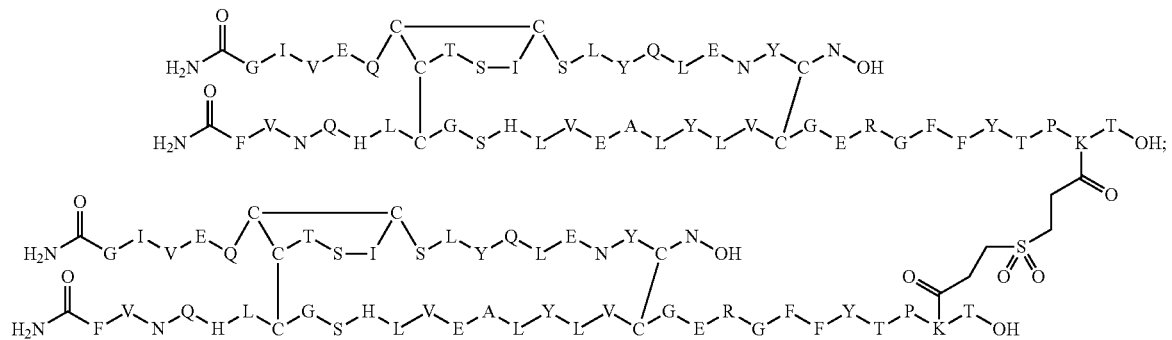
Dimer 21
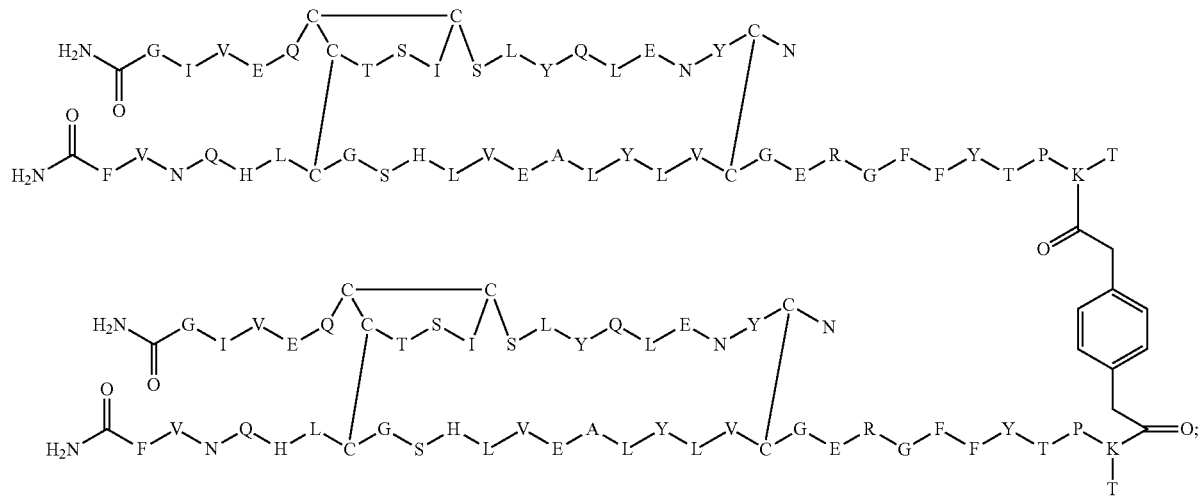

Dimer 22
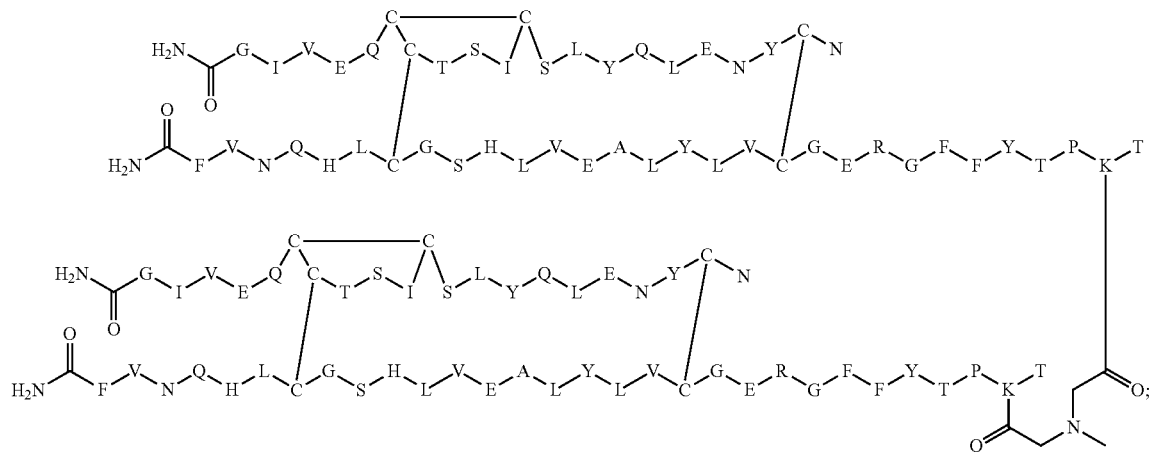
Dimer 23
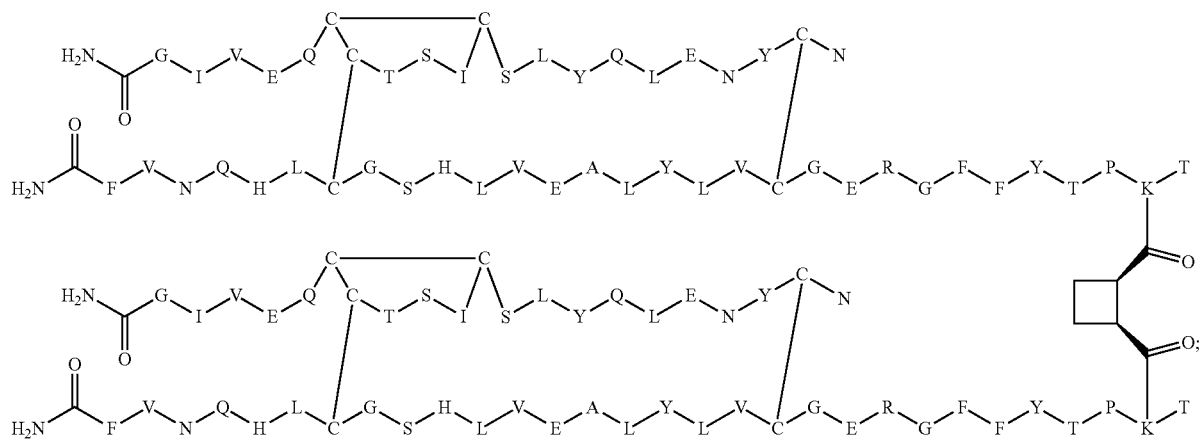
Dimer 24
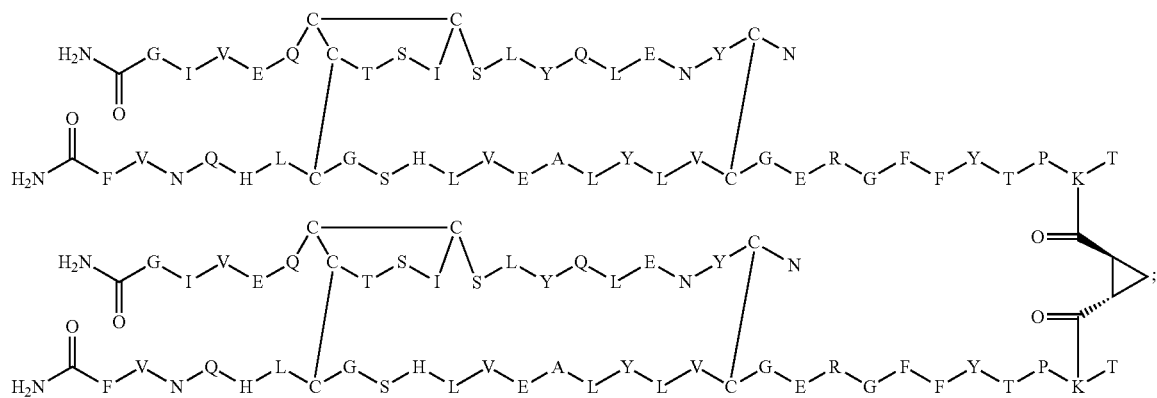

Dimer 25
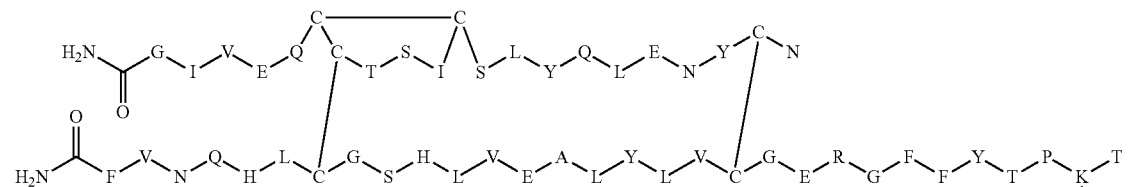
Dimer 26
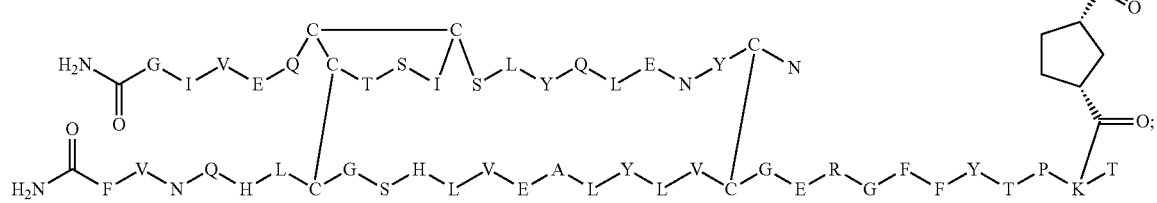
Dimer 27
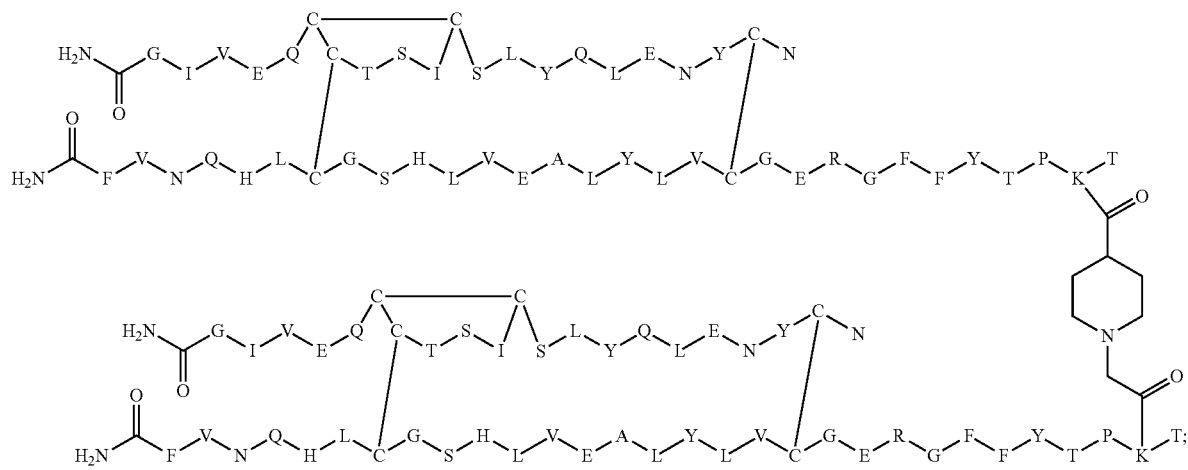

-continued
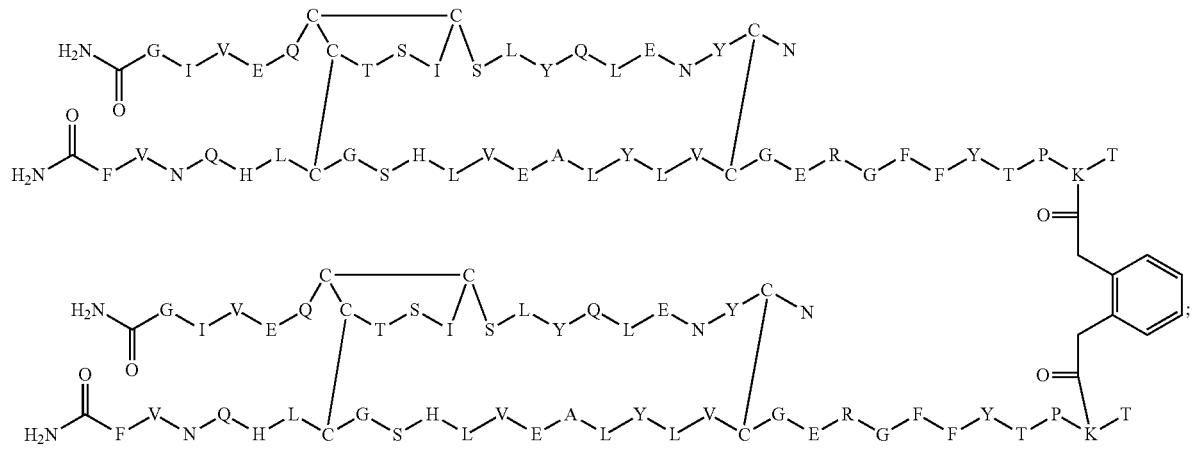
Dimer 28
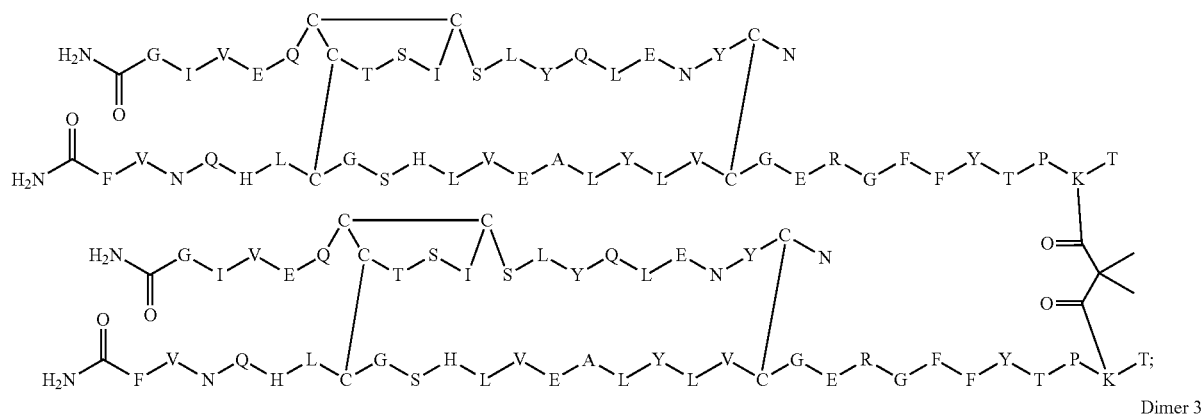
Dimer 29
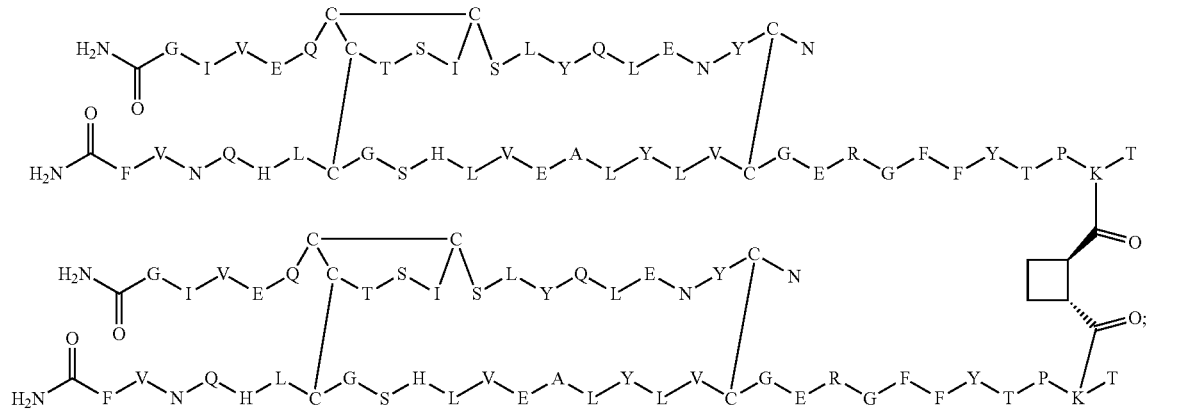
Dimer 30
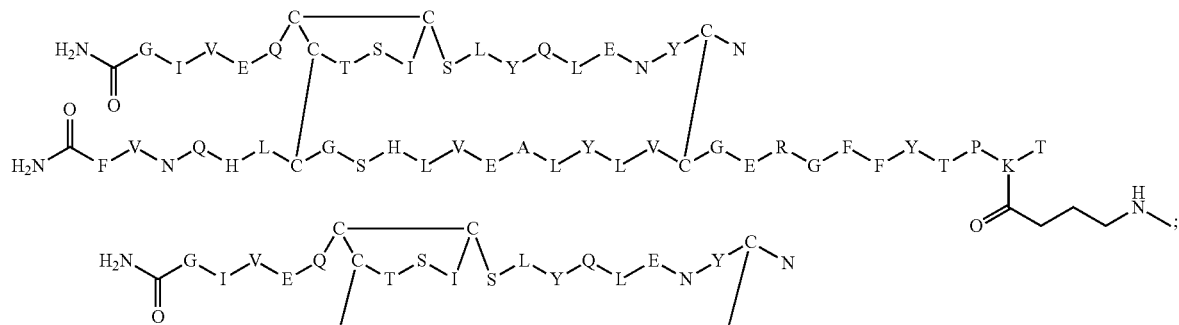
Dimer 31

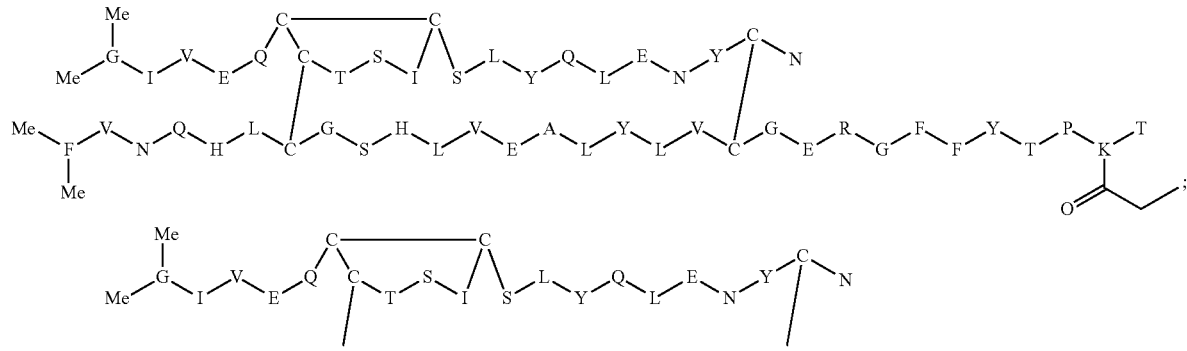
Dimer 32
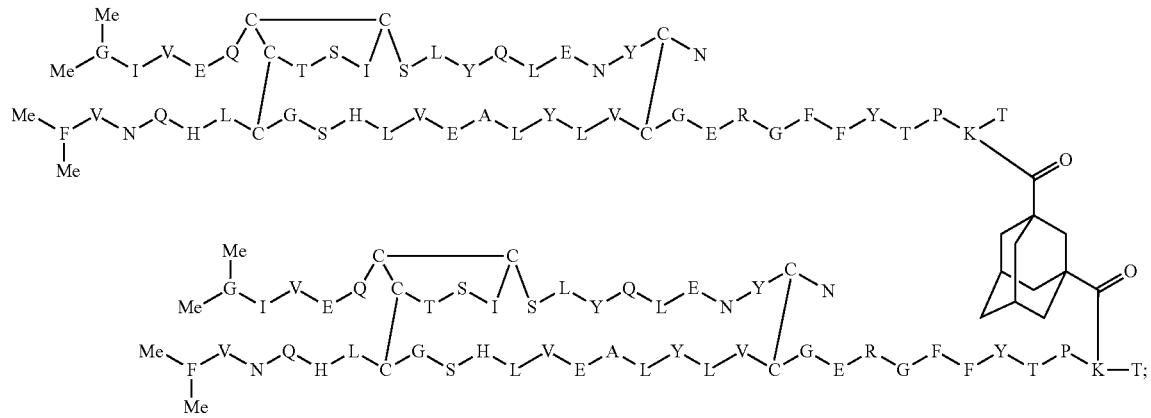
Dimer 35
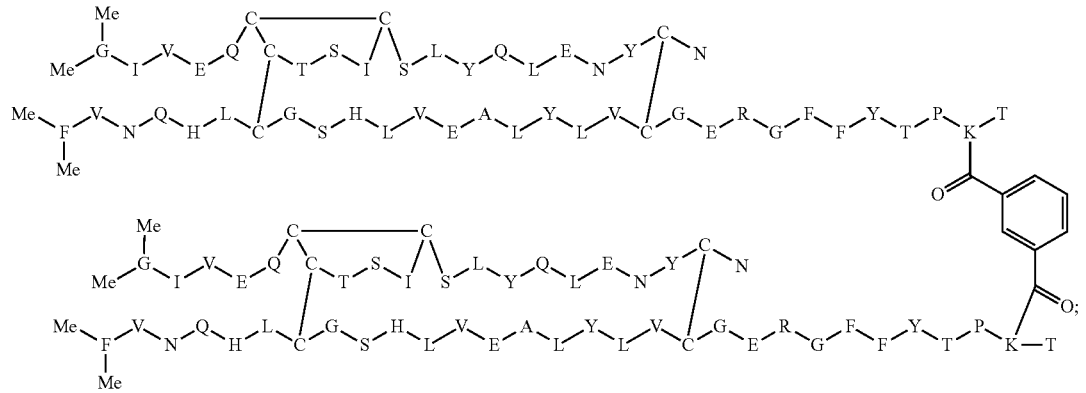
Dimer 36

Dimer 37
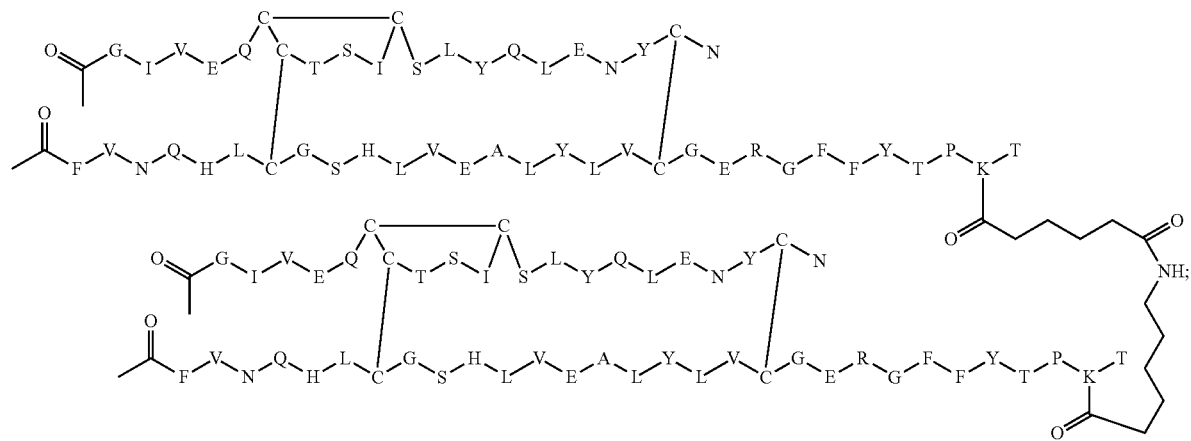
Dimer 38
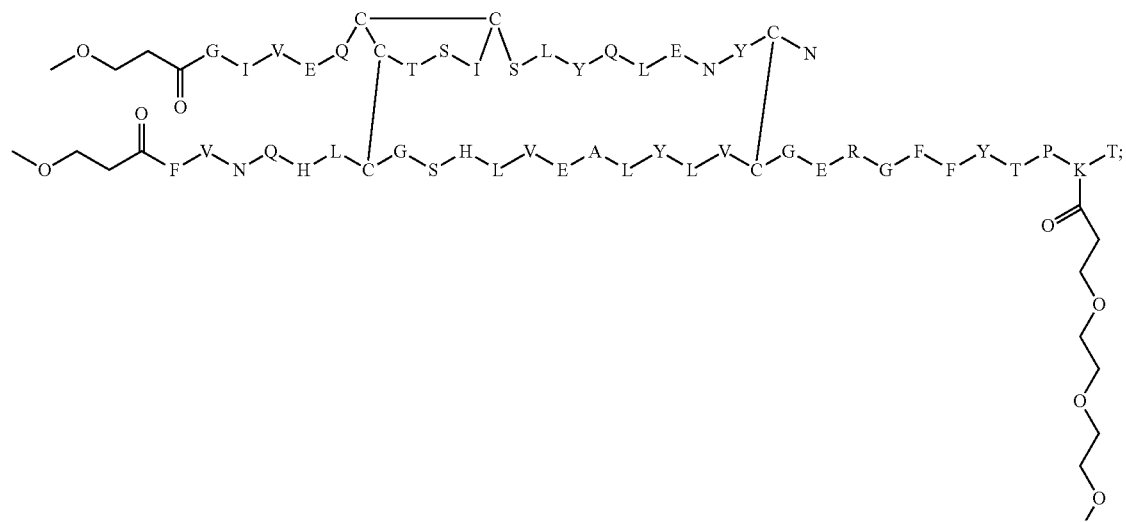
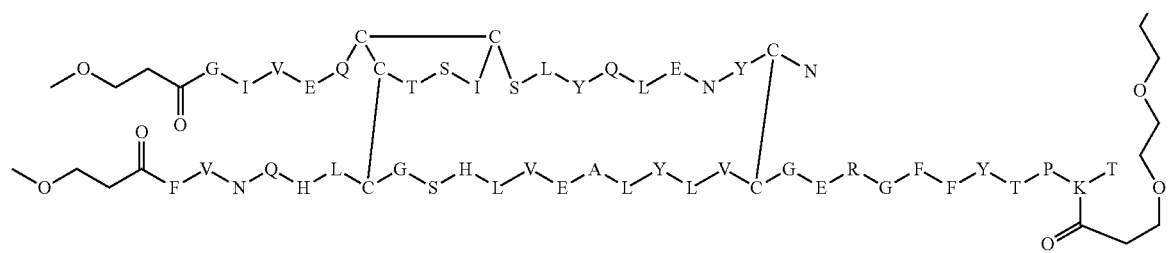

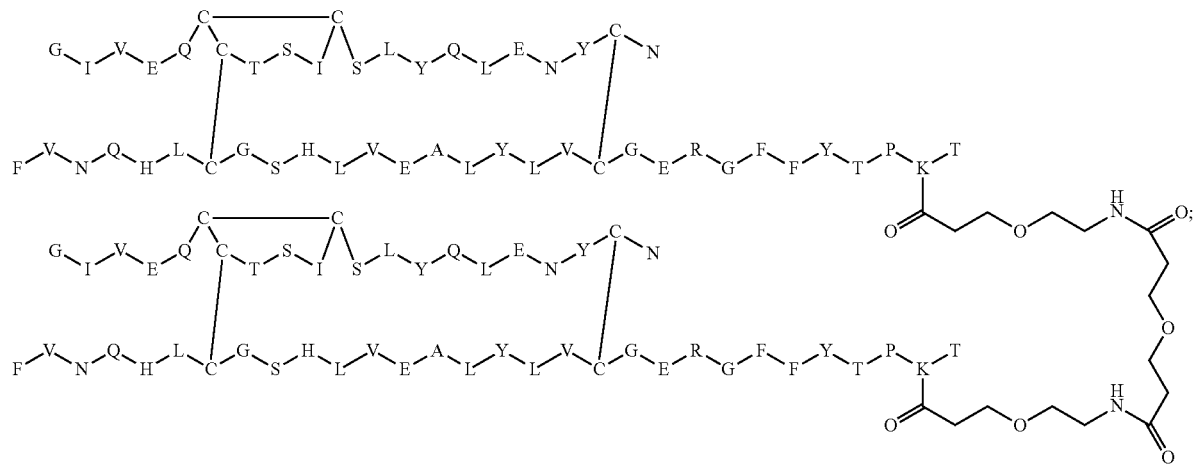
Dimer 39
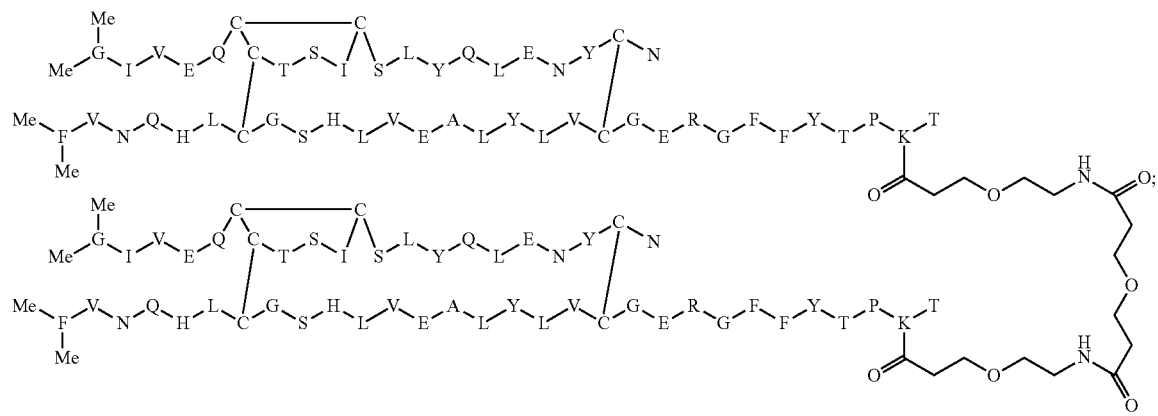
Dimer 40
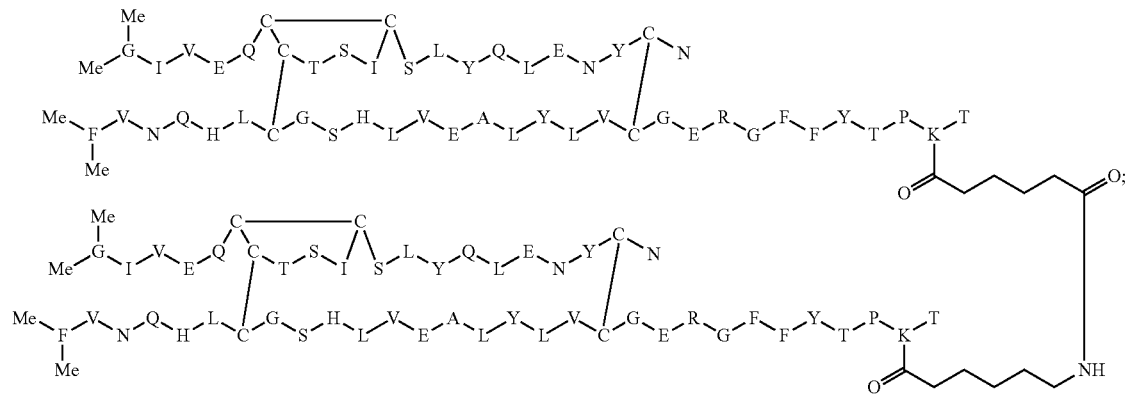
Dimer 41

-continued
Dimer 42
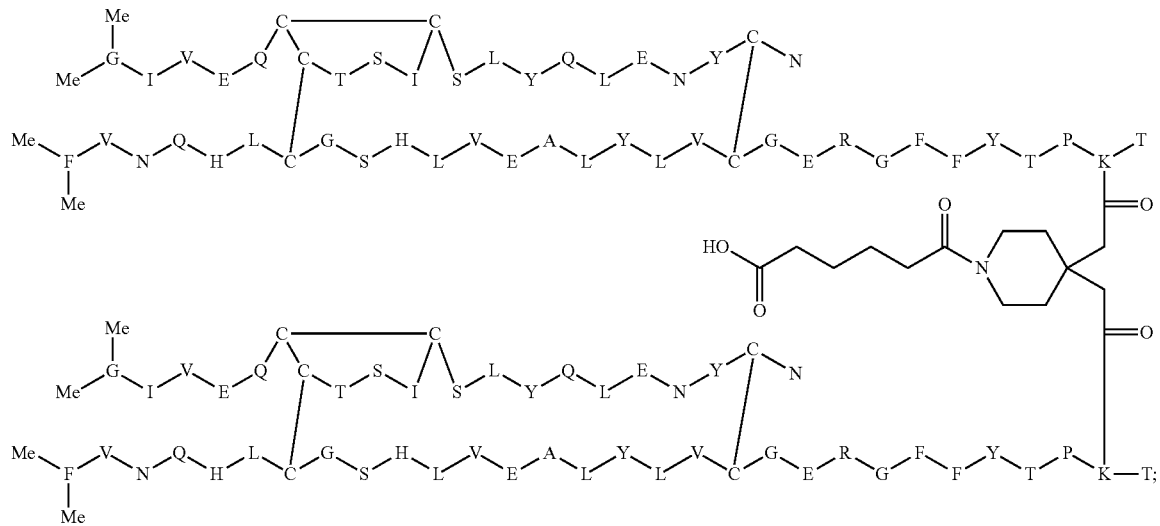
Dimer 43
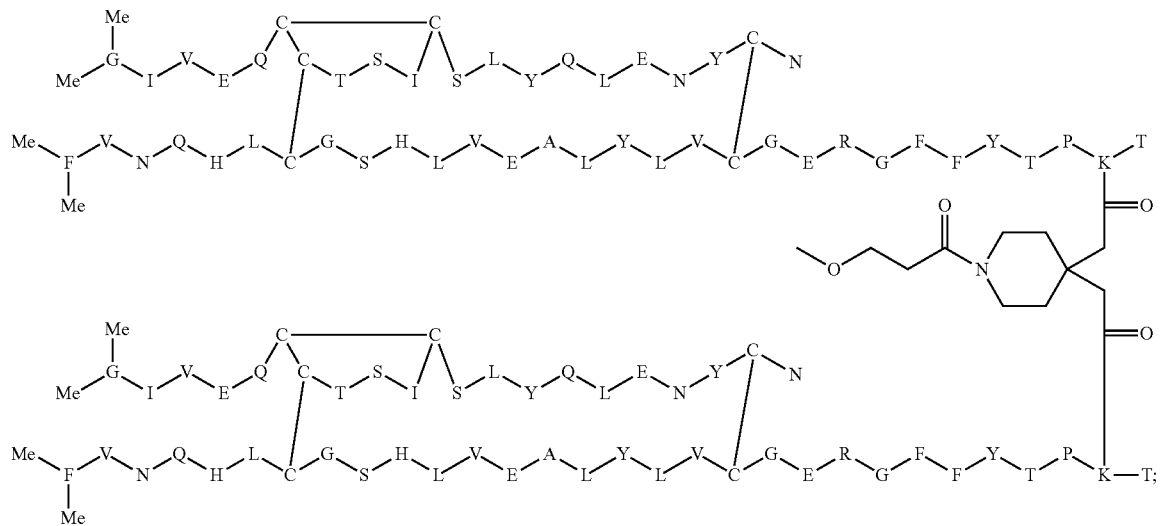
Dimer 44
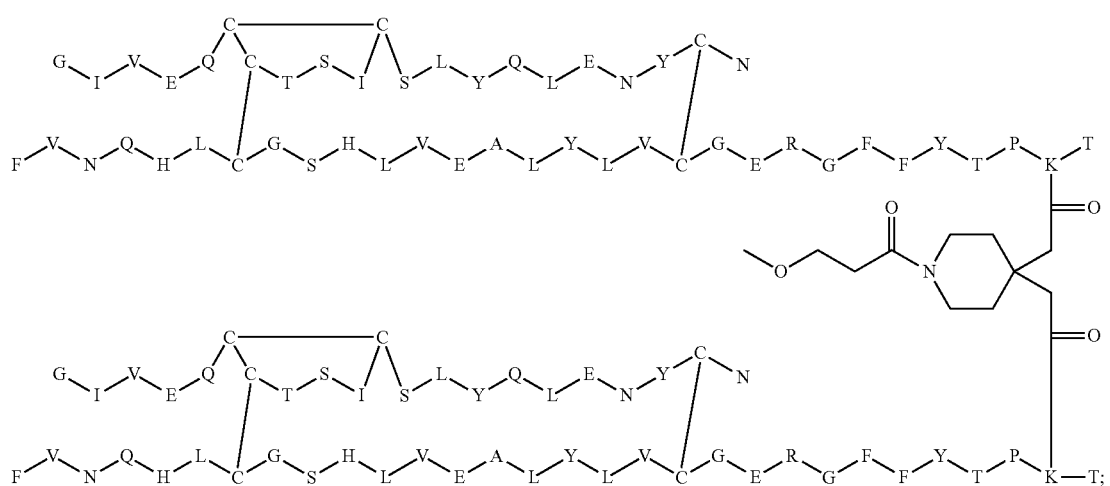

-continued
Dimer 45
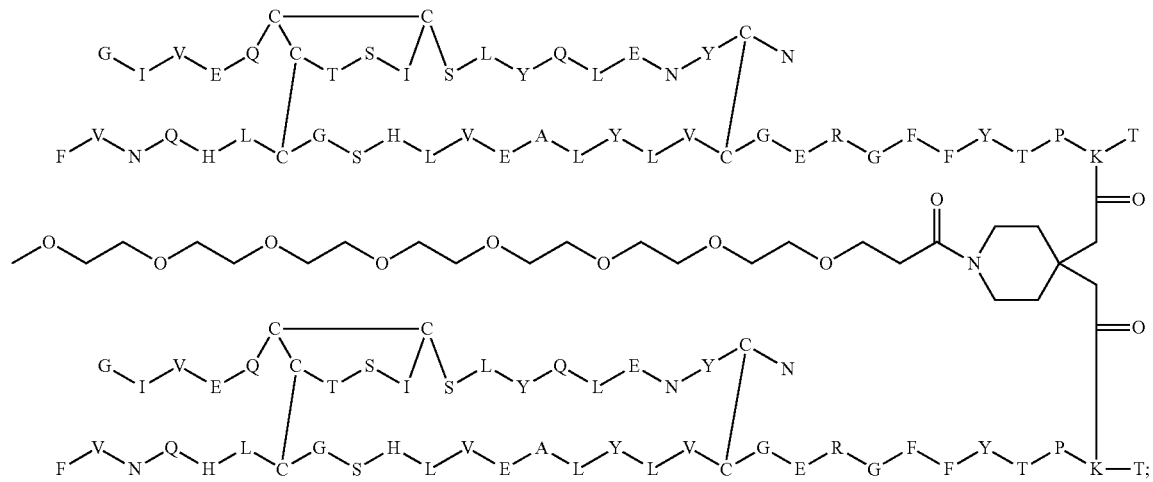
Dimer 46
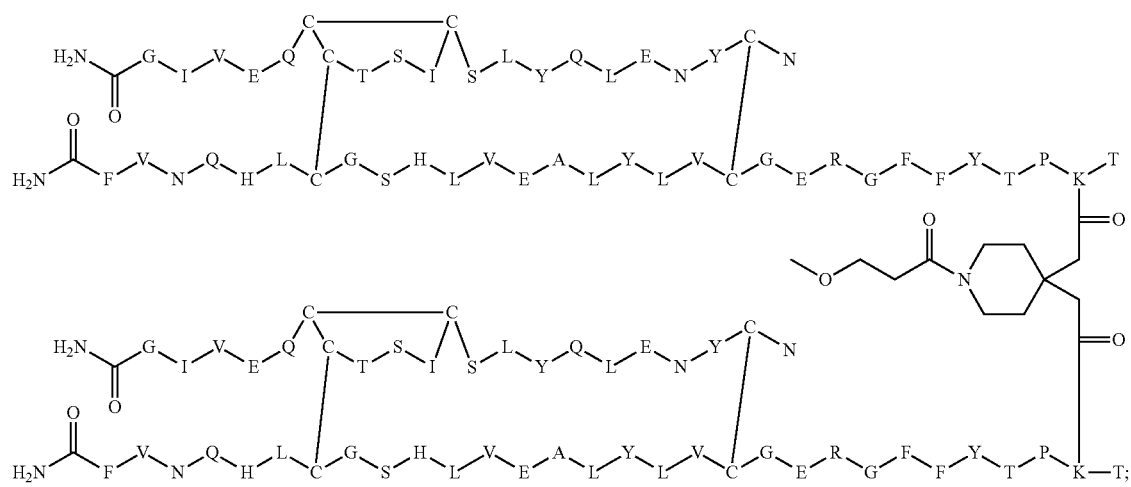
Dimer 47
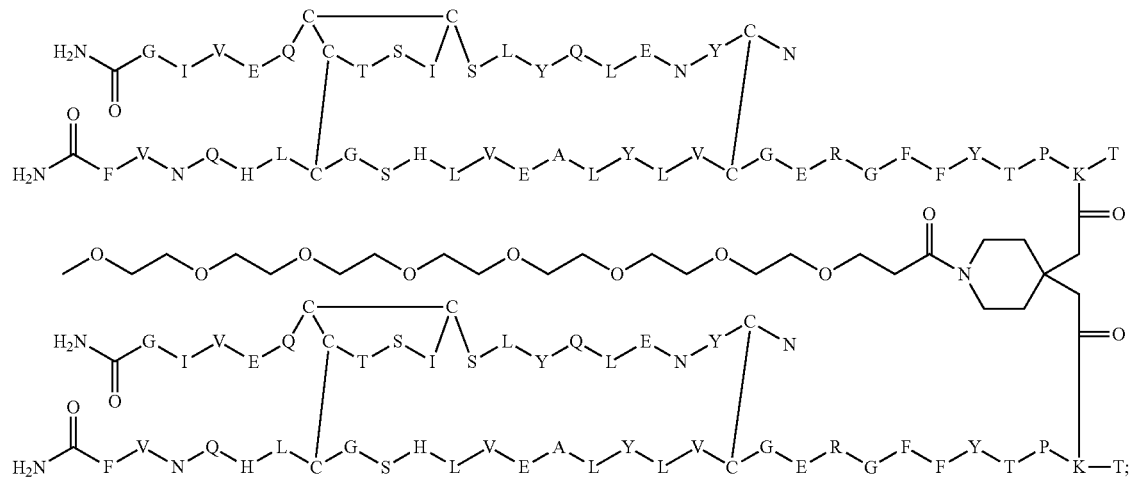

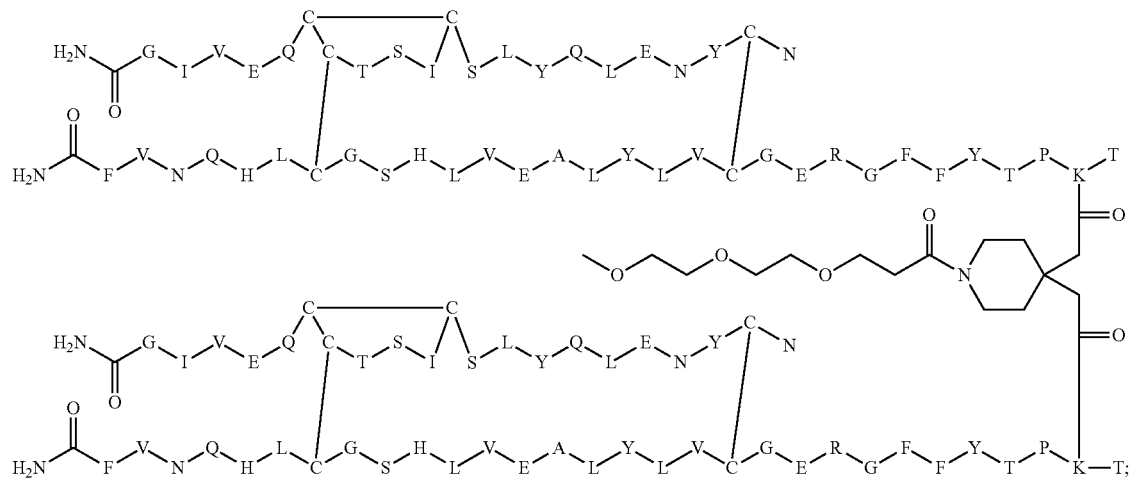
Dimer 48
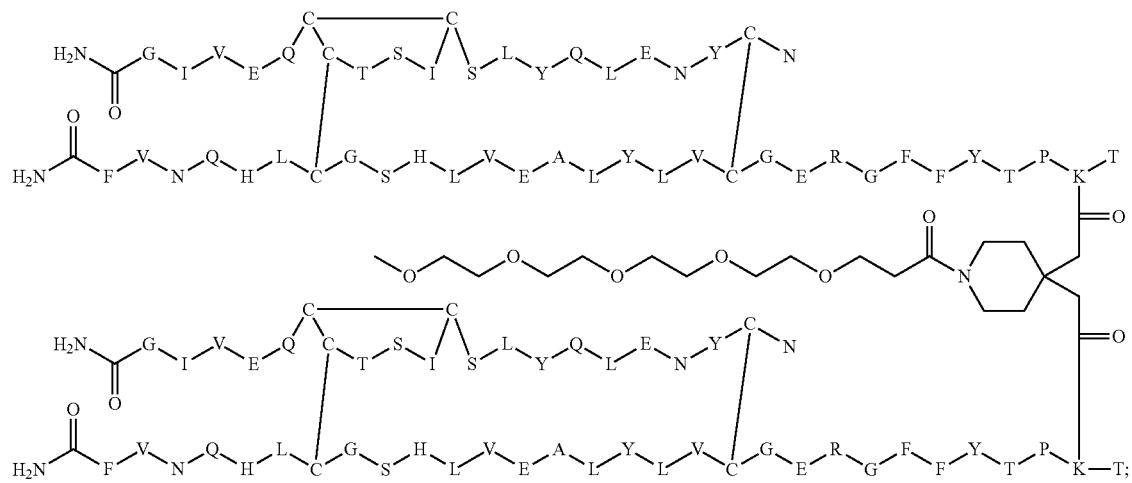
Dimer 49
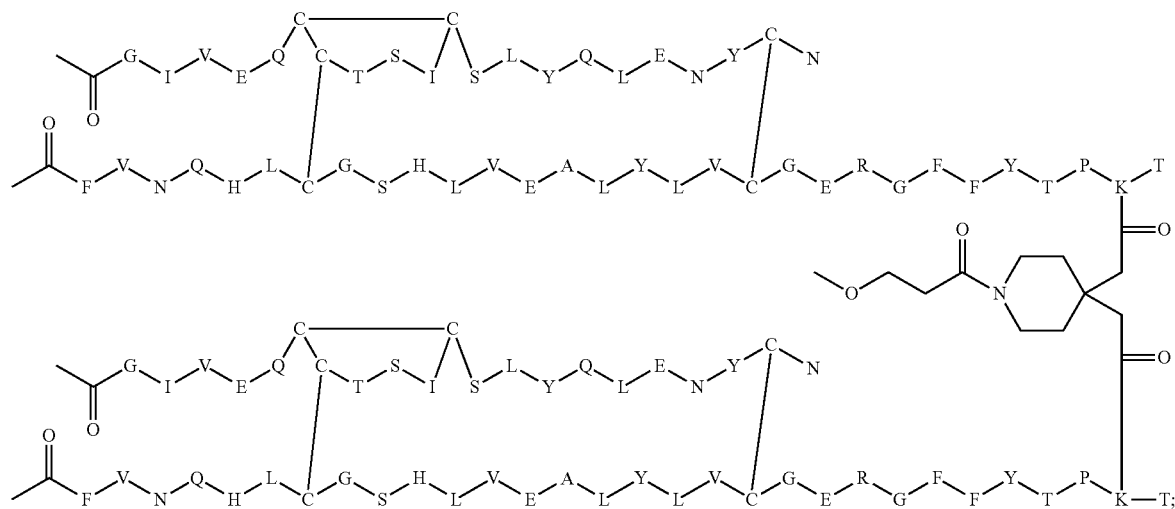
Dimer 50

Dimer 51
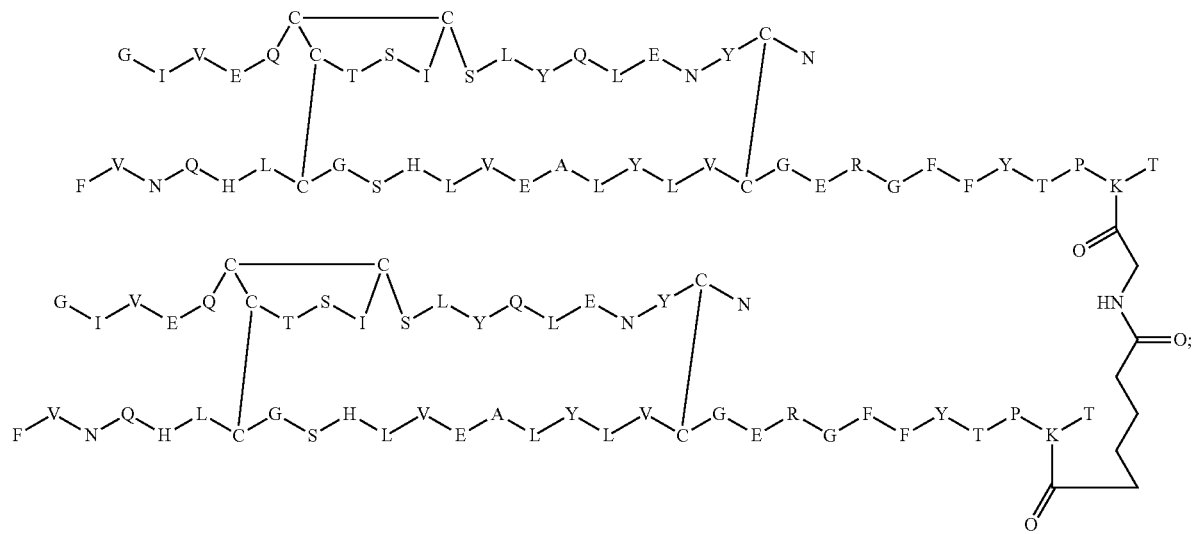
Dimer 52
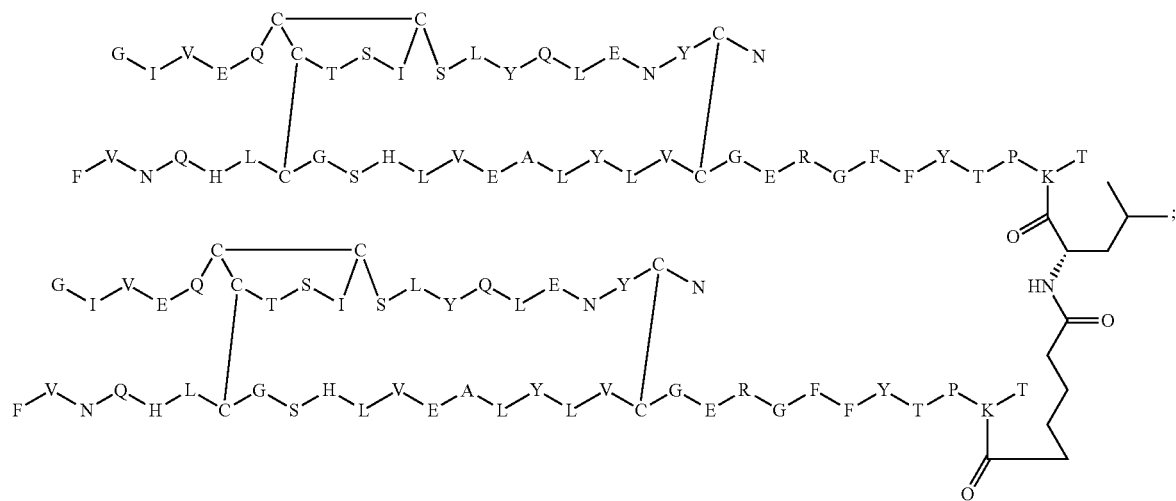

Dimer 53
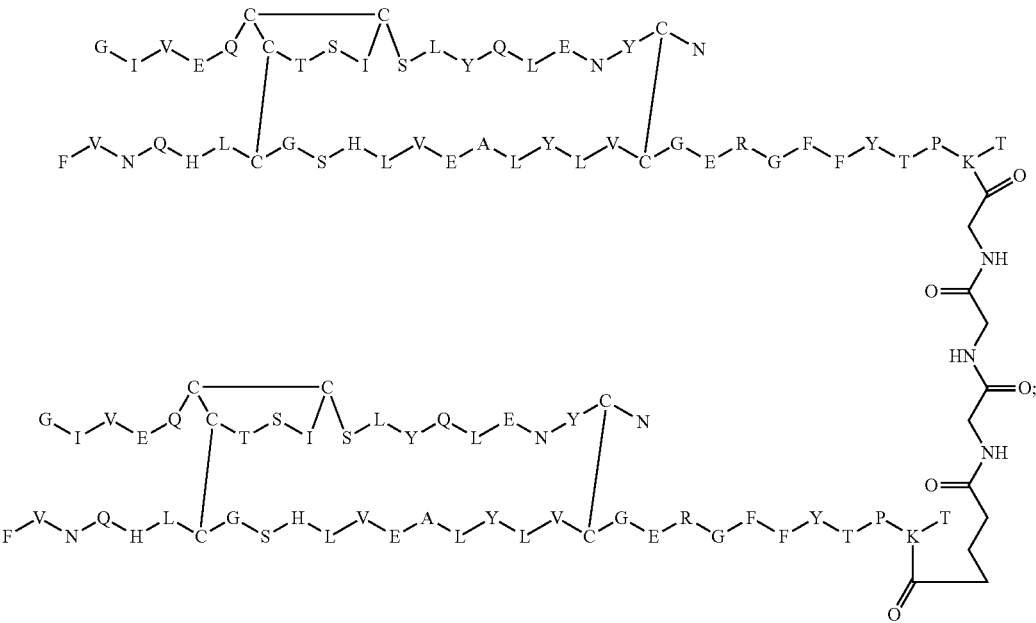
Dimer 54
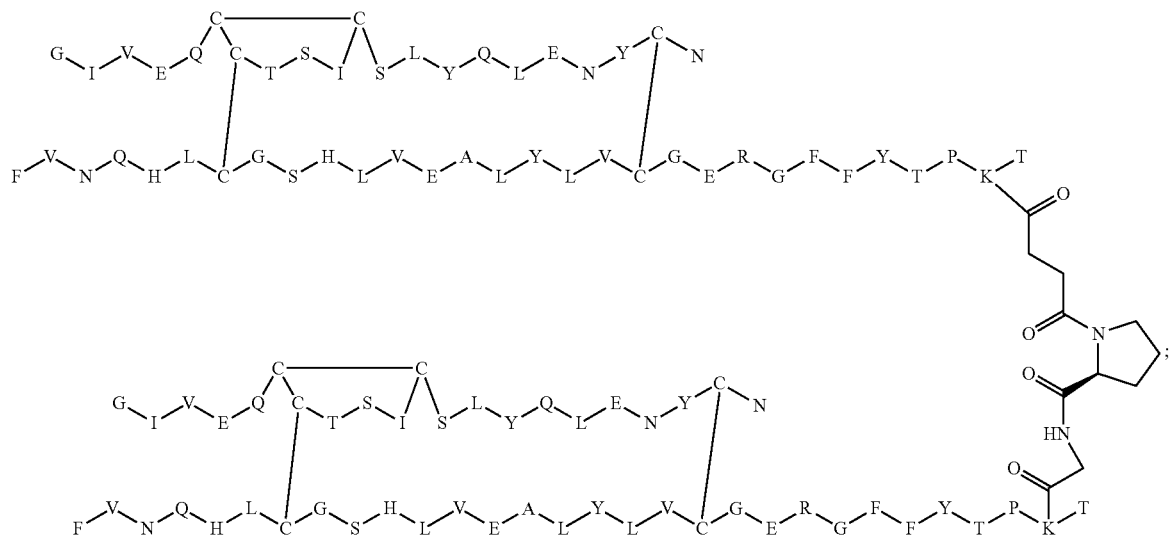

Dimer 55
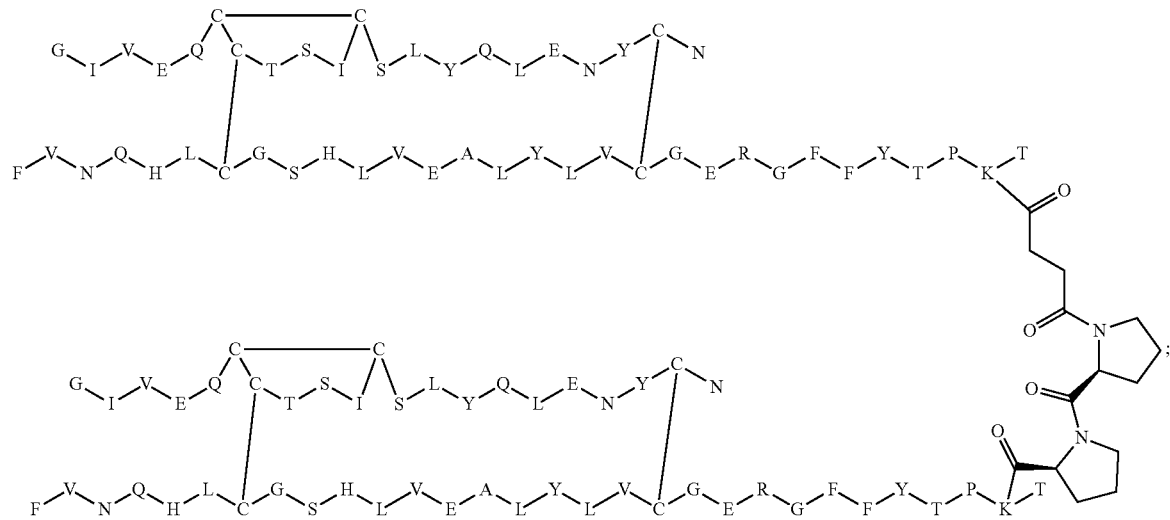
Dimer 56
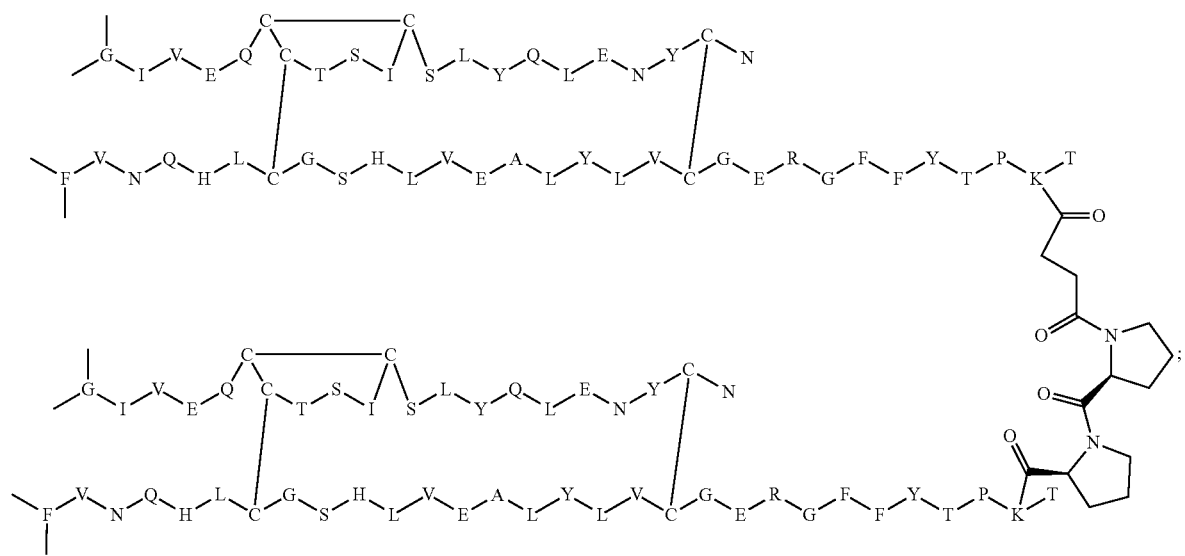

Dimer 57
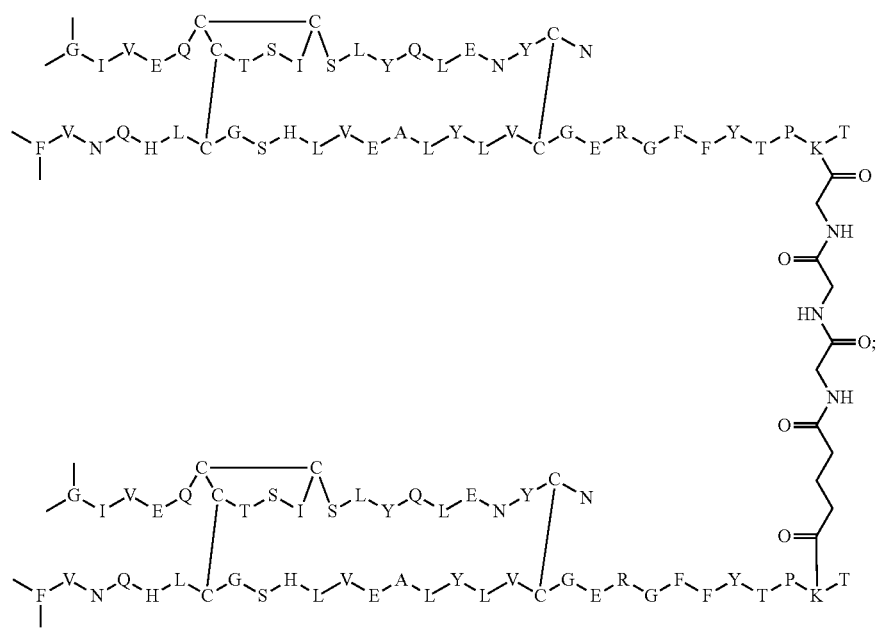
Dimer 58
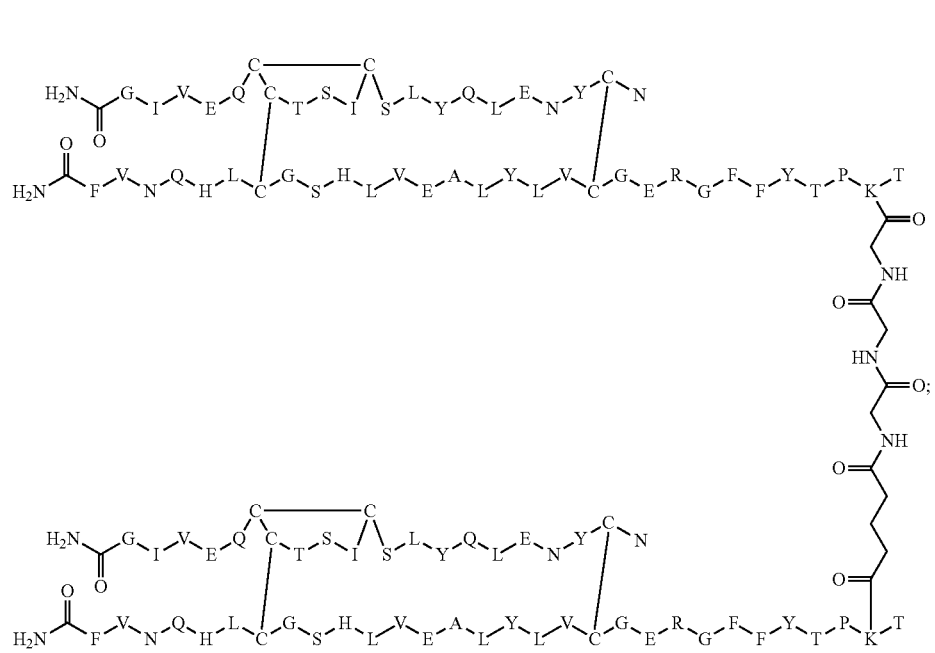

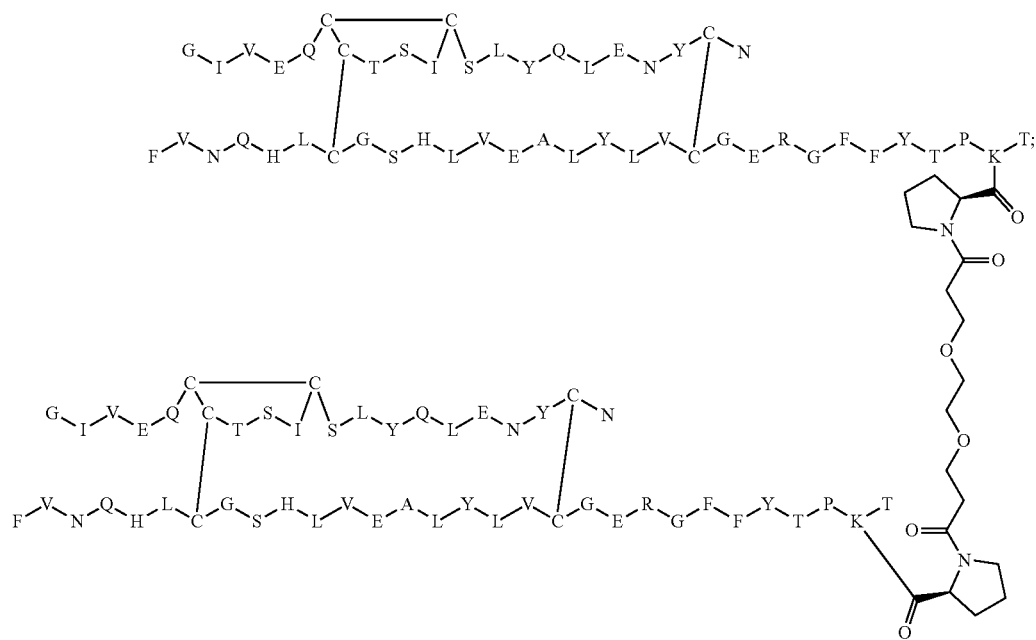
Dimer 59
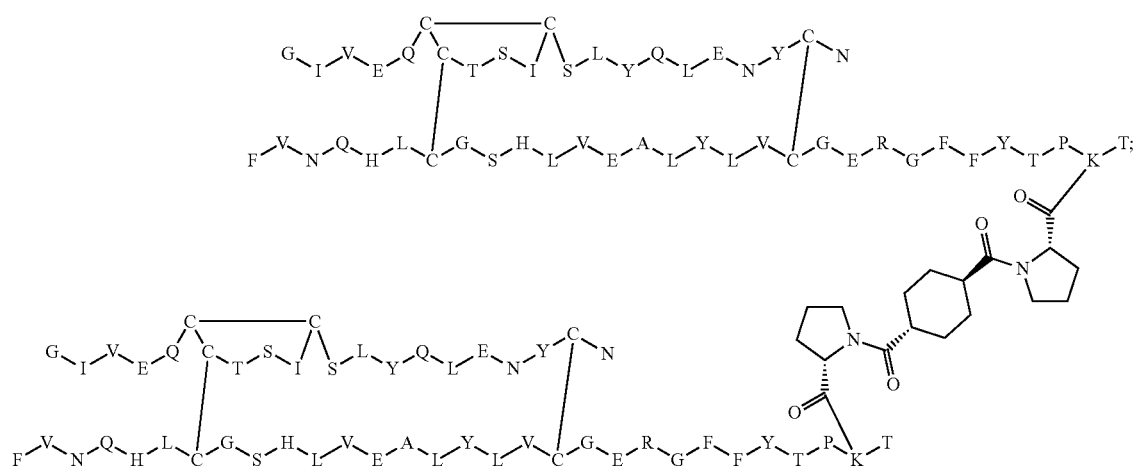
Dimer 60

-continued
Dimer 61
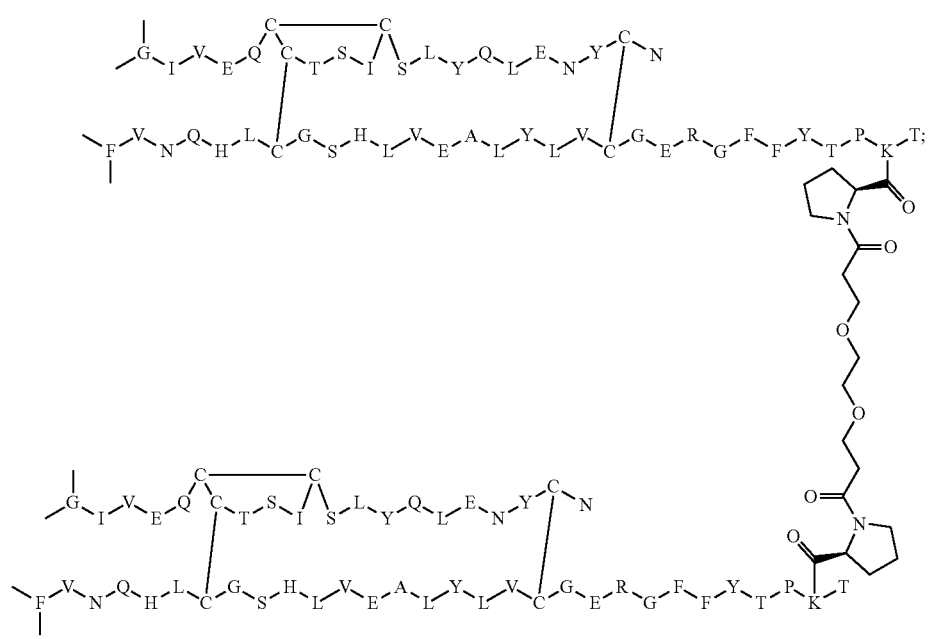
Dimer 62
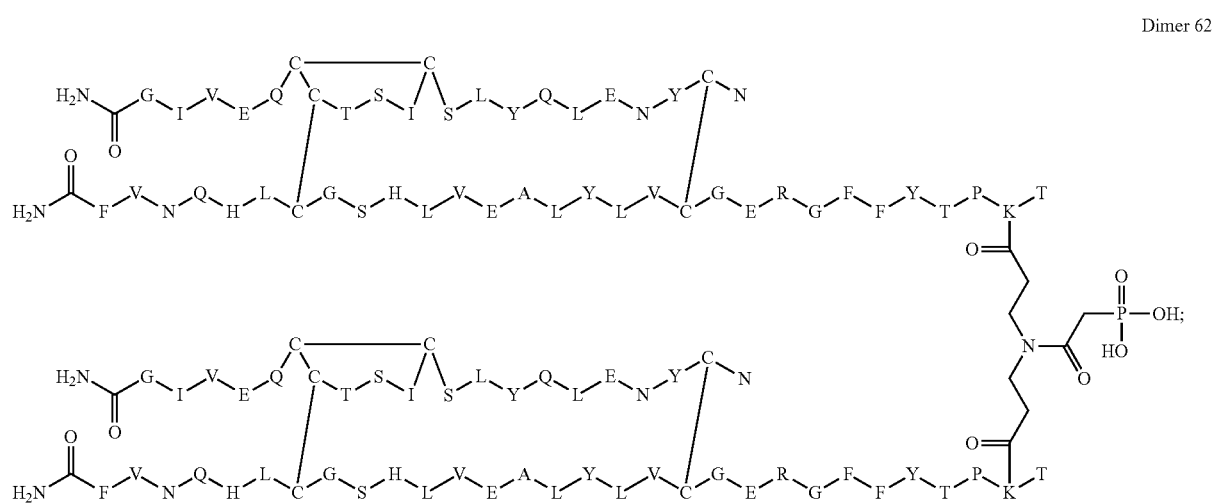

Dimer 64
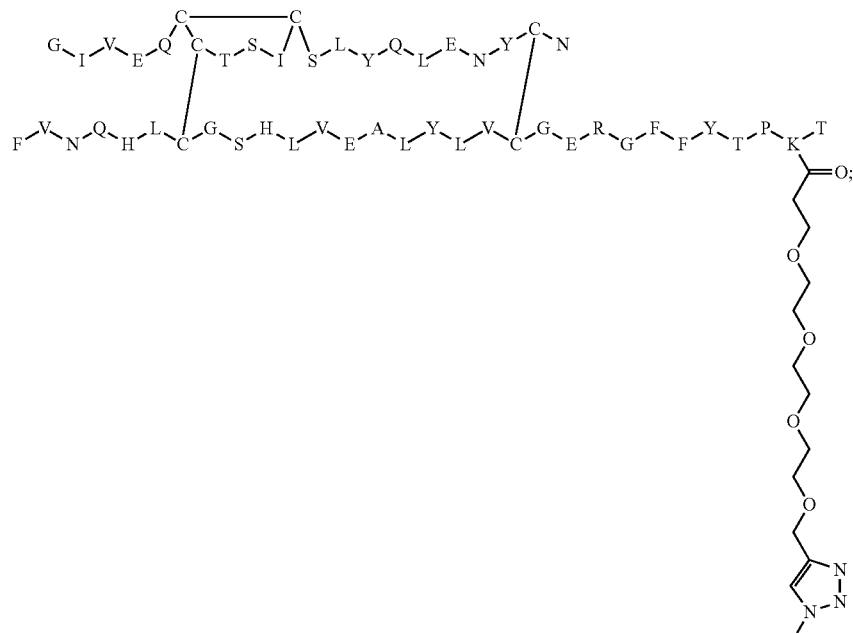
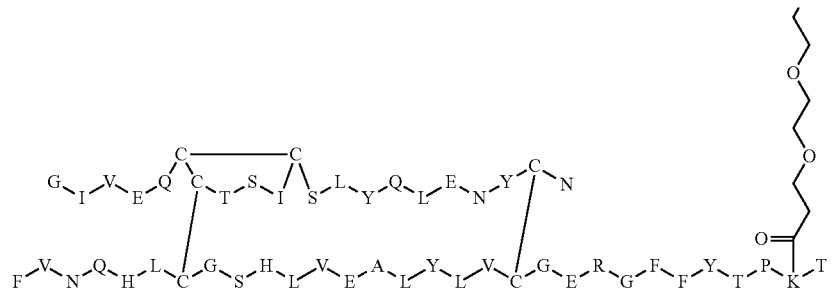
Dimer 65
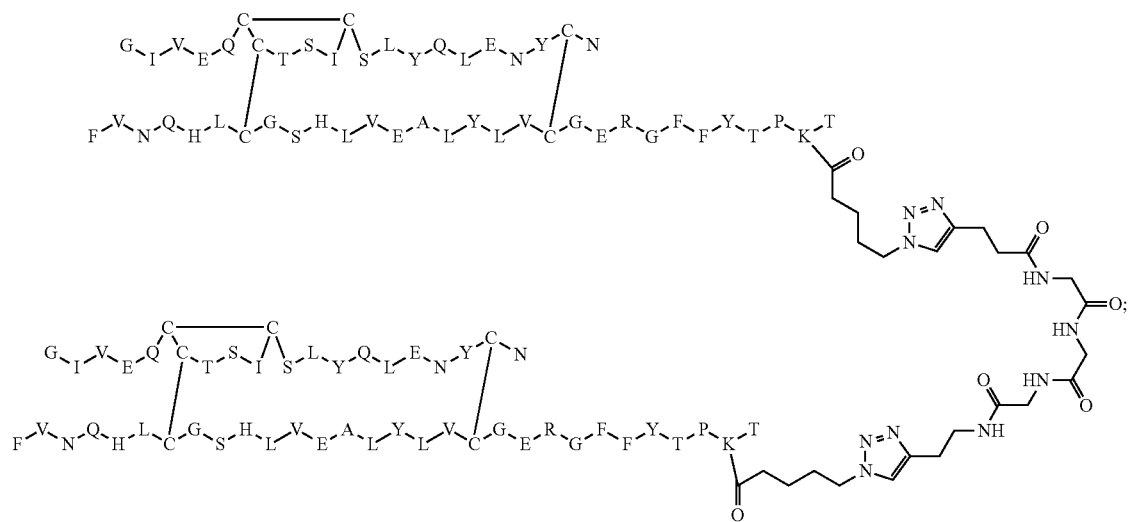

-continued
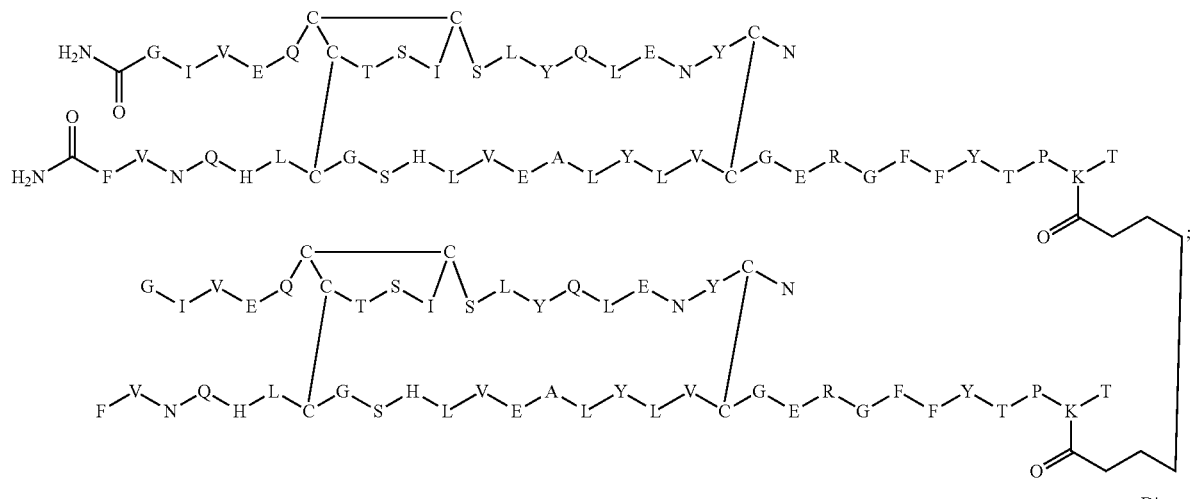
Dimer 66
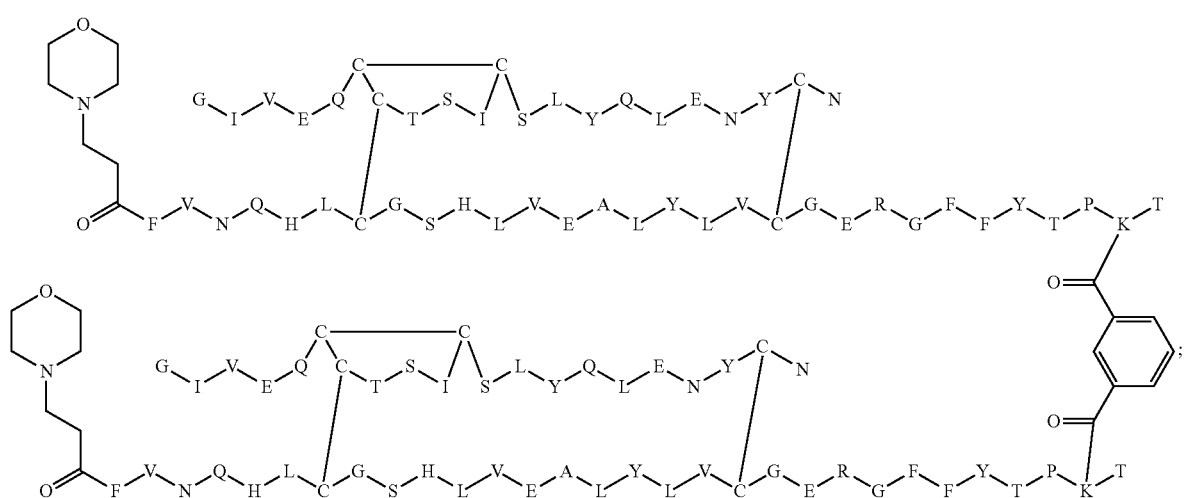
Dimer 69
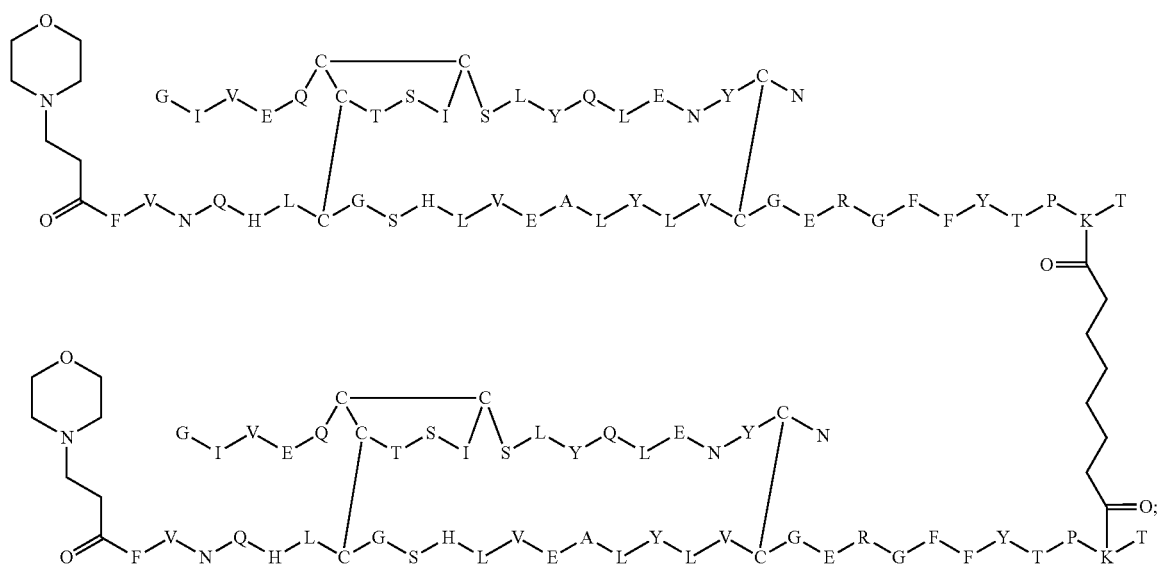
Dimer 70

-continued
Dimer 71
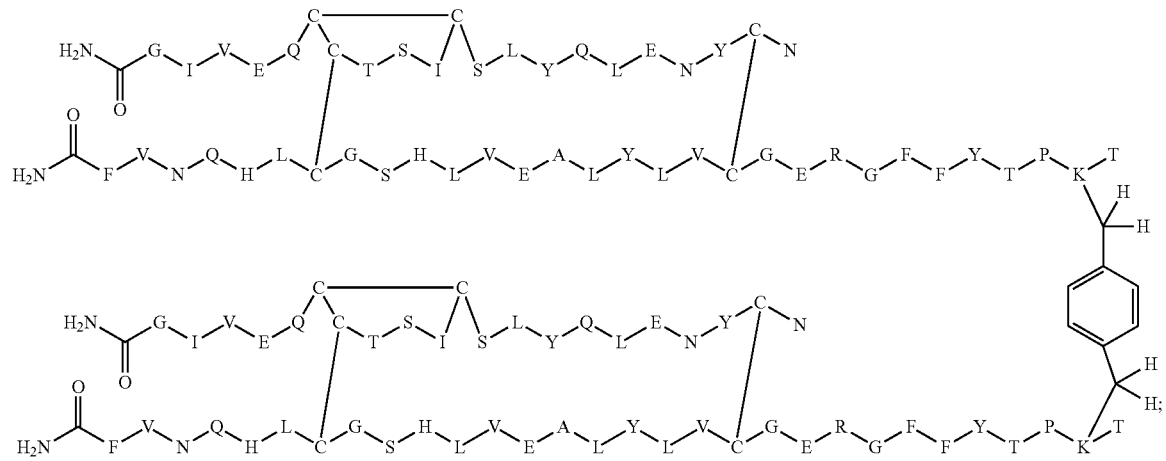
Dimer 72
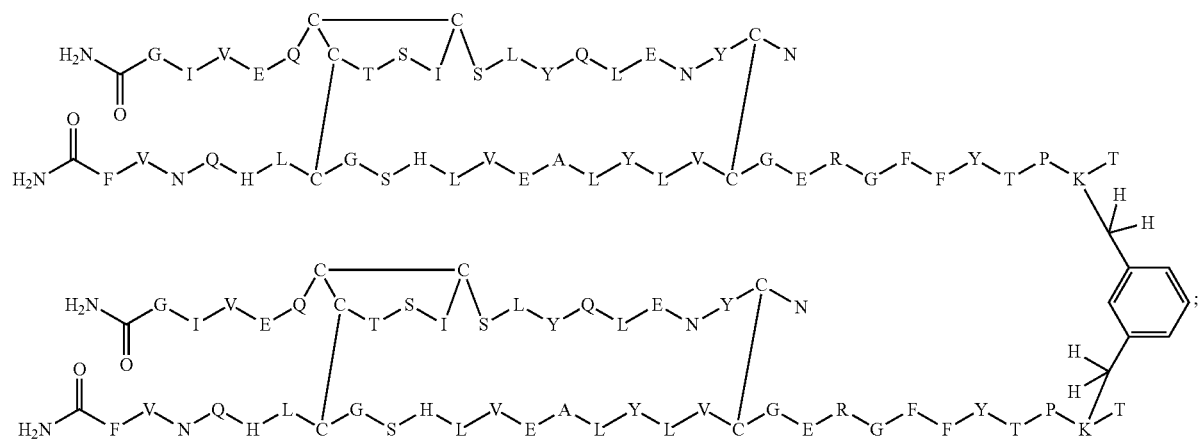
Dimer 73
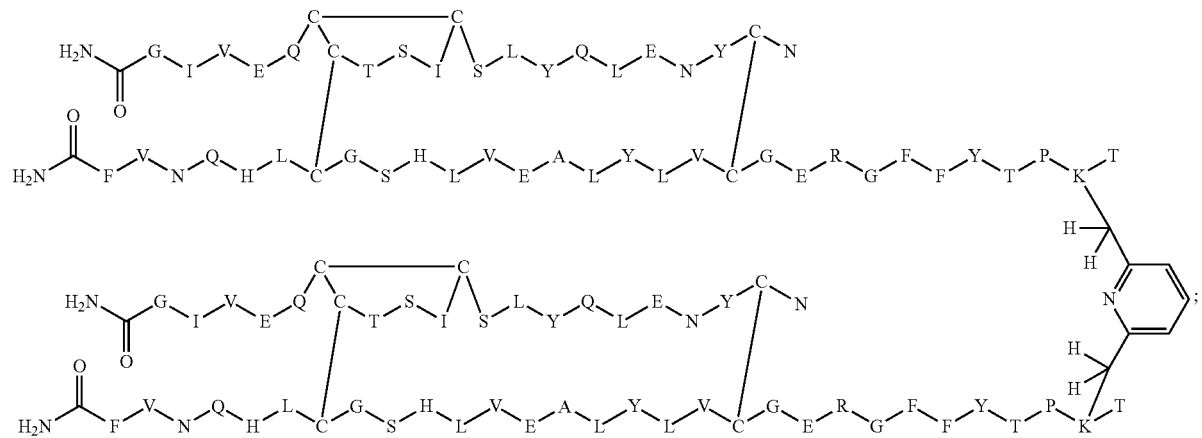

Dimer 74
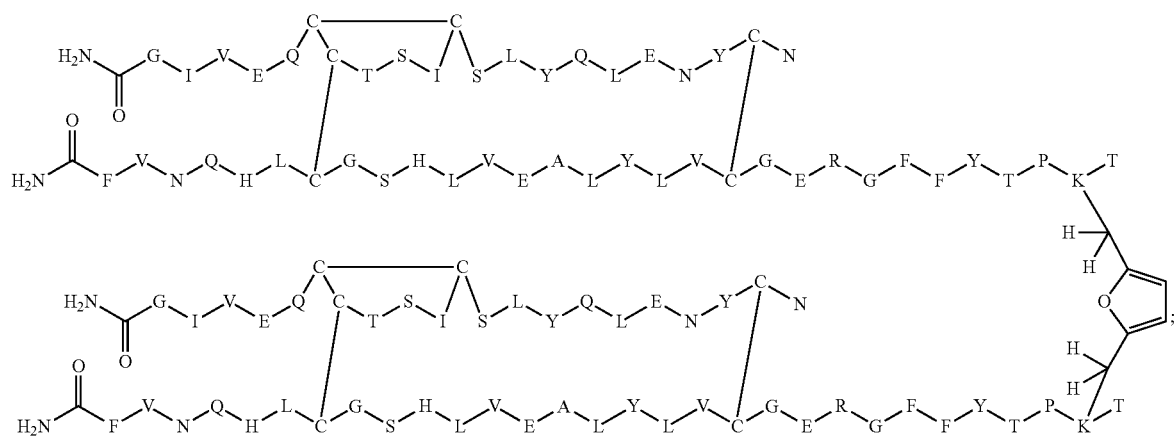
Dimer 75
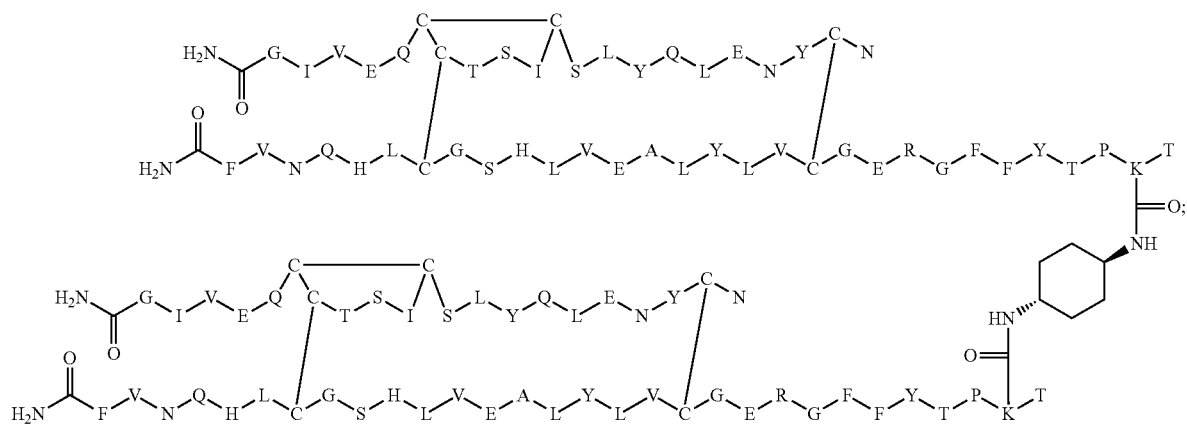
Dimer 76
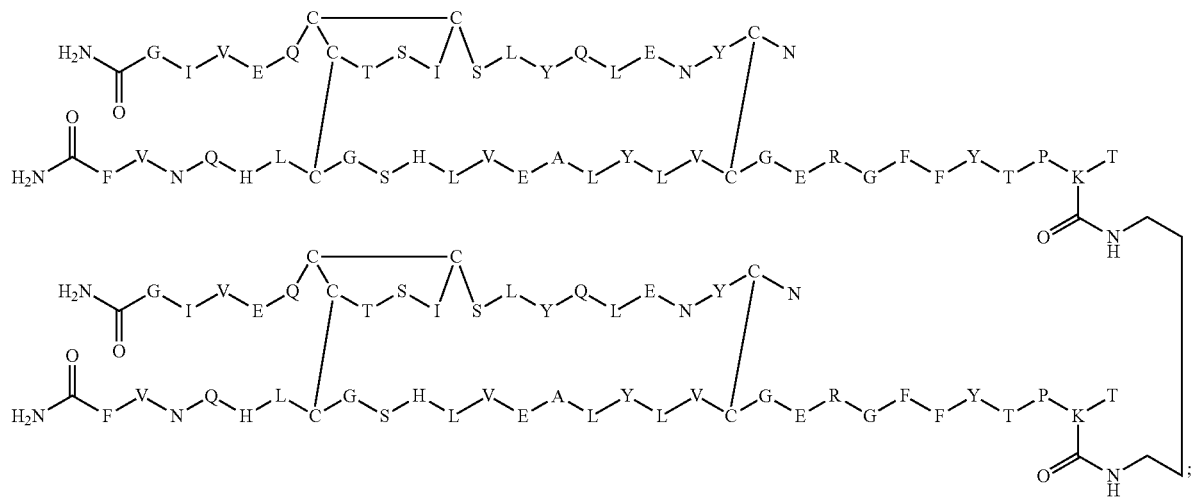

Dimer 77
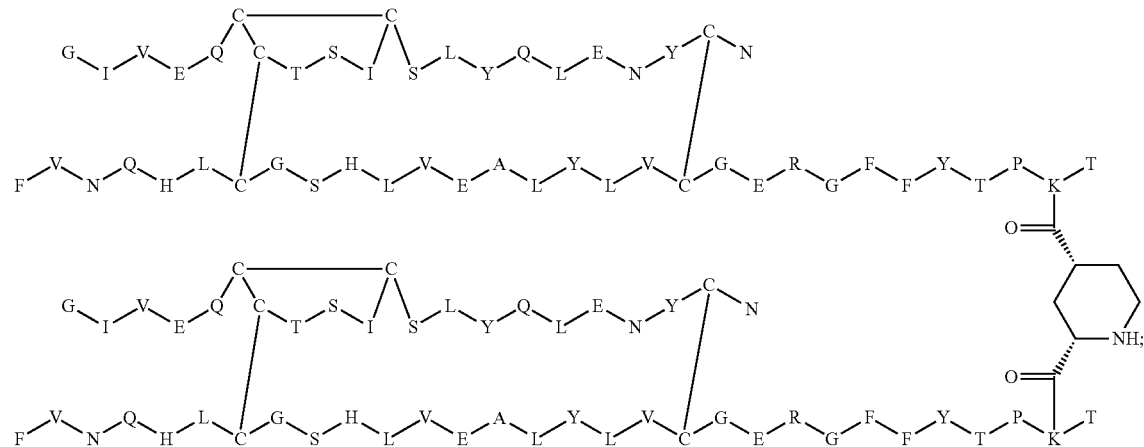
Dimer 78
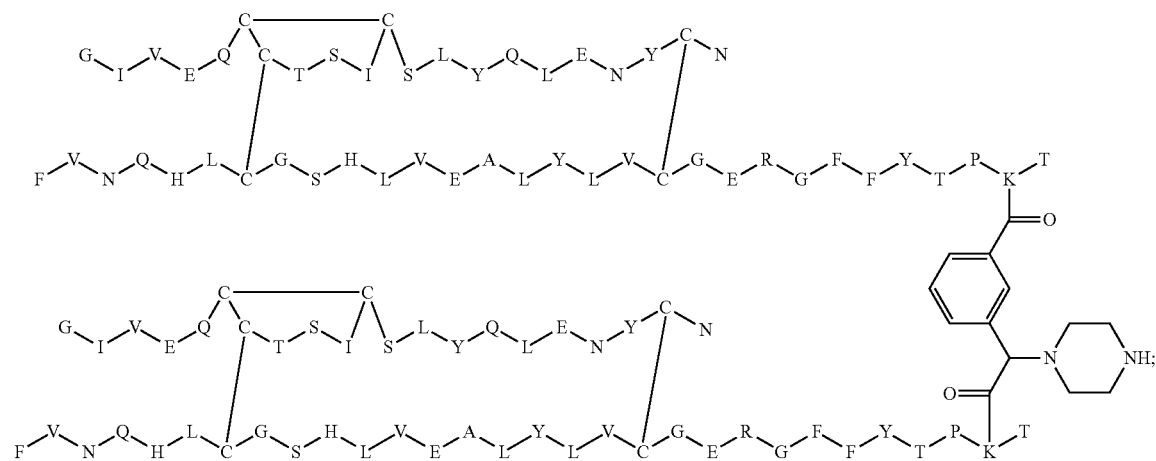
Dimer 79
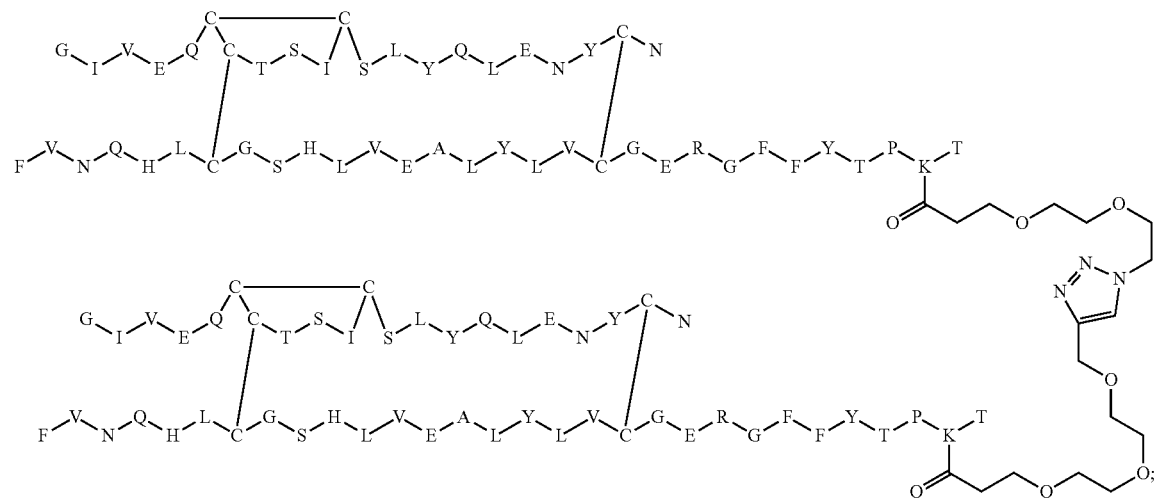

Dimer 82
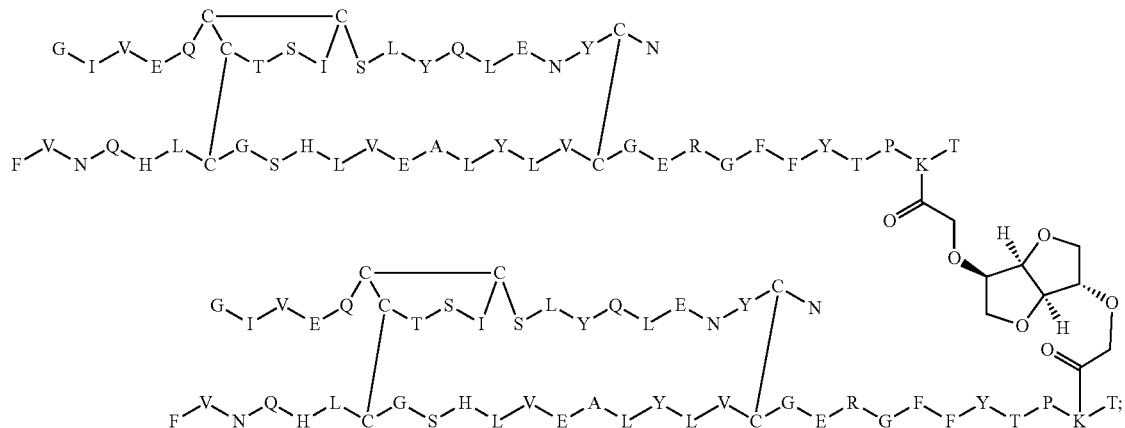
Dimer 83
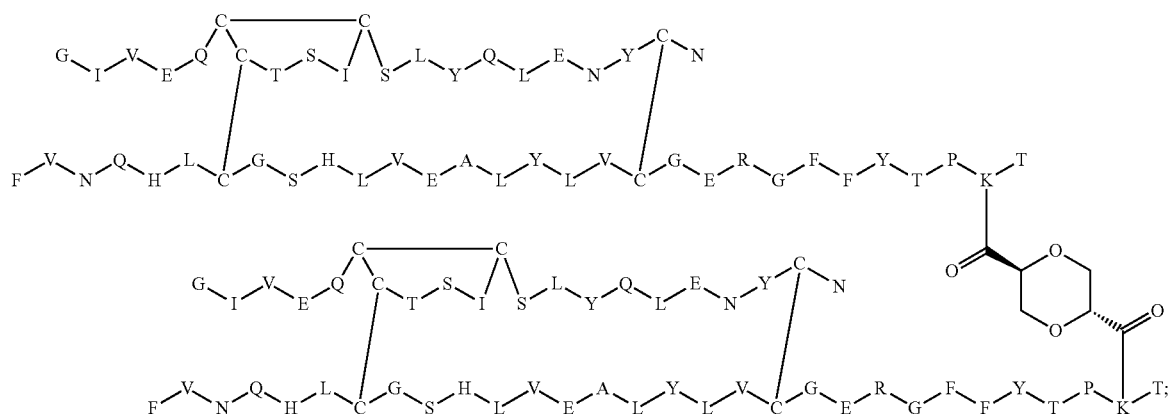
Dimer 84
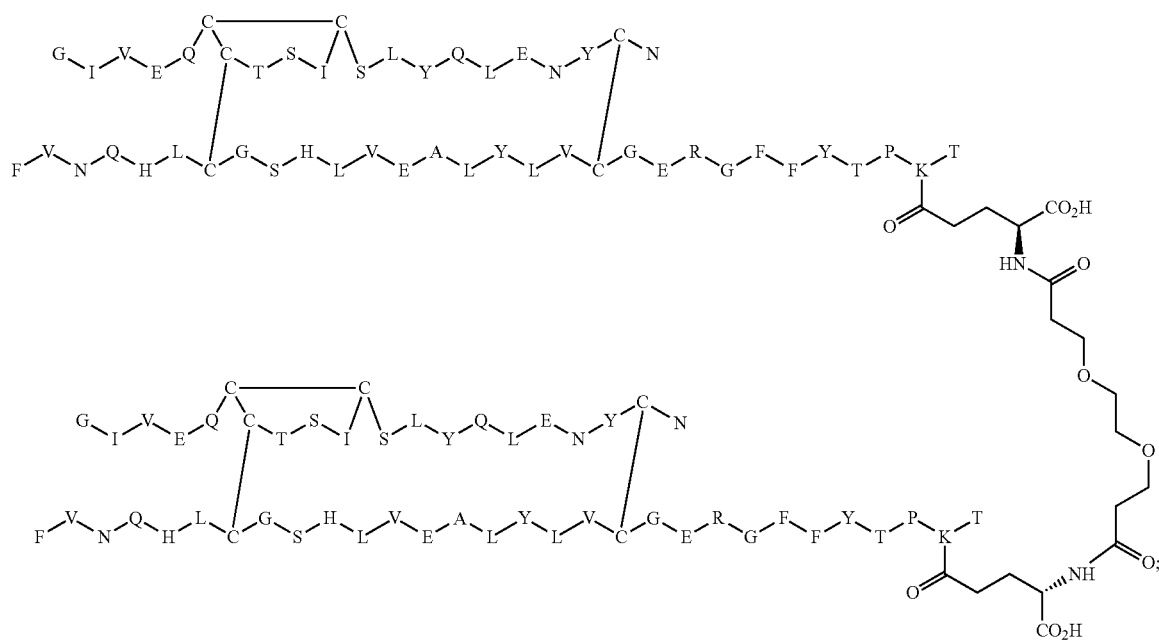

-continued

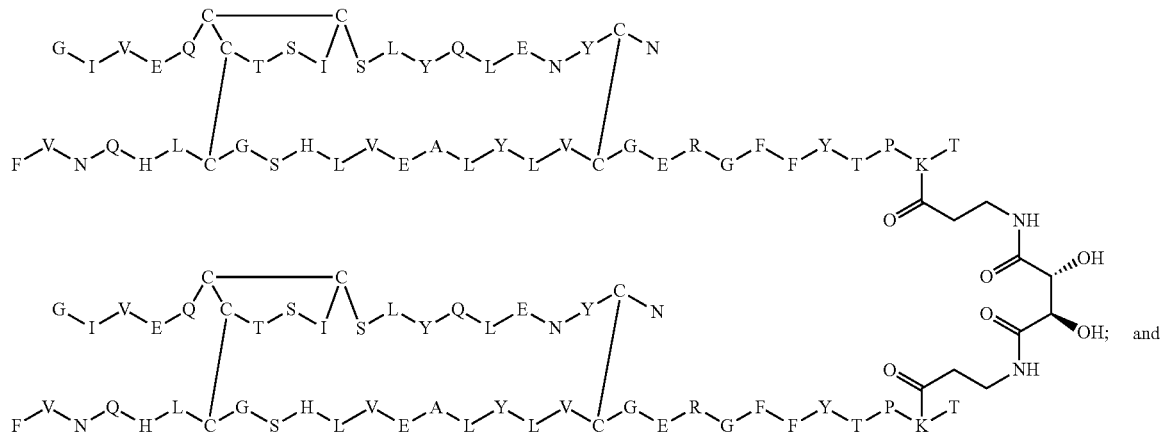

Dimer 85

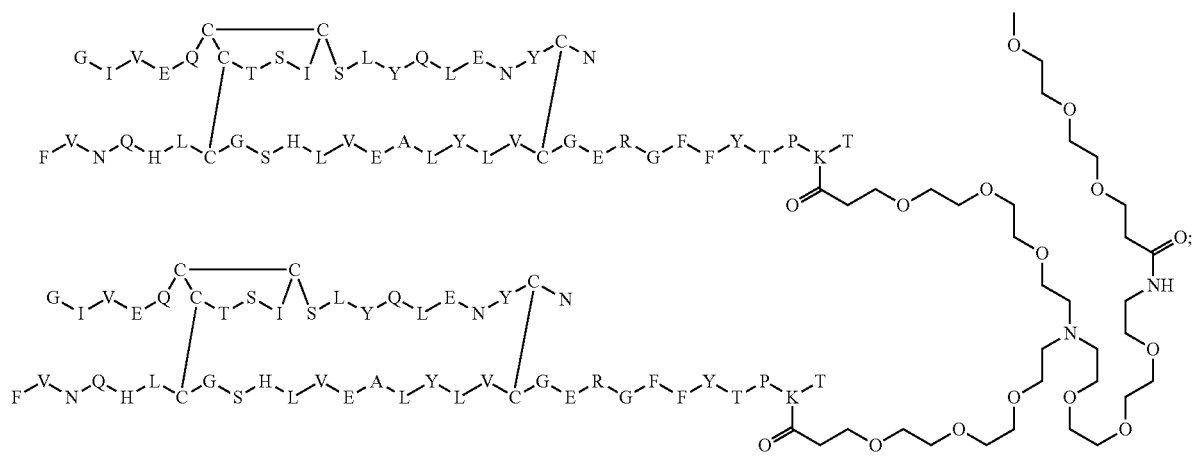

Dimer 86 wherein the disulfide linkages between the $Cys_6$ and $Cys_{11}$ residues of the A-chain polypeptide and the disulfide linkages between the $Cys_7$ and $Cys_{20}$ of the A-chain to the $Cys_7$ and $Cys_{19}$ of the B-chain polypeptide, respectively, are represented by the solid line therebetween; wherein the linking moieties are covalently linked to the epsilon amino acid of the shown lysine residue wherein the A-chain polypeptide for Dimers 1-32, 35-62, 64-66, 69-79 and 82-86 has the amino acid sequence shown in SEQ ID NO: 1; and the B-chain polypeptide for Dimers 1-32, 35-62, 64-66, 69-79 and 82-86 has the amino acid sequence shown in SEQ ID NO: 2.

2. A composition comprising the insulin receptor partial agonist of claim 1 and a GLP-1 receptor agonist.

3. A method for treating diabetes comprising administering to an individual with diabetes a therapeutically effective amount of a composition comprising the insulin receptor partial agonist of claim 1.

4. The method of claim 3, wherein the diabetes is Type 1 diabetes, Type 2 diabetes, or gestational diabetes.

5. A composition for the treatment of diabetes comprising the insulin receptor partial agonist of claim 1.

6. The composition of claim 5, wherein the diabetes is Type 1 diabetes, Type 2 diabetes, or gestational diabetes.

* * * * *

```
                        SEQUENCE LISTING

<160> NUMBER OF SEQ ID NOS: 11

<210> SEQ ID NO 1
<211> LENGTH: 21
<212> TYPE: PRT
<213> ORGANISM: Homo sapiens

<400> SEQUENCE: 1

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 2
<211> LENGTH: 30
<212> TYPE: PRT
<213> ORGANISM: Homo sapiens

<400> SEQUENCE: 2

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 3
<211> LENGTH: 21
<212> TYPE: PRT
<213> ORGANISM: Artificial Sequence
<220> FEATURE:
```

```
<223> OTHER INFORMATION: Insulin A chain mutiens
<220> FEATURE:
<221> NAME/KEY: MISC_FEATURE
<222> LOCATION: (2)..(2)
<223> OTHER INFORMATION: Xaa is isoleucine or threonine
<220> FEATURE:
<221> NAME/KEY: MISC_FEATURE
<222> LOCATION: (3)..(3)
<223> OTHER INFORMATION: Xaa is valine, glycine, or leucine
<220> FEATURE:
<221> NAME/KEY: MISC_FEATURE
<222> LOCATION: (8)..(8)
<223> OTHER INFORMATION: Xaa is threonine or histidine
<220> FEATURE:
<221> NAME/KEY: MISC_FEATURE
<222> LOCATION: (17)..(17)
<223> OTHER INFORMATION: Xaa is glutamic acid or glutamine
<220> FEATURE:
<221> NAME/KEY: MISC_FEATURE
<222> LOCATION: (19)..(19)
<223> OTHER INFORMATION: Xaa is tyrosine, 4-methoxy-phenylalanine,
     alanine, or 4-amino phenylalanine
<220> FEATURE:
<221> NAME/KEY: misc_feature
<222> LOCATION: (21)..(21)
<223> OTHER INFORMATION: Xaa can be any naturally occurring amino acid
<220> FEATURE:
<221> NAME/KEY: MISC_FEATURE
<222> LOCATION: (23)..(23)
<223> OTHER INFORMATION: Xaa is asparagine or glycine

<400> SEQUENCE: 3

Gly Xaa Xaa Glu Gln Cys Cys Xaa Ser Ile Cys Ser Leu Tyr Gln Leu
1               5                   10                  15

Xaa Asn Xaa Cys Xaa
            20

<210> SEQ ID NO 4
<211> LENGTH: 25
<212> TYPE: PRT
<213> ORGANISM: Artificial Sequence
<220> FEATURE:
<223> OTHER INFORMATION: Insulin B chain variants
<220> FEATURE:
<221> NAME/KEY: MISC_FEATURE
<222> LOCATION: (1)..(1)
<223> OTHER INFORMATION: Xaa is histidine or threonine
<220> FEATURE:
<221> NAME/KEY: MISC_FEATURE
<222> LOCATION: (1)..(25)
<223> OTHER INFORMATION: With the proviso that at least one of 24 or 25
     is lysine
<220> FEATURE:
<221> NAME/KEY: MISC_FEATURE
<222> LOCATION: (5)..(5)
<223> OTHER INFORMATION: Xaa is alanine, glycine, or serine
<220> FEATURE:
<221> NAME/KEY: MISC_FEATURE
<222> LOCATION: (6)..(6)
<223> OTHER INFORMATION: Xaa is histidine, aspartic acid, glutamic acid,
     homocysteic acid, or cysteic acid
<220> FEATURE:
<221> NAME/KEY: MISC_FEATURE
<222> LOCATION: (21)..(21)
<223> OTHER INFORMATION: Xaa is proline or lysine
<220> FEATURE:
<221> NAME/KEY: MISC_FEATURE
<222> LOCATION: (24)..(24)
<223> OTHER INFORMATION: Xaa is proline or lysine
<220> FEATURE:
<221> NAME/KEY: MISC_FEATURE
<222> LOCATION: (25)..(25)
<223> OTHER INFORMATION: Xaa is proline or lysine

<400> SEQUENCE: 4
```

-continued

```
Xaa Leu Cys Gly Xaa Xaa Leu Val Glu Ala Leu Tyr Leu Val Cys Gly
1               5                   10                  15

Glu Arg Gly Phe Xaa Tyr Thr Xaa Xaa
            20                  25
```

<210> SEQ ID NO 5
<211> LENGTH: 32
<212> TYPE: PRT
<213> ORGANISM: Artificial Sequence
<220> FEATURE:
<223> OTHER INFORMATION: Insulin B chain variants
<220> FEATURE:
<221> NAME/KEY: MISC_FEATURE
<222> LOCATION: (1)..(1)
<223> OTHER INFORMATION: Xaa is phenylalanine or desamino-phenylalanine
<220> FEATURE:
<221> NAME/KEY: MISC_FEATURE
<222> LOCATION: (1)..(32)
<223> OTHER INFORMATION: With the proviso that at least one of 28 or 29
      is lysine
<220> FEATURE:
<221> NAME/KEY: MISC_FEATURE
<222> LOCATION: (5)..(5)
<223> OTHER INFORMATION: Xaa is histidine or threonine
<220> FEATURE:
<221> NAME/KEY: MISC_FEATURE
<222> LOCATION: (6)..(6)
<223> OTHER INFORMATION: Xaa is glycine or leucine
<220> FEATURE:
<221> NAME/KEY: MISC_FEATURE
<222> LOCATION: (9)..(9)
<223> OTHER INFORMATION: Xaa is alanine, glycine, or serine
<220> FEATURE:
<221> NAME/KEY: MISC_FEATURE
<222> LOCATION: (10)..(10)
<223> OTHER INFORMATION: Xaa is histidine, aspartic acid, glutamic acid,
      homocysteic acid, or cysteic acid
<220> FEATURE:
<221> NAME/KEY: MISC_FEATURE
<222> LOCATION: (25)..(25)
<223> OTHER INFORMATION: Xaa is phenyalanine or aspartic acid
<220> FEATURE:
<221> NAME/KEY: MISC_FEATURE
<222> LOCATION: (28)..(28)
<223> OTHER INFORMATION: Xaa is aspartic acid, proline, or lysine
<220> FEATURE:
<221> NAME/KEY: MISC_FEATURE
<222> LOCATION: (29)..(29)
<223> OTHER INFORMATION: Xaa is lysine or proline
<220> FEATURE:
<221> NAME/KEY: MISC_FEATURE
<222> LOCATION: (30)..(30)
<223> OTHER INFORMATION: Xaa is threonine, alanine, or absent
<220> FEATURE:
<221> NAME/KEY: MISC_FEATURE
<222> LOCATION: (31)..(31)
<223> OTHER INFORMATION: Xaa is arginine or absent
<220> FEATURE:
<221> NAME/KEY: MISC_FEATURE
<222> LOCATION: (32)..(32)
<223> OTHER INFORMATION: Xaa is arginine or absent

<400> SEQUENCE: 5

```
Xaa Val Asn Gln Xaa Xaa Cys Gly Xaa Xaa Leu Val Glu Ala Leu Tyr
1               5                   10                  15

Leu Val Cys Gly Glu Arg Gly Phe Xaa Tyr Thr Xaa Xaa Xaa Xaa Xaa
            20                  25                  30
```

<210> SEQ ID NO 6
<211> LENGTH: 30
<212> TYPE: PRT
<213> ORGANISM: Artificial Sequence
<220> FEATURE:
<223> OTHER INFORMATION: Insulin lispro B chain

<400> SEQUENCE: 6

Phe Val Asn Gln His Leu Cys Gly Ser His Leu Val Glu Ala Leu Tyr
1               5                   10                  15

Leu Val Cys Gly Glu Arg Gly Phe Phe Tyr Thr Lys Pro Thr
            20                  25                  30

<210> SEQ ID NO 7
<211> LENGTH: 21
<212> TYPE: PRT
<213> ORGANISM: Artificial Sequence
<220> FEATURE:
<223> OTHER INFORMATION: Insulin glargine A chain

<400> SEQUENCE: 7

Gly Ile Val Glu Gln Cys Cys Thr Ser Ile Cys Ser Leu Tyr Gln Leu
1               5                   10                  15

Glu Asn Tyr Cys Gly
            20

<210> SEQ ID NO 8
<211> LENGTH: 32
<212> TYPE: PRT
<213> ORGANISM: Artificial Sequence
<220> FEATURE:
<223> OTHER INFORMATION: Insulin glargine B chain

<400> SEQUENCE: 8

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30

<210> SEQ ID NO 9
<211> LENGTH: 30
<212> TYPE: PRT
<213> ORGANISM: Artificial Sequence
<220> FEATURE:
<223> OTHER INFORMATION: Insulin aspart B chain

<400> SEQUENCE: 9

Phe Val Asn Gln His Leu Cys Gly Ser His Leu Val Glu Ala Leu Tyr
1               5                   10                  15

Leu Val Cys Gly Glu Arg Gly Phe Phe Tyr Thr Asp Lys Thr
            20                  25                  30

<210> SEQ ID NO 10
<211> LENGTH: 29
<212> TYPE: PRT
<213> ORGANISM: Artificial Sequence
<220> FEATURE:
<223> OTHER INFORMATION: Des30 B chain

<400> SEQUENCE: 10

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys
            20                  25

<210> SEQ ID NO 11
<211> LENGTH: 21
<212> TYPE: PRT
<213> ORGANISM: Artificial Sequence
<220> FEATURE:

<223> OTHER INFORMATION: A chain Y19A
<400> SEQUENCE: 11
Gly Ile Val Glu Gln Cys Cys Thr Ser Ile Cys Ser Leu Tyr Gln Leu
1               5                   10                  15
Glu Asn Ala Cys Asn
            20